United States Patent
Ni et al.

(10) Patent No.: US 9,656,959 B2
(45) Date of Patent: *May 23, 2017

(54) SUBSTITUTED PYRIDINES AS SODIUM CHANNEL BLOCKERS

(75) Inventors: Chiyou Ni, Belle Mead, NJ (US); Minnie Park, Princeton Junction, NJ (US); Bin Shao, Richboro, PA (US); Laykea Tafesse, Robbinsville, NJ (US); Jiangchao Yao, Princeton, NJ (US); Mark A. Youngman, North Wales, PA (US); Xiaoming Zhou, Monmouth Junction, NJ (US)

(73) Assignee: Purdue Pharma L.P., Stamford, CT (US)

( * ) Notice: Subject to any disclaimer, the term of this patent is extended or adjusted under 35 U.S.C. 154(b) by 135 days.

This patent is subject to a terminal disclaimer.

(21) Appl. No.: 13/996,082

(22) PCT Filed: Dec. 21, 2011

(86) PCT No.: PCT/IB2011/003137
§ 371 (c)(1),
(2), (4) Date: Sep. 9, 2013

(87) PCT Pub. No.: WO2012/085650
PCT Pub. Date: Jun. 28, 2012

(65) Prior Publication Data
US 2014/0005212 A1    Jan. 2, 2014

Related U.S. Application Data

(60) Provisional application No. 61/426,318, filed on Dec. 22, 2010.

(51) Int. Cl.
| | | |
|---|---|---|
| C07D 213/75 | (2006.01) |
| C07D 401/02 | (2006.01) |
| C07D 401/12 | (2006.01) |
| C07D 401/14 | (2006.01) |
| C07D 213/76 | (2006.01) |
| C07D 213/81 | (2006.01) |
| C07D 413/12 | (2006.01) |

(52) U.S. Cl.
CPC ......... *C07D 213/75* (2013.01); *C07D 213/76* (2013.01); *C07D 213/81* (2013.01); *C07D 401/02* (2013.01); *C07D 401/12* (2013.01); *C07D 401/14* (2013.01); *C07D 413/12* (2013.01)

(58) Field of Classification Search
None
See application file for complete search history.

(56) References Cited

U.S. PATENT DOCUMENTS

| | | | |
|---|---|---|---|
| 6,281,211 B1 | 8/2001 | Cai et al. |
| 6,335,354 B2 | 1/2002 | Hogenkamp |
| 6,414,011 B1 | 7/2002 | Hogenkamp et al. |
| 6,479,484 B1 | 11/2002 | Lan et al. |
| 6,500,825 B2 | 12/2002 | Lan et al. |
| 6,613,803 B1 | 9/2003 | Wang et al. |
| 6,638,947 B2 | 10/2003 | Wang et al. |
| 6,696,442 B2 | 2/2004 | Wang et al. |
| 6,737,418 B2 | 5/2004 | Hogenkamp et al. |
| 6,770,661 B2 | 8/2004 | Shao et al. |
| 6,867,210 B2 | 3/2005 | Hogenkamp et al. |
| 6,919,363 B2 | 7/2005 | Hogenkamp et al. |
| 6,979,686 B1 | 12/2005 | Naraian et al. |
| 7,022,714 B2 | 4/2006 | Sun et al. |
| 7,078,426 B2 | 7/2006 | Hogenkamp et al. |
| 7,091,210 B2 | 8/2006 | Lan et al. |
| 7,105,549 B2 | 9/2006 | Shao et al. |
| 7,169,782 B2 | 1/2007 | Sun et al. |
| 7,229,993 B2 | 6/2007 | Goehring et al. |
| 7,393,872 B2 | 7/2008 | Lan |

(Continued)

FOREIGN PATENT DOCUMENTS

| | | |
|---|---|---|
| CA | 2137443 A1 * | 6/1995 |
| EP | 1 402 900 A1 | 3/2004 |
| EP | 1 481 965 A1 | 12/2004 |
| WO | WO-99/39712 | 8/1999 |
| WO | WO-01/74779 | 10/2001 |
| WO | WO-03/022285 | 3/2003 |
| WO | 2005/070916 A1 | 8/2005 |
| WO | 2006/119390 A1 | 11/2006 |
| WO | 2007/050348 A2 | 5/2007 |
| WO | WO 2007/078523 * | 7/2007 |

(Continued)

OTHER PUBLICATIONS

Dörwald, F. Zaragoza. Side Reactions in Organic Synthesis: A Guide to Successful Synthesis Design, Weinheim: WILEY-VCH Verlag GmbH & Co. KGaA, 2005, Preface).*

(Continued)

*Primary Examiner* — Kortney L Klinkel
*Assistant Examiner* — William Lee
(74) *Attorney, Agent, or Firm* — Purdue Pharma L.P.; Alan L. Koller; Weiying Yang

(57) ABSTRACT

The invention relates to substituted pyridine compounds of Formula I: (I) and the pharmaceutically acceptable salts, prodrugs, and solvates thereof, wherein $R^{1a}$, $R^{1b}$, $R^{2a}$, $R^{2b}$, $R^{2c}$, $A^1$, $A^2$, and X are defined as set forth in the specification. The invention is also directed to the use of compounds of Formula I to treat a disorder responsive to the blockade of sodium channels. Compounds of the present invention are especially useful for treating pain.

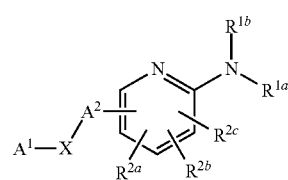

I

24 Claims, No Drawings

(56) References Cited

U.S. PATENT DOCUMENTS

| | | |
|---|---|---|
| 7,541,465 B2 | 6/2009 | Lan et al. |
| 7,579,367 B2 | 8/2009 | Shao et al. |
| 7,872,127 B2 | 1/2011 | Lan et al. |
| 7,943,643 B2 | 5/2011 | Shao et al. |
| 8,426,431 B2 | 4/2013 | Lan et al. |
| 9,045,435 B2 | 6/2015 | Goehring et al. |
| 9,056,832 B2 * | 6/2015 | Ni .................. C07D 213/30 |
| 9,120,752 B2 * | 9/2015 | Kyle ................. C07D 213/81 |
| 9,120,786 B2 | 9/2015 | Tadesse et al. |
| 9,168,255 B2 | 10/2015 | Goehring et al. |
| 9,206,127 B2 | 12/2015 | Tafesse et al. |
| 2003/0225080 A1 | 12/2003 | Wang et al. |
| 2003/0236256 A1 | 12/2003 | Eberle et al. |
| 2004/0054186 A1 | 3/2004 | Das et al. |
| 2004/0097569 A1 | 5/2004 | Sun et al. |
| 2004/0152696 A1 | 8/2004 | Sun et al. |
| 2004/0176364 A1 | 9/2004 | Sun et al. |
| 2004/0192691 A1 | 9/2004 | Hogenkamp et al. |
| 2005/0043305 A1 | 2/2005 | Hogenkamp et al. |
| 2005/0222027 A1 | 10/2005 | Chiang et al. |
| 2008/0187575 A1 | 8/2008 | Klebl et al. |
| 2013/0289044 A1 | 10/2013 | Goehring et al. |
| 2013/0296281 A1 | 11/2013 | Kyle et al. |
| 2013/0303526 A1 | 11/2013 | Ni et al. |
| 2013/0303568 A1 | 11/2013 | Lan et al. |
| 2013/0345211 A1 | 12/2013 | Kyle et al. |
| 2014/0249128 A1 | 9/2014 | Yu et al. |
| 2014/0288092 A1 | 9/2014 | Yao |
| 2014/0303139 A1 | 10/2014 | Ni et al. |
| 2014/0309228 A1 | 10/2014 | Engel |
| 2014/0315783 A1 | 10/2014 | Shao |
| 2015/0057300 A1 | 2/2015 | Tafesse et al. |
| 2015/0133500 A1 | 5/2015 | Tafesse et al. |
| 2015/0141434 A1 | 5/2015 | Park |
| 2015/0259293 A1 | 9/2015 | Ni et al. |
| 2015/0284383 A1 | 10/2015 | Lynch et al. |
| 2015/0335642 A1 | 11/2015 | Shao |
| 2015/0336974 A1 | 11/2015 | Youngman |
| 2015/0344465 A1 | 12/2015 | Kyle et al. |
| 2015/0353512 A1 | 12/2015 | Tadesse et al. |
| 2016/0009659 A1 | 1/2016 | Lockman et al. |
| 2016/0031873 A1 | 2/2016 | Yao et al. |
| 2016/0052911 A1 | 2/2016 | Yao |
| 2016/0145210 A1 | 5/2016 | Tafesse |
| 2016/0207923 A1 | 7/2016 | Youngman et al. |

FOREIGN PATENT DOCUMENTS

| | | | |
|---|---|---|---|
| WO | WO 2009/004430 | * | 1/2009 |
| WO | 2009/049181 A1 | | 4/2009 |
| WO | 2009/140517 A1 | | 11/2009 |
| WO | 2010/030967 A1 | | 3/2010 |
| WO | WO 2010/052569 | * | 5/2010 |
| WO | WO 2010/138600 | * | 5/2010 |
| WO | WO 2010/150192 | * | 6/2010 |
| WO | 2011/019780 A1 | | 2/2011 |
| WO | WO-2014/016673 A1 | | 1/2014 |
| WO | WO-2014/151393 A2 | | 9/2014 |
| WO | WO-2015/031036 | | 3/2015 |
| WO | WO-2015/094443 | | 6/2015 |
| WO | WO-2015/099841 | | 7/2015 |
| WO | WO-2015/112801 | | 7/2015 |
| WO | WO-2016/134283 | | 8/2016 |

OTHER PUBLICATIONS

Jordan, V. C. (Nature Reviews: Drug Discovery, 2, 2003, 205-213).*
International Search Report mailed on Mar. 13, 2012 in corresponding International Application No. PCT/IB2011/003137 with Written Opinions.
Hubner et al., Hum. Mol. Genet. 11:2435-2445 (2002).
Yogeeswari et al, Curr. Drug Target 5:589-602 (2004).
Noble, Proc. Natl. Acad. Sci. USA 99:5755-5756 (2002).
Cannon, Kidney Int. 57:772-779 (2000).
Wood et al., J. Neurobiol., 61:55-71 (2004).
Chahine et al., CNS & Neurological Disorders—Drug Targets 7:144-158 (2008).
Kyle and Ilyin, J. Med. Chem. 50:2583-2588 (2007).
Liu et al., Am. J. Pharmacogenomics 3:173-179 (2003).
Srivatsa et al., Curr. Cardiol. Rep. 4:401-410 (2002).
Black et al., Proc. Natl. Acad. Sci. USA 97:11598-115602 (2000).
Laird et al., J. Neurosci. 22:8352-8356 (2002).
Toledo-Aral et al., Proc. Natl. Acad. Sci. USA 94:1527-1532 (1997).
Nassar et al., Proc Natl. Acad. Sci. USA 101:12706-12711 (2004).
Clare et al., Drug Discovery Today 5:506-510 (2000).
Lai et al., Annu. Rev. Pharmacol. Toxicol. 44:371-397 (2004).
Catterall, Trends Pharmacol. Sci. 8:57-65 (1987).
Graham et al., J. Pharmacol. Exp. Ther. 269:854-859 (1994).
Brown et al., British J. Pharmacol. 115:1425-1432 (1995).
Baker et al., Trends in Pharmacological Sciences 22:27-31 (2001).
Lai et al., Current Opinion in Neurobiology 13:291-297 (2003).
Meisler and Kearney, J. Clin. Invest. 115:2010-2017 (2005).
Taylor and Meldrum, Trends Pharmacol. Sci. 16:309-316 (1995).
Moller, Am. J. Otol. 18:577-585 (1997).
Tonndorf, Hear. Res. 28:271-275 (1987).
Simpson, et al., TiP. 20:12-18 (1999).
Majumdar, B. et al., Clin. Otolaryngol. 8:175-180 (1983).
Donaldson, Laryngol. Otol. 95:947-951 (1981).
Shao et al., "Phenoxyphenyl Pyridines as novel State-Dependent, High-Potency Sodium Channel Inhibitors", J. Med. Chem., vol. 47, No. 17, 4277-4285 (2004).
Anger et al., J Med. Chem. 44:115-137 (2001).

* cited by examiner

SUBSTITUTED PYRIDINES AS SODIUM CHANNEL BLOCKERS

BACKGROUND OF THE INVENTION

Field of the Invention

This invention is in the field of medicinal chemistry. The invention relates to novel substituted pyridine compounds and the use of these compounds as blockers of voltage-gated sodium (Na$^+$) channels.

Background Art

Voltage-gated sodium channels (VGSCs) are found in all excitable cells. In neuronal cells of the central nervous system (CNS) and peripheral nervous system (PNS) sodium channels are primarily responsible for generating the rapid upstroke of the action potential. In this manner sodium channels are essential to the initiation and propagation of electrical signals in the nervous system. Proper function of sodium channels is therefore necessary for normal function of the neuron. Consequently, aberrant sodium channel function is thought to underlie a variety of medical disorders (See Hubner et al., *Hum. Mol. Genet.* 11:2435-2445 (2002) for a general review of inherited ion channel disorders) including epilepsy (Yogeeswari et al, *Curr. Drug Target* 5:589-602 (2004)), arrhythmia (Noble, *Proc. Natl. Acad. Sci. USA* 99:5755-5756 (2002)), myotonia (Cannon, *Kidney Int.* 57:772-779 (2000)), and pain (Wood et al., *J. Neurobiol.*, 61:55-71 (2004)).

VGSCs are composed of one α-subunit, which forms the core of the channel and is responsible for voltage-dependent gating and ion permeation, and several auxiliary β-subunits (see, e.g., Chahine et al., *CNS & Neurological Disorders—Drug Targets* 7:144-158 (2008) and Kyle and Ilyin, *J. Med. Chem.* 50:2583-2588 (2007)). α-Subunits are large proteins composed of four homologous domains. Each domain contains six α-helical transmembrane spanning segments. There are currently nine known members of the family of voltage-gated sodium channel α-subunits. Names for this family include SCNx, SCNAx, and Na$_v$x.x (see Table 1, below). The VGSC family has been phylogenetically divided into two subfamilies Na$_v$1.x (all but SCN6A) and Na$_v$2.x (SCN6A). The Na$_v$1.x subfamily can be functionally subdivided into two groups, those which are sensitive to blocking by tetrodotoxin (TTX-sensitive or TTX-s) and those which are resistant to blocking by tetrodotoxin (TTX-resistant or TTX-r).

There are three members of the subgroup of TTX-resistant sodium channels. The SCN5A gene product (Na$_v$1.5, HI) is almost exclusively expressed in cardiac tissue and has been shown to underlie a variety of cardiac arrhythmias and other conduction disorders (Liu et al., *Am. J. Pharmacogenomics* 3:173-179 (2003)). Consequently, blockers of Na$_v$1.5 have found clinical utility in treatment of such disorders (Srivatsa et al., *Curr. Cardiol. Rep.* 4:401-410 (2002)). The remaining TTX-resistant sodium channels, Na$_v$1.8 (SCN10A, PN3, SNS) and Na$_v$1.9 (SCN11A, NaN, SNS2) are expressed in the peripheral nervous system and show preferential expression in primary nociceptive neurons. Human genetic variants of these channels have not been associated with any inherited clinical disorder. However, aberrant expression of Na$_v$1.8 has been found in the CNS of human multiple sclerosis (MS) patients and also in a rodent model of MS (Black et al., *Proc. Natl. Acad. Sci. USA* 97:11598-115602 (2000)). Evidence for involvement in nociception is both associative (preferential expression in nociceptive neurons) and direct (genetic knockout). Na$_v$1.8-null mice exhibited typical nociceptive behavior in response to acute noxious stimulation but had significant deficits in referred pain and hyperalgesia (Laird et al., *J. Neurosci.* 22:8352-8356 (2002)).

TABLE 1

Voltage-gated sodium channel gene family

| Type | Gene Symbol | Tissue Distribution | TTX IC$_{50}$ (nM) | Disease Association | Indications |
|---|---|---|---|---|---|
| Na$_v$1.1 | SCN1A | CNS/PNS | 10 | Epilepsy | Pain, seizures, neurodegeneration |
| Na$_v$1.2 | SCN2A | CNS | 10 | Epilepsy | Epilepsy, neurodegeneration |
| Na$_v$1.3 | SCN3A | CNS | 15 | — | Pain |
| Na$_v$1.4 | SCN4A | Skeletal muscle | 25 | Myotonia | Myotonia |
| Na$_v$1.5 | SCN5A | Heart muscle | 2,000 | Arrhythmia | Arrhythmia |
| Na$_v$1.6 | SCN8A | CNS/PNS | 6 | — | Pain, movement disorders |
| Na$_v$1.7 | SCN9A | PNS | 25 | Erythermalgia | Pain |
| Na$_v$1.8 | SCN10A | PNS | 50,000 | — | Pain |
| Na$_v$1.9 | SCN11A | PNS | 1,000 | — | Pain |

The Na$_v$1.7 (PN1, SCN9A) VGSC is sensitive to blocking by tetrodotoxin and is preferentially expressed in peripheral sympathetic and sensory neurons. The SCN9A gene has been cloned from a number of species, including human, rat, and rabbit and shows ~90% amino acid identity between the human and rat genes (Toledo-Aral et al., *Proc. Natl. Acad. Sci. USA* 94:1527-1532 (1997)).

An increasing body of evidence suggests that Na$_v$1.7 plays a key role in various pain states, including acute, inflammatory and/or neuropathic pain. Deletion of the SCN9A gene in nociceptive neurons of mice led to an increase in mechanical and thermal pain thresholds and reduction or abolition of inflammatory pain responses (Nassar et al., *Proc Natl. Acad. Sci. USA* 101:12706-12711 (2004)).

Sodium channel-blocking agents have been reported to be effective in the treatment of various disease states, and have found particular use as local anesthetics, e.g., lidocaine and bupivacaine, and in the treatment of cardiac arrhythmias, e.g., propafenone and amiodarone, and epilepsy, e.g., lamotrigine, phenyloin and carbamazepine (see Clare et al., *Drug Discovery Today* 5:506-510 (2000); Lai et al., *Annu.*

Rev. Pharmacol. Toxicol. 44:371-397 (2004); Anger et al., *J. Med. Chem.* 44:115-137 (2001), and Catterall, *Trends Pharmacol. Sci.* 8:57-65 (1987)). Each of these agents is believed to act by interfering with the rapid influx of sodium ions.

Other sodium channel blockers such as BW619C89 and lifarizine have been shown to be neuroprotective in animal models of global and focal ischemia (Graham et al., *J. Pharmacol. Exp. Ther.* 269:854-859 (1994); Brown et al., *British J. Pharmacol.* 115:1425-1432 (1995)). It has also been reported that sodium channel-blocking agents can be useful in the treatment of pain, including acute, chronic, inflammatory, neuropathic, and other types of pain such as rectal, ocular, and submandibular pain typically associated with paroxysmal extreme pain disorder; see, for example, Kyle and Ilyin., *J. Med. Chem.* 50:2583-2588 (2007); Wood et al., *J. Neurobiol.* 61:55-71 (2004); Baker et al., *TRENDS in Pharmacological Sciences* 22:27-31 (2001); and Lai et al., *Current Opinion in Neurobiology* 13:291-297 (2003); the treatment of neurological disorders such as epilepsy, seizures, epilepsy with febrile seizures, epilepsy with benign familial neonatal infantile seizures, inherited pain disorders, e.g., primary erythermalgia and paroxysmal extreme pain disorder, familial hemiplegic migraine, and movement disorder; and the treatment of other psychiatric disorders such as autism, cerebellar atrophy, ataxia, and mental retardation; see, for example, Chahine et al., *CNS & Neurological Disorders—Drug Targets* 7:144-158 (2008) and Meisler and Kearney, *J. Clin. Invest.* 115:2010-2017 (2005). In addition to the above-mentioned clinical uses, carbamazepine, lidocaine and phenyloin are used to treat neuropathic pain, such as from trigeminal neuralgia, diabetic neuropathy and other forms of nerve damage (Taylor and Meldrum, *Trends Pharmacol. Sci.* 16:309-316 (1995)). Furthermore, based on a number of similarities between chronic pain and tinnitus, (Moller, *Am. J. Otol.* 18:577-585 (1997); Tonndorf, *Hear. Res.* 28:271-275 (1987)) it has been proposed that tinnitus should be viewed as a form of chronic pain sensation (Simpson, et al., *TiP.* 20:12-18 (1999)). Indeed, lidocaine and carbamazepine have been shown to be efficacious in treating tinnitus (Majumdar, B. et al., *Clin. Otolaryngol.* 8:175-180 (1983); Donaldson, *Laryngol. Otol.* 95:947-951 (1981)).

Many patients with either acute or chronic pain disorders respond poorly to current pain therapies, and the development of resistance or insensitivity to opiates is common. In addition, many of the currently available treatments have undesirable side effects.

In view of the limited efficacy and/or unacceptable side-effects of the currently available agents, there is a pressing need for more effective and safer analgesics that work by blocking sodium channels.

BRIEF SUMMARY OF THE INVENTION

The present invention is related to the use of substituted pyridine compounds represented by Formulae I-XVI, below, and the pharmaceutically acceptable salts, prodrugs and solvates thereof (collectively referred to herein as "Compounds of the Invention"), as blockers of sodium ($Na^+$) channels.

The present invention is also related to treating a disorder responsive to the blockade of sodium channels in a mammal suffering from excess activity of said channels by administering an effective amount of a Compound of the Invention as described herein. Some compounds useful in the present invention have not been heretofore reported. Thus, one aspect of the present invention is directed to novel compounds of Formula I-XVI, as well as their pharmaceutically acceptable salts, prodrugs and solvates.

Another aspect of the present invention is directed to the use of the novel compounds of Formulae I-XVI, and their pharmaceutically acceptable salts, prodrugs and solvates, as blockers of sodium channels.

A further aspect of the present invention is to provide a method for treating pain (e.g., acute pain, chronic pain, which includes but is not limited to, neuropathic pain, postoperative pain, and inflammatory pain, or surgical pain) by administering an effective amount of a Compound of the Invention to a mammal in need of such treatment. Specifically, the present invention provides a method for preemptive or palliative treatment of pain by administering an effective amount of a Compound of the Invention to a mammal in need of such treatment. A further aspect of the present invention is to provide a method for treating stroke, neuronal damage resulting from head trauma, epilepsy, seizures, general epilepsy with febrile seizures, severe myoclonic epilepsy in infancy, neuronal loss following global and focal ischemia, migraine, familial primary erythromelalgia, paroxysmal extreme pain disorder, cerebellar atrophy, ataxia, dystonia, tremor, mental retardation, autism, a neurodegenerative disorder (e.g., Alzheimer's disease, amyotrophic lateral sclerosis (ALS), or Parkinson's disease), manic depression, tinnitus, myotonia, a movement disorder, or cardiac arrhythmia, or providing local anesthesia, by administering an effective amount of a Compound of the Invention to a mammal in need of such treatment.

A further aspect of the present invention is to provide a pharmaceutical composition useful for treating a disorder responsive to the blockade of sodium ion channels, said pharmaceutical composition containing an effective amount of a Compound of the Invention in a mixture with one or more pharmaceutically acceptable carriers.

Also, an aspect of the present invention is to provide a method of modulating sodium channels in a mammal, wherein said method comprises administering to the mammal an effective amount of at least one Compound of the Invention.

A further aspect of the present invention is to provide a Compound of the Invention for use in treating pain in a mammal, e.g., acute pain, chronic pain, which includes but is not limited to, neuropathic pain, postoperative pain, and inflammatory pain, or surgical pain.

A further aspect of the present invention is to provide a Compound of the Invention for use in treating stroke, neuronal damage resulting from head trauma, epilepsy, seizures, general epilepsy with febrile seizures, severe myoclonic epilepsy in infancy, neuronal loss following global and focal ischemia, migraine, familial primary erythromelalgia, paroxysmal extreme pain disorder, cerebellar atrophy, ataxia, dystonia, tremor, mental retardation, autism, a neurodegenerative disorder (e.g., Alzheimer's disease, amyotrophic lateral sclerosis (ALS), or Parkinson's disease), manic depression, tinnitus, myotonia, a movement disorder, or cardiac arrhythmia, or providing local anesthesia, in a mammal.

A further aspect of the present invention is to provide radiolabeled Compounds of the Invention and the use of such compounds as radioligands in any appropriately selected competitive binding assays and screening methodologies. Thus, the present invention further provides a method for screening a candidate compound for its ability to bind to a sodium channel or sodium channel subunit using a radiolabeled Compound of the Invention. In certain embodiments, the compound is radiolabeled with $^3H$, $^{11}C$, or $^{14}$C. This competitive binding assay can be conducted using any appropriately selected methodology. In one embodiment, the screening method comprises: i) introducing a fixed concentration of the radiolabeled compound to an in vitro preparation comprising a soluble or membrane-associated sodium channel, subunit or fragment under conditions that permit the radiolabeled compound to bind to the channel, subunit or fragment, respectively, to form a conjugate; ii) titrating the conjugate with a candidate compound; and iii) determining the ability of the candidate compound to displace the radiolabeled compound from said channel, subunit or fragment.

A further aspect of the present invention is to provide the use of a Compound of the Invention in the manufacture of a medicament for treating pain in a mammal. In one embodiment, the invention provides the use of a Compound of the Invention in the manufacture of a medicament for palliative or preemptive treatment of pain, such as acute pain, chronic pain, or surgical pain.

A further aspect of the present invention is to provide the use of a Compound of the Invention in the manufacture of a medicament for treating stroke, neuronal damage resulting from head trauma, epilepsy, seizures, general epilepsy with febrile seizures, severe myoclonic epilepsy in infancy, neuronal loss following global and focal ischemia, migraine, familial primary erythromelalgia, paroxysmal extreme pain disorder, cerebellar atrophy, ataxia, dystonia, tremor, mental retardation, autism, a neurodegenerative disorder (e.g., Alzheimer's disease, amyotrophic lateral sclerosis (ALS), or Parkinson's disease), manic depression, tinnitus, myotonia, a movement disorder, or cardiac arrhythmia, or providing local anesthesia, in a mammal.

Additional embodiments and advantages of the invention will be set forth in part in the description that follows, and will flow from the description, or can be learned by practice of the invention. The embodiments and advantages of the invention will be realized and attained by means of the elements and combinations particularly pointed out in the appended claims.

It is to be understood that both the foregoing summary and the following detailed description are exemplary and explanatory only and are not restrictive of the invention as claimed.

DETAILED DESCRIPTION OF THE INVENTION

One aspect of the present invention is based on the use of compounds of Formula I, and the pharmaceutically acceptable salts, prodrugs and solvates thereof, as blockers of Na$^+$ channels. In view of this property, compounds of Formula I, and the pharmaceutically acceptable salts, prodrugs and solvates thereof, are useful for treating disorders responsive to the blockade of sodium ion channels.

In one embodiment, compounds useful in this aspect of the invention are compounds represented by Formula I:

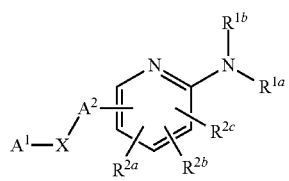

I wherein:
A$^1$ is selected from the group consisting of:
  optionally substituted cycloalkyl;
  optionally substituted heterocyclo;
  optionally substituted aryl; and
  optionally substituted heteroaryl;
X is selected from the group consisting of:
  —O—;
  —S—;
  —SO—;
  —SO$_2$—
  —(CR$^3$R$^4$)$_m$—;
  —NR$^5$—;
  —SO$_2$NH—; and
  —NHSO$_2$—
wherein:
each R$^3$ and R$^4$, which can be identical or different, are selected from the group consisting of:
  hydrogen;
  halo; and
  optionally substituted alkyl; or
each R$^3$ and R$^4$ taken together with the carbon atom to which they are attached form a 3- to 8-membered optionally substituted cycloalkyl or optionally substituted heterocyclo;
m is 0, 1, 2, or 3; and
R$^5$ is selected from the group consisting of hydrogen and optionally substituted alkyl;
A$^2$ is selected from the group consisting of optionally substituted aryl and optionally substituted heteroaryl;
R$^{1a}$ is selected from the group consisting of:
  optionally substituted alkyl;
  (heterocyclo)alkyl;
  (heteroaryl)alkyl;
  (amino)alkyl;
  (alkylamino)alkyl;
  (dialkylamino)alkyl;
  (carboxamido)alkyl;
  (cyano)alkyl;
  alkoxyalkyl;
  hydroxyalkyl;
  heteroalkyl;
  optionally substituted heterocyclo;
  —SO$_2$R$^6$; and
  —COR$^7$;
wherein:
R$^6$ is selected from the group consisting of:
  optionally substituted alkyl;
  optionally substituted cycloalkyl;
  optionally substituted aryl;
  optionally substituted heteroaryl;
  amino;
  alkylamino;
  dialkylamino;
  cycloalkylamino;
  heterocycloalkylamino;
  heteroarylamino;
  arylamino; and
  optionally substituted alkenyl;
R$^7$ is selected from the group consisting of:
  optionally substituted heteroaryl;
  b)

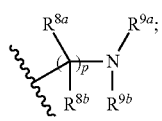

and
  c) hydroxyalkyl;
wherein:
p is 0, 1, or 2;

each $R^{8a}$ and $R^{8b}$, which can be identical or different, are selected from the group consisting of:
  hydrogen;
  optionally substituted alkyl;
  aralkyl;
  (heterocyclo)alkyl;
  (heteroaryl)alkyl;
  (amino)alkyl;
  (alkylamino)alkyl;
  (dialkylamino)alkyl;
  (carboxamido)alkyl;
  (cyano)alkyl;
  hydroxyalkyl;
  optionally substituted cycloalkyl;
  optionally substituted aryl;
  optionally substituted heterocyclo; and
  optionally substituted heteroaryl;
$R^{9a}$ is selected from the group consisting of:
  hydrogen;
  optionally substituted alkyl;
  —$COR^{10}$;
  —$SO_2R^{11}$; and
  —$R^{25}$;
  wherein:
$R^{10}$ is selected from the group consisting of:
  optionally substituted alkyl;
  aralkyl;
  (heterocyclo)alkyl;
  (heteroaryl)alkyl;
  (amino)alkyl;
  (alkylamino)alkyl;
  (dialkylamino)alkyl;
  (carboxamido)alkyl;
  (cyano)alkyl;
  alkoxyalkyl;
  hydroxyalkyl;
  heteroalkyl;
  optionally substituted cycloalkyl;
  optionally substituted aryl;
  optionally substituted heterocyclo;
  optionally substituted heteroaryl;
  amino;
  alkylamino;
  dialkylamino;
  cycloalkylamino;
  heterocycloalkylamino;
  heteroarylamino;
  arylamino;
  alkoxy; and
  haloalkyl
$R^{11}$ is selected from the group consisting of:
  optionally substituted alkyl;
  aralkyl;
  (heterocyclo)alkyl;
  (heteroaryl)alkyl;
  (amino)alkyl;
  (alkylamino)alkyl;
  (dialkylamino)alkyl;
  (carboxamido)alkyl;
  (cyano)alkyl;
  alkoxyalkyl;
  hydroxyalkyl;
  heteroalkyl;
  optionally substituted cycloalkyl;
  optionally substituted aryl;
  optionally substituted heterocyclo;
  optionally substituted heteroaryl;
  amino;
  alkylamino;
  dialkylamino;
  cycloalkylamino;
  heterocycloalkylamino;
  heteroarylamino; and
  arylamino;
$R^{9b}$ is selected from the group consisting of hydrogen and optionally substituted alkyl; or
$R^{9a}$ and $R^{9b}$ taken together with the nitrogen atom to which they are attached form a 3- to 8-membered optionally substituted heterocyclo;
$R^{1b}$ is selected from the group consisting of:
  hydrogen;
  optionally substituted alkyl;
  (heterocyclo)alkyl;
  (heteroaryl)alkyl;
  (amino)alkyl;
  (alkylamino)alkyl;
  (dialkylamino)alkyl;
  (carboxamido)alkyl;
  (cyano)alkyl;
  alkoxyalkyl; and
  hydroxyalkyl; or
$R^{1a}$ and $R^{1b}$ taken together with the nitrogen atom to which they are attached form a 3- to 8-membered optionally substituted heterocyclo;
$R^{2a}$, $R^{2b}$, and $R^{2c}$, which can be identical or different, are selected from the group consisting of:
  hydrogen;
  halo;
  nitro;
  cyano;
  hydroxy;
  amino;
  alkylamino;
  dialkylamino;
  haloalkyl;
  hydroxyalkyl;
  alkoxy;
  haloalkoxy;
  aryloxy;
  aralkyloxy;
  alkylthio;
  carboxamido;
  sulfonamido;
  alkylcarbonyl;
  arylcarbonyl;
  alkylsulfonyl;
  arylsulfonyl;
  ureido;
  guanidino;
  carboxy;
  carboxyalkyl;
  optionally substituted alkyl,
  (amino)alkyl; and
  (diamino)alkyl; and
$R^{25}$ is:

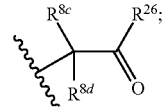

$R^{8c}$ and $R^{8d}$, which can be identical or different, are selected from the group consisting of:
  hydrogen;
  optionally substituted alkyl;
  aralkyl;
  (heterocyclo)alkyl;

(heteroaryl)alkyl;
(amino)alkyl;
(alkylamino)alkyl;
(dialkylamino)alkyl;
(carboxamido)alkyl;
(cyano)alkyl;
alkoxyalkyl;
hydroxyalkyl;
optionally substituted cycloalkyl;
optionally substituted aryl;
optionally substituted heterocyclo; and
optionally substituted heteroaryl; and
$R^{26}$ is selected from the group consisting of:
hydroxy;
alkoxy;
amino;
alkylamino;
dialkylamino;
hydroxyalkylamino;
arylamino; and
cycloalkylamino,
and the pharmaceutically acceptable salts, solvates, and prodrugs thereof.

The $A^1$-X-$A^2$- group can be at any of the four available carbon atoms of the pyridine ring. In one embodiment, Compounds of the Invention are compounds having Formula I, with the proviso that when $R^{1a}$ and $R^{1b}$ taken together with the nitrogen atom to which they are attached form a 3- to 8-membered optionally substituted heterocyclo or when $R^{1a}$ is alkoxyalkyl, alkyl or alkylaminoalkyl, then X is selected from the group consisting of:
—O—;
—S—;
—SO—;
—SO$_2$—
—(CR$^3$R$^4$)$_m$—;
—SO$_2$NH—; and
—NHSO$_2$— and
the pharmaceutically acceptable salts, solvates, and prodrugs thereof.

In one embodiment, Compounds of the Invention are compounds having Formula I, with the proviso that when $A^2$ pyrrolopyridine and X is X is —(CR$^3$R$^4$)$_m$—, then m is 1, 2, or 3,
and the pharmaceutically acceptable salts, solvates, and prodrugs thereof.

In one embodiment, Compounds of the Invention are compounds having Formula I, with the proviso that when $R^7$ is:

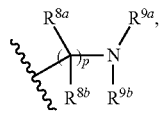

and X is —(CR$^3$R$^4$)$_m$—, then m is 1, 2, or 3, and the pharmaceutically acceptable salts, solvates, and prodrugs thereof.

In one embodiment, Compounds of the Invention are compounds having Formula I, with the proviso that when $R^7$ is optionally substituted heteroaryl, then $A^1$ is selected from the group consisting of optionally substituted aryl and optionally substituted heteroaryl, and the pharmaceutically acceptable salts, solvates, and prodrugs thereof.

In one embodiment, Compounds of the Invention are compounds having Formula I, wherein:
$R^7$ is selected from the group consisting of:
optionally substituted heteroaryl; and
b)

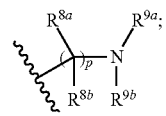

X is selected from the group consisting of:
—O—;
—S—;
—SO—;
—SO$_2$—
—(CR$^3$R$^4$)$_m$—;
—NR$^5$—; and
—SO$_2$NH—; and
$R^{9a}$ is selected from the group consisting of:
hydrogen;
optionally substituted alkyl;
—COR$^{10}$; and
—SO$_2$R$^{11}$,
and the pharmaceutically acceptable salts, solvates, and prodrugs thereof.

In one embodiment, Compounds of the Invention are compounds having Formula II:

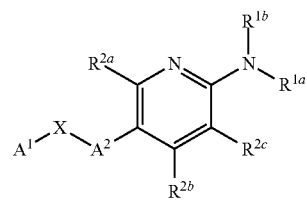

and the pharmaceutically acceptable salts, solvates, and prodrugs thereof, wherein $R^{1a}$, $R^{1b}$, $R^{2a}$, $R^{2b}$, $R^{2c}$, $A^1$, $A^2$, and X are as defined above in connection with Formula I.

In one embodiment, Compounds of the Invention are compounds having Formula III:

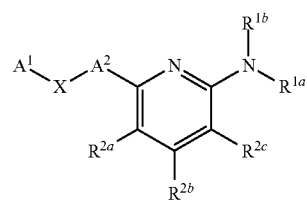

and the pharmaceutically acceptable salts, solvates, and prodrugs thereof, wherein $R^{1a}$, $R^{1b}$, $R^{2a}$, $R^{2b}$, $R^{2c}$, $A^1$, $A^2$, and X are as defined above in connection with Formula I.

In one embodiment, Compounds of the Invention are compounds having any of Formulae I-III wherein $R^{1a}$ is —SO$_2$R$^6$, and the pharmaceutically acceptable salts, solvates, and prodrugs thereof.

In one embodiment, Compounds of the Invention are compounds having any of Formulae I-III wherein $R^{1a}$ is —COR$^7$, $R^7$ is:

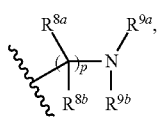

and p is 1, and the pharmaceutically acceptable salts, solvates, and prodrugs thereof.

In one embodiment, Compounds of the Invention are compounds having any of Formulae I-III wherein:
$R^{1a}$ is —COR$^7$;
$R^7$ is hydroxyalkyl; and
X is selected from the group consisting of:
—O—;
—S—;
—SO—;
—SO$_2$—;
—(CR$^3$R$^4$)$_m$—; and
—NR$^5$—, and the pharmaceutically acceptable salts, solvates, and prodrugs thereof.

In one embodiment, Compounds of the Invention are compounds having any of Formulae I-III wherein:
$R^{1a}$ is —COR$^7$;
$R^7$ a $C_{2-4}$ dihydroxyalkyl; and
X is selected from the group consisting of:
—O—;
—S—;
—SO—;
—SO$_2$—;
—(CR$^3$R$^4$)$_m$—; and
—NR$^5$—, and the pharmaceutically acceptable salts, solvates, and prodrugs thereof.

In one embodiment, Compounds of the Invention are compounds having any of Formulae I-III wherein:
$R^{1a}$ is —COR$^7$;
$R^7$ is selected from the group consisting of:

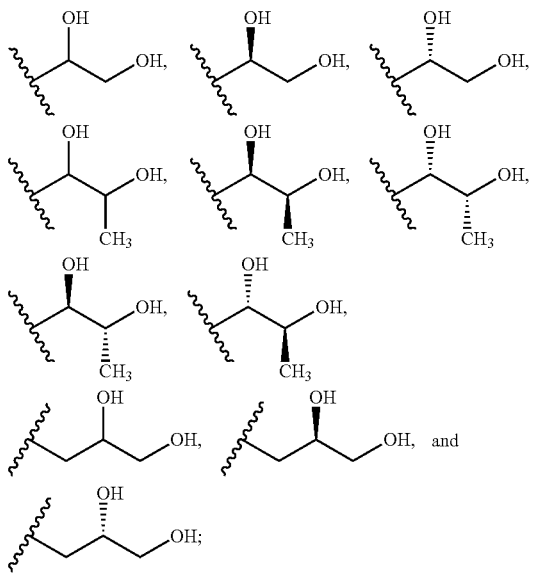

and
X is selected from the group consisting of:
—O—;
—S—;
—SO—;
—SO$_2$—;
—(CR$^3$R$^4$)$_m$—; and
—NR$^5$—, and the pharmaceutically acceptable salts, solvates, and prodrugs thereof.

In one embodiment, Compounds of the Invention are compounds having Formula IV:

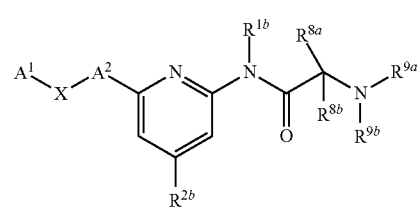

and the pharmaceutically acceptable salts, solvates, and prodrugs thereof, wherein $R^{1b}$, $R^{2b}$, $R^{8a}$, $R^{8b}$, $R^{9a}$, $R^{9b}$, $A^1$, $A^2$, and X are as defined above in connection with Formula I.

In one embodiment, Compounds of the Invention are compounds having Formula V:

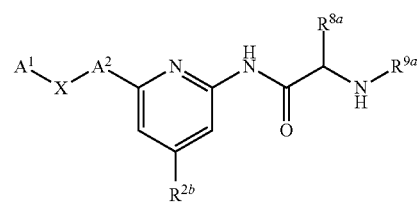

and the pharmaceutically acceptable salts, solvates, and prodrugs thereof, wherein $R^{2b}$, $R^{8a}$, $R^{9a}$, $A^1$, $A^2$, and X are as defined above in connection with Formula I.

In one embodiment, Compounds of the Invention are compounds having Formula VI:

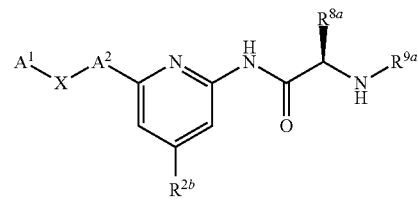

and the pharmaceutically acceptable salts, solvates, and prodrugs thereof, wherein $R^{2b}$, $R^{8a}$, $R^{9a}$, $A^1$, $A^2$, and X are as defined above in connection with Formula I.

In one embodiment, Compounds of the Invention are compounds having Formula VII:

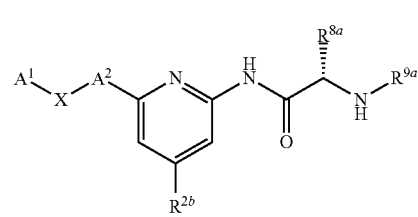

and the pharmaceutically acceptable salts, solvates, and prodrugs thereof, wherein $R^{2b}$, $R^{8a}$, $R^{9a}$, $A^1$, $A^2$, and X are as defined above in connection with Formula I.

In one embodiment, Compounds of the Invention are compounds having any of Formulae I-VII wherein $R^{9a}$ is —$COR^{10}$, and the pharmaceutically acceptable salts, solvates, and prodrugs thereof. In one embodiment, $R^{10}$ is selected from the group consisting of $C_1$-$C_4$ alkyl, $C_{1-4}$ haloalkyl, $C_3$-$C_6$ cycloalkyl, optionally substituted aryl, optionally substituted heteroaryl, amino, and (amino)alkyl.

In one embodiment, Compounds of the Invention are compounds having any of Formulae I-VII wherein $R^{8a}$ is selected from the group consisting of hydrogen, $C_{1-6}$ alkyl, hydroxyalkyl, (carboxamido)alkyl, aralkyl, and (heteroaryl)alkyl, and the pharmaceutically acceptable salts, solvates, and prodrugs thereof.

In one embodiment, Compounds of the Invention are compounds having any of Formulae I-VII wherein $R^{9a}$ is —$SO_2R^{11}$, and the pharmaceutically acceptable salts, solvates, and prodrugs thereof. In one embodiment, $R^{11}$ is $C_1$-$C_4$ alkyl.

In one embodiment, Compounds of the Invention are compounds having Formula VIII:

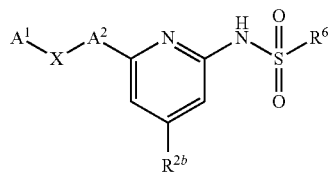

VIII and the pharmaceutically acceptable salts, solvates, and prodrugs thereof, wherein $R^{2b}$, $R^6$, $A^1$, $A^2$, and X are as defined above in connection with Formula I. In one embodiment, $R^6$ is selected from the group consisting of $C_1$-$C_4$ alkyl, $C_3$-$C_6$ cycloalkyl, optionally substituted aryl, optionally substituted heteroaryl, optionally substituted alkenyl, amino, and (amino)alkyl.

In one embodiment, Compounds of the Invention are compounds having Formula IX:

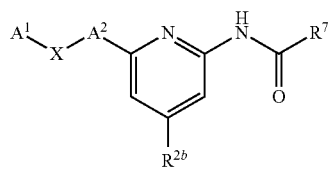

IX and the pharmaceutically acceptable salts, solvates, and prodrugs thereof, wherein $R^{2b}$, $A^1$, and $A^2$ are as defined above in connection with Formula I, $R^7$ is hydroxyalkyl, and X is selected from the group consisting of —O—; —S—; —SO—; —$SO_2$—; —$(CR^3R^4)_m$—; and —$NR^5$—. In one embodiment, $R^7$ is monohydroxyalkyl. In one embodiment, $R^7$ is a dihydroxyalkyl. In one embodiment, $R^7$ is a $C_{2-4}$ dihydroxyalkyl. In one embodiment, $R^7$ is selected from the group consisting of:

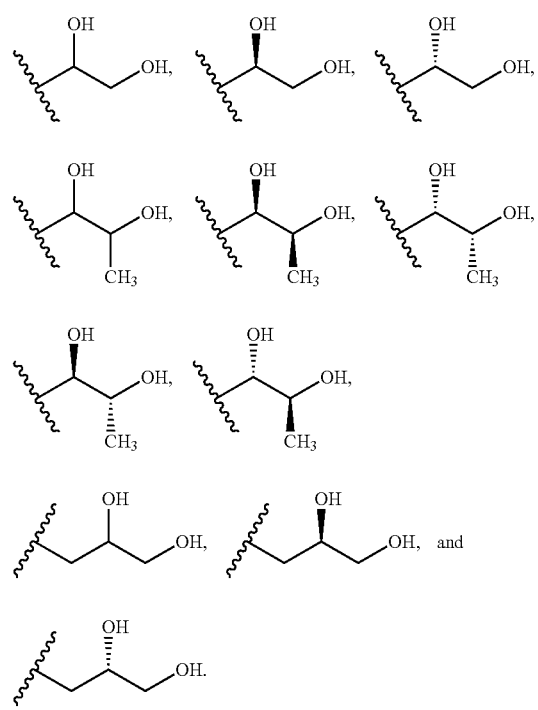

In one embodiment, Compounds of the Invention are compounds having Formula X:

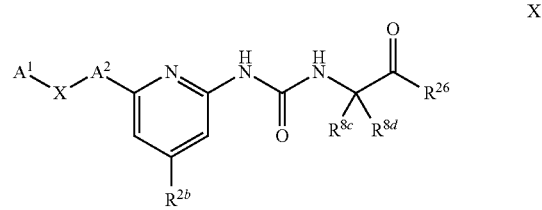

X and the pharmaceutically acceptance salts, solvates, and prodrugs thereof, wherein $R^{2b}$, $R^{8c}$, $R^{8d}$, $R^{26}$, $A^1$, $A^2$, and X are as defined above in connection with Formula I. In one embodiment, $R^{26}$ is hydroxy. In one embodiment, $R^{26}$ is alkoxy. In one embodiment, $R^{26}$ is amino.

In one embodiment, Compounds of the Invention are compounds having Formula XI:

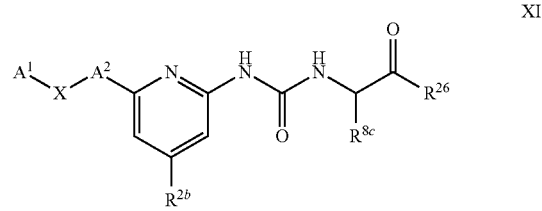

XI and the pharmaceutically acceptable salts, solvates, and prodrugs thereof, wherein $R^{2b}$, $R^{8c}$, $R^{26}$, $A^1$, $A^2$, and X are as defined above in connection with Formula I. In one embodiment, $R^{26}$ is hydroxy. In one embodiment, $R^{26}$ is alkoxy. In one embodiment, $R^{26}$ is amino.

In one embodiment, Compounds of the Invention are compounds having Formula XII:

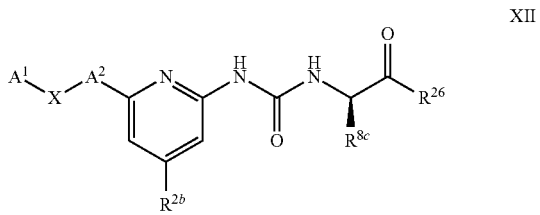

XII and the pharmaceutically acceptable salts, solvates, and prodrugs thereof, wherein $R^{2b}$, $R^{8c}$, $R^{26}$, $A^1$, $A^2$, and X are as defined above in connection with Formula I. In one embodiment, $R^{26}$ is hydroxy. In one embodiment, $R^{26}$ is alkoxy. In one embodiment, $R^{26}$ is amino.

In one embodiment, Compounds of the Invention are compounds having Formula XIII:

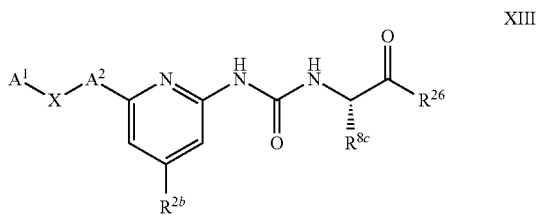

XIII and the pharmaceutically acceptable salts, solvates, and prodrugs thereof, wherein $R^{2b}$, $R^{8c}$, $R^{26}$, $A^1$, $A^2$, and X are as defined above in connection with Formula I. In one embodiment, $R^{26}$ is hydroxy. In one embodiment, $R^{26}$ is alkoxy. In one embodiment, $R^{26}$ is amino. In one embodiment, Compounds of the Invention are compounds having any one of Formulae X-XIII, and the pharmaceutically acceptable salts, solvates, and prodrugs thereof, wherein $R^{8c}$ is selected from the group consisting of hydrogen, alkyl, (heterocyclo)alkyl, (heteroaryl)alkyl, and (carboxamido)alkyl, and $R^{26}$ is amino.

In one embodiment, Compounds of the Invention are compounds having Formula XIV:

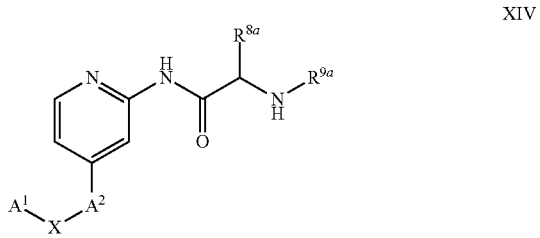

XIV and the pharmaceutically acceptable salts, solvates, and prodrugs thereof, wherein $R^{8a}$, $R^{9a}$, $A^1$, $A^2$, and X are as defined above in connection with Formula I.

In one embodiment, Compounds of the Invention are compounds having Formula XV:

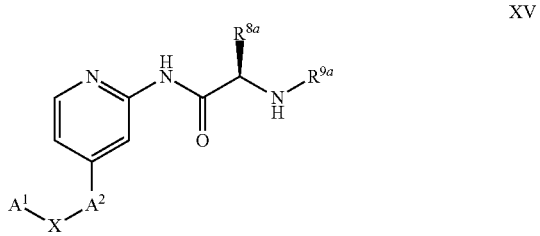

XV and the pharmaceutically acceptable salts, solvates, and prodrugs thereof, wherein $R^{8a}$, $R^{9a}$, $A^1$, $A^2$, and X are as defined above in connection with Formula I.

In one embodiment, Compounds of the Invention are compounds having Formula XVI:

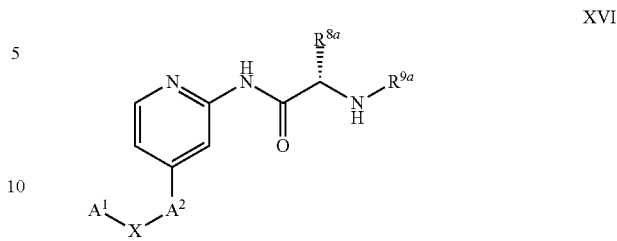

XVI and the pharmaceutically acceptable salts, solvates, and prodrugs thereof, wherein $R^{8a}$, $R^{9a}$, $A^1$, $A^2$, and X are as defined above in connection with Formula I.

In one embodiment, Compounds of the Invention are compounds having any of Formulae XIV-XVI wherein $R^{9a}$ is —$COR^{10}$, and the pharmaceutically acceptable salts, solvates, and prodrugs thereof. In one embodiment, $R^{10}$ is selected from the group consisting of $C_1$-$C_4$ alkyl, $C_{1-4}$ haloalkyl, $C_3$-$C_6$ cycloalkyl, optionally substituted aryl, optionally substituted heteroaryl, amino, and (amino)alkyl.

In one embodiment, Compounds of the Invention are compounds having any of Formulae XIV-XVI wherein $R^{8a}$ is selected from the group consisting of hydrogen, $C_{1-6}$ alkyl, hydroxyalkyl, (carboxamido)alkyl, aralkyl, and (heteroaryl)alkyl, and the pharmaceutically acceptable salts, solvates, and prodrugs thereof.

In one embodiment, Compounds of the Invention are compounds having any of Formulae I-XVI wherein X is —O—, and the pharmaceutically acceptable salts, solvates, and prodrugs thereof.

In one embodiment, Compounds of the Invention are compounds having any of Formulae I-XVI wherein $A^2$ is optionally substituted phenyl, and the pharmaceutically acceptable salts, solvates, and prodrugs thereof.

In one embodiment, Compounds of the Invention are compounds having any of Formulae I-XVI wherein $R^{1b}$ is selected from the group consisting of hydrogen and hydroxyalkyl, and the pharmaceutically acceptable salts, solvates, and prodrugs thereof.

In one embodiment, Compounds of the Invention are compounds having any of Formulae I-XVI wherein $R^{2b}$ is selected from the group consisting of hydrogen, halo, e.g., chloro, $C_{1-4}$ alkyl, and hydroxyalkyl, and the pharmaceutically acceptable salts, solvates, and prodrugs thereof.

In one embodiment, Compounds of the Invention are compounds having any of Formulae I-XVI wherein $A^1$ is selected from the group consisting of optionally substituted aryl and optionally substituted heteroaryl; X is —O—; and $A^2$ is optionally substituted phenyl, and the pharmaceutically acceptable salts, solvates, and prodrugs thereof.

In one embodiment, Compounds of the Invention are compounds having any of Formulae I-XVI wherein $A^1$ selected from the group consisting of optionally substituted phenyl; optionally substituted 2-pyridyl (i.e., pyridin-2-yl); optionally substituted 3-pyridyl (i.e., pyridin-3-yl); and optionally substituted 4-pyridyl (i.e., pyridin-4-yl), and the pharmaceutically acceptable salts, solvates, and prodrugs thereof.

In one embodiment, Compounds of the Invention are compounds having any of Formulae I-XVI wherein the optional substituents of the $A^1$ group are selected from the group consisting of halo, cyano, haloalkyl, and $C_{1-4}$ alkyl, and the pharmaceutically acceptable salts, solvates, and prodrugs thereof.

In one embodiment, Compounds of the Invention are compounds having any of Formulae I-XVI wherein $A^1$-X-$A^2$- is:

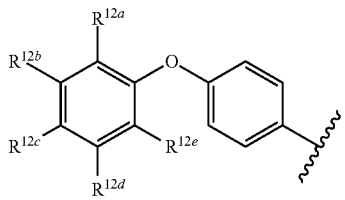

wherein:
$R^{12a}$, $R^{12b}$, $R^{12c}$, $R^{12d}$, and $R^{12e}$, which can be identical or different, are selected from the group consisting of:
hydrogen;
halo;
nitro;
cyano;
hydroxy;
amino;
alkylamino;
dialkylamino;
haloalkyl;
hydroxyalkyl;
alkoxy;
haloalkoxy;
aryloxy;
aralkyloxy;
alkylthio;
carboxamido;
sulfonamido;
alkylcarbonyl;
arylcarbonyl;
alkylsulfonyl;
arylsulfonyl;
ureido;
guanidino;
carboxy;
carboxyalkyl;
alkyl;
optionally substituted cycloalkyl;
optionally substituted alkenyl;
optionally substituted alkynyl;
optionally substituted aryl;
optionally substituted heteroaryl; and
optionally substituted heterocyclo; or
$R^{12a}$ and $R^{12b}$, or $R^{12b}$ and $R^{12c}$, or $R^{12c}$ and $R^{12d}$, or $R^{12d}$ and $R^{12e}$, taken together with the carbon atoms to which they are attached form a 5- or 6-membered optionally substituted cycloalkyl or heterocyclo group, and the pharmaceutically acceptable salts, solvates, and prodrugs thereof.

In one embodiment, Compounds of the Invention are compounds having any of Formulae I-XVI, wherein $A^1$-X-$A^2$- is:

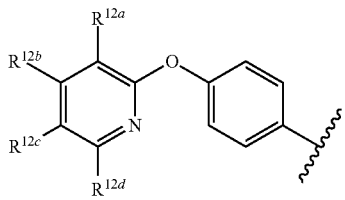

wherein $R^{12a}$, $R^{12b}$, $R^{12c}$, and $R^{12d}$ are as defined above, and the pharmaceutically acceptable salts, solvates, and prodrugs thereof.

In one embodiment, Compounds of the Invention are compounds having any of Formulae I-XVI wherein $A^1$-X-$A^2$- is:

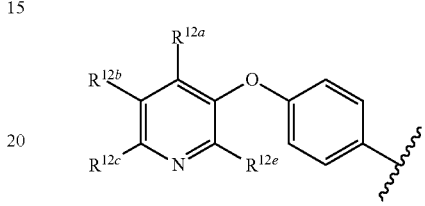

wherein $R^{12a}$, $R^{12b}$, $R^{12c}$, and $R^{12e}$ are as defined above, and the pharmaceutically acceptable salts, solvates, and prodrugs thereof.

In one embodiment, Compounds of the Invention are compounds having any of Formulae I-XVI wherein $A^1$-X-$A^2$- is:

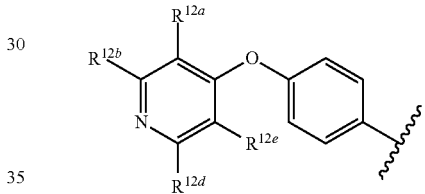

wherein $R^{12a}$, $R^{12b}$, $R^{12d}$, $R^{12e}$ are as defined above, and the pharmaceutically acceptable salts, solvates, and prodrugs thereof.

In one embodiment, Compounds of the Invention are compounds having any of Formulae I-XVI wherein $R^{12a}$, $R^{12b}$, $R^{12c}$, $R^{12d}$, and $R^{12e}$, which can be identical or different, are selected from the group consisting of hydrogen, halo, cyano, haloalkyl, and $C_{1-4}$ alkyl, and the pharmaceutically acceptable salts, solvates, and prodrugs thereof. In one embodiment, one or two of $R^{12a}$, $R^{12b}$, $R^{12c}$, $R^{12d}$, and $R^{12e}$ are halo, e.g., fluoro or chloro, or haloalkyl, e.g., trifluoromethyl, and the others are hydrogen. In one embodiment, $R^{12c}$ is halo or haloalkyl.

In another embodiment, Compounds of the Invention include the compound examples of TABLE 2, and the pharmaceutically acceptable salts, prodrugs, and solvates thereof. The chemical names of the compound examples are provided in TABLE 3.

TABLE 2

| Compound Example No. | Structure |
|---|---|
| 3 | 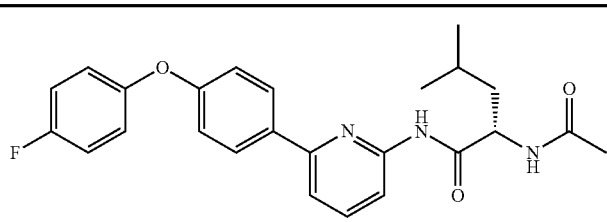 |

TABLE 2-continued
| Compound Example No. | Structure |
|---|---|
| 4 | 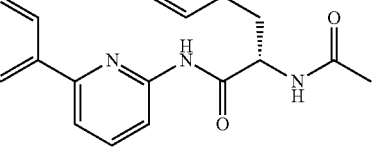 |
| 7 | 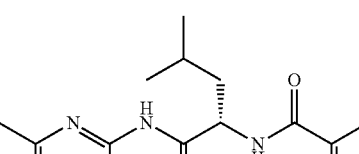 |
| 8 | 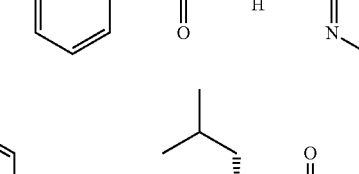 |
| 9 | 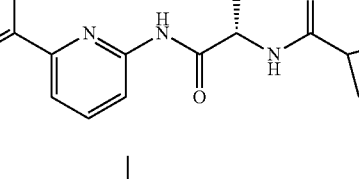 |
| 10 | 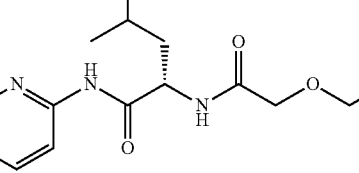 |
| 11 | 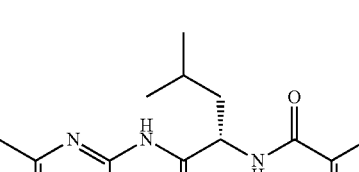 |
| 12 | 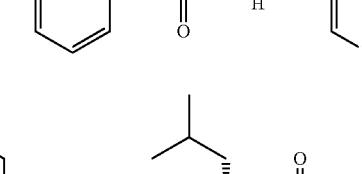 |

TABLE 2-continued

| Compound Example No. | Structure |
|---|---|
| 13 | 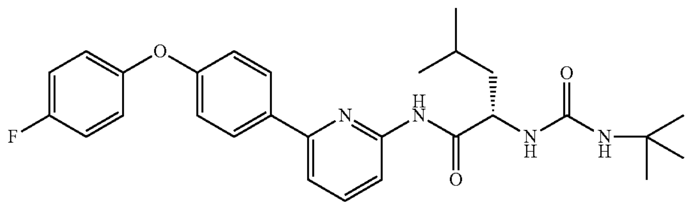 [SMILES: CC(C)C[C@H](NC(=O)NC(C)(C)C)C(=O)Nc1cccc(-c2ccc(Oc3ccc(F)cc3)cc2)n1] |
| 15 | 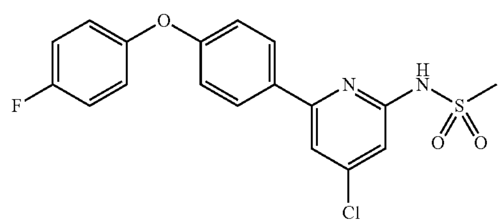 [SMILES: CS(=O)(=O)Nc1cc(Cl)cc(-c2ccc(Oc3ccc(F)cc3)cc2)n1] |
| 17 | 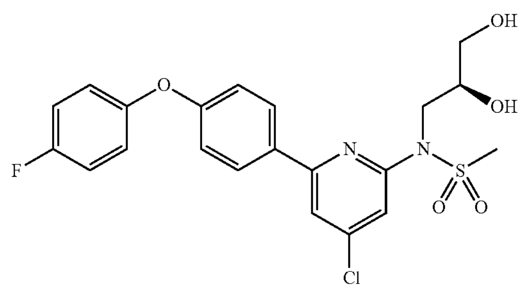 [SMILES: CS(=O)(=O)N(C[C@H](O)CO)c1cc(Cl)cc(-c2ccc(Oc3ccc(F)cc3)cc2)n1] |
| 18 | 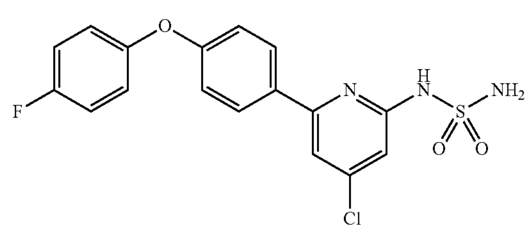 [SMILES: NS(=O)(=O)Nc1cc(Cl)cc(-c2ccc(Oc3ccc(F)cc3)cc2)n1] |
| 24 | 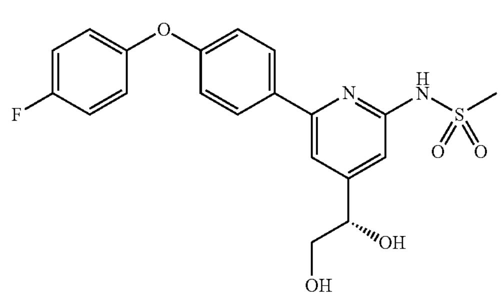 [SMILES: CS(=O)(=O)Nc1cc([C@H](O)CO)cc(-c2ccc(Oc3ccc(F)cc3)cc2)n1] |
| 26 | 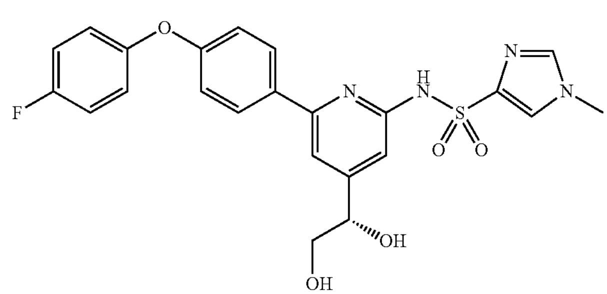 [SMILES: Cn1cnc(S(=O)(=O)Nc2cc([C@H](O)CO)cc(-c3ccc(Oc4ccc(F)cc4)cc3)n2)c1] |

TABLE 2-continued

| Compound Example No. | Structure |
|---|---|
| 27 | 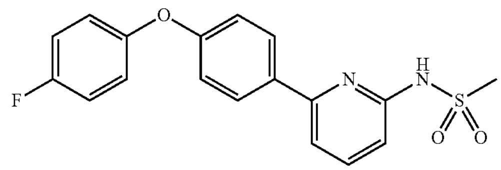 [SMILES: CS(=O)(=O)Nc1cccc(-c2ccc(Oc3ccc(F)cc3)cc2)n1] |
| 28 | 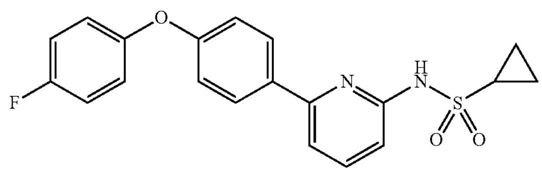 [SMILES: O=S(=O)(Nc1cccc(-c2ccc(Oc3ccc(F)cc3)cc2)n1)C1CC1] |
| 29 | 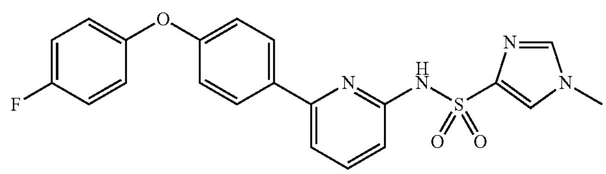 [SMILES: Cn1cnc(S(=O)(=O)Nc2cccc(-c3ccc(Oc4ccc(F)cc4)cc3)n2)c1] |
| 31 | 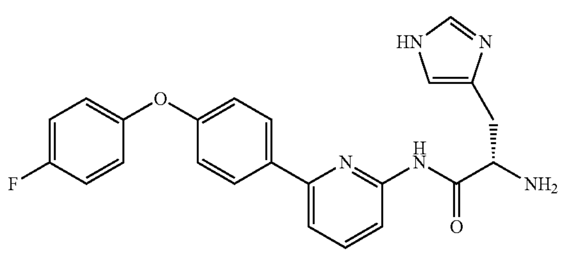 [SMILES: N[C@@H](Cc1c[nH]cn1)C(=O)Nc1cccc(-c2ccc(Oc3ccc(F)cc3)cc2)n1] |
| 32 | 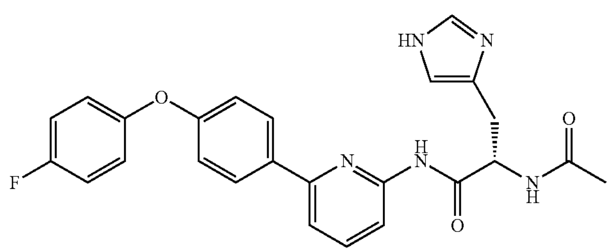 [SMILES: CC(=O)N[C@@H](Cc1c[nH]cn1)C(=O)Nc1cccc(-c2ccc(Oc3ccc(F)cc3)cc2)n1] |
| 33 | 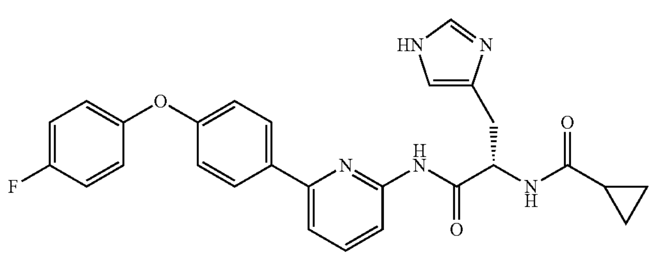 [SMILES: O=C(N[C@@H](Cc1c[nH]cn1)C(=O)Nc1cccc(-c2ccc(Oc3ccc(F)cc3)cc2)n1)C1CC1] |

TABLE 2-continued

| Compound Example No. | Structure |
|---|---|
| 34 | 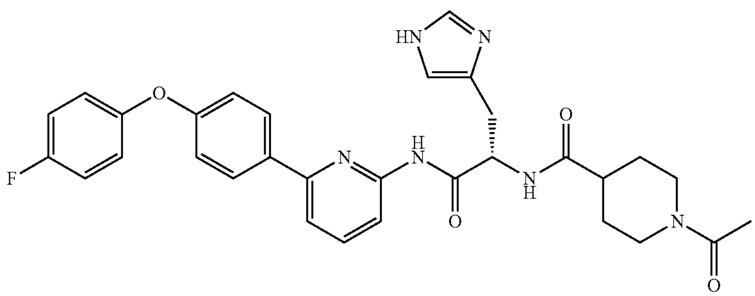 [SMILES: CC(=O)N1CCC(C(=O)N[C@@H](Cc2c[nH]cn2)C(=O)Nc2cccc(-c3ccc(Oc4ccc(F)cc4)cc3)n2)CC1] |
| 35 | 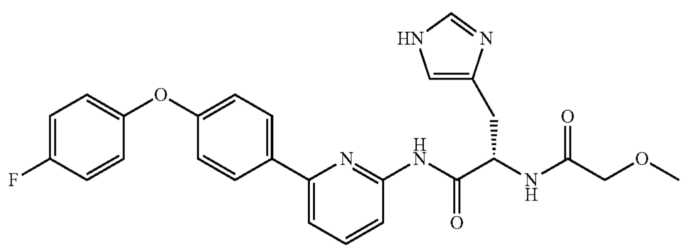 [SMILES: COCC(=O)N[C@@H](Cc1c[nH]cn1)C(=O)Nc1cccc(-c2ccc(Oc3ccc(F)cc3)cc2)n1] |
| 36 | 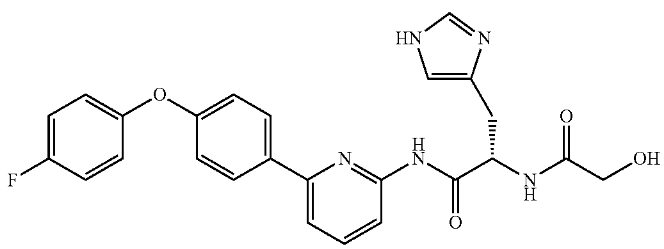 [SMILES: O=C(CO)N[C@@H](Cc1c[nH]cn1)C(=O)Nc1cccc(-c2ccc(Oc3ccc(F)cc3)cc2)n1] |
| 37 | 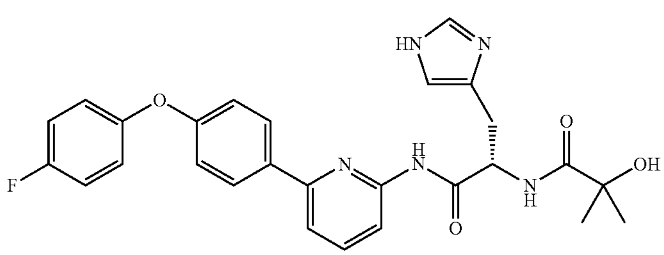 [SMILES: CC(C)(O)C(=O)N[C@@H](Cc1c[nH]cn1)C(=O)Nc1cccc(-c2ccc(Oc3ccc(F)cc3)cc2)n1] |
| 38 | 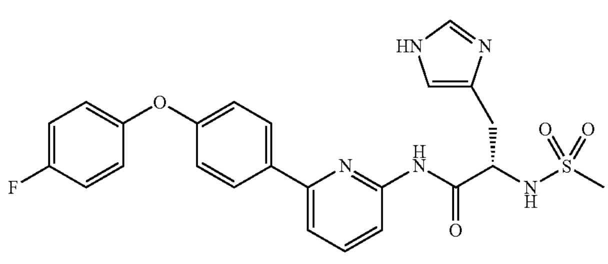 [SMILES: CS(=O)(=O)N[C@@H](Cc1c[nH]cn1)C(=O)Nc1cccc(-c2ccc(Oc3ccc(F)cc3)cc2)n1] |

TABLE 2-continued

| Compound Example No. | Structure |
|---|---|
| 40 | 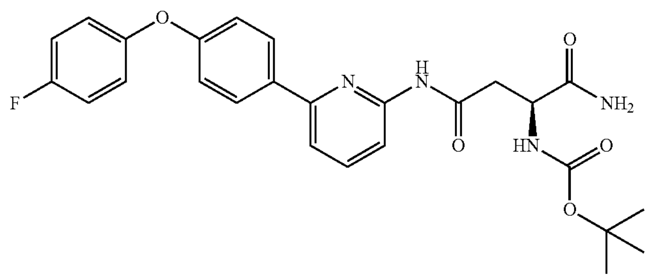 [SMILES: CC(C)(C)OC(=O)N[C@@H](CC(=O)Nc1cccc(-c2ccc(Oc3ccc(F)cc3)cc2)n1)C(N)=O] |
| 41 | 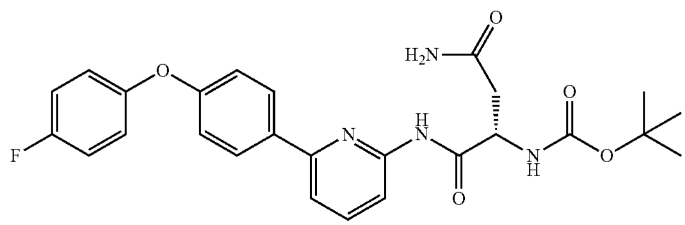 [SMILES: CC(C)(C)OC(=O)N[C@@H](CC(N)=O)C(=O)Nc1cccc(-c2ccc(Oc3ccc(F)cc3)cc2)n1] |
| 44 | 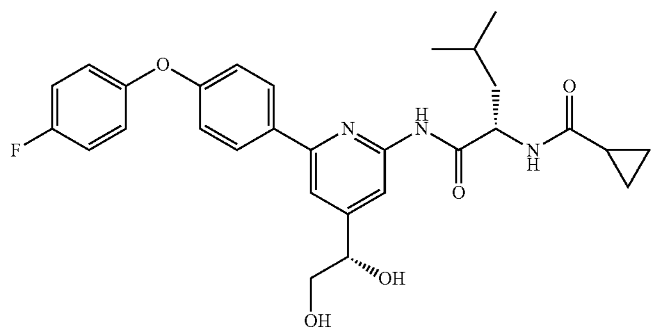 [SMILES: CC(C)C[C@H](NC(=O)C1CC1)C(=O)Nc1cc([C@H](O)CO)cc(-c2ccc(Oc3ccc(F)cc3)cc2)n1] |
| 45 | 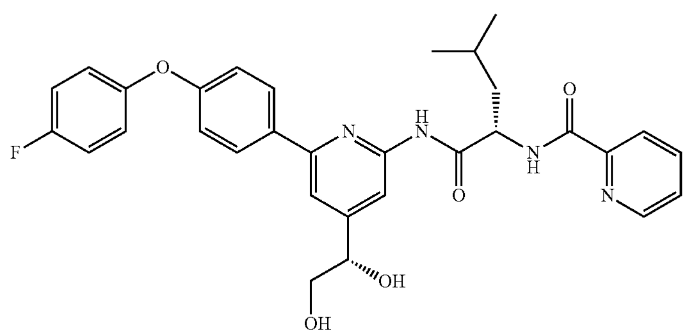 [SMILES: CC(C)C[C@H](NC(=O)c1ccccn1)C(=O)Nc1cc([C@H](O)CO)cc(-c2ccc(Oc3ccc(F)cc3)cc2)n1] |
| 50 | 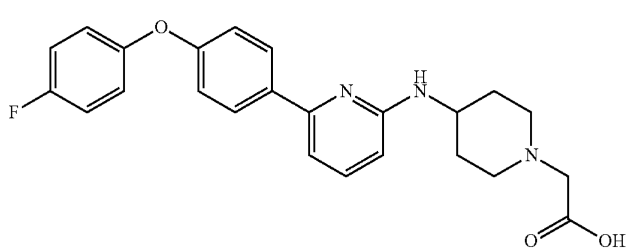 [SMILES: O=C(O)CN1CCC(Nc2cccc(-c3ccc(Oc4ccc(F)cc4)cc3)n2)CC1] |

TABLE 2-continued
| Compound Example No. | Structure |
|---|---|
| 53 | 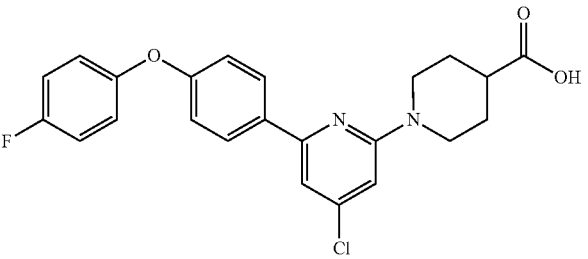 [SMILES: O=C(O)C1CCN(c2cc(Cl)cc(-c3ccc(Oc4ccc(F)cc4)cc3)n2)CC1] |
| 54 | 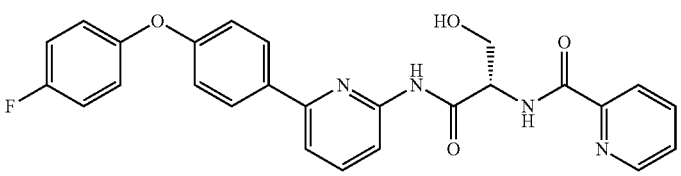 [SMILES: O=C(N[C@@H](CO)C(=O)Nc1cccc(-c2ccc(Oc3ccc(F)cc3)cc2)n1)c1ccccn1] |
| 55 | 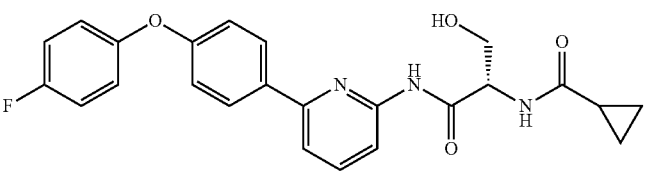 [SMILES: O=C(N[C@@H](CO)C(=O)Nc1cccc(-c2ccc(Oc3ccc(F)cc3)cc2)n1)C1CC1] |
| 56 | 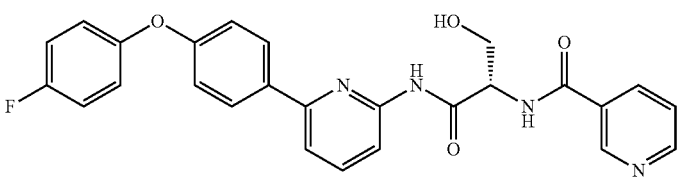 [SMILES: O=C(N[C@@H](CO)C(=O)Nc1cccc(-c2ccc(Oc3ccc(F)cc3)cc2)n1)c1cccnc1] |
| 57 | 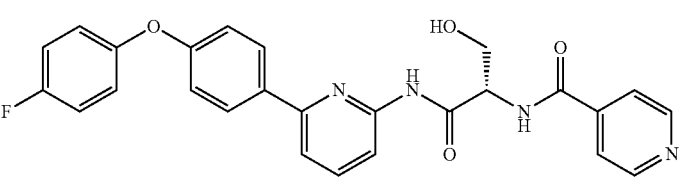 [SMILES: O=C(N[C@@H](CO)C(=O)Nc1cccc(-c2ccc(Oc3ccc(F)cc3)cc2)n1)c1ccncc1] |
| 58 | 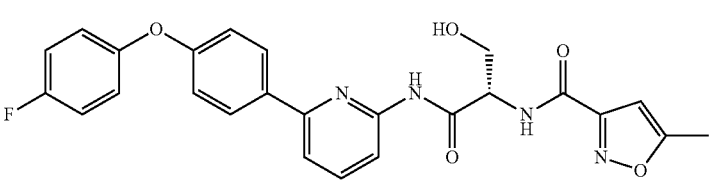 [SMILES: Cc1cc(C(=O)N[C@@H](CO)C(=O)Nc2cccc(-c3ccc(Oc4ccc(F)cc4)cc3)n2)no1] |
| 59 | 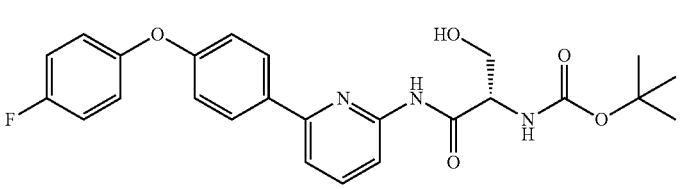 [SMILES: CC(C)(C)OC(=O)N[C@@H](CO)C(=O)Nc1cccc(-c2ccc(Oc3ccc(F)cc3)cc2)n1] |
| 60 | 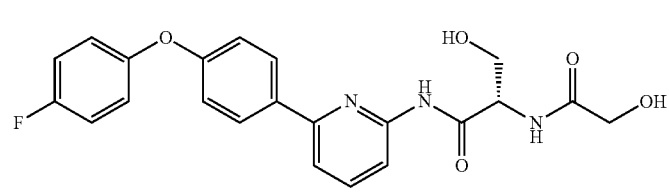 [SMILES: O=C(CO)N[C@@H](CO)C(=O)Nc1cccc(-c2ccc(Oc3ccc(F)cc3)cc2)n1] |

TABLE 2-continued
| Compound Example No. | Structure |
|---|---|
| 61 | 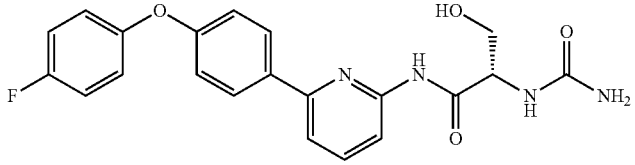 [SMILES: NC(=O)N[C@@H](CO)C(=O)Nc1cccc(-c2ccc(Oc3ccc(F)cc3)cc2)n1] |
| 62 | 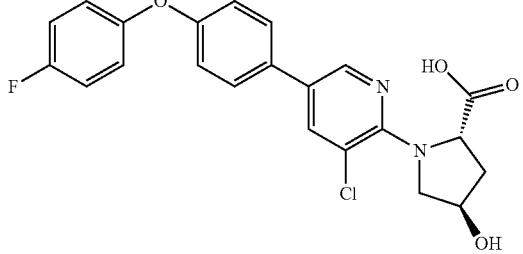 |
| 63 | 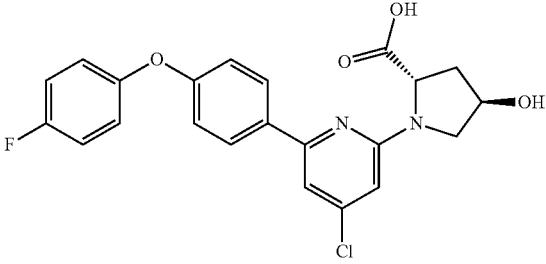 [SMILES: O=C(O)[C@@H]1C[C@@H](O)CN1c1cc(Cl)cc(-c2ccc(Oc3ccc(F)cc3)cc2)n1] |
| 64 | 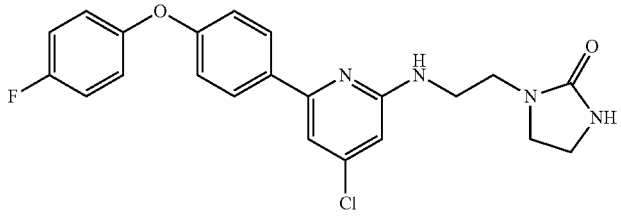 [SMILES: O=C1NCCN1CCNc1cc(Cl)cc(-c2ccc(Oc3ccc(F)cc3)cc2)n1] |
| 65 | 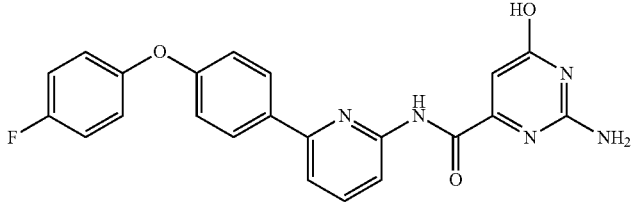 [SMILES: Nc1nc(O)cc(C(=O)Nc2cccc(-c3ccc(Oc4ccc(F)cc4)cc3)n2)n1] |
| 66 | 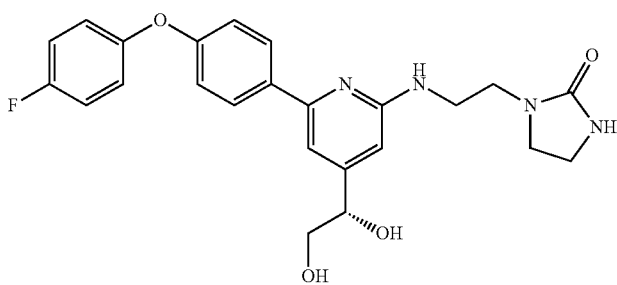 [SMILES: O=C1NCCN1CCNc1cc([C@H](O)CO)cc(-c2ccc(Oc3ccc(F)cc3)cc2)n1] |

TABLE 2-continued

| Compound Example No. | Structure |
|---|---|
| 67 | 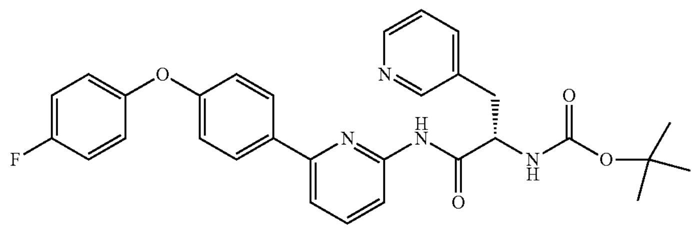 [SMILES: CC(C)(C)OC(=O)N[C@@H](Cc1cccnc1)C(=O)Nc1cccc(-c2ccc(Oc3ccc(F)cc3)cc2)n1] |
| 68 | 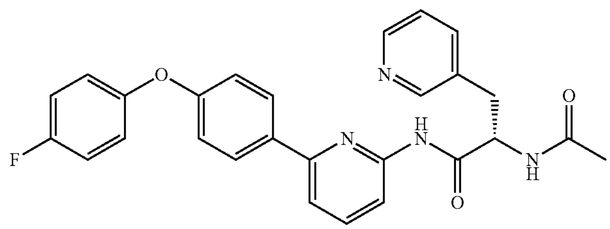 [SMILES: CC(=O)N[C@@H](Cc1cccnc1)C(=O)Nc1cccc(-c2ccc(Oc3ccc(F)cc3)cc2)n1] |
| 69 | 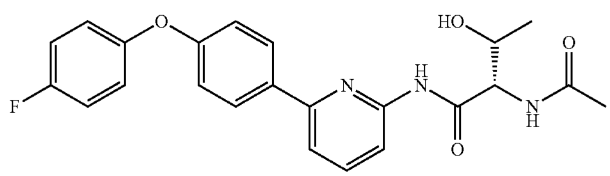 [SMILES: CC(=O)N[C@H](C(=O)Nc1cccc(-c2ccc(Oc3ccc(F)cc3)cc2)n1)C(C)O] |
| 70 | 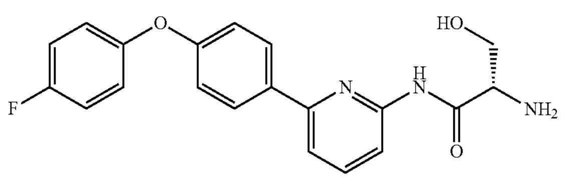 [SMILES: N[C@@H](CO)C(=O)Nc1cccc(-c2ccc(Oc3ccc(F)cc3)cc2)n1] |
| 71 | 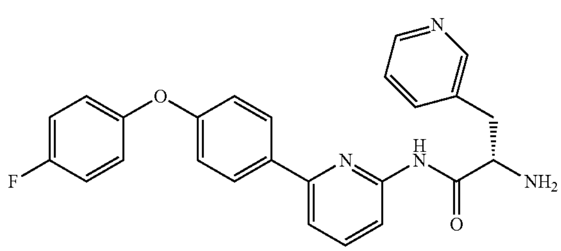 [SMILES: N[C@@H](Cc1cccnc1)C(=O)Nc1cccc(-c2ccc(Oc3ccc(F)cc3)cc2)n1] |
| 72 | 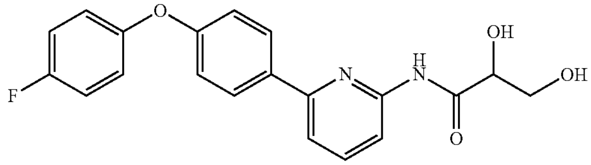 [SMILES: O=C(Nc1cccc(-c2ccc(Oc3ccc(F)cc3)cc2)n1)C(O)CO] |
| 73 | 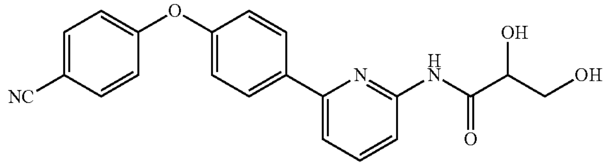 [SMILES: N#Cc1ccc(Oc2ccc(-c3cccc(NC(=O)C(O)CO)n3)cc2)cc1] |

TABLE 2-continued

| Compound Example No. | Structure |
|---|---|
| 74 | 4-trifluoromethyl-3-cyanophenoxy-phenyl-pyridine-NH-C(O)-CH(OH)-CH2OH |
| 75 | 4-cyano-3-trifluoromethylphenoxy-phenyl-pyridine-NH-C(O)-CH(OH)-CH2OH |
| 76 | 4-trifluoromethylphenoxy-phenyl-pyridine-NH-C(O)-CH(OH)-CH2OH |
| 77 | 4-fluorophenoxy-phenyl-pyridine-NH-C(O)-CH(NHAc)-CH2-(1-methylimidazol-4-yl) |
| 78 | 4-fluorophenoxy-phenyl-pyridine-NH-C(O)-CH(NH-C(O)-C(CH3)2OH)-CH2-(1-methylimidazol-4-yl) |

TABLE 2-continued
| Compound Example No. | Structure |
|---|---|
| 79 | 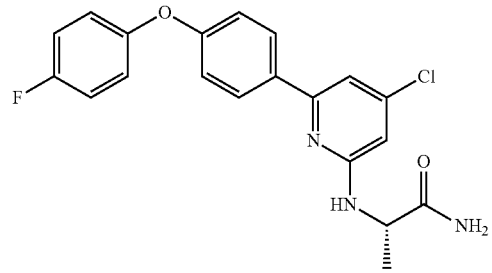 [SMILES: C[C@H](Nc1cc(Cl)cc(-c2ccc(Oc3ccc(F)cc3)cc2)n1)C(N)=O] |
| 80 | 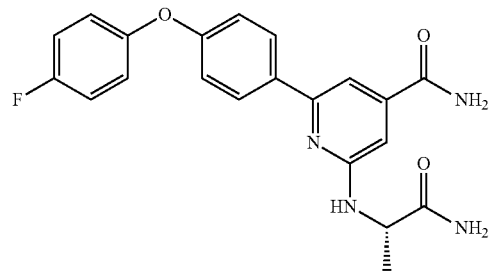 [SMILES: C[C@H](Nc1cc(C(N)=O)cc(-c2ccc(Oc3ccc(F)cc3)cc2)n1)C(N)=O] |
| 81 | 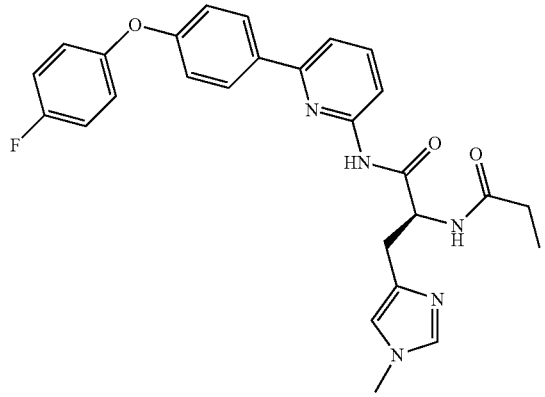 [SMILES: CCC(=O)N[C@@H](Cc1cn(C)cn1)C(=O)Nc1cccc(-c2ccc(Oc3ccc(F)cc3)cc2)n1] |
| 82 | 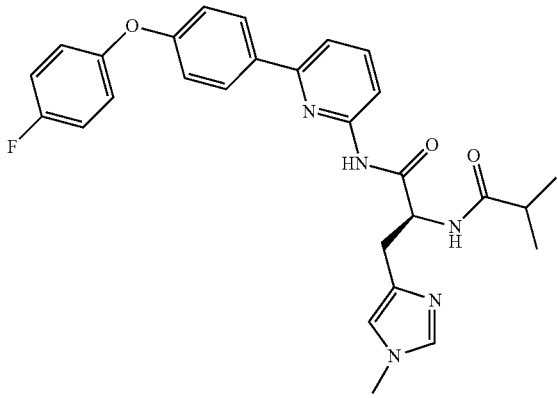 [SMILES: CC(C)C(=O)N[C@@H](Cc1cn(C)cn1)C(=O)Nc1cccc(-c2ccc(Oc3ccc(F)cc3)cc2)n1] |

TABLE 2-continued
| Compound Example No. | Structure |
|---|---|
| 83 | 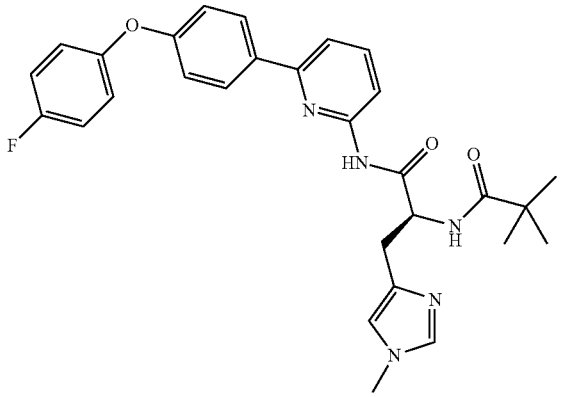 [SMILES: Cn1cnc(C[C@H](NC(=O)C(C)(C)C)C(=O)Nc2cccc(-c3ccc(Oc4ccc(F)cc4)cc3)n2)c1] |
| 84 | 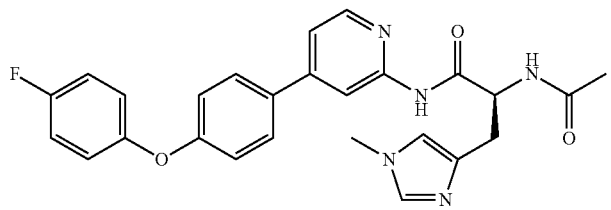 [SMILES: CC(=O)N[C@@H](Cc1cn(C)cn1)C(=O)Nc1cc(-c2ccc(Oc3ccc(F)cc3)cc2)ccn1] |
| 85 | 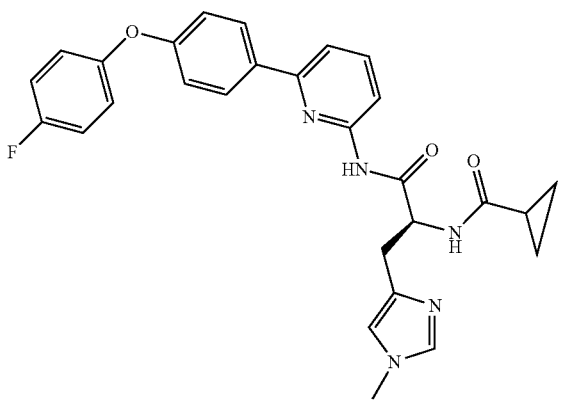 [SMILES: Cn1cnc(C[C@H](NC(=O)C2CC2)C(=O)Nc2cccc(-c3ccc(Oc4ccc(F)cc4)cc3)n2)c1] |
| 86 | 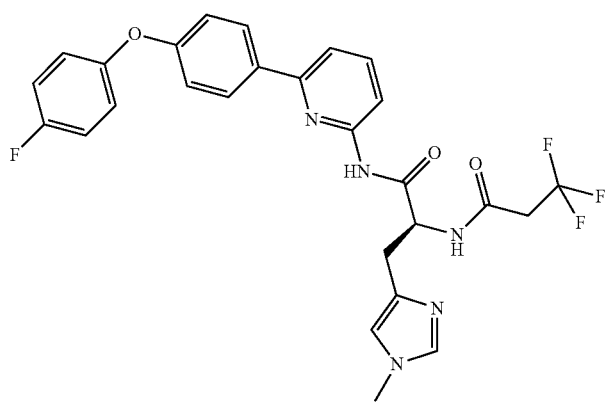 [SMILES: Cn1cnc(C[C@H](NC(=O)CC(F)(F)F)C(=O)Nc2cccc(-c3ccc(Oc4ccc(F)cc4)cc3)n2)c1] |

TABLE 2-continued

| Compound Example No. | Structure |
|---|---|
| 87 | 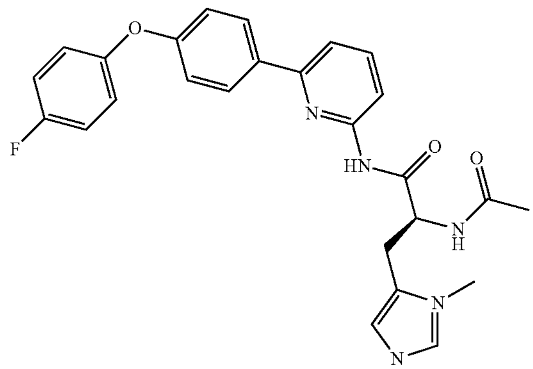 |
| 88 | 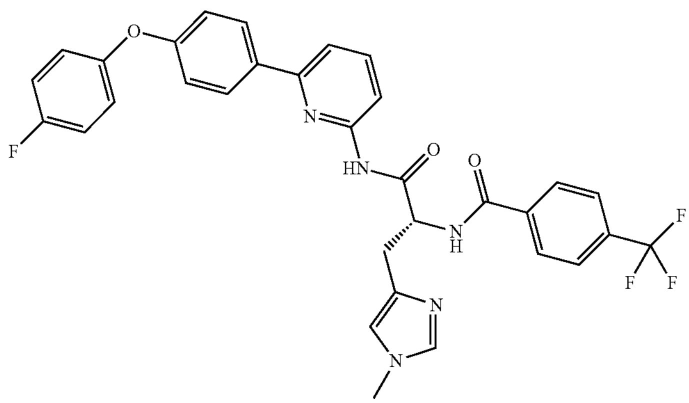 [SMILES: Cn1cnc(C[C@@H](NC(=O)c2ccc(C(F)(F)F)cc2)C(=O)Nc2cccc(-c3ccc(Oc4ccc(F)cc4)cc3)n2)c1] |
| 89 | 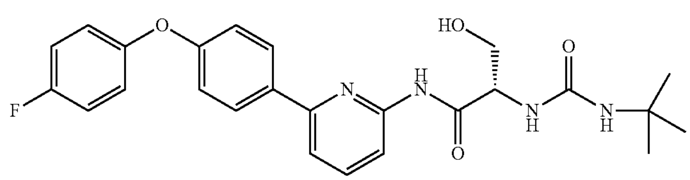 [SMILES: CC(C)(C)NC(=O)N[C@@H](CO)C(=O)Nc1cccc(-c2ccc(Oc3ccc(F)cc3)cc2)n1] |
| 90 | 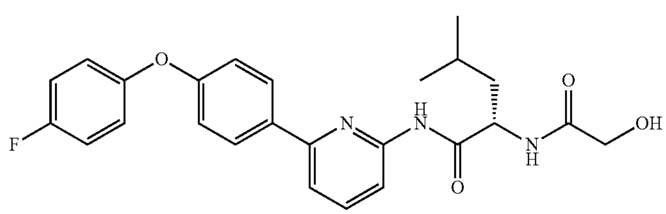 [SMILES: CC(C)C[C@H](NC(=O)CO)C(=O)Nc1cccc(-c2ccc(Oc3ccc(F)cc3)cc2)n1] |
| 91 | 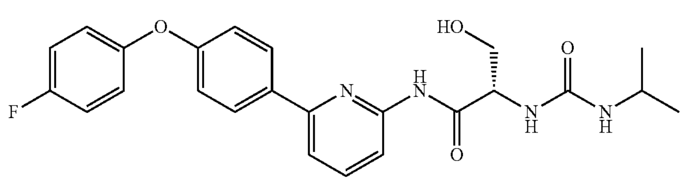 [SMILES: CC(C)NC(=O)N[C@@H](CO)C(=O)Nc1cccc(-c2ccc(Oc3ccc(F)cc3)cc2)n1] |
| 92 | 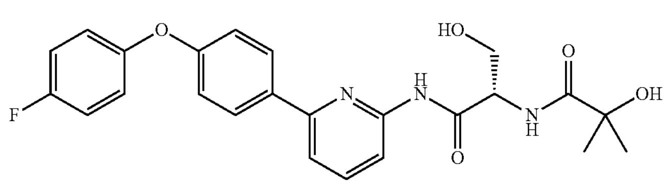 [SMILES: CC(C)(O)C(=O)N[C@@H](CO)C(=O)Nc1cccc(-c2ccc(Oc3ccc(F)cc3)cc2)n1] |

TABLE 2-continued

| Compound Example No. | Structure |
|---|---|
| 93 | 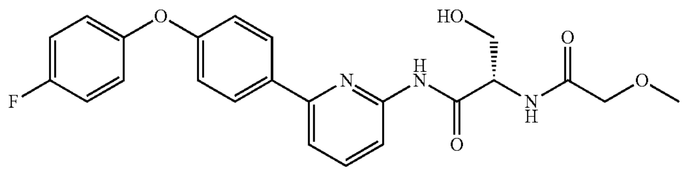 [SMILES: COCC(=O)N[C@@H](CO)C(=O)Nc1cccc(-c2ccc(Oc3ccc(F)cc3)cc2)n1] |
| 94 | 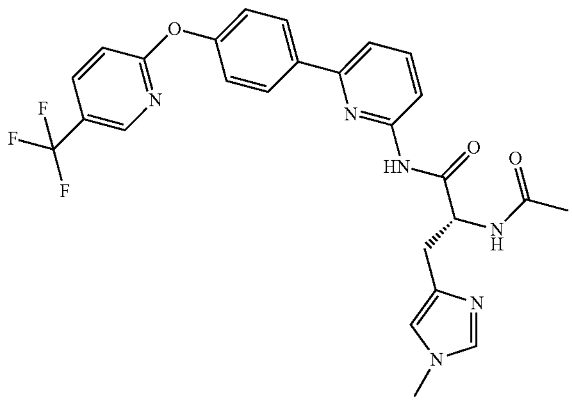 [SMILES: CC(=O)N[C@H](Cc1cn(C)cn1)C(=O)Nc1cccc(-c2ccc(Oc3ccc(C(F)(F)F)cn3)cc2)n1] |
| 95 | 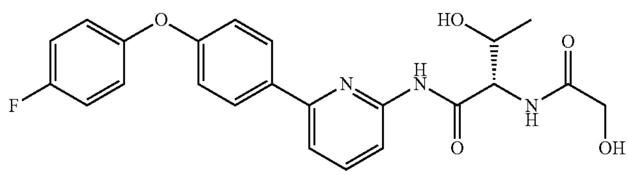 [SMILES: CC(O)[C@H](NC(=O)CO)C(=O)Nc1cccc(-c2ccc(Oc3ccc(F)cc3)cc2)n1] |
| 96 | 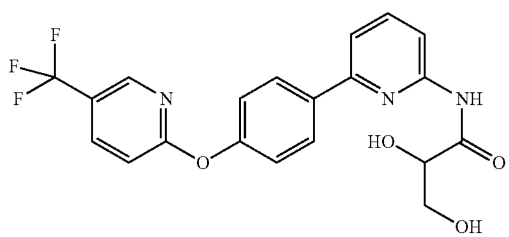 [SMILES: O=C(Nc1cccc(-c2ccc(Oc3ccc(C(F)(F)F)cn3)cc2)n1)C(O)CO] |
| 97 | 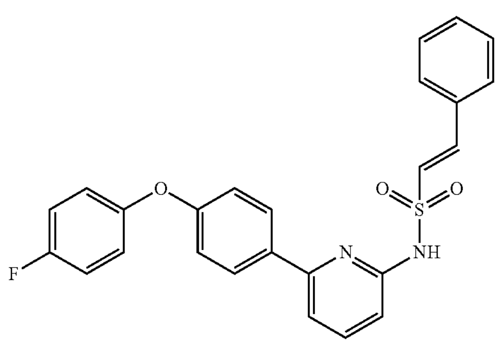 [SMILES: O=S(=O)(/C=C/c1ccccc1)Nc1cccc(-c2ccc(Oc3ccc(F)cc3)cc2)n1] |
| 98 | 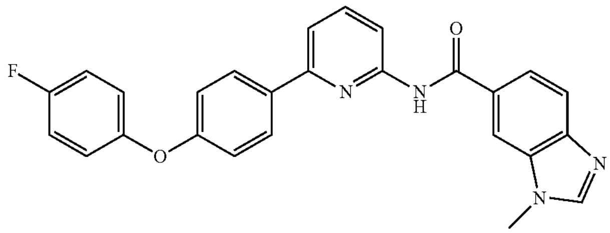 [SMILES: Cn1cnc2ccc(C(=O)Nc3cccc(-c4ccc(Oc5ccc(F)cc5)cc4)n3)cc21] |

TABLE 2-continued

| Compound Example No. | Structure |
|---|---|
| 99 | 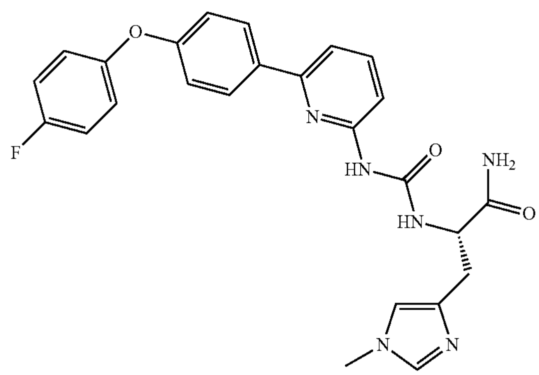 [SMILES: Cn1cnc(C[C@H](NC(=O)Nc2cccc(-c3ccc(Oc4ccc(F)cc4)cc3)n2)C(N)=O)c1] |
| 100 | 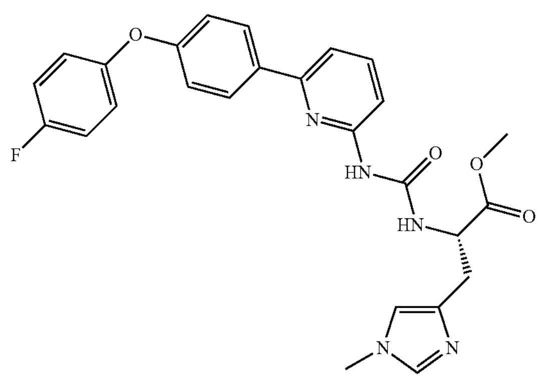 [SMILES: COC(=O)[C@H](Cc1cn(C)cn1)NC(=O)Nc1cccc(-c2ccc(Oc3ccc(F)cc3)cc2)n1] |
| 101 | 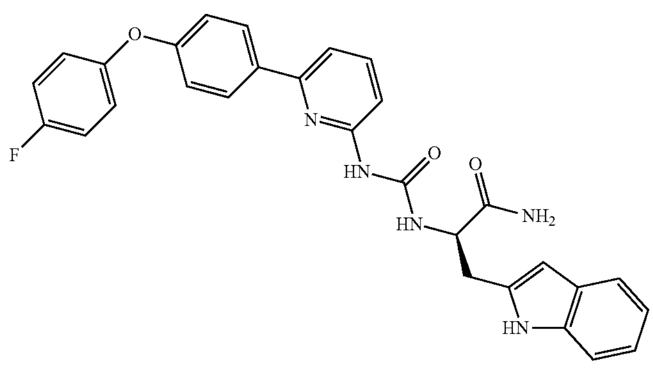 [SMILES: NC(=O)[C@@H](Cc1cc2ccccc2[nH]1)NC(=O)Nc1cccc(-c2ccc(Oc3ccc(F)cc3)cc2)n1] |
| 102 | 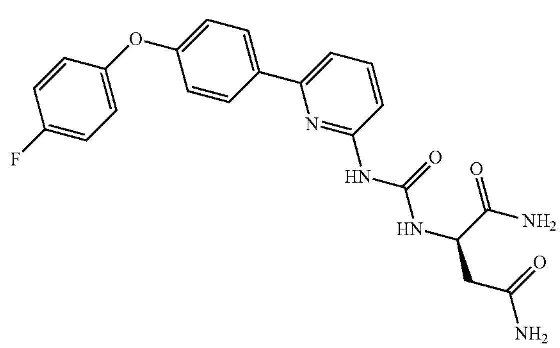 [SMILES: NC(=O)C[C@@H](NC(=O)Nc1cccc(-c2ccc(Oc3ccc(F)cc3)cc2)n1)C(N)=O] |

TABLE 2-continued

| Compound Example No. | Structure |
|---|---|
| 103 | *(structure shown)* |

TABLE 3

| Compound Example No. | Chemical Name |
|---|---|
| 3 | (S)-2-acetamido-N-(6-(4-(4-fluorophenoxy)phenyl)pyridin-2-yl)-4-methylpentanamide |
| 4 | (S)-2-acetamido-N-(6-(4-(4-fluorophenoxy)phenyl)pyridin-2-yl)-3-phenylpropanamide |
| 7 | (S)-N-(1-((6-(4-(4-fluorophenoxy)phenyl)pyridin-2-yl)amino)-4-methyl-1-oxopentan-2-yl)picolinamide |
| 8 | (S)-N-(1-((6-(4-(4-fluorophenoxy)phenyl)pyridin-2-yl)amino)-4-methyl-1-oxopentan-2-yl)cyclopropanecarboxamide |
| 9 | (S)-N-(6-(4-(4-fluorophenoxy)phenyl)pyridin-2-yl)-2-(2-(2-methoxyethoxy)acetamido)-4-methylpentanamide |
| 10 | (S)-N-(1-((6-(4-(4-fluorophenoxy)phenyl)pyridin-2-yl)amino)-4-methyl-1-oxopentan-2-yl)nicotinamide |
| 11 | (S)-N-(6-(4-(4-fluorophenoxy)phenyl)pyridin-2-yl)-2-(3-isopropylureido)-4-methylpentanamide |
| 12 | (S)-N-(6-(4-(4-fluorophenoxy)phenyl)pyridin-2-yl)-4-methyl-2-ureidopentanamide |
| 13 | (S)-2-(3-(tert-butyl)ureido)-N-(6-(4-(4-fluorophenoxy)phenyl)pyridin-2-yl)-4-methylpentanamide |
| 15 | N-(4-chloro-6-(4-(4-fluorophenoxy)phenyl)pyridin-2-yl)methanesulfonamide |
| 17 | (S)-N-(4-chloro-6-(4-(4-fluorophenoxy)phenyl)pyridin-2-yl)-N-(2,3-dihydroxypropyl)methanesulfonamide |
| 18 | N-(4-chloro-6-(4-(4-fluorophenoxy)phenyl)pyridin-2-yl)sulfamide |
| 24 | (S)-N-(4-(1,2-dihydroxyethyl)-6-(4-(4-fluorophenoxy)phenyl)pyridin-2-yl)methanesulfonamide |
| 26 | (S)-N-(4-(1,2-dihydroxyethyl)-6-(4-(4-fluorophenoxy)phenyl)pyridin-2-yl)-1-methyl-1H-imidazole-4-sulfonamide |
| 27 | N-(6-(4-(4-fluorophenoxy)phenyl)pyridin-2-yl)methanesulfonamide |
| 28 | N-(6-(4-(4-fluorophenoxy)phenyl)pyridin-2-yl)cyclopropane Sulfonamide |
| 29 | N-(6-(4-(4-fluorophenoxy)phenyl)pyridin-2-yl)-1-methyl-1H-imidazole-4-sulfonamide |
| 31 | (S)-2-amino-N-(6-(4-(4-fluorophenoxy)phenyl)pyridin-2-yl)-3-(1H-imidazol-4-yl)propanamide |
| 32 | (S)-2-acetamido-N-(6-(4-(4-fluorophenoxy)phenyl)pyridin-2-yl)-3-(1H-imidazol-4-yl)propanamide |
| 33 | (S)-N-(1-((6-(4-(4-fluorophenoxy)phenyl)pyridin-2-yl)amino)-3-(1H-imidazol-4-yl)-1-oxopropan-2-yl)cyclopropanecarboxamide |
| 34 | (S)-1-acetyl-N-(1-((6-(4-(4-fluorophenoxy)phenyl)pyridin-2-yl)amino)-3-(1H-imidazol-4-yl)-1-oxopropan-2-yl)piperidine-4-carboxamide |
| 35 | (S)-N-(6-(4-(4-fluorophenoxy)phenyl)pyridin-2-yl)-3-(1H-imidazol-4-yl)-2-(2-methoxyacetamido)propanamide |
| 36 | (S)-N-(6-(4-(4-fluorophenoxy)phenyl)pyridin-2-yl)-2-(2-hydroxyacetamido)-3-(1H-imidazol-4-yl)propanamide |

TABLE 3-continued

| Compound Example No. | Chemical Name |
|---|---|
| 37 | (S)-N-(6-(4-(4-fluorophenoxy)phenyl)pyridin-2-yl)-2-(2-hydroxy-2-methylpropanamido)-3-(1H-imidazol-4-yl)propanamide |
| 38 | (S)-N-(6-(4-(4-fluorophenoxy)phenyl)pyridin-2-yl)-3-(1H-imidazol-4-yl)-2-(methylsulfonamido)propanamide |
| 40 | (S)-tert-butyl (1-amino-4-((6-(4-(4-fluorophenoxy)phenyl)pyridin-2-yl)amino)-1,4-dioxobutan-2-yl)carbamate |
| 41 | (S)-tert-butyl (4-amino-1-((6-(4-(4-fluorophenoxy)phenyl)pyridin-2-yl)amino)-1,4-dioxobutan-2-yl)carbamate |
| 44 | N-((S)-1-((4-((S)-1,2-dihydroxyethyl)-6-(4-(4-fluorophenoxy)phenyl)pyridin-2-yl)amino)-4-methyl-1-oxopentan-2-yl)cyclopropanecarboxamide |
| 45 | N-((S)-1-((4-((S)-1,2-dihydroxyethyl)-6-(4-(4-fluorophenoxy)phenyl)pyridin-2-yl)amino)-4-methyl-1-oxopentan-2-yl)picolinamide |
| 50 | 2-(4-((6-(4-(4-fluorophenoxy)phenyl)pyridin-2-yl)amino)piperidin-1-yl)acetic acid |
| 53 | 1-(4-chloro-6-(4-(4-fluorophenoxy)phenyl)pyridin-2-yl)piperidine-4-carboxylic acid |
| 54 | Pyridine-2-carboxylic acid ((S)-1-{6-[4-(4-fluoro-phenoxy)-phenyl]-pyridin-2-ylcarbamoyl}-2-hydroxy-ethyl)-amide |
| 55 | Cyclopropanecarboxylic acid ((S)-1-{6-[4-(4-fluoro-phenoxy)-phenyl]-pyridin-2-ylcarbamoyl}-2-hydroxy-ethyl)-amide |
| 56 | N-((S)-1-{6-[4-(4-Fluoro-phenoxy)-phenyl]-pyridin-2-ylcarbamoyl}-2-hydroxy-ethyl)-nicotinamide |
| 57 | N-((S)-1-{6-[4-(4-Fluoro-phenoxy)-phenyl]-pyridin-2-ylcarbamoyl}-2-hydroxy-ethyl)-isonicotinamide |
| 58 | 5-Methyl-isoxazole-3-carboxylic acid ((S)-1-{6-[4-(4-fluoro-phenoxy)-phenyl]-pyridin-2-ylcarbamoyl}-2-hydroxy-ethyl)-amide |
| 59 | ((S)-1-{6-[4-(4-Fluoro-phenoxy)-phenyl]-pyridin-2-ylcarbamoyl}-2-hydroxy-ethyl)-carbamic acid tert-butyl ester |
| 60 | (S)-N-{6-[4-(4-Fluoro-phenoxy)-phenyl]-pyridin-2-yl}-3-hydroxy-2-(2-hydroxy-acetylamino)-propionamide |
| 61 | (S)-N-{6-[4-(4-Fluoro-phenoxy)-phenyl]-pyridin-2-yl}-3-hydroxy-2-ureido-propionamide |
| 62 | (2S,4R)-1-(3-chloro-5-(4-(4-fluorophenoxy)phenyl)pyridin-2-yl)-4-hydroxypyrrolidine-2-carboxylic acid |
| 63 | (2S,4R)-1-(4-chloro-6-(4-(4-fluorophenoxy)phenyl)pyridin-2-yl)-4-hydroxypyrrolidine-2-carboxylic acid |
| 64 | 1-(2-((4-chloro-6-(4-(4-fluorophenoxy)phenyl)pyridin-2-yl)amino)ethyl)imidazolidin-2-one |
| 65 | 2-amino-N-(6-(4-(4-fluorophenoxy)phenyl)pyridin-2-yl)-6-hydroxypyrimidine-4-carboxamide |
| 66 | (S)-1-(2-((4-(1,2-dihydroxyethyl)-6-(4-(4-fluorophenoxy)phenyl)pyridin-2-yl)amino)ethyl)imidazolidin-2-one |
| 67 | ((S)-1-{6-[4-(4-Fluoro-phenoxy)-phenyl]-pyridin-2-ylcarbamoyl}-2-pyridin-3-yl-ethyl)-carbamic acid tert-butyl ester |
| 68 | (S)-2-Acetylamino-N-{6-[4-(4-fluoro-phenoxy)-phenyl]-pyridin-2-yl}-3-pyridin-3-yl-propionamide |
| 69 | (S)-2-Acetylamino-N-{6-[4-(4-fluoro-phenoxy)-phenyl]-pyridin-2-yl}-3-hydroxy-butyramide |
| 70 | (S)-2-Amino-N-{6-[4-(4-fluoro-phenoxy)-phenyl]-pridin-2-yl}-3-hydroxy-propionamide |
| 71 | (S)-2-Amino-N-{6-[4-(4-fluoro-phenoxy)-phenyl]-pyridin-2-yl}-3-pyridin-3-yl-propionamide |
| 72 | N-(6-(4-(4-fluorophenoxy)phenyl)pyridin-2-yl)-2,3-dihydroxypropanamide |
| 73 | N-(6-(4-(4-cyanophenoxy)phenyl)pyridin-2-yl)-2,3-dihydroxypropanamide |
| 74 | N-(6-(4-(3-cyano-4-(trifluoromethyl)phenoxy)phenyl)pyridin-2-yl)-2,3-dihydroxypropanamide |
| 75 | N-(6-(4-(4-cyano-3-(trifluoromethyl)phenoxy)phenyl)pyridin-2-yl)-2,3-dihydroxypropanamide |
| 76 | 2,3-dihydroxy-N-(6-(4-(4-(trifluoromethyl)phenoxy)phenyl)pyridin-2-yl)propanamide |
| 77 | (S)-2-acetamido-N-(6-(4-(4-fluorophenoxy)phenyl)pyridin-2-yl)-3-(1-methyl-1H-imidazol-4-yl)propanamide |
| 78 | (R)-N-(6-(4-(4-fluorophenoxy)phenyl)pyridin-2-yl)-2-(2-hydroxy-2-methylpropanamido)-3-(1-methyl-1H-imidazol-4-yl)propanamide |

TABLE 3-continued

| Compound Example No. | Chemical Name |
|---|---|
| 79 | (S)-2-((4-chloro-6-(4-(4-fluorophenoxy)phenyl)pyridin-2-yl)amino)propanamide |
| 80 | (S)-2-((1-amino-1-oxopropan-2-yl)amino)-6-(4-(4-fluorophenoxy)phenyl)isonicotinamide |
| 81 | (S)-N-(6-(4-(4-fluorophenoxy)phenyl)pyridin-2-yl)-3-(1-methyl-1H-imidazol-4-yl)-2-propionamidopropanamide |
| 82 | (S)-N-(6-(4-(4-fluorophenoxy)phenyl)pyridin-2-yl)-2-isobutyramido-3-(1-methyl-1H-imidazol-4-yl)propanamide |
| 83 | (S)-N-(6-(4-(4-fluorophenoxy)phenyl)pyridin-2-yl)-3-(1-methyl-1H-imidazol-4-yl)-2-pivalamidopropanamide |
| 84 | (S)-2-acetamido-N-(4-(4-(4-fluorophenoxy)phenyl)pyridin-2-yl)-3-(1-methyl-1H-imidazol-4-yl)propanamide |
| 85 | (S)-N-(1-((6-(4-(4-fluorophenoxy)phenyl)pyridin-2-yl)amino)-3-(1-methyl-1H-imidazol-4-yl)-1-oxopropan-2-yl)cyclopropanecarboxamide |
| 86 | (S)-3,3,3-trifluoro-N-(1-((6-(4-(4-fluorophenoxy)phenyl)pyridin-2-yl)amino)-3-(1-methyl-1H-imidazol-4-yl)-1-oxopropan-2-yl)propanamide |
| 87 | (S)-2-acetamido-N-(6-(4-(4-fluorophenoxy)phenyl)pyridin-2-yl)-3-(1-methyl-1H-imidazol-5-yl)propanamide |
| 88 | (R)-N-(1-((6-(4-(4-fluorophenoxy)phenyl)pyridin-2-yl)amino)-3-(1-methyl-1H-imidazol-4-yl)-1-oxopropan-2-yl)-4-(trifluoromethyl)benzamide |
| 89 | (S)-2-(3-(tert-butyl)ureido)-N-(6-(4-(4-fluorophenoxy)phenyl)pyridin-2-yl)-3-hydroxypropanamide |
| 90 | (S)-N-(6-(4-(4-fluorophenoxy)phenyl)pyridin-2-yl)-2-(2-hydroxyacetamido)-4-methylpentanamide |
| 91 | (S)-N-(6-(4-(4-fluorophenoxy)phenyl)pyridin-2-yl)-3-hydroxy-2-(3-isopropylureido)propanamide |
| 92 | (S)-N-(6-(4-(4-fluorophenoxy)phenyl)pyridin-2-yl)-3-hydroxy-2-(2-hydroxy-2-methylpropanamido)propanamide |
| 93 | (S)-N-(6-(4-(4-fluorophenoxy)phenyl)pyridin-2-yl)-3-hydroxy-2-(2-methoxyacetamido)propanamide |
| 94 | (R)-2-acetamido-3-(1-methyl-1H-imidazol-4-yl)-N-(6-(4-((5-(trifluoromethyl)pyridin-2-yl)oxy)phenyl)pyridin-2-yl)propanamide |
| 95 | (2S,3S)-N-(6-(4-(4-fluorophenoxy)phenyl)pyridin-2-yl)-3-hydroxy-2-(2-hydroxyacetamido)butanamide |
| 96 | 2,3-dihydroxy-N-(6-(4-((5-(trifluoromethyl)pyridin-2-yl)oxy)phenyl)pyridin-2-yl)propanamide |
| 97 | (E)-N-(6-(4-(4-fluorophenoxy)phenyl)pyridin-2-yl)-2-phenylethenesulfonamide |
| 98 | N-(6-(4-(4-fluorophenoxy)phenyl)pyridin-2-yl)-1-methyl-1H-benzo[d]imidazole-6-carboxamide |
| 99 | (S)-2-(3-(6-(4-(4-fluorophenoxy)phenyl)pyridin-2-yl)ureido)-3-(1-methyl-1H-imidazol-4-yl)propanamide |
| 100 | (S)-methyl 2-(3-(6-(4-(4-fluorophenoxy)phenyl)pyridin-2-yl)ureido)-3-(1-methyl-1H-imidazol-4-yl)propanoate |
| 101 | (R)-2-(3-(6-(4-(4-fluorophenoxy)phenyl)pyridin-2-yl)ureido)-3-(1H-indol-2-yl)propanamide |
| 102 | (R)-2-(3-(6-(4-(4-fluorophenoxy)phenyl)pyridin-2-yl)ureido)succinamide |
| 103 | (R)-2-(3-(6-(4-(4-fluorophenoxy)phenyl)pyridin-2-yl)ureido)-3-(1H-imidazol-5-yl)propanamide |

For the purpose of the present disclosure, the term "alkyl" as used by itself or as part of another group refers to a straight- or branched-chain aliphatic hydrocarbon containing one to twelve carbon atoms (i.e., $C_{1-12}$ alkyl) or the number of carbon atoms designated (i.e., a $C_1$ alkyl such as methyl, a $C_2$ alkyl such as ethyl, a $C_3$ alkyl such as propyl or isopropyl, etc.). In one embodiment, the alkyl group is chosen from a straight chain $C_{1-10}$ alkyl group. In another embodiment, the alkyl group is chosen from a branched chain $C_{1-10}$ alkyl group. In another embodiment, the alkyl group is chosen from a straight chain $C_{1-6}$ alkyl group. In another embodiment, the alkyl group is chosen from a branched chain $C_{3-6}$ alkyl group. In another embodiment, the alkyl group is chosen from a straight chain $C_{1-4}$ alkyl group. In another embodiment, the alkyl group is chosen from a straight chain $C_{2-4}$ alkyl group. In another embodiment, the alkyl group is chosen from a branched chain $C_{3-4}$ alkyl group. Non-limiting exemplary alkyl groups include methyl, ethyl, propyl, isopropyl, butyl, sec-butyl, tert-butyl, isobutyl, 3-pentyl, hexyl, heptyl, octyl, nonyl, decyl, and the like. Non-limiting exemplary $C_{1-4}$ alkyl groups include methyl, ethyl, propyl, isopropyl, butyl, sec-butyl, tert-butyl, and iso-butyl.

For the purpose of the present disclosure, the term "optionally substituted alkyl" as used by itself or as part of another group means that the alkyl as defined above is either unsubstituted or substituted with one, two, or three substituents independently chosen from nitro, haloalkoxy, aryloxy, aralkyloxy, alkylthio, sulfonamido, alkylcarbonyl, arylcarbonyl, alkylsulfonyl, arylsulfonyl, ureido, guanidino, carboxy, carboxyalkyl, cycloalkyl, and the like. In one embodiment, the optionally substituted alkyl is substituted with two substituents. In another embodiment, the optionally substituted alkyl is substituted with one substituent. Non-limiting exemplary optionally substituted alkyl groups include —CH$_2$CH$_2$NO$_2$, —CH$_2$CH$_2$CO$_2$H, —CH$_2$CH$_2$SO$_2$CH$_3$, —CH$_2$CH$_2$COPh, and the like.

For the purpose of the present disclosure, the term "cycloalkyl" as used by itself or as part of another group refers to saturated and partially unsaturated (e.g. containing one or two double bonds) cyclic aliphatic hydrocarbons containing one to three rings having from three to twelve carbon atoms (i.e., C$_{3-12}$ cycloalkyl) or the number of carbons designated. In one embodiment, the cycloalkyl group has two rings. In one embodiment, the cycloalkyl group has one ring. In another embodiment, the cycloalkyl group is chosen from a C$_{3-8}$ cycloalkyl group. In another embodiment, the cycloalkyl group is chosen from a C$_{3-6}$ cycloalkyl group. Non-limiting exemplary cycloalkyl groups include cyclopropyl, cyclobutyl, cyclopentyl, cyclohexyl, cycloheptyl, cyclooctyl, norbornyl, decalin, adamantyl, cyclohexenyl, and the like.

For the purpose of the present disclosure, the term "optionally substituted cycloalkyl" as used by itself or as part of another group means that the cycloalkyl as defined above is either unsubstituted or substituted with one, two, or three substituents independently chosen from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, and (heteroaryl)alkyl. In one embodiment, the optionally substituted cycloalkyl is substituted with two substituents. In another embodiment, the optionally substituted cycloalkyl is substituted with one substituent. Non-limiting exemplary optionally substituted cycloalkyl groups include:

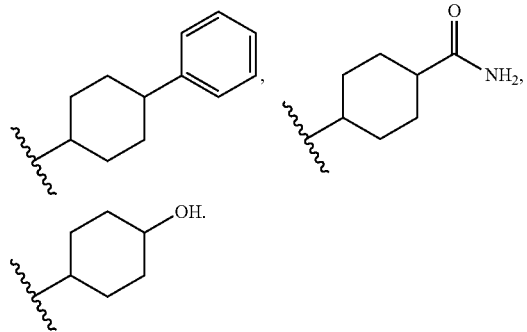

For the purpose of the present disclosure, the term "alkenyl" as used by itself or as part of another group refers to an alkyl group as defined above containing one, two or three carbon-to-carbon double bonds. In one embodiment, the alkenyl group is chosen from a C$_{2-6}$ alkenyl group. In another embodiment, the alkenyl group is chosen from a C$_{2-4}$ alkenyl group. Non-limiting exemplary alkenyl groups include ethenyl, propenyl, isopropenyl, butenyl, sec-butenyl, pentenyl, and hexenyl.

For the purpose of the present disclosure, the term "optionally substituted alkenyl" as used herein by itself or as part of another group means the alkenyl as defined above is either unsubstituted or substituted with one, two or three substituents independently chosen from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, or heterocyclo.

For the purpose of the present disclosure, the term "alkynyl" as used by itself or as part of another group refers to an alkyl group as defined above containing one to three carbon-to-carbon triple bonds. In one embodiment, the alkynyl has one carbon-to-carbon triple bond. In one embodiment, the alkynyl group is chosen from a C$_{2-6}$ alkynyl group. In another embodiment, the alkynyl group is chosen from a C$_{2-4}$ alkynyl group. Non-limiting exemplary alkynyl groups include ethynyl, propynyl, butynyl, 2-butynyl, pentynyl, and hexynyl groups.

For the purpose of the present disclosure, the term "optionally substituted alkynyl" as used herein by itself or as part of another group means the alkynyl as defined above is either unsubstituted or substituted with one, two or three substituents independently chosen from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, or heterocyclo.

For the purpose of the present disclosure, the term "haloalkyl" as used by itself or as part of another group refers to an alkyl group as defined above substituted by one or more fluorine, chlorine, bromine and/or iodine atoms. In one embodiment, the alkyl group is substituted by one, two, or three fluorine and/or chlorine atoms. In another embodiment, the haloalkyl group is chosen from a C$_{1-4}$ haloalkyl group. Non-limiting exemplary haloalkyl groups include fluoromethyl, difluoromethyl, trifluoromethyl, pentafluoroethyl, 1,1-difluoroethyl, 2,2-difluoroethyl, 2,2,2-trifluoroethyl, 3,3,3-trifluoropropyl, 4,4,4-trifluorobutyl, and trichloromethyl groups.

For the purpose of the present disclosure, the term "hydroxyalkyl" as used by itself or as part of another group refers to an alkyl group as defined above substituted with one or more, e.g., one, two, or three, hydroxy groups. In one embodiment, the hydroxyalkyl is a monohydroxyalkyl, i.e., substituted with exactly one hydroxy group. In another embodiment, the hydroxyalkyl is a dihydroxyalkyl, i.e., substituted with exactly two hydroxy groups. In another embodiment, the hydroxyalkyl group is chosen from a C$_{1-4}$ hydroxyalkyl group. In another embodiment, the hydroxyalkyl group is chosen from a C$_{2-4}$ hydroxyalkyl group. Non-limiting exemplary hydroxyalkyl groups include hydroxymethyl, hydroxyethyl, hydroxypropyl and hydroxybutyl groups, such as 1-hydroxyethyl, 2-hydroxyethyl, 1,2-dihydroxyethyl, 2-hydroxypropyl, 3-hydroxypropyl, 3-hydroxybutyl, 4-hydroxybutyl, 2-hydroxy-1-methylpropyl, and 1,3-dihydroxyprop-2-yl.

For the purpose of the present disclosure, the term "alkoxy" as used by itself or as part of another group refers to an optionally substituted alkyl, optionally substituted cycloalkyl, optionally substituted alkenyl or optionally substituted alkynyl attached to a terminal oxygen atom. In one embodiment, the alkoxy group is chosen from a C$_{1-4}$ alkoxy group. In another embodiment, the alkoxy group is chosen from a $C_{1-4}$ alkyl attached to a terminal oxygen atom, e.g., methoxy, ethoxy, and tert-butoxy.

For the purpose of the present disclosure, the term "alkylthio" as used by itself or as part of another group refers to a sulfur atom substituted by an optionally substituted alkyl group. In one embodiment, the alkylthio group is chosen from a $C_{1-4}$ alkylthio group. Non-limiting exemplary alkylthio groups include —$SCH_3$, and —$SCH_2CH_3$.

For the purpose of the present disclosure, the term "alkoxyalkyl" as used by itself or as part of another group refers to any of the above-mentioned alkyl groups substituted with any of the above-mentioned alkoxy groups. Non-limiting exemplary alkoxyalkyl groups include methoxymethyl, methoxyethyl, methoxypropyl, methoxybutyl, ethoxymethyl, ethoxyethyl, ethoxypropyl, ethoxybutyl, propoxymethyl, iso-propoxymethyl, propoxyethyl, propoxypropyl, butoxymethyl, tert-butoxymethyl, isobutoxymethyl, sec-butoxymethyl, and pentyloxymethyl.

For the purpose of the present disclosure, the term "heteroalkyl" as used by itself or part of another group refers to a stable straight or branched chain hydrocarbon radical containing 1 to 10 carbon atoms and at least two heteroatoms, which can be the same or different, selected from O, N, or S, wherein: 1) the nitrogen atom(s) and sulfur atom(s) can optionally be oxidized; and/or 2) the nitrogen atom(s) can optionally be quaternized. The heteroatoms can be placed at any interior position of the heteroalkyl group or at a position at which the heteroalkyl group is attached to the remainder of the molecule. In one embodiment, the heteroalkyl group contains two oxygen atoms. Non-limiting exemplary heteroalkyl groups include —$CH_2OCH_2CH_2OCH_3$, —$OCH_2CH_2OCH_2CH_2OCH_3$, —$CH_2NHCH_2CH_2OCH_2$, —$OCH_2CH_2NH_2$, and —$NHCH_2CH_2N(H)CH_3$.

For the purpose of the present disclosure, the term "haloalkoxy" as used by itself or as part of another group refers to a haloalkyl attached to a terminal oxygen atom. Non-limiting exemplary haloalkoxy groups include fluoromethoxy, difluoromethoxy, trifluoromethoxy, and 2,2,2-trifluoroethoxy.

For the purpose of the present disclosure, the term "aryl" as used by itself or as part of another group refers to a monocyclic or bicyclic aromatic ring system having from six to fourteen carbon atoms (i.e., $C_6$-$C_{14}$ aryl). Non-limiting exemplary aryl groups include phenyl (abbreviated as "Ph"), naphthyl, phenanthryl, anthracyl, indenyl, azulenyl, biphenyl, biphenylenyl, and fluorenyl groups. In one embodiment, the aryl group is chosen from phenyl and naphthyl.

For the purpose of the present disclosure, the term "optionally substituted aryl" as used herein by itself or as part of another group means that the aryl as defined above is either unsubstituted or substituted with one to five substituents independently chosen from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, or (heteroaryl)alkyl. In one embodiment, the optionally substituted aryl is an optionally substituted phenyl. In one embodiment, the optionally substituted phenyl has four substituents. In another embodiment, the optionally substituted phenyl has three substituents. In another embodiment, the optionally substituted phenyl has two substituents.

In another embodiment, the optionally substituted phenyl has one substituent. Non-limiting exemplary substituted aryl groups include 2-methylphenyl, 2-methoxyphenyl, 2-fluorophenyl, 2-chlorophenyl, 2-bromophenyl, 3-methylphenyl, 3-methoxyphenyl, 3-fluorophenyl, 3-chlorophenyl, 4-methylphenyl, 4-ethylphenyl, 4-methoxyphenyl, 4-fluorophenyl, 4-chlorophenyl, 2,6-di-fluorophenyl, 2,6-di-chlorophenyl, 2-methyl, 3-methoxyphenyl, 2-ethyl, 3-methoxyphenyl, 3,4-di-methoxyphenyl, 3,5-di-fluorophenyl 3,5-di-methylphenyl and 3,5-dimethoxy, 4-methylphenyl, 2-fluoro-3-chlorophenyl, and 3-chloro-4-fluorophenyl. The term optionally substituted aryl is meant to include groups having fused optionally substituted cycloalkyl and fused optionally substituted heterocyclo rings. Examples include

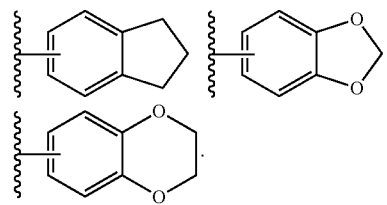

For the purpose of the present disclosure, the term "aryloxy" as used by itself or as part of another group refers to an optionally substituted aryl attached to a terminal oxygen atom. A non-limiting exemplary aryloxy group is PhO—.

For the purpose of the present disclosure, the term "aralkyloxy" as used by itself or as part of another group refers to an aralkyl group attached to a terminal oxygen atom. A non-limiting exemplary aralkyloxy group is $PhCH_2O$—.

For the purpose of the present disclosure, the term "heteroaryl" or "heteroaromatic" refers to monocyclic and bicyclic aromatic ring systems having 5 to 14 ring atoms, wherein at least one carbon atom of one or both of the rings is replaced with a heteroatom independently selected from nitrogen, oxygen, and sulfur. In one embodiment the heteroaryl contains 1, 2, 3, or 4 heteroatoms independently chosen from oxygen, nitrogen and sulfur. In one embodiment, the heteroaryl has three heteroatoms. In another embodiment, the heteroaryl has two heteroatoms. In another embodiment, the heteroaryl has one heteroatom. In one embodiment, the heteroaryl is a 5-membered heteroaryl. In another embodiment, the heteroaryl is a 6-membered heteroaryl. Non-limiting exemplary heteroaryl groups include thienyl, benzo[b]thienyl, naphtho[2,3-b]thienyl, thianthrenyl, furyl, benzofuryl, pyranyl, isobenzofuranyl, benzooxazonyl, chromenyl, xanthenyl, 2H-pyrrolyl, pyrrolyl, imidazolyl, pyrazolyl, pyridyl, pyrazinyl, pyrimidinyl, pyridazinyl, isoindolyl, 3H-indolyl, indolyl, indazolyl, purinyl, isoquinolyl, quinolyl, phthalazinyl, naphthyridinyl, cinnolinyl, quinazolinyl, pteridinyl, 4aH-carbazolyl, carbazolyl, β-carbolinyl, phenanthridinyl, acridinyl, pyrimidinyl, phenanthrolinyl, phenazinyl, thiazolyl, isothiazolyl, phenothiazolyl, isoxazolyl, furazanyl, benzimidazolyl, and phenoxazinyl. In one embodiment, the heteroaryl is chosen from thienyl (e.g., thien-2-yl and thien-3-yl), furyl (e.g., 2-furyl and 3-furyl), pyrrolyl (e.g., 1H-pyrrol-2-yl and 1H-pyrrol-3-yl), imidazolyl (e.g., 2H-imidazol-2-yl and 2H-imidazol-4-yl), pyrazolyl (e.g., 1H-pyrazol-3-yl, 1H-pyrazol-4-yl, and 1H-pyrazol-5-yl), pyridyl (e.g., pyridin-2-yl, pyridin-3-yl, and pyridin-4-yl), pyrimidinyl (e.g., pyrimidin-2-yl, pyrimidin-4-yl, pyrimidin-5-yl, and pyrimidin-5-yl), thiazolyl (e.g., thiazol-2-yl, thiazol-4-yl, and thiazol-5-yl), isothiazolyl (e.g., isothiazol-3-yl, isothiazol-4-yl, and isothiazol-5-yl), oxazolyl (e.g., oxazol-2-yl, oxazol-4-yl, and oxazol-5-yl) and isoxazolyl (e.g., isoxazol-3-yl, isoxazol-4-yl, and isoxazol-5-yl). The term "heteroaryl" is also meant to include possible N-oxides. Exemplary N-oxides include pyridyl N-oxide and the like.

For the purpose of the present disclosure, the term "optionally substituted heteroaryl" as used by itself or as part of another group means that the heteroaryl as defined above is either unsubstituted or substituted with one to four substituents, e.g., one or two substituents, independently chosen from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, and (heteroaryl)alkyl.

In one embodiment, the optionally substituted heteroaryl has one substituent. In one embodiment, the optionally substituted is an optionally substituted pyridyl, i.e., 2-, 3-, or 4-pyridyl. Any available carbon or nitrogen atom can be substituted. In another embodiment, the optionally substituted heteroaryl is an optionally substituted indole.

For the purpose of the present disclosure, the term "heterocyclo" as used by itself or as part of another group refers to saturated and partially unsaturated (e.g. containing one or two double bonds) cyclic groups containing one, two, or three rings having from 3 to 14 ring members. A 3-membered heterocyclo can contain up to 1 heteroatom, a 4-membered heterocyclo can contain up to 2 heteroatoms, a 5-membered heterocyclo can contain up to 4 heteroatoms, and a 6-membered heterocyclo can contain up to 4 heteroatoms, and a 7-membered heterocyclo can contain up to 5 heteroatoms. Each heteroatom is independently selected from oxygen, sulfur, including sulfoxide and sulfone, and/or nitrogen atoms, which can be quaternized. The term "heterocyclo" is meant to include cyclic ureido groups such as 2-imidazolidinone. In one embodiment, the heterocyclo group is chosen from a 5- or 6-membered cyclic group containing one ring and one or two oxygen and/or nitrogen atoms. The heterocyclo can be optionally linked to the rest of the molecule through a carbon or nitrogen atom. Non-limiting exemplary heterocyclo groups include 2-imidazolidinone, piperidinyl, morpholinyl, piperazinyl, and pyrrolidinyl.

For the purpose of the present disclosure, the term "optionally substituted heterocyclo" as used herein by itself or part of another group means the heterocyclo as defined above is either unsubstituted or substituted with one to four substituents independently selected from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo) alkyl, (heteroaryl)alkyl, and the like. Substitution may occur on any available carbon or nitrogen atom. An optionally substituted heterocyclo can be fused to an aryl group to provide an optionally substituted aryl as described above. Non-limiting exemplary optionally substituted heterocyclo groups include:

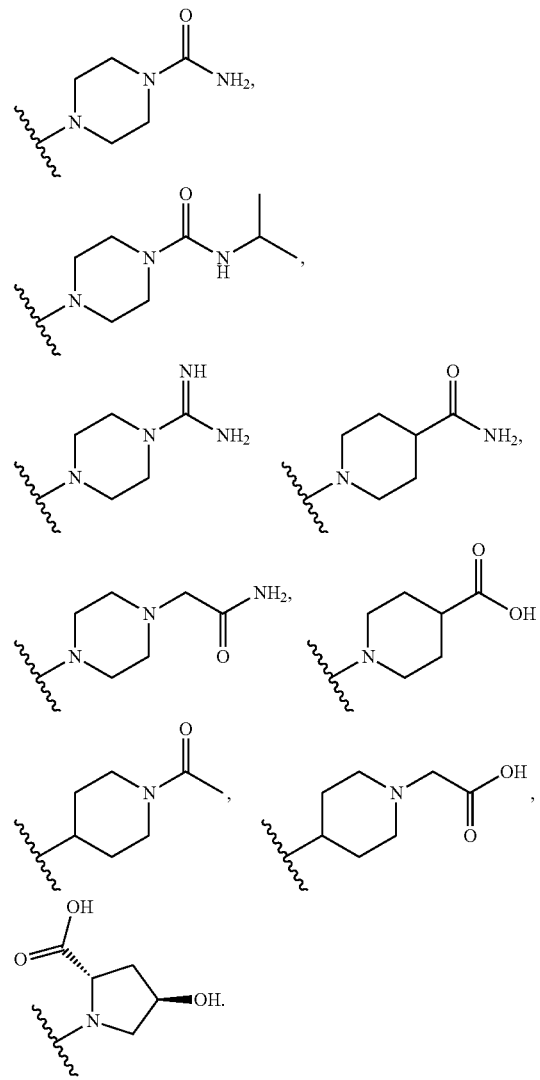

For the purpose of the present disclosure, the term "amino" as used by itself or as part of another group refers to —$NH_2$.

For the purpose of the present disclosure, the term "(amino)alkyl" as used by itself or as part of another group refers to any of the above-mentioned alkyl groups substituted with an amino group. Non-limiting exemplary amino alkyl groups include —$CH_2NH_2$, —$CH_2CH_2NH_2$, —$CH_2CH_2CH_2NH_2$, —$CH_2CH_2CH_2CH_2NH_2$ and the like.

For the purpose of the present disclosure, the term "diaminoalkyl" as used by itself or as part of another group refers any of the above-mentioned alkyl groups substituted with two amino groups.

For the purpose of the present disclosure, the term "alkylamino" as used by itself or as part of another group refers to —$NHR^{13}$, wherein $R^{13}$ is any alkyl group as "alkyl" is defined above.

For the purpose of the present disclosure, the term "dialkylamino" as used by itself or as part of another group refers to —$NR^{14a}R^{14b}$ wherein $R^{14a}$ and $R^{14b}$) are each independently any alkyl group as "alkyl" is defined above.

For the purpose of the present disclosure, the term "hydroxyalkylamino" as used by itself or as part of another group refers to —NHR$^{15}$, wherein R$^{15}$ is any hydroxyalkyl group as "hydroxyalkyl" is defined above.

For the purpose of the present disclosure, the term "arylamino" as used by itself or as part of another group refers to —NR$^{16a}$R$^{16b}$ wherein R$^{16a}$ is any optionally substituted aryl group as "aryl" is defined above and R$^{16b}$ is hydrogen or any alkyl group as "alkyl" is defined above. For the purpose of the present disclosure, the term "cycloalkylamino" as used by itself or as part of another group refers to —NR$^{17a}$R$^{17b}$ wherein R$^{17a}$ is any optionally substituted cycloalkyl group as "cycloalkyl" is defined above and R$^{17b}$ is hydrogen or any alkyl group as "alkyl" is defined above.

For the purpose of the present disclosure, the term "heteroarylamino" as used by itself or as part of another group refers to —NR$^{18a}$R$^{18b}$ wherein R$^{18a}$ is any optionally substituted heteroaryl group as "heteroaryl" is defined above and R$^{18b}$ is hydrogen or any alkyl group as "alkyl" is defined above.

For the purpose of the present disclosure, the term "heterocycloamino" as used by itself or as part of another group refers to —NR$^{19a}$R$^{19b}$ wherein R$^{19a}$ is any optionally substituted heterocyclo group as "heterocyclo" is defined above and R$^{19b}$ is hydrogen or any alkyl group as "alkyl" is defined above.

For the purpose of the present disclosure, the term "(alkylamino)alkyl" as used by itself or as part of another group refers to any alkyl group as "alkyl" is defined above substituted by any alkylamino group as "alkylamino" is defined above.

For the purpose of the present disclosure, the term "(dialkylamino)alkyl" as used by itself or as part of another group refers to any alkyl group as "alkyl" is defined above substituted by any dialkylamino group as "dialkylamino" is defined above.

For the purpose of the present disclosure, the term "(cyano)alkyl" as used by itself or as part of another group refers to any alkyl group as "alkyl" is defined above substituted with one or more cyano, e.g., —CN, groups. Non-limiting exemplary (cyano)alkyl groups include —CH$_2$CN, —CH$_2$CH$_2$CN, —CH$_2$CH$_2$CH$_2$CN, and —CH$_2$CH$_2$CH$_2$CH$_2$CN.

For the purpose of the present disclosure, the term "carboxamido" as used by itself or as part of another group refers to a radical of formula —C(=O)NR$^{20a}$R$^{20b}$, wherein R$^{20a}$ and R$^{20b}$ are each independently hydrogen, optionally substituted alkyl, optionally substituted aryl, or optionally substituted heteroaryl, or R$^{20a}$ and R$^{20b}$ together with the nitrogen to which they are attached from a 3- to 8-membered heterocyclo group. In one embodiment, R$^{20a}$ and R$^{20b}$ are each independently hydrogen or optionally substituted alkyl. Non-limiting exemplary carboxamido groups include —CONH$_2$, —CON(H)CH$_3$, CON(CH$_3$)$_2$, and CON(H)Ph.

For the purpose of the present disclosure, the term "(carboxamido)alkyl" as used by itself or as part of another group refers to any of the above-mentioned alkyl groups substituted with a carboxamido group. Non-limiting exemplary (carboxamido)alkyl groups include —CH$_2$CONH$_2$, —C(H)CH$_3$CONH$_2$, and —CH$_2$CON(H)CH$_3$.

For the purpose of the present disclosure, the term "sulfonamido" as used by itself or as part of another group refers to a radical of the formula —SO$_2$NR$^{21a}$R$^{21b}$, wherein R$^{21a}$ and R$^{21b}$ are each independently hydrogen, optionally substituted alkyl, or optionally substituted aryl, or R$^{21a}$ and R$^{21b}$ taken together with the nitrogen to which they are attached from a 3- to 8-membered heterocyclo group. Non-limiting exemplary sulfonamido groups include —SO$_2$NH$_2$, —SO$_2$N(H)CH$_3$, and —SO$_2$N(H)Ph.

For the purpose of the present disclosure, the term "alkylcarbonyl" as used by itself or as part of another group refers to a carbonyl group, i.e., —C(=O)—, substituted by any of the above-mentioned optionally substituted alkyl groups. A non-limiting exemplary alkylcarbonyl group is —COCH$_3$.

For the purpose of the present disclosure, the term "arylcarbonyl" as used by itself or as part of another group refers to a carbonyl group, i.e., —C(=O)—, substituted by any of the above-mentioned optionally substituted aryl groups. A non-limiting exemplary arylcarbonyl group is —COPh.

For the purpose of the present disclosure, the term "alkylsulfonyl" as used by itself or as part of another group refers to a sulfonyl group, i.e., —SO$_2$—, substituted by any of the above-mentioned optionally substituted alkyl groups. A non-limiting exemplary alkylsulfonyl group is —SO$_2$CH$_3$.

For the purpose of the present disclosure, the term "arylsulfonyl" as used by itself or as part of another group refers to a sulfonyl group, i.e., —SO$_2$—, substituted by any of the above-mentioned optionally substituted aryl groups. A non-limiting exemplary arylsulfonyl group is —SO$_2$Ph.

For the purpose of the present disclosure, the term "mercaptoalkyl" as used by itself or as part of another group refers to any of the above-mentioned alkyl groups substituted by a —SH group.

For the purpose of the present disclosure, the term "carboxy" as used by itself or as part of another group refers to a radical of the formula —COOH.

For the purpose of the present disclosure, the term "carboxyalkyl" as used by itself or as part of another group refers to any of the above-mentioned alkyl groups substituted with a —COOH. A non-limiting exemplary carboxyalkyl group is —CH$_2$CO$_2$H.

For the purpose of the present disclosure, the term "aralkyl" as used by itself or as part of another group refers to any of the above-mentioned alkyl groups substituted with one, two, or three optionally substituted aryl groups. In one embodiment, the aralkyl group is a C$_{1-4}$ alkyl substituted with one optionally substituted aryl group. Non-limiting exemplary aralkyl groups include benzyl, trityl and phenethyl.

For the purpose of the present disclosure, the term "ureido" as used by itself or as part of another group refers to a radical of the formula —NR$^{22a}$—C(=O)—NR$^{22b}$R$^{22c}$, wherein R$^{22a}$ is R$^{22b}$ and R$^{22c}$ are hydrogen, optionally substituted alkyl, or optionally substituted aryl, and R$^{22b}$ and R$^{22c}$ are each independently hydrogen, optionally substituted alkyl, or optionally substituted aryl, or R$^{22b}$ and R$^{22c}$ taken together with the nitrogen to which they are attached form a 4- to 8-membered heterocyclo group. Non-limiting exemplary ureido groups include —NH—C(C=O)—NH$_2$ and NH—C(C=O)—NHCH$_3$.

For the purpose of the present disclosure, the term "guanidino" as used by itself or as part of another group refers to a radical of the formula —NR$^{23a}$—C(=NR$^{24}$)—NR$^{23b}$R$^{23c}$, wherein R$^{23a}$, R$^{23b}$, and R$^{23c}$ are each independently hydrogen, optionally substituted alkyl, or optionally substituted aryl, and R$^{24}$ is hydrogen, alkyl, cyano, alkylsulfonyl, alkylcarbonyl, carboxamido, or sulfonamido. Non-limiting exemplary guanidino groups include —NH—C(C=NH)—NH$_2$, —NH—C(C=NCN)—NH$_2$, —NH—C(C=NH)—NHCH$_3$ and the like.

For the purpose of the present disclosure, the term "azido" as used by itself or as part of another group refers to a radical of the formula —N$_3$.

For the purpose of the present disclosure, the term "(heterocyclo)alkyl" as used by itself or as part of another group refers to any of the above-mentioned alkyl groups substituted with one, two, or three optionally substituted heterocyclo groups. In one embodiment, the (heterocyclo)alkyl group is a $C_{1-4}$ alkyl substituted with one optionally substituted heterocyclo group. Non-limiting exemplary (heterocyclo)alkyl groups include:

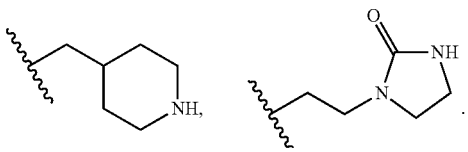 [SMILES: *CC1CCNCC1 ; *CCN1CCNC1=O]

For the purpose of the present disclosure, the term "(heteroaryl)alkyl" as used by itself or as part of another group refers to any of the above-mentioned alkyl groups substituted with one, two, or three optionally substituted heteroaryl groups. In one embodiment, the (heteroaryl)alkyl group is a $C_{1-4}$ alkyl substituted with one optionally substituted heteroaryl group. Non-limiting exemplary (heteroaryl)alkyl groups include:

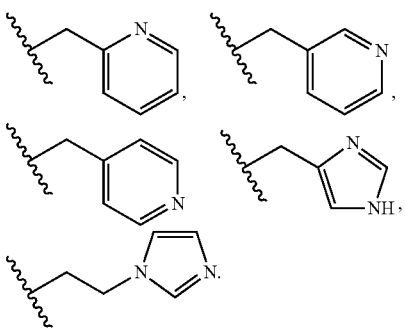

For the purpose of the present disclosure, the term "alkylcarbonylamino" as used by itself or as part of another group refers to an alkylcarbonyl group attached to an amino nitrogen. A non-limiting exemplary alkylcarbonylamino group is —NHCOCH$_3$.

The present invention disclosed herein is also meant to encompass prodrugs of any of the disclosed compounds. As used herein, prodrugs are considered to be any covalently bonded carriers that release the active parent drug in vivo. In general, such prodrugs will be functional derivatives of compounds of any of Formulae I-XVI, which will be readily convertible in vivo, e.g., by being metabolized, into the required compound of Formulae I-XVI. Conventional procedures for the selection and preparation of suitable prodrug derivatives are described in, for example, *Design of Prodrugs*, H. Bundgaard ed., Elsevier (1985); "Drug and Enzyme Targeting, Part A," K. Widder et al. eds., Vol. 112 in *Methods in Enzymology*, Academic Press (1985); Bundgaard, "Design and Application of Prodrugs," Chapter 5 (pp. 113-191) in *A Textbook of Drug Design and Development*, P. Krogsgaard-Larsen and H. Bundgaard eds., Harwood Academic Publishers (1991); Bundgaard et al., *Adv. Drug Delivery Revs.* 8:1-38 (1992); Bundgaard et al., *J. Pharmaceut. Sci.* 77:285 (1988); and Kakeya et al., *Chem. Pharm. Bull.* 32:692 (1984). Non-limiting examples of prodrugs include esters or amides of compounds of any of Formulae I-XVI having hydroxyalkyl or aminoalkyl as a substituent, and these can be prepared by reacting such parent compounds with anhydrides such as succinic anhydride.

The invention disclosed herein is also intended to encompass any of the disclosed compounds being isotopically-labelled (i.e., radiolabeled) by having one or more atoms replaced by an atom having a different atomic mass or mass number. Examples of isotopes that can be incorporated into the disclosed compounds include isotopes of hydrogen, carbon, nitrogen, oxygen, phosphorous, fluorine and chlorine, such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F, and $^{36}$Cl, respectively, and preferably $^3$H, $^{11}$C, and $^{14}$C. Isotopically-labeled compounds of the present invention can be prepared by methods known in the art.

The present invention is also directed to $^3$H, $^{11}$C, or $^{14}$C radiolabeled compounds of any of Formulae I-XVI, as well as their pharmaceutically acceptable salts, prodrugs and solvates, and the use of any such compounds as radioligands for their ability to bind to the sodium channel. For example, one use of the labeled compounds of the present invention is the characterization of specific receptor binding. Another use of a labeled Compound of the Invention is an alternative to animal testing for the evaluation of structure-activity relationships. For example, the receptor assay can be performed at a fixed concentration of a labeled Compound of the Invention and at increasing concentrations of a test compound in a competition assay. For example, a tritiated compound of any of Formulae I-XVI can be prepared by introducing tritium into the particular compound, for example, by catalytic dehalogenation with tritium. This method may include reacting a suitably halogen-substituted precursor of the compound with tritium gas in the presence of a suitable catalyst, for example, Pd/C, in the presence or absence of a base. Other suitable methods for preparing tritiated compounds can be found in Filer, *Isotopes in the Physical and Biomedical Sciences, Vol. 1, Labeled Compounds (Part A)*, Chapter 6 (1987). $^{14}$C-labeled compounds can be prepared by employing starting materials having a $^{14}$C carbon.

Some of the compounds disclosed herein may contain one or more asymmetric centers and may thus give rise to enantiomers, diastereomers, and other stereoisomeric forms. The present invention is meant to encompass the use of all such possible forms, as well as their racemic and resolved forms and mixtures thereof. The individual enantiomers can be separated according to methods known in the art in view of the present disclosure. When the compounds described herein contain olefinic double bonds or other centers of geometric asymmetry, and unless specified otherwise, it is intended that they include both E and Z geometric isomers. All tautomers are intended to be encompassed by the present invention as well.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" refers to a carbon atom to which four different groups are attached.

The terms "enantiomer" and "enantiomeric" refer to a molecule that cannot be superimposed on its mirror image and hence is optically active wherein the enantiomer rotates the plane of polarized light in one direction and its mirror image compound rotates the plane of polarized light in the opposite direction.

The term "racemic" refers to a mixture of equal parts of enantiomers and which mixture is optically inactive.

The term "resolution" refers to the separation or concentration or depletion of one of the two enantiomeric forms of a molecule.

The terms "a" and "an" refer to one or more.

The term "treat," "treating" or "treatment" is meant to encompass administering to a subject a Compound of the Invention for the purposes of amelioration or cure, including preemptive and palliative treatment.

The term "about," as used herein in connection with a measured quantity, refers to the normal variations in that measured quantity, as expected by the skilled artisan making the measurement and exercising a level of care commensurate with the objective of measurement and the precision of the measuring equipment.

The invention disclosed herein also encompasses the use of salts of the disclosed compounds, including all non-toxic pharmaceutically acceptable salts thereof of the disclosed compounds. Examples of pharmaceutically acceptable addition salts include inorganic and organic acid addition salts and basic salts. The pharmaceutically acceptable salts include, but are not limited to, metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, phosphate, sulphate and the like; organic acid salts such as citrate, lactate, tartrate, maleate, fumarate, mandelate, acetate, dichloroacetate, trifluoroacetate, oxalate, formate and the like; sulfonates such as methanesulfonate, benzenesulfonate, p-toluenesulfonate and the like; and amino acid salts such as arginate, asparginate, glutamate and the like.

Acid addition salts can be formed by mixing a solution of the particular Compound of the Invention with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, dichloroacetic acid, or the like. Basic salts can be formed by mixing a solution of the Compound of the Invention with a solution of a pharmaceutically acceptable non-toxic base such as sodium hydroxide, potassium hydroxide, choline hydroxide, sodium carbonate and the like.

The invention disclosed herein is also meant to encompass solvates of any of the disclosed compounds. Solvates typically do not significantly alter the physiological activity or toxicity of the compounds, and as such may function as pharmacological equivalents. The term "solvate" as used herein is a combination, physical association and/or solvation of a Compound of the Invention with a solvent molecule such as, e.g., a disolvate, monosolvate or hemisolvate, where the ratio of solvent molecule to the Compound of the Invention is 2:1, 1:1 or 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. Compounds of any of Formulae I-XVI can be present as solvated forms with a pharmaceutically acceptable solvent, such as water, methanol, ethanol, and the like, and it is intended that the invention includes both solvated and unsolvated forms of compounds of any of Formulae I-XVI. One type of solvate is a hydrate. A "hydrate" relates to a particular subgroup of solvates where the solvent molecule is water. Solvates typically can function as pharmacological equivalents. Preparation of solvates is known in the art. See, for example, M. Caira et a.l, *J. Pharmaceut. Sci.*, 93(3):601-611 (2004), which describes the preparation of solvates of fluconazole with ethyl acetate and with water. Similar preparation of solvates, hemisolvates, hydrates, and the like are described by E. C. van Tonder et al., *AAPS Pharm. Sci. Tech.*, 5(1):Article 12 (2004), and A. L. Bingham et al., *Chem. Commun.*: 603-604 (2001). A typical, non-limiting, process of preparing a solvate would involve dissolving a compound of any of Formulae I-XVI in a desired solvent (organic, water, or a mixture thereof) at temperatures above 20° C. to about 25° C., then cooling the solution at a rate sufficient to form crystals, and isolating the crystals by known methods, e.g., filtration. Analytical techniques such as infrared spectroscopy can be used to confirm the presence of the solvent in a crystal of the solvate.

Since compounds of Formulae I-XVI are blockers of sodium ($Na^+$) channels, a number of diseases and conditions mediated by sodium ion influx can be treated by employing these compounds. The present invention is thus directed generally to a method for treating a disorder responsive to the blockade of sodium channels in an animal suffering from, or at risk of suffering from, said disorder, said method comprising administering to the animal an effective amount of a compound represented by any of defined Formulae I-XVI, or a pharmaceutically acceptable salt, prodrug, or solvate thereof.

The present invention is further directed to a method of modulating sodium channels in an animal in need thereof, said method comprising administering to the animal a modulating-effective amount of at least one compound represented by any of defined Formulae I-XVI, or a pharmaceutically acceptable salt, prodrug, or solvate thereof.

More specifically, the present invention provides a method of treating stroke, neuronal damage resulting from head trauma, epilepsy, neuronal loss following global and focal ischemia, pain (e.g., acute pain, chronic pain, which includes but is not limited to neuropathic pain, postoperative pain, and inflammatory pain, or surgical pain), a neurodegenerative disorder (e.g., Alzheimer's disease, amyotrophic lateral sclerosis (ALS), or Parkinson's disease), migraine, manic depression, tinnitus, myotonia, a movement disorder, or cardiac arrhythmia, or providing local anesthesia. In one embodiment, the invention provides a method of treating pain. In another embodiment, the type of pain is chronic pain. In another embodiment, the type of pain is neuropathic pain. In another embodiment, the type of pain is postoperative pain. In another embodiment, the type of pain is inflammatory pain. In another embodiment, the type of pain is surgical pain. In another embodiment, the type of pain is acute pain. In another embodiment, the treatment of pain (e.g., chronic pain, such as neuropathic pain, postoperative pain, or inflammatory pain, acute pain or surgical pain) is preemptive. In another embodiment, the treatment of pain is palliative. In each instance, such method of treatment requires administering to an animal in need of such treatment an amount of a Compound of the Invention that is therapeutically effective in achieving said treatment. In one embodiment, the amount of such compound is the amount that is effective to block sodium channels in vivo.

Chronic pain includes, but is not limited to, inflammatory pain, postoperative pain, cancer pain, osteoarthritis pain associated with metastatic cancer, trigeminal neuralgia, acute herpetic and postherpetic neuralgia, diabetic neuropathy, causalgia, brachial plexus avulsion, occipital neuralgia, reflex sympathetic dystrophy, fibromyalgia, gout, phantom limb pain, burn pain, and other forms of neuralgia, neuropathic, and idiopathic pain syndromes. Chronic somatic pain generally results from inflammatory responses to tissue injury such as nerve entrapment, surgical procedures, cancer or arthritis (Brower, *Nature Biotechnology* 2000; 18: 387-391).

The inflammatory process is a complex series of biochemical and cellular events activated in response to tissue injury or the presence of foreign substances (Levine, *Inflammatory Pain, In: Textbook of Pain*, Wall and Melzack eds., 3$^{rd}$ ed., 1994). Inflammation often occurs at the site of injured tissue, or foreign material, and contributes to the process of tissue repair and healing. The cardinal signs of inflammation include erythema (redness), heat, edema (swelling), pain and loss of function (ibid.). The majority of patients with inflammatory pain do not experience pain continually, but rather experience enhanced pain when the inflamed site is moved or touched. Inflammatory pain includes, but is not limited to, that associated with osteoarthritis and rheumatoid arthritis.

Chronic neuropathic pain is a heterogenous disease state with an unclear etiology. In chronic neuropathic pain, the pain can be mediated by multiple mechanisms. This type of pain generally arises from injury to the peripheral or central nervous tissue. The syndromes include pain associated with spinal cord injury, multiple sclerosis, post-herpetic neuralgia, trigeminal neuralgia, phantom pain, causalgia, and reflex sympathetic dystrophy and lower back pain. Chronic pain is different from acute pain in that patients suffer the abnormal pain sensations that can be described as spontaneous pain, continuous superficial burning and/or deep aching pain. The pain can be evoked by heat-, cold-, and mechano-hyperalgesia or by heat-, cold-, or mechano-allodynia.

Neuropathic pain can be caused by injury or infection of peripheral sensory nerves. It includes, but is not limited to, pain from peripheral nerve trauma, herpes virus infection, diabetes mellitus, causalgia, plexus avulsion, neuroma, limb amputation, and vasculitis. Neuropathic pain is also caused by nerve damage from chronic alcoholism, human immunodeficiency virus infection, hypothyroidism, uremia, or vitamin deficiencies. Stroke (spinal or brain) and spinal cord injury can also induce neuropathic pain. Cancer-related neuropathic pain results from tumor growth compression of adjacent nerves, brain, or spinal cord. In addition, cancer treatments, including chemotherapy and radiation therapy, can also cause nerve injury. Neuropathic pain includes but is not limited to pain caused by nerve injury such as, for example, the pain from which diabetics suffer.

The present invention is also directed to the use of a compound represented by any of defined Formulae I-XVI, or a pharmaceutically acceptable salt, prodrug, or solvate thereof, in the manufacture of a medicament for treating a disorder responsive to the blockade of sodium channels (e.g., any of the disorders listed above) in an animal suffering from said disorder.

The present invention is also directed to the use of a compound represented by any of defined Formulae I-XVI, or a pharmaceutically acceptable salt, prodrug, or solvate thereof, in the manufacture of a medicament, in particular a medicament for modulating sodium channels, in an animal in need thereof.

General Synthesis of Compounds

Compounds of the Invention are prepared using methods known to those skilled in the art in view of this disclosure. For example, compounds of Formula I wherein $R^{1a}$ is —$SO_2R^6$ or —$COR^7$ and $R^{1b}$ is hydrogen can be prepared according to General Scheme 1.

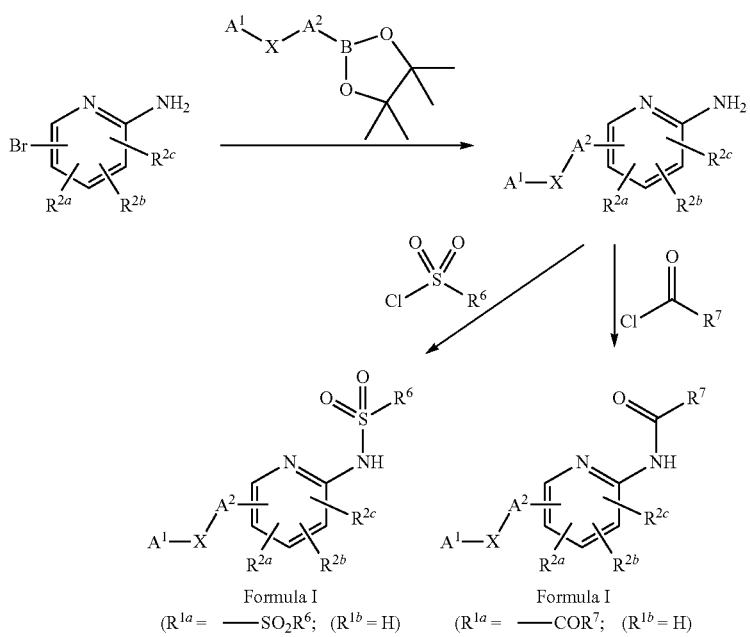

Compounds of Formula IV can be prepared according to General Scheme 2. When $R^{9a}$ of Formula IV is hydrogen, the compound can be further reacted, e.g., with $R^{10}COCl$, to give additional Compounds of the Invention.

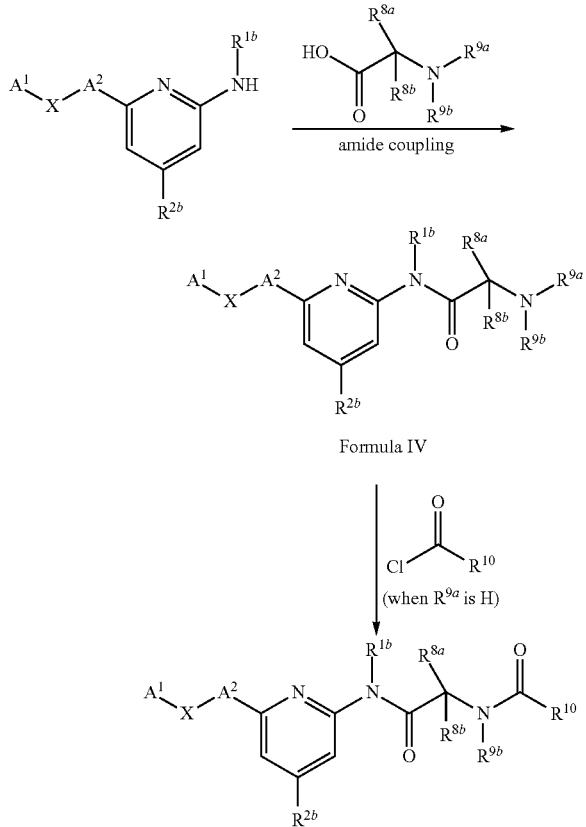

General Scheme 2

Formula IV

Compounds of Formula VIII can be prepared according to General Scheme 3.

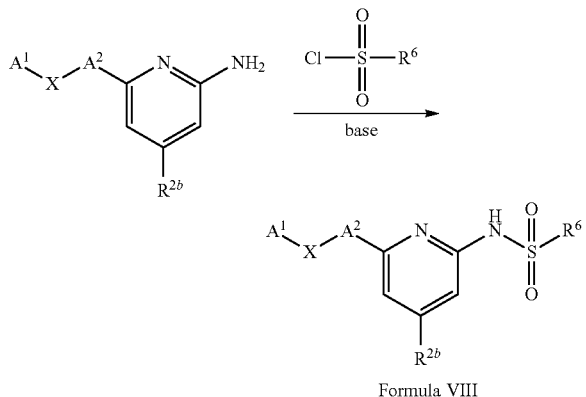

General Scheme 3

Formula VIII

Testing of Compounds

Representative Compounds of the present invention were assessed by sodium mobilization and/or electrophysiological assays for sodium channel blocker activity. One aspect of the present invention is based on the use of the compounds herein described as sodium channel blockers. Based upon this property, compounds of the invention are considered useful in treating a condition or disorder responsive to the blockade of sodium ion channels, e.g., stroke, neuronal damage resulting from head trauma, epilepsy, seizures, general epilepsy with febrile seizures, severe myoclonic epilepsy in infancy, neuronal loss following global and focal ischemia, migraine, familial primary erythromelalgia, paroxysmal extreme pain disorder, cerebellar atrophy, ataxia, dystonia, tremor, mental retardation, autism, a neurodegenerative disorder (e.g., Alzheimer's disease, amyotrophic lateral sclerosis (ALS), or Parkinson's disease), manic depression, tinnitus, myotonia, a movement disorder, cardiac arrhythmia, or providing local anesthesia. Compounds of the Invention are also expected to be effective in treating pain, e.g., acute pain, chronic pain, which includes but is not limited to, neuropathic pain, postoperative pain, and inflammatory pain, or surgical pain.

More specifically, the present invention is directed to compounds of Formulae I-XVI that are blockers of sodium channels. According to the present invention, those compounds having useful sodium channel blocking properties exhibit an $IC_{50}$ for $Na_v1.1$, $Na_v1.2$, $Na_v1.3$, $Na_v1.4$, $Na_v1.5$, $Na_v1.6$, $Na_v1.7$, $Na_v1.8$, and/or $Na_v1.9$ of about 100 µM or less, e.g., about 50 µM or less, about 10 µM or less, about 5 µM or less, or about 1 µM or less, in sodium mobilization and/or electrophysiological assays. In certain embodiments, Compounds of the Invention exhibit an $IC_{50}$ for $Na_v1.7$ of 100 µM or less, about 50 µM or less, about 10 µM or less, about 5 µM or less, about 1 µM or less, about 0.5 µM or less, or about 0.1 µM or less. Compounds of the Invention can be tested for their $Na^+$ channel blocking activity using methods known in the art and by the following fluorescence imaging and electrophysiological in vitro assays and/or in vivo assays.

In one embodiment, Compounds of the Invention demonstrate substantially no penetration across the CNS blood-brain barrier in a mammal. Such compounds are referred to as "peripherally restricted" as a means to designate their PNS versus CNS tissue selectivity.

In one embodiment, the PNS:CNS concentration ratio of a peripherally restricted Compound of the Invention is about 5:1, about 10:1, about 20:1, about 30:1; about 50:1; about 100:1, about 250:1, about 500:1, about 1000:1, about 5,000:1, about 10,000:1, or more. Compounds of the Invention can be tested for their ability to penetrate the central nervous system using in vitro and in vivo methods known in the art.

In Vitro Assay Protocols

FLIPR® Assays

Recombinant $Na_v1.7$ Cell Line:

In vitro assays were performed in a recombinant cell line expressing cDNA encoding the alpha subunit ($Na_v1.7$, SCN9a, PN1, NE) of human $Na_v1.7$ (Accession No. NM_002977). The cell line was provided by investigators at Yale University (Cummins et al, *J. Neurosci.* 18(23): 9607-9619 (1998)). For dominant selection of the $Na_v1.7$-expressing clones, the expression plasmid co-expressed the neomycin resistance gene. The cell line was constructed in the human embryonic kidney cell line, HEK293, under the influence of the CMV major late promoter, and stable clones were selected using limiting dilution cloning and antibiotic selection using the neomycin analogue, G418. Recombinant beta and gamma subunits were not introduced into this cell line. Additional cell lines expressing recombinant $Na_v1.7$ cloned from other species can also be used, alone or in combination with various beta subunits, gamma subunits or chaperones.

Non-Recombinant Cell Lines Expressing Native $Na_v1.7$:

Alternatively, in vitro assays can be performed in a cell line expressing native, non-recombinant $Na_v1.7$, such as the ND7 mouse neuroblastoma X rat dorsal root ganglion (DRG) hybrid cell line ND7/23, available from the European Cell Culture Collection (Cat. No. 92090903, Salisbury, Wiltshire, United Kingdom). The assays can also be performed in other cell lines expressing native, non-recombinant $Na_v1.7$, from various species, or in cultures of fresh or preserved sensory neurons, such as dorsal root ganglion (DRG) cells, isolated from various species. Primary screens or counter-screens of other voltage-gated sodium channels can also be performed, and the cell lines can be constructed using methods known in the art, purchased from collaborators or commercial establishments, and they can express either recombinant or native channels. The primary counter-screen is for one of the central neuronal sodium channels, $Na_v1.2$ (rBIIa), expressed in HEK293 host cells (Ilyin et al., *Br. J. Pharmacol.* 144:801-812 (2005)). Pharmacological profiling for these counter-screens is carried out under conditions similar to the primary or alternative $Na_v1.7$ assays described below.

Cell Maintenance:

Unless otherwise noted, cell culture reagents were purchased from Mediatech of Herndon, Va. The recombinant $Na_v1.7$/HEK293 cells were routinely cultured in growth medium consisting of Dulbecco's minimum essential medium containing 10% fetal bovine serum (FBS, Hyclone, Thermo Fisher Scientific, Logan, Utah), 100 U/mL penicillin, 100 µg/mL streptomycin, 2-4 mM L-glutamine, and 500 mg/mL G418. For natural, non-recombinant cell lines, the selective antibiotic was omitted, and additional media formulations can be applied as needed.

Assay Buffer:

The assay buffer was formulated by removing 120 mL from a 1 L bottle of fresh, sterile $dH_2O$ (Mediatech, Herndon, Va.) and adding 100 mL of 10×HBSS that does not contain $Ca^{++}$ or $Mg^{++}$ (Gibco, Invitrogen, Grand Island, N.Y.) followed by 20 mL of 1.0 M Hepes, pH 7.3 (Fisher Scientific, BP299-100). The final buffer consisted of 20 mM Hepes, pH 7.3, 1.261 mM $CaCl_2$, 0.493 mM $MgCl_2$, 0.407 mM $Mg(SO)_4$, 5.33 mM KCl, 0.441 mM $KH_2PO_4$, 137 mM NaCl, 0.336 mM $Na_2HPO_4$ and 0.556 mM D-glucose (Hanks et al., *Proc. Soc. Exp. Biol. Med.* 71:196 (1949)), and the simple formulation was typically the basic buffer throughout the assay (i.e., all wash and addition steps).

CoroNa™ Green AM $Na^+$ Dye for Primary Fluorescence Assay:

The fluorescence indicator used in the primary fluorescence assay was the cell permeant version of CoroNa™ Green (Invitrogen, Molecular Probes, Eugene, Oreg.), a dye that emits light in the fluorescence range (Harootunian et al., *J. Biol. Chem.* 264(32):19458-19467 (1989)). The intensity of this emission, but not the wavelength range, is increased when the dye is exposed to $Na^+$ ions, which it can bind with partial selectivity. Cells expressing $Na_v1.7$ or other sodium channels were loaded with the CoroNa™ Green dye immediately in advance of the fluorescence assay, and then, after agonist stimulation, the mobilization of $Na^+$ ions was detected as the $Na^+$ ions flowed from the extracellular fluid into the cytoplasm through the activated sodium channel pores. The dye was stored in the dark as a lyophilized powder, and then an aliquot was dissolved immediately before the cell loading procedure, according to the instructions of the manufacturer to a stock concentration of 10 mM in DMSO. It was then diluted in the assay buffer to a 4× concentrated working solution, so that the final concentration of dye in the cell loading buffer was 5 µM.

Membrane Potential Dye for Alternative Fluorescence Assays:

A fluorescence indicator that can be used in alternative fluorescence assays is the blue version membrane potential dye (MDS, Molecular Devices, Sunnyvale, Calif.), a dye that detects changes in molecules following a change in membrane potential. An increase in fluorescence is expected if agonist stimulation provokes a change in membrane potential. Cells expressing $Na_v1.7$ or other sodium channels are incubated with the membrane potential dye 30-60 minutes before the fluorescence assay. In the case of the KCl pre-stimulation version of the assay, the dye and all other components are washed out immediately before the assay, and the dye is then replaced. In the version lacking KCl pre-stimulation, the dye remains on the cells and is not washed out or replaced. The dye is stored in the dark as a lyophilized powder, and then an aliquot dissolved in assay buffer to form a 20×-concentrated stock solution that can be used for several weeks.

Agonists:

In the fluorescence assays, two agonists were used in combination, namely 1) veratridine; and 2) the venom from the yellow scorpion, *Leiurus quinquestriatus hebraeus*. Veratridine is an alkaloid small molecule that facilitates the capture of channel openings by inhibiting inactivation, and the scorpion venom is a natural preparation that includes peptide toxins selective for different subsets of voltage-gated sodium channels. These scorpion toxins inhibit the fast inactivation of their cognate target channels. Stock solutions of the agonists were prepared to 40 mM in DMSO (veratridine) and 1 mg/mL in $dH_2O$ (scorpion venom), and then diluted to make a 4× or 2× stock (depending on the particular assay) in assay buffer, the final concentration being 100 µM (veratridine) and 10 µg/mL (scorpion venom). Both of the agonists were purchased from Sigma Aldrich, St. Louis, Mo.

Test Compounds:

Test compounds were dissolved in DMSO to yield 10 mM stock solutions. The stock solutions were further diluted using DMSO in 1:3 serial dilution steps with 10 points (10,000 µM, 3,333 µM, 1,111 µM, 370 µM, 123 µM, 41 µM, 14 µM, 4.6 µM, 1.5 µM and 0.5 µM). The stock solutions were further diluted in assay buffer (1:125) as 4× stock serial dilutions with a DMSO concentration of 0.8% (final [DMSO], in the assay, from the compounds component=0.2%), so that the compounds' final concentrations in the assay were 20 µM, 6.7 µM, 2.2 µM, 0.74 µM, 0.25 µM and 0.08 µM, 0.03 µM, 0.01 µM, 0.003 µM and 0.001 µM. If a particular test article appeared to be especially potent, then the concentration curve was adjusted, e.g., to 10-fold lower concentrations, in order to perform the dose-response in a more relevant concentration range. Compound dilutions were added during the dye-loading and pre-stimulation step, and then again during the fluorescence assay, early in the kinetic read. Compound dilutions were added in duplicate rows across the middle 80 wells of the 96-well plate, whereas the fully stimulated and the fully inhibited controls (positive and negative) were located in the top 4 side wells and the bottom 4 side wells, respectively, on the left and right sides of the assay plate.

Data Analysis:

The data were analyzed according to methods known to those skilled in the art or using the GraphPad® Prism 4.0 Program (available from GraphPad Software, San Diego, Calif.) to determine the $IC_{50}$ value for the test article. At least one standard reference compound was evaluated during each experiment.

FLIPR® or FLIPR$^{TETRA}$® Sodium Dye Assay with KCl and Test Article Pre-Incubation:

Cells were prepared by plating the recombinant HEK293 cells or other host cells expressing either recombinant or non-recombinant, native, $Na_V1.7$ alpha subunit, alone or in combination with various beta and gamma subunits at a density of ~40,000 cells/well into a 96-well black, clear-bottom, PDL-coated plate. The assay can be adapted to 384-well or 1,536-well format, if desired, using proportionately fewer cells and less media. The plate was then incubated in growth media, with or without selective antibiotic, overnight at 37° C. at 5% $CO_2$, 95% humidity, in preparation for the assay. For counter-screens of other voltage-gated sodium channels, the procedure was very similar, though optimal densities of cells, media and subsequent assay components can be fine-tuned for the particular cell line or isoform.

The next day, at the start of the assay, the media was flicked from the cells and the wells were washed once with 50 μl/well assay buffer (1× Hank's balanced salt solution without sodium bicarbonate or phenol red, 20 mM Hepes, pH 7.3) and then pre-incubated with the test articles, CoroNa™ Green AM sodium dye (for cell loading) and KCl for re-polarization and synchronization of the channels in the entire population of cells. For this dye-loading and pre-stimulation step, the components were added as follows, immediately after the wash step: 1) first, the compound dilutions and controls were added as 4× concentrates in assay buffer at 50 μL/well; 2) CoroNa™ Green AM dye was diluted from the stock solution to 20 μM in assay buffer (4× concentrate) and added to the plate at 50 μL/well; and 3) finally, a solution of 180 mM KCl (2×) was prepared by diluting a 2M stock solution into assay buffer and the solution was added to the cells at 100 μl/well. The cells were incubated at 25° C. in the dark for 30 min. before their fluorescence was measured.

The plates containing dye-loaded cells were then flicked to remove the pre-incubation components and washed once with 100 μL/well assay buffer. A 100 μL/well aliquot of assay buffer was added back to the plate, and the real-time assay was commenced. The fluorescence of cells was measured using a fluorescence plate reader (FLIPR$^{TETRA}$® or FLIPR384®, MDS, Molecular Devices, Sunnyvale, Calif.). Samples were excited by either a laser or a PMT light source (Excitation wavelength=470-495 nM) and the emissions were filtered (Emission wavelength=515-575 nM). The additions of compound and the channel activators in this cell-based, medium-to-high throughput assay were performed on the fluorescence plate reader and the results (expressed as relative fluorescence units) were captured by means of camera shots every 1-3 sec., then displayed in real-time and stored. Generally, there was a 15 sec. base line, with camera shots taken every 1.5 sec., then the test compounds were added, then another 120 sec. baseline was conducted, with camera shots taken every 3 sec.; and finally, the agonist solution (containing veratridine and scorpion venom) was added. The amplitude of fluorescence increase, resulting from the binding of $Na^+$ ions to the CoroNa™ Green dye, was captured for 180 sec. thereafter. Results were expressed in relative fluorescence units (RFU) and can be determined by using the maximum signal during the latter part of the stimulation; or the maximum minus the minimum during the whole agonist stimulation period; or by taking the area under the curve for the whole stimulation period.

The assay can be performed as a screening assay as well with the test articles present in standard amounts (e.g., 10 μM) in only one or two wells of a multi-well plate during the primary screen. Hits in this screen will typically be profiled more exhaustively (multiple times), subjected to dose-response or competition assays and tested in counter screens against other voltage-gate sodium channels or other biologically relevant target molecules.

FLIPR® or FLIPR$^{TETRA}$® Membrane Potential Assay with KCl and Test Article Pre-Incubation:

Cells are prepared by plating the recombinant HEK293 cells or other host cells expressing either recombinant or non-recombinant, native, $Na_V1.7$ alpha subunit, alone or in combination with various beta and gamma subunits at a density of 40,000 cells/well into a 96-well black, clear-bottom, PDL-coated plate. The assay can be adapted to 384-well or 1,536-well format, if desired, using proportionately fewer cells and less media. The plate is then incubated in growth media, with or without selective antibiotic, overnight at 37° C. at 5% $CO_2$, 95% humidity, in preparation for the assay (see, e.g., Benjamin et. al., *J. Biomol. Screen* 10(4):365-373 (2005)). For screens and counter-screens of other voltage-gated sodium channels, the assay protocol is similar, though optimal densities of cells, media and subsequent assay components can be fine-tuned for the particular cell line or sodium channel isoform being tested.

The next day, at the start of the assay, the media is flicked from the cells and the wells are washed once with 50 μL/well assay buffer (1× Hank's balanced salt solution without sodium bicarbonate or phenol red, 20 mM Hepes, pH 7.3) and then pre-incubated with the test articles, the membrane potential dye (for cell loading), and the KCl for re-polarization and synchronization of the channels in the entire population of cells. For this dye-loading and pre-stimulation step, the components are added as follows, immediately after the wash step: 1) first, the compound dilutions and controls are added as 4× concentrates in assay buffer at 50 μL/well; 2) membrane potential dye is diluted from the stock solution in assay buffer (4× concentrate) and added to the plate at 50 μL/well; and 3) finally, a solution of 180 mM KCl (2×) is prepared by diluting a 2M stock solution into assay buffer and the solution added to the cells at 100 μL/well. The cells are incubated at 37° C. in the dark for 30-60 min. before their fluorescence is measured.

The plates containing dye-loaded cells are then flicked to remove the pre-incubation components and washed once with 50 μL/well assay buffer. A 50 μL/well aliquot of membrane potential dye is added back to the plate, and the real-time assay is commenced. The fluorescence of cells is measured using a fluorescence plate reader (FLIPR$^{TETRA}$® or FLIPR384®, MDS, Molecular Devices, Sunnyvale, Calif.). Samples are excited by either a laser or a PMT light source (Excitation wavelength=510-545 nM) and the emissions are filtered (Emission wavelength=565-625 nM). The additions of the compounds (first) and then the channel activators (later) in this are performed on the fluorescence plate reader and the results, expressed as relative fluorescence units (RFU), are captured by means of camera shots every 1-3 sec., then displayed in real-time and stored. Generally, there is a 15 sec. base line, with camera shots taken every 1.5 sec., then the test compounds are added, then another 120 sec. baseline is conducted, with camera shots taken every 3 sec.; and finally, the agonist solution (containing veratridine and scorpion venom) is added. The amplitude of fluorescence increase, resulting from the detection of membrane potential change, is captured for ~120 sec. thereafter. Results are expressed in relative fluorescence units (RFU) and can be determined by using the maximum signal during the latter part of the stimulation; or the maximum minus the minimum during the whole stimulation period; or by taking the area under the curve for the whole stimulation period.

The assay can be performed as a screening assay as well with the test articles present in standard amounts (e.g., 10 µM) in only one or two wells of a multi-well plate during the primary screen. Hits in this screen are typically profiled more exhaustively (multiple times), subjected to dose-response or competition assays and tested in counter screens against other voltage-gate sodium channels or other biologically relevant target molecules.

FLIPR® or FLIPR$^{TETRA}$® Sodium Dye Assay without KCl and Test Article Pre-Incubation:

Cells are prepared by plating the recombinant HEK293 cells or other host cells expressing either recombinant or non-recombinant, native, Na$_v$1.7 alpha subunit, alone or in combination with various beta and gamma subunits at a density of 40,000 cells/well into a 96-well black, clear-bottom, PDL-coated plate. The assay can be adapted to 384-well or 1,536-well format, if desired, using proportionately fewer cells and less media. The plate is then incubated in growth media, with or without selective antibiotic, overnight at 37° C. at 5% $CO_2$, 95% humidity, in preparation for the assay. For counter-screens of other voltage-gated sodium channels, the procedure is very similar, though optimal densities of cells, media and subsequent assay components can be fine-tuned for the particular cell line or isoform.

The next day, at the start of the assay, the media is flicked from the cells and the wells washed once with 50 µL/well assay buffer (1× Hank's balanced salt solution without sodium bicarbonate or phenol red, 20 mM Hepes, pH 7.3). Membrane potential dye is then added to each well of the 96-well plate (50 µL/well), from a freshly diluted sample of the stock (now at 4× concentration) in the assay buffer. The cells are incubated at 37° C. in the dark for 30-60 min. before their fluorescence is measured.

In this standard membrane potential assay, the 96-well plate containing dye-loaded cells is then loaded directly onto the plate reader without aspirating the dye solution and without any further washing of the cells. The fluorescence of cells is measured using a fluorescence plate reader (FLIPR$^{TETRA}$® or FLIPR384®, MDS, Molecular Devices, Sunnyvale, Calif.). Samples are excited by either a laser or a PMT light source (Excitation wavelength=510-545 nM) and the emissions are filtered (Emission wavelength=565-625 nM). The additions of the compounds (first, 50 µL/well from a 4× stock plate) and then the channel activators (later, 100 µL/well from a 2× stock solution) in this kinetic assay are performed on the fluorescence plate reader and the results, expressed as relative fluorescence units (RFU), are captured by means of camera shots every 1-3 sec., then displayed in real-time and stored. Generally, there is a 15 sec. base line, with camera shots taken every 1.5 sec., then the test compounds are added, then another 120 sec. baseline is conducted, with camera shots taken every 3 sec.; and finally, the agonist solution (containing veratridine and scorpion venom) is added. The amplitude of fluorescence increase, resulting from the detection of membrane potential change, is captured for 120 sec. thereafter. Results are expressed in relative fluorescence units (RFU) and can be determined by using the maximum signal during the latter part of the stimulation; or the maximum minus the minimum during the whole stimulation period; or by taking the area under the curve for the whole stimulation period.

The assay can be performed as a screening assay as well, with the test articles present in standard amounts (e.g., 10 µM) in only one or two wells of a multi-well plate during the primary screen. Hits in this screen are typically profiled more exhaustively (multiple times), subjected to dose-response or competition assays and tested in counter screens against other voltage-gate sodium channels or other biologically relevant target molecules.

Electrophysiology Assay

Cells:

The hNa$_v$1.7 expressing HEK-293 cells were plated on 35 mm culture dishes pre-coated with poly-D-lysine in standard DMEM culture media (Mediatech, Inc., Herndon, Va.) and incubated in a 5% $CO_2$ incubator at 37° C. Cultured cells were used approximately 12-48 hours after plating.

Electrophysiology:

On the day of experimentation, the 35 mm dish was placed on the stage of an inverted microscope equipped with a perfusion system that continuously perfuses the culture dish with fresh recording media. A gravity driven superfusion system was used to apply test solutions directly to the cell under evaluation. This system consists of an array of glass pipette connected to a motorized horizontal translator. The outlet of the shooter was positioned approximately 100 µm from the cell of interest.

Whole cell currents were recorded using the whole-cell patch clamp configuration using an Axopatch 200B amplifier (Axon Instruments, Foster City Calif.), 1322A A/D converter (Axon Instruments) and pClamp software (v. 8; Axon Instruments) and stored on a personal computer. Gigaseals were formed and the whole-cell configuration was established in voltage clamp mode, and membrane currents generated by hNa$_v$1.7 were recorded in gap-free mode. Borosilicate glass pipettes have resistance values between 1.5 and 2.0 MΩ when filled with pipette solution and series resistance (<5 MΩ) was compensated 75-80%. Signals were sampled at 50 kHz and low pass filtered at 3 kHz.

Voltage Protocols:

After establishing the whole-cell configuration in voltage clamp mode, voltage protocols were run to establish the 1) test potential, 2) holding potential, and 3) the conditioning potential for each cell.

After establishing the whole-cell configuration in voltage clamp mode, a standard I-V protocol was run to determine the potential at which the maximal current ($I_{max}$) is elicited. This potential was the test potential ($V_t$). To determine a conditioning potential at which 100% of channels were in the inactivated state, a standard steady-state inactivation (SSIN) protocol was run using a series of fifteen 100 ms-long depolarizing prepulses, incrementing in 10 mV steps, immediately followed by a 5 ms testing pulse, $V_t$, to $V_{max}$. This protocol also permitted determination of the holding potential at which all channels are in the resting state.

For compounds causing significant retardation of recovery from inactivation, an estimate of the affinity for the inactivated state of the channel ($K_i$) was generated using the following protocol. From the negative, no residual inactivation, holding potential, the cell was depolarized to the conditioning voltage for 2-5 seconds, returned to the negative holding potential for 10-20 ms to relieve fast inactivation and then depolarized to the test potential for ~15 ms. This voltage protocol was repeated every 10-15 seconds, first to establish a baseline in the absence of the test compound, then in the presence of the test compound.

After a stable baseline was established, the test compound was applied and block of the current elicited by the test pulse assessed. In some cases, multiple cumulative concentrations were applied to identify a concentration that blocked between 40-60% of this current. Washout of the compound was attempted by superfusing with control solution once steady-state block was observed. An estimate of the K, was calculated as follows:

$$K_i=[drug]*\{FR/(1-FR)\}, \qquad \text{Eq. 1}$$

where [drug] is the concentration of a drug, and $$FR=I(\text{after drug})/I(\text{control}), \qquad \text{Eq. 2}$$

where I is the peak current amplitude. If multiple concentrations were used, $K_i$ was determined from the fit of a logistic equation to FRs plotted against corresponding drug concentrations.

In the alternative, the voltage clamp protocol to examine hNa$_v$1.7 currents was as follows. First, the standard current-voltage relationship was tested by pulsing the cell from the holding voltage ($V_h$) of −120 mV by a series of 5 msec long square-shaped test pulses incrementing in +10 mV steps over the membrane voltage range of −90 mV to +60 mV at the pace of stimulation of 0.5 Hz. This procedure determines the voltage that elicits the maximal current ($V_{max}$). Second, $V_h$ was re-set to −120 mV and a steady-state inactivation (SSIN) curve was taken by the standard double-pulse protocol: 100 ms depolarizing pre-pulse was incremented in steps of +10 mV (voltage range from −90 mV to 0 mV) immediately followed by the 5 ms long test pulse to −10 mV at the pace of stimulation of 0.2 Hz. This procedure determines the voltage of full inactivation ($V_{full}$). Third, the cell was repeatedly stimulated with the following protocol, first in the absence of the test compound then in its presence. The protocol consisted of depolarizing the cell from the holding potential of −120 mV to the $V_{full}$ value for 4.5 seconds then repolarizing the cell to the holding potential for 10 ms before applying the test pulse to the $V_{max}$ for 5 ms. The amount of inhibition produced by the test compound was determined by comparing the current amplitude elicited by the test pulse in the absence and presence of the compound.

In a further alternative, the voltage clamp protocol to examine hNa$_v$1.7 currents was as follows. After establishing the whole-cell configuration in voltage clamp mode, two voltage protocols were run to establish: 1) the holding potential; and 2) the test potential for each cell.

Resting Block:

To determine a membrane potential at which the majority of channels are in the resting state, a standard steady-state inactivation (SSIN) protocol was run using 100 ms pre-pulses×10 mV depolarizing steps. The holding potential for testing resting block (Vh$_1$) was 20 mV more hyperpolarized than the first potential where inactivation was observed with the inactivation protocol.

From this holding potential a standard I-V protocol was run to determine the potential at which the maximal current (Imax) is elicited. This potential was the test potential (Vt). The compound testing protocol was a series of 10 ms depolarizations from the Vh$_1$ (determined from the SSIN) to the Vt (determined from the I-V protocol) repeated every 10-15 seconds. After a stable baseline was established, a high concentration of a test compound (highest concentration solubility permits or that which provides ~50% block) was applied and block of the current assessed. Washout of the compound was attempted by superfusing with control solution once steady-state block was observed. The fractional response was calculated as follows:

$$K_r=[drug]*\{FR/(1-FR)\}, \qquad \text{Eq. 3}$$

where [drug] is the concentration of a drug, and $$FR=I(\text{after drug})/I(\text{control}), \qquad \text{Eq. 2}$$

where I is the peak current amplitude and was used for estimating resting block dissociation constant, $K_r$.

Block of Inactivated Channels:

To assess the block of inactivated channels the holding potential was depolarized such that 20-50% of the current amplitude was reduced when pulsed to the same Vt as above. The magnitude of this depolarization depends upon the initial current amplitude and the rate of current loss due to slow inactivation. This was the second holding potential (Vh$_2$). The current reduction was recorded to determine the fraction of available channels at this potential (h).

$$h=I@V_2/\text{Imax}. \qquad \text{Eq. 4}$$

At this membrane voltage a proportion of channels was in the inactivated state, and thus inhibition by a blocker includes interaction with both resting and inactivated channels.

To determine the potency of the test compound on inactivated channels, a series of currents were elicited by 10 ms voltage steps from Vh$_2$ to Vt every 10-15 seconds. After establishing a stable baseline, the low concentration of the compound was applied. In some cases, multiple cumulative concentrations will have to be applied to identify a concentration that blocks between 40-60% of the current. Washout is attempted to re-establish baseline. Fractional responses were measured with respect to a projected baseline to determine $K_{app}$.

$$K_{app}=[drug]*\{FR/(1-FR)\}, \qquad \text{Eq. 5}$$

where [drug] is the concentration of a drug.

This $K_{app}$ value, along with the calculated $K_r$ and h values, were used to calculate the affinity of the compound for the inactivated channels ($K_i$) using the following equation:

$$K_i=(1-h)/((1/K_{app})-(h/K_r)). \qquad \text{Eq. 6}$$

Solutions and Chemicals:

For electrophysiological recordings the external solution was either standard, DMEM supplemented with 10 mM HEPES (pH adjusted to 7.34 with NaOH and the osmolarity adjusted to 320) or Tyrodes salt solution (Sigma, USA) supplemented with 10 mM HEPES (pH adjusted to 7.4 with NaOH; osmolarity=320). The internal pipette solution contained (in mM): NaCl (10), CsF (140), CaCl$_2$ (1), MgCl$_2$ (5), EGTA (11), HEPES (10: pH 7.4, 305 mOsm). Compounds were prepared first as series of stock solutions in DMSO and then dissolved in external solution; DMSO content in final dilutions did not exceed 0.3%. At this concentration, DMSO did not affect sodium currents. Vehicle solution used to establish base line was also contacting 0.3% DMSO.

Data Analysis:

Data was analyzed off-line using Clampfit software (pClamp, v.8; Axon Instruments) and graphed using Graph-Pad Prizm (v. 4.0) software.

In Vivo Assay for Pain

The compounds can be tested for their antinociceptive activity in the formalin model as described in Hunskaar et al., *J. Neurosci. Methods* 14: 69-76 (1985). Male Swiss Webster NIH mice (20-30 g; Harlan, San Diego, Calif.) can be used in all experiments. Food is withdrawn on the day of experiment. Mice are placed in Plexiglass jars for at least 1 hour to acclimate to the environment. Following the acclimation period, mice are weighed and given either the compound of interest administered i.p. or p.o., or the appropriate volume of vehicle (for example, 10% Tween-80 or 0.9% saline, and other pharmaceutically acceptable vehicles) as control. Fifteen minutes after the i.p. dosing, and 30 minutes after the p.o. dosing mice are injected with formalin (20 μL of 5% formaldehyde solution in saline) into the dorsal surface of the right hind paw. Mice are transferred to the Plexiglass jars and monitored for the amount of time spent licking or biting the injected paw. Periods of licking and biting are recorded in 5-minute intervals for 1 hour after the formalin injection. All experiments are done in a blinded manner during the light cycle. The early phase of the formalin response is measured as licking/biting between 0-5 minutes, and the late phase is measured from 15-50 minutes. Differences between vehicle and drug treated groups can be analyzed by one-way analysis of variance (ANOVA). A P value <0.05 is considered significant. Compounds are considered to be efficacious for treating acute and chronic pain if they have activity in blocking both the early and second phase of formalin-induced paw-licking activity.

In Vivo Assays for Inflammatory or Neuropathic Pain

Test Animals:

Each experiment uses rats weighing between 200-260 g at the start of the experiment. The rats are group-housed and have free access to food and water at all times, except prior to oral administration of a test compound when food is removed for 16 hours before dosing. A control group acts as a comparison to rats treated with a compound of Formulae I-XVI. The control group is administered the carrier as used for the test compound. The volume of carrier administered to the control group is the same as the volume of carrier and test compound administered to the test group.

Inflammatory Pain:

To assess the actions of the compounds of Formulae I-XVI on the treatment of inflammatory pain the Freund's complete adjuvant ("FCA") model of inflammatory pain is used. FCA-induced inflammation of the rat hind paw is associated with the development of persistent inflammatory mechanical and thermal hyperalgesia and provides reliable prediction of the anti-hyperalgesic action of clinically useful analgesic drugs (Bartho et al., *Naunyn-Schmiedeberg's Archives of Pharmacol.* 342:666-670 (1990)). The left hind paw of each animal is administered a 50 μL intraplantar injection of 50% FCA. 24 hour post injection, the animal is assessed for response to noxious mechanical stimuli by determining the paw withdrawal threshold (PWT), or to noxious thermal stimuli by determining the paw withdrawal latency (PWL), as described below. Rats are then administered a single injection of either a test compound or 30 mg/Kg of a positive control compound (indomethacin). Responses to noxious mechanical or thermal stimuli are then determined 1, 3, 5 and 24 hours post administration (admin). Percentage reversal of hyperalgesia for each animal is defined as:

$$\% \text{ reversal} = \frac{[(\text{post administration } PWT \text{ or } PWL) - (\text{pre-administration } PWT \text{ or } PWL)]}{[(\text{baseline } PWT \text{ or } PWL) - (\text{pre-administration } PWT \text{ or } PWL)]} \times 100$$

Neuropathic Pain:

To assess the actions of the test compounds for the treatment of neuropathic pain the Seltzer model or the Chung model can be used.

In the Seltzer model, the partial sciatic nerve ligation model of neuropathic pain is used to produce neuropathic hyperalgesia in rats (Seltzer et al., *Pain* 43:205-218 (1990)). Partial ligation of the left sciatic nerve is performed under isoflurane/$O_2$ inhalation anesthesia. Following induction of anesthesia, the left thigh of the rat is shaved and the sciatic nerve exposed at high thigh level through a small incision and is carefully cleared of surrounding connective tissues at a site near the trocanther just distal to the point at which the posterior biceps semitendinosus nerve branches off of the common sciatic nerve. A 7-0 silk suture is inserted into the nerve with a ⅜ curved, reversed-cutting mini-needle and tightly ligated so that the dorsal ⅓ to ½ of the nerve thickness is held within the ligature. The wound is closed with a single muscle suture (4-0 nylon (Vicryl)) and vetbond tissue glue. Following surgery, the wound area is dusted with antibiotic powder. Sham-treated rats undergo an identical surgical procedure except that the sciatic nerve is not manipulated. Following surgery, animals are weighed and placed on a warm pad until they recover from anesthesia. Animals are then returned to their home cages until behavioral testing begins. The animals are assessed for response to noxious mechanical stimuli by determining PWT, as described below, prior to surgery (baseline), then immediately prior to and 1, 3, and 5 hours after drug administration for rear paw of the animal. Percentage reversal of neuropathic hyperalgesia is defined as:

$$\% \text{ reversal} = \frac{[(\text{post administration } PWT) - (\text{pre-administration } PWT)]}{[(\text{baseline } PWT) - (\text{pre-administration } PWT)]} \times 100$$

In the Chung model, the spinal nerve ligation model of neuropathic pain is used to produce mechanical hyperalgesia, thermal hyperalgesia and tactile allodynia in rats. Surgery is performed under isoflurane/$O_2$ inhalation anesthesia. Following induction of anesthesia a 3 cm incision is made and the left paraspinal muscles are separated from the spinous process at the $L_4$-$S_2$ levels. The $L_6$ transverse process is carefully removed with a pair of small rongeurs to identify visually the $L_4$-$L_6$ spinal nerves. The left $L_5$ (or $L_5$ and $L_6$) spinal nerve(s) is (are) isolated and tightly ligated with silk thread. A complete hemostasis is confirmed and the wound is sutured using non-absorbable sutures, such as nylon sutures or stainless steel staples. Sham-treated rats undergo an identical surgical procedure except that the spinal nerve(s) is (are) not manipulated. Following surgery animals are weighed, administered a subcutaneous (s.c.) injection of saline or ringers lactate, the wound area is dusted with antibiotic powder and they are kept on a warm pad until they recover from the anesthesia. Animals are then returned to their home cages until behavioral testing begins. The animals are assessed for response to noxious mechanical stimuli by determining PWT, as described below, prior to surgery (baseline), then immediately prior to and 1, 3, and 5 hours after being administered a compound of Formulae I-XVI for the left rear paw of the animal. The animals can also be assessed for response to noxious thermal stimuli or for tactile allodynia, as described below. The Chung model for neuropathic pain is described in Kim et al., *Pain* 50(3): 355-363 (1992).

Tactile Allodynia:

Sensitivity to non-noxious mechanical stimuli can be measured in animals to assess tactile allodynia. Rats are transferred to an elevated testing cage with a wire mesh floor and allowed to acclimate for five to ten minutes. A series of von Frey monofilaments are applied to the plantar surface of the hindpaw to determine the animal's withdrawal threshold. The first filament used possesses a buckling weight of 9.1 gms (0.96 log value) and is applied up to five times to see if it elicits a withdrawal response. If the animal has a withdrawal response, then the next lightest filament in the series would be applied up to five times to determine if it also could elicit a response. This procedure is repeated with subsequent lesser filaments until there is no response and the identity of the lightest filament that elicits a response is recorded. If the animal does not have a withdrawal response from the initial 9.1 gms filament, then subsequent filaments of increased weight are applied until a filament elicits a response and the identity of this filament is recorded. For each animal, three measurements are made at every time point to produce an average withdrawal threshold determination. Tests can be performed prior to, and at 1, 2, 4 and 24 hours post drug administration.

Mechanical Hyperalgesia:

Sensitivity to noxious mechanical stimuli can be measured in animals using the paw pressure test to assess mechanical hyperalgesia. In rats, hind paw withdrawal thresholds ("PWT"), measured in grams, in response to a noxious mechanical stimulus are determined using an analgesymeter (Model 7200, commercially available from Ugo Basile of Italy), as described in Stein (*Biochemistry & Behavior* 31: 451-455 (1988)). The rat's paw is placed on a small platform, and weight is applied in a graded manner up to a maximum of 250 grams. The endpoint is taken as the weight at which the paw is completely withdrawn. PWT is determined once for each rat at each time point. PWT can be measured only in the injured paw, or in both the injured and non-injured paw. In one non-limiting embodiment, mechanical hyperalgesia associated with nerve injury induced pain (neuropathic pain) can be assessed in rats. Rats are tested prior to surgery to determine a baseline, or normal, PWT. Rats are tested again 2 to 3 weeks post-surgery, prior to, and at different times after (e.g., 1, 3, 5 and 24 hr) drug administration. An increase in PWT following drug administration indicates that the test compound reduces mechanical hyperalgesia.

In Vivo Assay for Anticonvulsant Activity

The Compounds of the Invention can be tested for in vivo anticonvulsant activity after i.v., p.o., or i.p. injection using any of a number of anticonvulsant tests in mice, including the maximum electroshock seizure test (MES). Maximum electroshock seizures are induced in male NSA mice weighing between 15-20 g and in male Sprague-Dawley rats weighing between 200-225 g by application of current (for mice: 50 mA, 60 pulses/sec, 0.8 msec pulse width, 1 sec duration, D.C.; for rats: 99 mA, 125 pulses/sec, 0.8 msec pulse width, 2 sec duration, D.C.) using a Ugo Basile ECT device (Model 7801). Mice are restrained by gripping the loose skin on their dorsal surface and saline-coated corneal electrodes are held lightly against the two corneae. Rats are allowed free movement on the bench top and ear-clip electrodes are used. Current is applied and animals are observed for a period of up to 30 seconds for the occurrence of a tonic hindlimb extensor response. A tonic seizure is defined as a hindlimb extension in excess of 90 degrees from the plane of the body. Results can be treated in a quantal manner.

Pharmaceutical Compositions

Although a Compound of the Invention can be administered to a mammal in the form of a raw chemical without any other components present, the compound is preferably administered as part of a pharmaceutical composition containing the compound combined with a suitable pharmaceutically acceptable carrier. Such a carrier can be selected from pharmaceutically acceptable excipients and auxiliaries.

Pharmaceutical compositions within the scope of the present invention include all compositions where a Compound of the Invention is combined with a pharmaceutically acceptable carrier. In one embodiment, the compound is present in the composition in an amount that is effective to achieve its intended therapeutic purpose. While individual needs may vary, a determination of optimal ranges of effective amounts of each compound is within the skill of the art. Typically, a compound can be administered to a mammal, e.g., a human, orally at a dose of from about 0.0025 to about 1500 mg per kg body weight of the mammal, or an equivalent amount of a pharmaceutically acceptable salt, prodrug, or solvate thereof, per day to treat the particular disorder. A useful oral dose of a Compound of the Invention administered to a mammal is from about 0.0025 to about 50 mg per kg body weight of the mammal, or an equivalent amount of the pharmaceutically acceptable salt, prodrug, or solvate thereof. For intramuscular injection, the dose is typically about one-half of the oral dose.

A unit oral dose may comprise from about 0.01 to about 50 mg, and preferably about 0.1 to about 10 mg, of the compound. The unit dose can be administered one or more times daily, e.g., as one or more tablets or capsules, each containing from about 0.01 to about 50 mg of the compound, or an equivalent amount of a pharmaceutically acceptable salt, prodrug or solvate thereof.

A pharmaceutical composition of the present invention can be administered to any animal that may experience the beneficial effects of a Compound of the Invention. Foremost among such animals are mammals, e.g., humans and companion animals, although the invention is not intended to be so limited.

A pharmaceutical composition of the present invention can be administered by any means that achieves its intended purpose. For example, administration can be by the oral, parenteral, subcutaneous, intravenous, intramuscular, intraperitoneal, transdermal, intranasal, transmucosal, rectal, intravaginal or buccal route, or by inhalation. The dosage administered and route of administration will vary, depending upon the circumstances of the particular subject, and taking into account such factors as age, gender, health, and weight of the recipient, condition or disorder to be treated, kind of concurrent treatment, if any, frequency of treatment, and the nature of the effect desired.

In one embodiment, a pharmaceutical composition of the present invention can be administered orally and is formulated into tablets, dragees, capsules or an oral liquid preparation. In one embodiment, the oral formulation comprises extruded multiparticulates comprising the Compound of the Invention.

Alternatively, a pharmaceutical composition of the present invention can be administered rectally, and is formulated in suppositories.

Alternatively, a pharmaceutical composition of the present invention can be administered by injection.

Alternatively, a pharmaceutical composition of the present invention can be administered transdermally.

Alternatively, a pharmaceutical composition of the present invention can be administered by inhalation or by intranasal or transmucosal administration.

Alternatively, a pharmaceutical composition of the present invention can be administered by the intravaginal route.

A pharmaceutical composition of the present invention can contain from about 0.01 to 99 percent by weight, and preferably from about 0.25 to 75 percent by weight, of active compound(s).

A method of the present invention, such as a method for treating a disorder responsive to the blockade of sodium channels in an animal in need thereof, can further comprise administering a second therapeutic agent to the animal in combination with a Compound of the Invention. In one embodiment, the other therapeutic agent is administered in an effective amount.

Effective amounts of the other therapeutic agents are known to those skilled in the art. However, it is well within the skilled artisan's purview to determine the other therapeutic agent's optimal effective-amount range.

A Compound of the Invention (i.e., the first therapeutic agent) and the second therapeutic agent can act additively or, in one embodiment, synergistically. Alternatively, the second therapeutic agent can be used to treat a disorder or condition that is different from the disorder or condition for which the first therapeutic agent is being administered, and which disorder or condition may or may not be a condition or disorder as defined herein. In one embodiment, a Compound of the Invention is administered concurrently with a second therapeutic agent; for example, a single composition comprising both an effective amount of a compound of any of Formulae I-XVI, and an effective amount of the second therapeutic agent can be administered. Accordingly, the present invention further provides a pharmaceutical composition comprising a combination of a Compound of the Invention, the second therapeutic agent, and a pharmaceutically acceptable carrier. Alternatively, a first pharmaceutical composition comprising an effective amount of a compound of any of Formulae I-XVI and a second pharmaceutical composition comprising an effective amount of the second therapeutic agent can be concurrently administered. In another embodiment, an effective amount of a Compound of the Invention is administered prior or subsequent to administration of an effective amount of the second therapeutic agent. In this embodiment, the Compound of the Invention is administered while the second therapeutic agent exerts its therapeutic effect, or the second therapeutic agent is administered while the Compound of the Invention exerts its therapeutic effect for treating a disorder or condition.

The second therapeutic agent can be an opioid agonist, a non-opioid analgesic, a non-steroidal anti-inflammatory agent, an antimigraine agent, a Cox-II inhibitor, a β-adrenergic blocker, an anticonvulsant, an antidepressant, an anticancer agent, an agent for treating addictive disorder, an agent for treating Parkinson's disease and parkinsonism, an agent for treating anxiety, an agent for treating epilepsy, an agent for treating a seizure, an agent for treating a stroke, an agent for treating a pruritic condition, an agent for treating psychosis, an agent for treating ALS, an agent for treating a cognitive disorder, an agent for treating a migraine, an agent for treating vomiting, an agent for treating dyskinesia, or an agent for treating depression, or a mixture thereof.

Examples of useful opioid agonists include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable salts thereof, and mixtures thereof.

In certain embodiments, the opioid agonist is selected from codeine, hydromorphone, hydrocodone, oxycodone, dihydrocodeine, dihydromorphine, morphine, tramadol, oxymorphone, pharmaceutically acceptable salts thereof, and mixtures thereof.

Examples of useful non-opioid analgesics include non-steroidal anti-inflammatory agents, such as aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam, and pharmaceutically acceptable salts thereof, and mixtures thereof. Examples of other suitable non-opioid analgesics include the following, non limiting, chemical classes of analgesic, antipyretic, nonsteroidal antiinflammatory drugs: salicylic acid derivatives, including aspirin, sodium salicylate, choline magnesium trisalicylate, salsalate, diflunisal, salicylsalicylic acid, sulfasalazine, and olsalazin; para aminophennol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid, and meclofenamic acid; enolic acids, including oxicams (piroxicam, tenoxicam), and pyrazolidinediones (phenylbutazone, oxyphenthartazone); and alkanones, including nabumetone. For a more detailed description of the NSAIDs, see Paul A. Insel, *Analgesic Antipyretic and Antiinflammatory Agents and Drugs Employed in the Treatment of Gout*, in Goodman & Gilman's *The Pharmacological Basis of Therapeutics* 617-57 (Perry B. Molinhoff and Raymond W. Ruddon eds., 9th ed 1996) and Glen R. Hanson, *Analgesic, Antipyretic and Anti Inflammatory Drugs* in Remington: *The Science and Practice of Pharmacy* Vol. II 1196-1221 (A. R. Gennaro ed. 19th ed. 1995) which are hereby incorporated by reference in their entireties. Suitable Cox-II inhibitors and 5-lipoxygenase inhibitors, as well as combinations thereof, are described in U.S. Pat. No. 6,136,839, which is hereby incorporated by reference in its entirety. Examples of useful Cox II inhibitors include, but are not limited to, rofecoxib and celecoxib.

Examples of useful antimigraine agents include, but are not limited to, alpiropride, bromocriptine, dihydroergotamine, dolasetron, ergocornine, ergocorninine, ergocryptine, ergonovine, ergot, ergotamine, flumedroxone acetate, fonazine, ketanserin, lisuride, lomerizine, methylergonovine, methysergide, metoprolol, naratriptan, oxetorone, pizotyline, propranolol, risperidone, rizatriptan, sumatriptan, timolol, trazodone, zolmitriptan, and mixtures thereof.

Examples of useful β-adrenergic blockers include, but are not limited to, acebutolol, alprenolol, amosulabol, arotinolol, atenolol, befunolol, betaxolol, bevantolol, bisoprolol, bopindolol, bucumolol, bufetolol, bufuralol, bunitrolol, bupranolol, butidrine hydrochloride, butofilolol, carazolol, carteolol, carvedilol, celiprolol, cetamolol, cloranolol, dilevalol, epanolol, esmolol, indenolol, labetalol, levobunolol, mepindolol, metipranolol, metoprolol, moprolol, nadolol, nadoxolol, nebivalol, nifenalol, nipradilol, oxprenolol, penbutolol, pindolol, practolol, pronethalol, propranolol, sotalol, sulfinalol, talinolol, tertatolol, tilisolol, timolol, toliprolol, and xibenolol.

Examples of useful anticonvulsants include, but are not limited to, acetylpheneturide, albutoin, aloxidone, aminoglutethimide, 4-amino-3-hydroxybutyric acid, atrolactamide, beclamide, buramate, calcium bromide, carbamazepine, cinromide, clomethiazole, clonazepam, decimemide, diethadione, dimethadione, doxenitroin, eterobarb, ethadione, ethosuximide, ethotoin, felbamate, fluoresone, gabapentin, 5-hydroxytryptophan, lamotrigine, magnesium bromide, magnesium sulfate, mephenyloin, mephobarbital, metharbital, methetoin, methsuximide, 5-methyl-5-(3-phenanthryl)-hydantoin, 3-methyl-5-phenyl-hydantoin, narcobarbital, nimetazepam, nitrazepam, oxcarbazepine, paramethadione, phenacemide, phenetharbital, pheneturide, phenobarbital, phensuximide, phenylmethylbarbituric acid, phenyloin, phethenylate sodium, potassium bromide, pregabaline, primidone, progabide, sodium bromide, solanum, strontium bromide, suclofenide, sulthiame, tetrantoin, tiagabine, topiramate, trimethadione, valproic acid, valpromide, vigabatrin, and zonisamide.

Examples of useful antidepressants include, but are not limited to, binedaline, caroxazone, citalopram, (S)-citalopram, dimethazan, fencamine, indalpine, indeloxazine hydrocholoride, nefopam, nomifensine, oxitriptan, oxypertine, paroxetine, sertraline, thiazesim, trazodone, benmoxine, iproclozide, iproniazid, isocarboxazid, nialamide, octamoxin, phenelzine, cotinine, rolicyprine, rolipram, maprotiline, metralindole, mianserin, mirtazepine, adinazolam, amitriptyline, amitriptylinoxide, amoxapine, butriptyline, clomipramine, demexiptiline, desipramine, dibenzepin, dimetacrine, dothiepin, doxepin, fluacizine, imipramine, imipramine N-oxide, iprindole, lofepramine, melitracen, metapramine, nortriptyline, noxiptilin, opipramol, pizotyline, propizepine, protriptyline, quinupramine, tianeptine, trimipramine, adrafinil, benactyzine, bupropion, butacetin, dioxadrol, duloxetine, etoperidone, febarbamate, femoxetine, fenpentadiol, fluoxetine, fluvoxamine, hematoporphyrin, hypericin, levophacetoperane, medifoxamine, milnacipran, minaprine, moclobemide, nefazodone, oxaflozane, piberaline, prolintane, pyrisuccideanol, ritanserin, roxindole, rubidium chloride, sulpiride, tandospirone, thozalinone, tofenacin, toloxatone, tranylcypromine, L-tryptophan, venlafaxine, viloxazine, and zimeldine.

Examples of useful anticancer agents include, but are not limited to, acivicin, aclarubicin, acodazole hydrochloride, acronine, adozelesin, aldesleukin, altretamine, ambomycin, ametantrone acetate, aminoglutethimide, amsacrine, anastrozole, anthramycin, asparaginase, asperlin, azacitidine, azetepa, azotomycin, batimastat, benzodepa, bicalutamide, bisantrene hydrochloride, bisnafide dimesylate, bizelesin, bleomycin sulfate, brequinar sodium, bropirimine, busulfan, cactinomycin, calusterone, caracemide, carbetimer, carboplatin, carmustine, carubicin hydrochloride, carzelesin, cedefingol, chlorambucil, cirolemycin, and cisplatin.

Therapeutic agents useful for treating an addictive disorder include, but are not limited to, methadone, desipramine, amantadine, fluoxetine, buprenorphine, an opiate agonist, 3-phenoxypyridine, or a serotonin antagonist.

Examples of useful therapeutic agents for treating Parkinson's disease and parkinsonism include, but are not limited to, carbidopa/levodopa, pergolide, bromocriptine, ropinirole, pramipexole, entacapone, tolcapone, selegiline, amantadine, and trihexyphenidyl hydrochloride.

Examples of useful therapeutic agents for treating anxiety include, but are not limited to, benzodiazepines, such as alprazolam, brotizolam, chlordiazepoxide, clobazam, clonazepam, clorazepate, demoxepam, diazepam, estazolam, flumazenil, flurazepam, halazepam, lorazepam, midazolam, nitrazepam, nordazepam, oxazepam, prazepam, quazepam, temazepam, and triazolam; non-benzodiazepine agents, such as buspirone, gepirone, ipsapirone, tiospirone, zolpicone, zolpidem, and zaleplon; tranquilizers, such as barbituates, e.g., amobarbital, aprobarbital, butabarbital, butalbital, mephobarbital, methohexital, pentobarbital, phenobarbital, secobarbital, and thiopental; and propanediol carbamates, such as meprobamate and tybamate.

Examples of useful therapeutic agents for treating epilepsy or seizure include, but are not limited to, carbamazepine, ethosuximide, gabapentin, lamotrigine, phenobarbital, phenyloin, primidone, valproic acid, trimethadione, benzodiazepines, gamma-vinyl GABA, acetazolamide, and felbamate.

Examples of useful therapeutic agents for treating stroke include, but are not limited to, anticoagulants such as heparin, agents that break up clots such as streptokinase or tissue plasminogen activator, agents that reduce swelling such as mannitol or corticosteroids, and acetylsalicylic acid.

Examples of useful therapeutic agents for treating a pruritic condition include, but are not limited to, naltrexone; nalmefene; danazol; tricyclics such as amitriptyline, imipramine, and doxepin; antidepressants such as those given below; menthol; camphor; phenol; pramoxine; capsaicin; tar; steroids; and antihistamines.

Examples of useful therapeutic agents for treating psychosis include, but are not limited to, phenothiazines such as chlorpromazine hydrochloride, mesoridazine besylate, and thoridazine hydrochloride; thioxanthenes such as chloroprothixene and thiothixene hydrochloride; clozapine; risperidone; olanzapine; quetiapine; quetiapine fumarate; haloperidol; haloperidol decanoate; loxapine succinate; molindone hydrochloride; pimozide; and ziprasidone.

Examples of useful therapeutic agents for treating ALS include, but are not limited to, baclofen, neurotrophic factors, riluzole, tizanidine, benzodiazepines such as clonazepan and dantrolene.

Examples of useful therapeutic agents for treating cognitive disorders include, but are not limited to, agents for treating dementia such as tacrine; donepezil; ibuprofen; antipsychotic drugs such as thioridazine and haloperidol; and antidepressant drugs such as those given below.

Examples of useful therapeutic agents for treating a migraine include, but are not limited to, sumatriptan; methysergide; ergotamine; caffeine; and beta-blockers such as propranolol, verapamil, and divalproex.

Examples of useful therapeutic agents for treating vomiting include, but are not limited to, 5-HT3 receptor antagonists such as ondansetron, dolasetron, granisetron, and tropisetron; dopamine receptor antagonists such as prochlorperazine, thiethylperazine, chlorpromazine, metoclopramide, and domperidone; glucocorticoids such as dexamethasone; and benzodiazepines such as lorazepam and alprazolam.

Examples of useful therapeutic agents for treating dyskinesia include, but are not limited to, reserpine and tetrabenazine.

Examples of useful therapeutic agents for treating depression include, but are not limited to, tricyclic antidepressants such as amitryptyline, amoxapine, bupropion, clomipramine, desipramine, doxepin, imipramine, maprotiline, nefazadone, nortriptyline, protriptyline, trazodone, trimipramine, and venlafaxine; selective serotonin reuptake inhibitors such as citalopram, (S)-citalopram, fluoxetine, fluvoxamine, paroxetine, and setraline; monoamine oxidase inhibitors such as isocarboxazid, pargyline, phenelzine, and tranylcypromine; and psychostimulants such as dextroamphetamine and methylphenidate.

A pharmaceutical composition of the present invention is preferably manufactured in a manner which itself will be known in view of the instant disclosure, for example, by means of conventional mixing, granulating, dragee-making, dissolving, extrusion, or lyophilizing processes. Thus, pharmaceutical compositions for oral use can be obtained by combining the active compound with solid excipients, optionally grinding the resulting mixture and processing the mixture of granules, after adding suitable auxiliaries, if desired or necessary, to obtain tablets or dragee cores.

Suitable excipients include fillers such as saccharides (for example, lactose, sucrose, mannitol or sorbitol), cellulose preparations, calcium phosphates (for example, tricalcium phosphate or calcium hydrogen phosphate), as well as binders such as starch paste (using, for example, maize starch, wheat starch, rice starch, or potato starch), gelatin, tragacanth, methyl cellulose, hydroxypropylmethylcellulose, sodium carboxymethylcellulose, and/or polyvinyl pyrrolidone. If desired, one or more disintegrating agents can be added, such as the above-mentioned starches and also carboxymethyl-starch, cross-linked polyvinyl pyrrolidone, agar, or alginic acid or a salt thereof, such as sodium alginate.

Auxiliaries are typically flow-regulating agents and lubricants such as, for example, silica, talc, stearic acid or salts thereof (e.g., magnesium stearate or calcium stearate), and polyethylene glycol. Dragee cores are provided with suitable coatings that are resistant to gastric juices. For this purpose, concentrated saccharide solutions can be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropymethyl-cellulose phthalate can be used. Dye agents or pigments can be added to the tablets or dragee coatings, for example, for identification or in order to characterize combinations of active compound doses.

Examples of other pharmaceutical preparations that can be used orally include push-fit capsules made of gelatin, or soft, sealed capsules made of gelatin and a plasticizer such as glycerol or sorbitol. The push-fit capsules can contain a compound in the form of granules, which can be mixed with fillers such as lactose, binders such as starches, and/or lubricants such as talc or magnesium stearate and, optionally, stabilizers, or in the form of extruded multiparticulates. In soft capsules, the active compounds are preferably dissolved or suspended in suitable liquids, such as fatty oils or liquid paraffin. In addition, stabilizers can be added.

Possible pharmaceutical preparations for rectal administration include, for example, suppositories, which consist of a combination of one or more active compounds with a suppository base. Suitable suppository bases include natural and synthetic triglycerides, and paraffin hydrocarbons, among others. It is also possible to use gelatin rectal capsules consisting of a combination of active compound with a base material such as, for example, a liquid triglyceride, polyethylene glycol, or paraffin hydrocarbon.

Suitable formulations for parenteral administration include aqueous solutions of the active compound in a water-soluble form such as, for example, a water-soluble salt, alkaline solution, or acidic solution. Alternatively, a suspension of the active compound can be prepared as an oily suspension. Suitable lipophilic solvents or vehicles for such as suspension may include fatty oils (for example, sesame oil), synthetic fatty acid esters (for example, ethyl oleate), triglycerides, or a polyethylene glycol such as polyethylene glycol-400 (PEG-400). An aqueous suspension may contain one or more substances to increase the viscosity of the suspension, including, for example, sodium carboxymethyl cellulose, sorbitol, and/or dextran. The suspension may optionally contain stabilizers.

The following examples are illustrative, but not limiting, of the compounds, compositions and methods of the present invention. Suitable modifications and adaptations of the variety of conditions and parameters normally encountered in clinical therapy and which are obvious to those skilled in the art in view of this disclosure are within the spirit and scope of the invention.

EXAMPLES

Example 1

Synthesis of (S)-2-acetamido-N-(6-(4-(4-fluorophenoxy)phenyl)pyridin-2-yl)-4-methylpentanamide

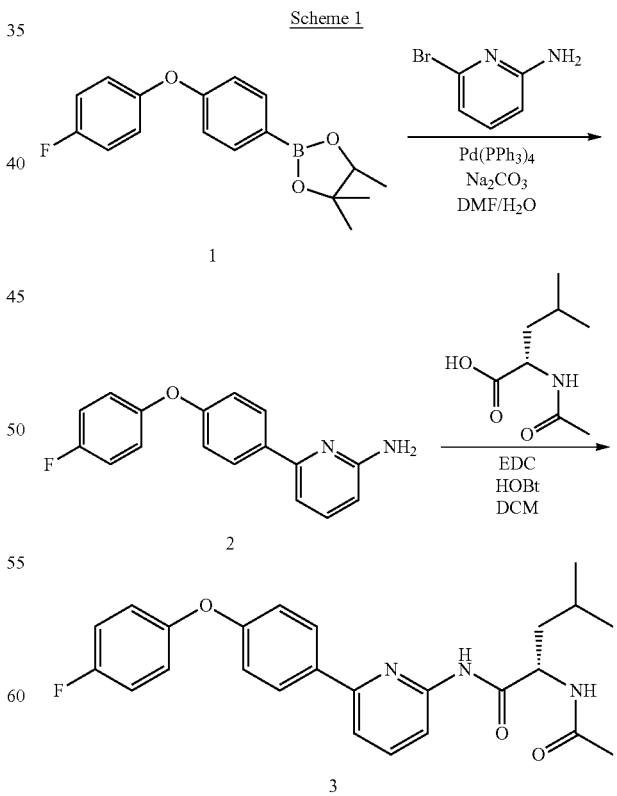

Compound 2: 2-(4-(4-Fluorophenoxy)phenyl)-4,4,5,5-tetramethyl-1,3,2-dioxaborolane (compound 1; 368 mg, 1.4 mmol), 6-bromopyridin-2-amine (250 mg, 1.4 mmol) and sodium carbonate (1.2 g, 11.2 mmol) were dissolved in DMF/H₂O (15 mL). Tetrakis(triphenylphosphine) palladium (81 mg, 0.07 mmol) was added thereto and the reaction mixture was refluxed for 4 h. The reaction mixture was cooled to room temperature and partitioned between EtOAc and water. The organic layer was separated and then dried over anhydrous Na₂SO₄. The solvent was evaporated and the oily residue was purified by column chromatography (silica gel, 30% EtOAc in hexane) to give 6-(4-(4-fluorophenoxy)phenyl)pyridin-2-amine as pale yellow oil (372 mg, 92%). R$_f$=0.6, eluent (1:1 EtOAc:hexanes), LC/MS: m/z=281 [M+H]⁺.

In an alternative procedure, to a solution of 6-bromopyridin-2-amine (4.329 g, 25.02 mmol, Aldrich) in dioxane (150 mL) was added compound 1 (7.88 g, 25.08 mmol), 2M aqueous Na₂CO₃ solution (25 mL, 50 mmol) and PdCl₂(dppf) (1.027 g, 1.26 mmol). The reaction vessel was heated at reflux under nitrogen overnight. After cooling, the reaction was partitioned between 100 mL EtOAc and 50 mL water. The organic layer was washed once with 25 mL brine, dried over Na₂SO₄, filtered and concentrated in vacuo. The residue was chromatographed over silica gel eluting with 20-50% EtOAc in hexanes. The product fractions were isolated and evaporated in vacuo to give 6-(4-(4-fluorophenoxy)phenyl)pyridin-2-amine as a thick pale yellow oil (5.994 g, 21.38 mmol, 85% yield, LC/MS: m/z=281.2 [M+H]⁺).

Compound 3: A mixture of AcN-(L)-Leu-OH (Sigma-Aldrich, 61.9 mg, 0.36 mmol), EDC (82 mg, 0.43 mmol), HOBt (58.0 mg, 0.43 mmol) in dry DCM was stirred for 1 h and compound 2 (100 mg, 0.36 mmol) was added thereto. The reaction mixture was allowed to stir overnight at room temperature. After the reaction was complete, it was quenched with saturated NH₄Cl. The aqueous layer was extracted with EtOAc and CHCl₃. The combined organic layers were dried over anhydrous Na₂SO₄ and concentrated to give oily residue. The residue was purified by preparative TLC (10% MeOH in DCM with 1% NH₄OH) to give (S)-2-acetamido-N-(6-(4-(4-fluorophenoxy)phenyl)pyridin-2-yl)-4-methylpentanamide (compound 3) as a white solid (61 mg, 39%). LC/MS: m/z=436 [M+H]⁺; ¹H NMR (400 MHz, CDCl₃): 8.52 (s, br, 1H), 8.01 (d, J=8.2 Hz, 1H), 7.86 (d, J=9.0 Hz, 2H), 7.68 (t, J=8.1 Hz, 2H), 7.37 (d, J=7.7 Hz, 2H), 6.93-7.02 (m, 6H), 5.90 (br, s, 1H), 4.53-4.66 (m, 1H), 2.0 (s, 3H), 1.60-1.78 (m, 2H), 1.49-1.60 (m, 1H), 0.91 (d, J=6.5 Hz, 3H), 0.90 (d, J=6.2 Hz, 3H). Unless otherwise indicated all ¹H NMR chemical shifts reported herein are denoted by the delta (δ) scale.

Example 2

Synthesis of (S)-2-acetamido-N-(6-(4-(4-fluorophenoxy)phenyl)pyridin-2-yl)-3-phenylpropanamide Scheme 2

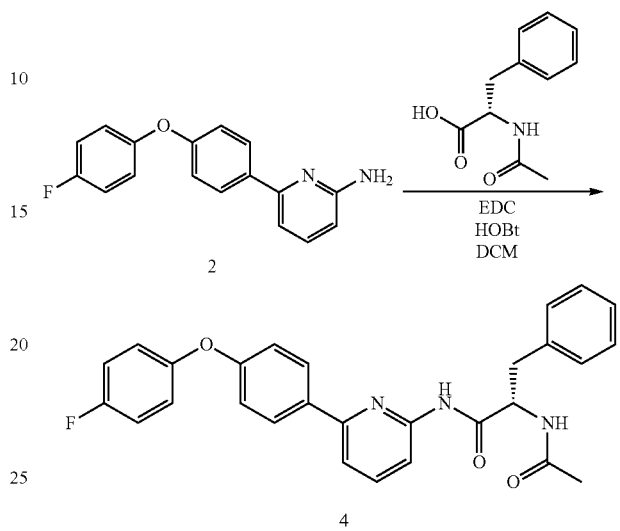

Compound 4: A mixture of AcN-(L)-Phe-OH (purchased from Sigma-Aldrich, 74.5 mg, 0.36 mmol), EDC (82 mg, 0.43 mmol), HOBt (58.0 mg, 0.43 mmol) in dry DCM was stirred for 1 h and compound 2 (100 mg, 0.36 mmol) was added thereto. The reaction mixture was stirred for 2 days at room temperature (67% conversion by LC/MS analysis) and it was quenched with saturated. NH₄Cl. The aqueous layer was extracted with EtOAC and CHCl₃. The combined organic layers were dried over anhydrous Na₂SO₄ and concentrated to give solid residue. The crude residue was purified by preparative TLC (1st purification: 50% EtOAc in hexanes; 2nd purification: 10% MeOH in DCM with 1% NH₄OH) to give (S)-2-acetamido-N-(6-(4-(4-fluorophenoxy)phenyl)pyridin-2-yl)-3-phenylpropanamide (compound 4) as a white solid (26 mg, 15%). LC/MS: m/z=470 [M+H]⁺; ¹H NMR (400 MHz, CDCl₃): 8.46-8.45 (br, s, 1H), 8.08 (d, J=8.3 Hz, 1H), 7.70 (dd, J=7.4 Hz, 8.0 Hz, 1H), 7.46 (d, J=7.7 Hz, 1H), 7.24-7.37 (m, 6H), 7.02-7.12 (m, 6H), 6.13 (s, br, 1H), 4.88 (m, 1H), 3.22 (d, J=7.1 Hz, 2H), 2.05 (s, 3H).

Example 3

Synthesis of (S)—N-(1-((6-(4-(4-fluorophenoxy)phenyl)pyridin-2-yl)amino)-4-methyl-1-oxopentan-2-yl)picolinamide Scheme 3

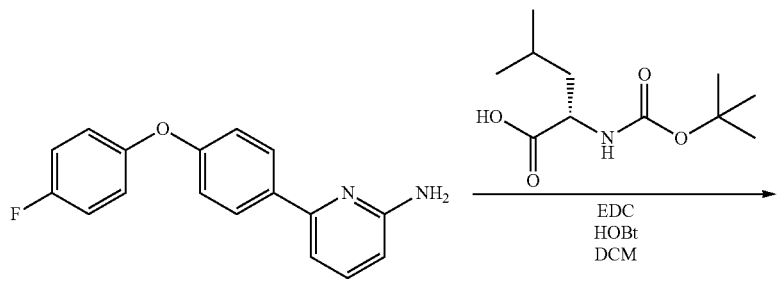

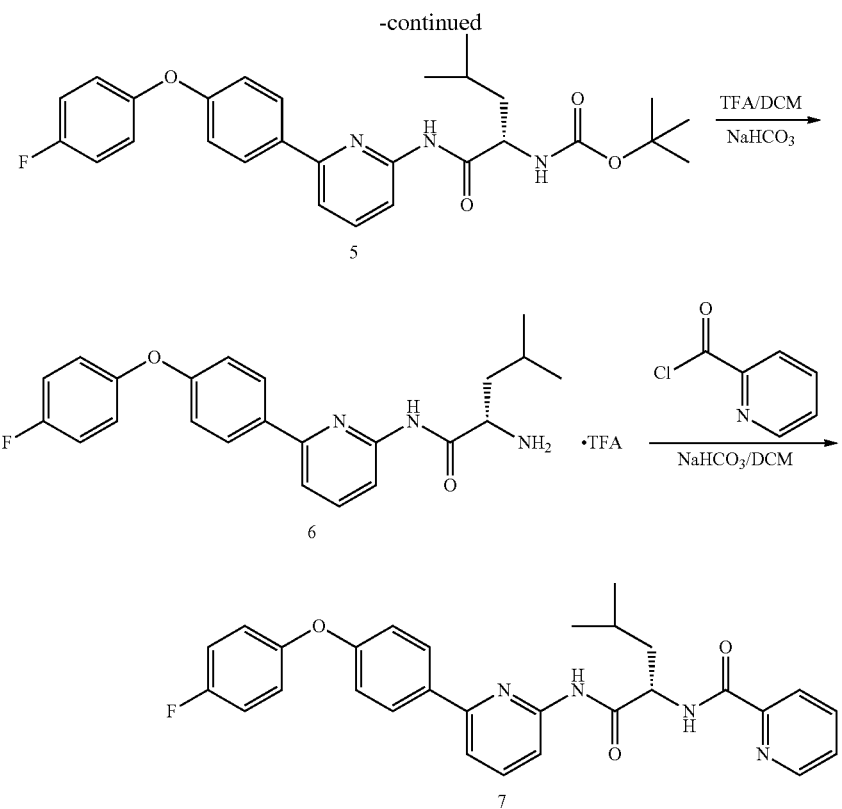

Compound 5: A mixture of Boc-Leu-OH (purchased from Sigma-Aldrich, 4.17 g, 18.0 mmol), EDC (4.1 g, 21.5 mmol), HOBt (2.9 g, 21.5 mmol) in dry DCM (300 mL) was stirred for 1 h at room temperature and compound 2 (5.0 g, 18.0 mmol) was added thereto. The reaction mixture was stirred for 12 h at room temperature. After the reaction was complete, it was quenched with saturated $NH_4Cl$. The aqueous layer was extracted with EtOAc and $CHCl_3$. The combined organic layers were dried over anhydrous $Na_2SO_4$ and concentrated to give oily residue which was then purified by column chromatography (silica gel, 30% EtOAc in hexane) to give compound 5 as pale yellow oil (4.0 g, 75% yield based on the recovered starting material (2.0 g)). LC/MS: m/z=496 [M+H]$^+$; $^1$H NMR (400 MHz, $CDCl_3$): 8.67 (br, s, 1H), 8.12 (d, J=8.33 Hz, 2H), 7.90 (d, J=8.99 Hz, 2H),), 7.76 (t, J=7.89 Hz, 1H), 7.42 (d, J=7.67 Hz, 1H), 7.00-7.09 (m, 5H), 4.86 (br, s, 1H), 4.31 (br, s, 1H), 1.48-1.87 (m, 3H), 1.45 (s, 9H), 0.95 (d, J=6.36 Hz, 6H).

Compound 6: Compound 5 (1.0 g, 2.0 mmol) was dissolved in dry DCM (15 mL) and treated with TFA (15 mL). The mixture was stirred for 1 h at room temperature and solvent was evaporated. The resulting residue was dissolved in a 5:1 mixture of THF:MeOH (10 mL) and $NaHCO_3$ (253 mg) was added thereto. The suspension was stirred for 10 min, diluted with DCM, and filtered. The solvent was evaporated and the compound 6 was obtained quantitatively as TFA salt which was used for the next step without further purification.

Compound 7: Compound 6 (50.0 mg, 0.10 mmol) was treated with picolinoyl chloride hydrochloride (14.2 mg, 0.10 mmol) in a 1:1 mixture of DCM/saturated $NaHCO_3$. After the reaction was complete, the organic layer was separated, washed with brine, dried over $Na_2SO_4$, and concentrated. The residue was purified by preparative TLC (10:1 DCM:MeOH) to give (S)—N-(1-((6-(4-(4-fluorophenoxy)phenyl)pyridin-2-yl)amino)-4-methyl-1-oxopentan-2-yl)picolinamide (compound 7) (25 mg, 51%). LC/MS: m/z=499 [M+H]$^+$; $^1$H NMR (400 MHz, $CD_3OD$): 8.63 (s, 1H), 8.59 (d, J=4.4 Hz, 1H), 8.43 (d, J=7.9 Hz, 1H), 8.21 (d, J=7.9 Hz, 1H), 8.12 (d, J=7.9 Hz, 1H), 7.83-7.95 (m, 3H), 7.74 (t, J=7.9 Hz, 1H), 7.41-7.48 (m, 1H), 7.42 (d, J=7.0 Hz, 1H), 6.99-7.08 (m, 6H), 4.78-4.88 (m, 1H), 1.93-2.03 (m, 1H), 1.74-1.90 (m, 1H), 1.0 (t, J=6.1 Hz, 6H).

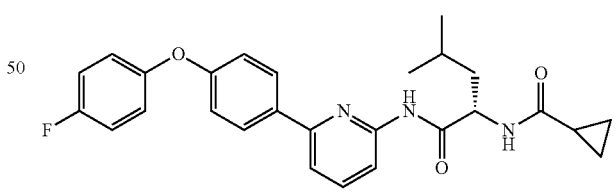

Compound 8: In a similar fashion, compound 6 (58.0 mg, 0.11 mmol) was treated with cyclopropanecarbonyl chloride (12.0 mg, 0.11 mmol) to give (S)—N-(1-((6-(4-(4-fluorophenoxy)phenyl)pyridin-2-yl)amino)-4-methyl-1-oxopentan-2-yl)cyclopropanecarboxamide (32 mg, 62%). LC/MS: m/z=463 [M+H]$^+$; $^1$H NMR (400 MHz, $CD_3OD$): 8.52 (s, 1H), 8.08 (d, J=7.89 Hz, 1H), 7.92 (d, J=8.77 Hz, 1H), 7.74 (t, J=7.89 Hz, 1H), 7.43 (d, J=7.89 Hz, 1H), 6.99-7.11 (m, 6H), 6.04-6.15 (m, 1H), 4.63-4.73 (m, 1H), 1.56-1.88 (m, 2H), 1.37-1.49 (m, 1H), 0.94-1.06 (m, 8H), 0.79 (d, J=7.89 Hz, 2H).

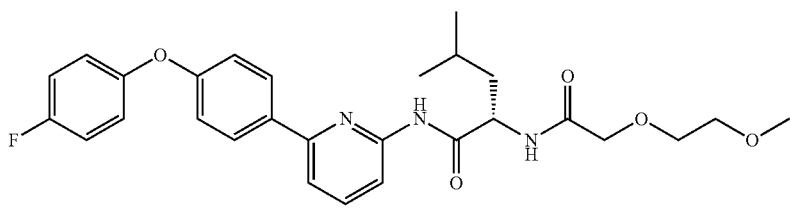 [SMILES: COCCOCC(=O)N[C@@H](CC(C)C)C(=O)Nc1cccc(-c2ccc(Oc3ccc(F)cc3)cc2)n1]

10

Compound 9: In a similar fashion, compound 6 (100.0 mg, 0.2 mmol) was treated with 2-(2-methoxyethoxy)acetyl chloride (30.5 mg, 0.2 mmol) to give S)—N-(6-(4-(4-fluorophenoxy)phenyl)pyridin-2-yl)-2-(2-(2-methoxyethoxy)acetamido)-4-methylpentanamide (65 mg, 65%). LC/MS: m/z=510 [M+H]$^+$; $^1$H NMR (400 MHz, CD$_3$OD): 8.65 (s, 1H), 8.03 (d, J=7.90 Hz, 1H), 7.86 (d, J=8.77 Hz, 2H), 7.67 (t, J=7.89 Hz, 1H), 7.47 (d, J=7.89 Hz, 1H), 7.36 (d, J=7.02 Hz, 1H), 6.91-7.03 (m, 6H), 4.52-4.63 (m, 1H), 4.01 (d, J=3.50 Hz, 2H), 3.63-3.70 (m, 2H), 3.48-3.57 (m, 2H), 3.37 (s, 3H), 1.43-2.02 (m, 3H), 0.92 (t, J=6.14 Hz, 6H).

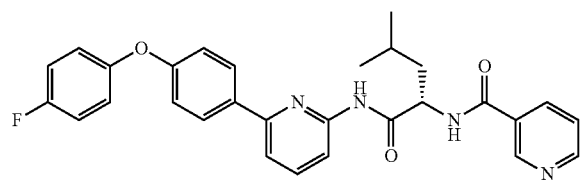 [SMILES: CC(C)C[C@H](NC(=O)c1cccnc1)C(=O)Nc1cccc(-c2ccc(Oc3ccc(F)cc3)cc2)n1]

Compound 10: In a similar fashion, compound 6 (53.3 mg, 0.1 mmol) was treated with nicotinyl chloride hydrochloride (14.1 mg, 0.1 mmol) to give S)—N-(1-((6-(4-(4-fluorophenoxy)phenyl)pyridin-2-yl)amino)-4-methyl-1-oxopentan-2-yl)nicotinamide (2.7 mg, 5.0%). LC/MS: m/z=499 [M+H]$^+$; $^1$H NMR (400 MHz, CD$_3$OD): 9.03 (s, 1H), 8.70 (dd, J=1.54, 5.26 Hz, 1H), 8.42-8.47 (m, 1H), 7.95 (d, J=8.77 Hz, 2H), 7.89-7.93 (m, 1H), 7.73 (t, J=8.11 Hz, 1H), 7.64 (m, 1H), 7.50 (d, J=7.24 Hz, 1H), 6.91-7.10 (m, 6H), 4.82 (br, s, 1H), 1.65-1.85 (m, 3H), 0.94 (dd, J=4.17 Hz, 6.14 Hz, 6H).

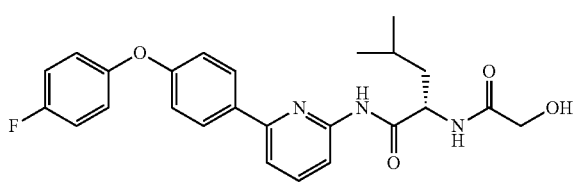 [SMILES: CC(C)C[C@H](NC(=O)CO)C(=O)Nc1cccc(-c2ccc(Oc3ccc(F)cc3)cc2)n1]

Compound 90: In similar fashion, compound 6 (as the HCl salt) (300 mg, 0.70 mmol) was treated with glycolic acid (53.2 mg, 0.7 mmol) in the presence of EDC (160 mg, 0.84 mmol), HOBt (113.4 mg, 0.84 mmol), DIEA (0.13 mL, 0.7 mmol) in dry DCM. The reaction mixture was stirred overnight at room temperature. After the reaction was complete, it was quenched with saturated NH$_4$Cl. The aqueous layer was extracted with EtOAc and CHCl$_3$. The organic phase was dried over anhydrous Na$_2$CO$_3$ and concentrated. The oily residue was purified by preparative TLC to give (S)—N-(6-(4-(4-fluorophenoxy)phenyl)pyridin-2-yl)-2-(2-hydroxyacetamido)-4-methylpentanamide (201 mg, 64%). $^1$H NMR (400 MHz, CD$_3$OD): 8.07 (1H, d, J=9.0 Hz), 8.02-8.07 (2H, m), 7.82 (1H, t, J=8.1 Hz), 7.60 (1H, d, J=7.7 Hz), 7.03-7.19 (6H, m), 4.72-4.73 (1H, m), 4.07 (12H, s), 1.72-1.80 (3H, m), 0.97-1.03 (6H, m); LC/MS: m/z=452.1 [M+H]$^+$.

Example 4

Synthesis of (S)—N-(6-(4-(4-fluorophenoxy)phenyl)pyridin-2-yl)-2-(3-isopropylureido)-4-methylpentanamide Scheme 4

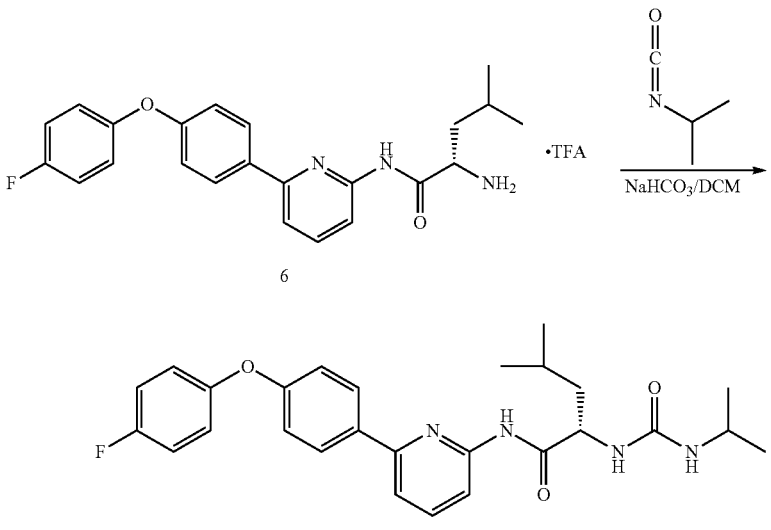

Compound 11: Compound 6 (100.0 mg, 0.2 mmol) in a mixture of DCM/saturated NaHCO₃ (1:1, 10 mL) was treated with isopropyl isocyanate (0.05 mL, 0.47 mmol) and stirred for 2 h at room temperature. After the reaction was complete, the mixture was diluted with DCM and dried over anhydrous Na₂CO₃. The solvent was evaporated and the residue was purified by preparative TLC (EtOAc:hexane=1:1) to give (S)—N-(6-(4-(4-fluorophenoxy)phenyl)pyridin-2-yl)-2-(3-isopropylureido)-4-methylpentanamide as a white solid (4.8 mg, 21%). LC/MS: m/z=479 [M+H]$^+$; $^1$H NMR (400 MHz, CD₃OD): 8.05 (d, J=8.99 Hz, 3H), 7.81 (t, J=8.33 Hz, 1H), 7.59 (d, J=7.67 Hz, 1H), 7.01-7.19 (m, 6H), 4.41-4.48 (m, 1H), 3.79-3.85 (m, 1H), 1.56-1.82 (m, 3H), 1.15 (dd, J=1.54 Hz, 6.58 Hz, 6H), 1.00 (dd, J=2.41 Hz, 6.58 Hz, 6H).

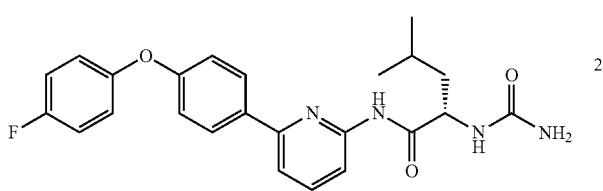

Compound 12: In a similar fashion, compound 6 (50.0 mg, 0.1 mmol) was treated with potassium cyanate (31.6 mg, 0.39 mmol) in water and stirred for 3 days at room temperature. After the reaction was complete, the reaction mixture was extracted with EtOAc. The organic phase was dried with anhydrous Na₂CO₃ and the solvent was evaporated. The residue was purified by preparative TLC (1:9 MeOH:DCM) to give (S)—N-(6-(4-(4-fluorophenoxy)phenyl)pyridin-2-yl)-4-methyl-2-ureidopentanamide as a white solid (17 mg, 33%). LC/MS: m/z=437 [M+H]$^+$; $^1$H NMR (400 MHz, CD₃OD): 8.07 (d, J=8.99 Hz, 3H), 7.81 (t, J=8.11 Hz, 1H), 7.59 (d, J=7.89 Hz, 1H), 7.06-7.19 (m, 3H), 7.05 (d, J=8.77 Hz, 2H), 4.41-4.48 (m, 1H), 1.56-1.87 (m, 3H), 1.01 (dd, J=2.86 Hz, 6.58 Hz, 6H).

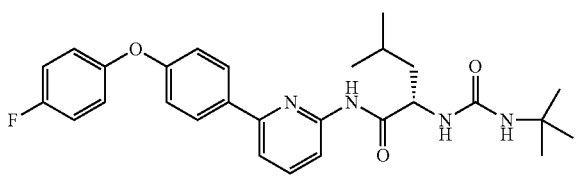 [SMILES: CC(C)C[C@H](NC(=O)NC(C)(C)C)C(=O)Nc1cccc(-c2ccc(Oc3ccc(F)cc3)cc2)n1]

Compound 13: In a similar fashion, compound 6 (439.0 mg, 0.87 mmol) in a mixture of DCM/saturated NaHCO₃ (1:1, 30 mL) was treated with t-butyl isocyanate (86 mg, 0.87 mmol) and stirred for 1 h at room temperature. After the reaction was complete, the mixture was diluted with DCM and dried over anhydrous Na₂CO₃. The solvent was evaporated and the residue was then purified by column chromatography (silica gel, 50% EtOAc in hexane) to give (S)-2-(3-(tert-butyl)ureido)-N-(6-(4-(4-fluorophenoxy)phenyl)pyridin-2-yl)-4-methylpentanamide as a white solid (268 mg, 62%). LC/MS: m/z=493 [M+H]$^+$; $^1$H NMR (400 MHz, CD₃OD): 8.78 (br, s, 1H), 8.10 (d, J=8.11 Hz, 1H), 7.92 (d, J=8.99 Hz, 2H), 7.71 (t, J=7.89 Hz, 1H), 7.41 (d, J=7.67 Hz, 1H), 6.99-7.10 (m, 6H), 4.75 (br, s, 1H), 4.44 (br, s, 2H), 1.71-1.82 (m, 2H), 1.52-1.60 (m, 1H), 1.32 (s, 9H), 0.97 (d, J=6.14 Hz, 6H).

Example 5

Synthesis of (S)—N-(4-chloro-6-(4-(4-fluorophenoxy)phenyl)pyridin-2-yl)-N-(2,3-dihydroxypropyl)methanesulfonamide Scheme 5

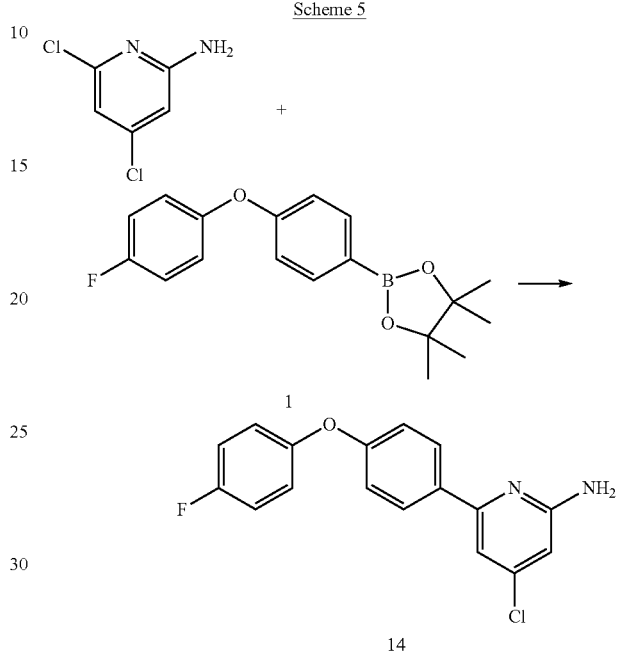

Compound 14: To a solution of the 4,6-dichloropyridin-2-amine (1.636 g, 10.04 mmol, Small Molecules, Inc.) in dioxane (100 mL) was added 2-(4-(4-fluorophenoxy)phenyl)-4,4,5,5-tetramethyl-1,3,2-dioxaborolane (compound 1, 3.157 g, 10.05 mmol), 2M aqueous Na₂CO₃ solution (10.0 mL, 20.0 mmol) and PdCl₂(dppf) (0.413 g, 0.51 mmol). The vessel was heated at reflux under nitrogen overnight. After cooling, the reaction was partitioned between 100 mL EtOAc and 50 mL water. The organics were isolated and the aqueous extracted once more with 25 mL EtOAc. The combined organic layers were washed once with 25 mL brine, dried over MgSO₄, filtered and concentrated in vacuo. The residue was chromatographed over silica gel eluting with 10-40% EtOAc in hexanes. The product fractions were isolated and evaporated in vacuo to yield 4-chloro-6-(4-(4-fluorophenoxy)phenyl)pyridin-2-amine (compound 14) as a thick yellow oil (2.215 g, 7.04 mmol, 70% yield, LC/MS: m/z=315.1 [M+H]$^+$).

Scheme 6

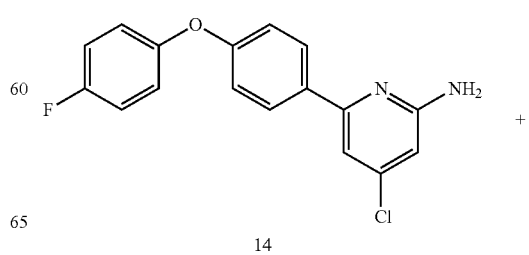

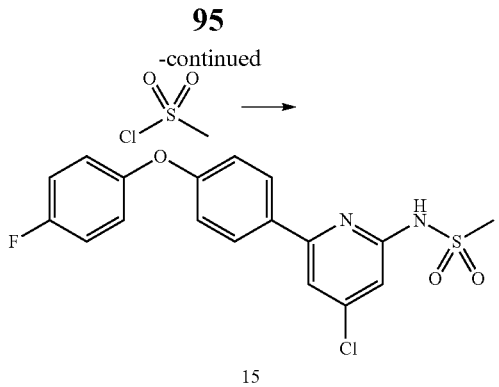

Compound 15: To a solution of compound 14 (0.496 g, 1.58 mmol) in DCM (5 mL) was added iPr₂NEt (0.42 mL, 2.41 mmol) and methanesulfonyl chloride (0.14 mL, 1.80 mmol, Aldrich). After 3 days additional methanesulfonyl chloride (0.14 mL, 1.80 mmol) was added. After one additional day more iPr₂NEt (0.42 mL, 2.41 mmol) and methanesulfonyl chloride (0.10 mL, 1.29 mmol) were successively added. After 2 days the reaction was quenched with 5 mL 1N aqueous NaOH. Acetonitrile (10 mL) was added to the reaction mixture and then heated at 50° C. for 3 days. The reaction was cooled and partitioned between 50 mL EtOAc and 25 mL water. The organic layer was washed once with 25 mL brine, dried over Na₂SO₄, filtered and evaporated in vacuo. The residue was chromatographed over silica gel eluting with 10-40% EtOAc in hexanes. The product fractions were isolated and evaporated in vacuo. The residue was triturated with 5 mL 10% EtOAc/hexanes, filtered, and rinsed once with 2 mL 10% EtOAc/Hexanes. The solid was dried under vacuum at 50° C. to yield N-(4-chloro-6-(4-(4-fluorophenoxy)phenyl)pyridin-2-yl)methanesulfonamide (compound 15) as a tan powder (0.345 g, 0.878 mmol, 56% yield, LC/MS: m/z=393.2 [M+H]⁺, ¹H NMR (400 MHz, DMSO-d₆): 10.88 (s, 1H), 8.11 (d, J=9.2 Hz, 2H), 7.72 (s, 1H), 7.32-7.24 (m, 2H), 7.20-7.13 (m, 2H), 7.08 (d, J=8.8 Hz, 2H), 6.89 (s, 1H), 3.42 (s, 3H).

Scheme 7

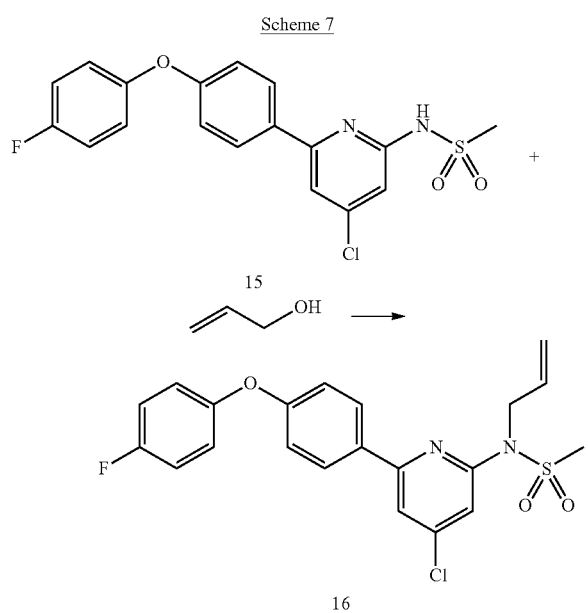

Compound 16: To a solution of triphenyl phosphine (0.215 g, 0.82 mmol, Aldrich) in THF (5 mL) was added a 40% DEAD solution in toluene (0.37 mL, 0.81 mmol, Aldrich). This reaction mixture was stirred for 3 minutes then added to a solution of compound 15 (0.290 g, 0.74 mmol) in THF (5 mL). The reaction mixture was stirred for another 2 minutes then allyl alcohol (0.07 mL, 1.0 mmol, Aldrich) was added. After 3 h to an additional amount of triphenyl phosphine (0.215 g, 0.82 mmol) in THF (5 mL) was added a 40% DEAD solution in toluene (0.37 mL, 0.81 mmol). This reaction mixture was stirred for 2 minutes then added to the sulfonamide reaction mixture. After 1 minute more allyl alcohol (0.07 mL, 1.0 mmol) was added. The reaction mixture was stirred for 3 days then evaporated in vacuo. The residue was chromatographed over silica gel eluting with 0-30% EtOAc in hexanes. The product fractions were isolated and evaporated in vacuo to give N-allyl-N-(4-chloro-6-(4-(4-fluorophenoxy)phenyl)pyridin-2-yl)methanesulfonamide (compound 16) as a colorless oil (0.311 g, 0.72 mmol, 97% yield, LC/MS: m/z=433.0 [M+H]⁺).

Scheme 8

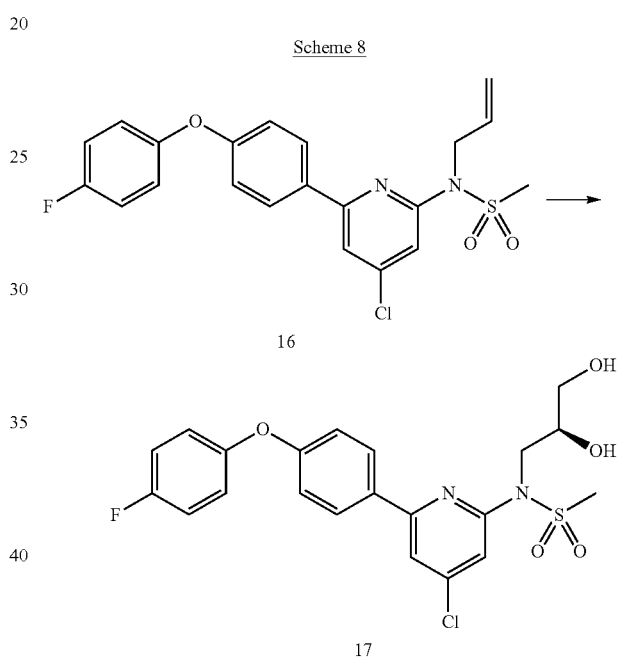

Compound 17: To a milky suspension of compound 16 (0.311 g, 0.72 mmol) in iPrOH (10 mL) and water (10 mL) was added AD-Mix α (0.978 g, Aldrich). The reaction mixture was stirred overnight then additional water (10 mL) and AD-Mix α (0.981 g) were added. After stirring overnight more iPrOH (10 mL), water (10 mL), and AD-Mix α (0.978 g) were added. After stirring overnight the reaction was partitioned between 200 mL EtOAc and 50 mL water. The organic layer was washed with 50 mL brine, dried over Na₂SO₄, filtered and evaporated in vacuo. The residue was chromatographed over silica gel eluting with 40-80% EtOAc in hexanes. The product fractions were isolated and evaporated in vacuo. The solid material was triturated with hexanes, filtered and dried under vacuum at 50° C. to give (S)—N-(4-chloro-6-(4-(4-fluorophenoxy)phenyl)pyridin-2-yl)-N-(2,3-dihydroxypropyl)methanesulfonamide (compound 17) as a white powder (0.090 g, 0.19 mmol, 26% yield, LC/MS: m/z=467.0 [M+H]⁺, ¹H NMR (400 MHz, DMSO-d₆): 8.13 (d, J=8.8 Hz, 2H), 7.89 (d, J=1.2 Hz, 1H), 7.46 (d, J=1.6 Hz, 1H), 7.31-7.25 (m, 2H), 7.20-7.15 (m, 2H), 7.08 (d, J=8.8 Hz, 2H), 5.00 (d, J=5.2 Hz, 1H), 4.68 (t, J=6.0 Hz, 1H), 4.10 (dd, J=14.8 Hz and 3.6 Hz, 1H), 3.86 (dd, J=14.8 Hz and 8.4 Hz, 1H), 3.67-3.58 (m, 1H), 3.41 (s, 3H), 3.34 (t, J=5.6 Hz, 2H).

Example 6

Synthesis of N-(4-chloro-6-(4-(4-fluorophenoxy)phenyl)pyridin-2-yl)sulfamide

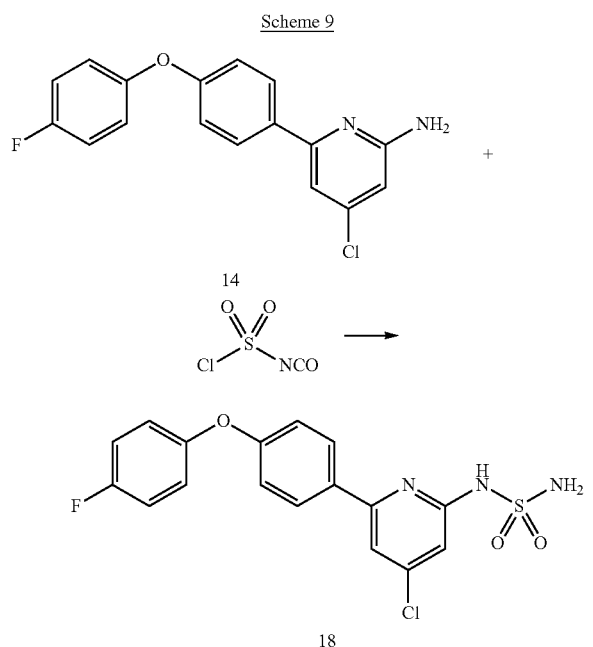

Compound 18: DCM (5 mL) was cooled with an ice bath in a sealed tube then charged with chlorosulfonyl isocyanate (0.25 mL, 2.87 mmol, Aldrich). A solution of t-butanol (0.39 mL, 4.08 mmol, Aldrich) was added to the reaction dropwise over ~3.5 minutes. The ice bath was removed and the reaction stirred for 10 minutes. This mixture was added to an ice-cooled solution of 4-chloro-6-(4-(4-fluorophenoxy)phenyl)pyridin-2-amine (compound 14, 0.630 g, 2.00 mmol) in DCM (5 mL) containing iPr₂NEt (0.52 mL, 2.99 mmol). After 10 minutes the ice bath was removed and the reaction stirred at ambient temperature for 3 days. The reaction was evaporated in vacuo and the residue was chromatographed over silica gel eluting with 10-50% EtOAc in hexanes. The product fractions were isolated and evaporated in vacuo. The solid residue was triturated with 5 mL 10% EtOAc/hexanes, filtered and washed once with 1 mL 10% EtOAc/hexanes. The solid was dried under vacuum at 50° C. to give N-(4-chloro-6-(4-(4-fluorophenoxy)phenyl)pyridin-2-yl)sulfamide (compound 18) as an off-white powder. (0.125 g, 0.32 mmol, 16% yield, LC/MS: m/z=394.0 [M+H]⁺, ¹H NMR (400 MHz, DMSO-d₆): 10.61 (s, 1H), 8.14 (d, J=8.8 Hz, 2H), 7.64 (d, J=1.6 Hz, 1H), 7.33-7.24 (m, 4H), 7.19-7.13 (m, 2H), 7.05 (d, J=8.8 Hz, 2H), 7.02 (d, J=1.6 Hz, 1H).

Example 7

Synthesis of (S)—N-(4-(1,2-dihydroxyethyl)-6-(4-(4-fluorophenoxy)phenyl)pyridin-2-yl)methanesulfonamide

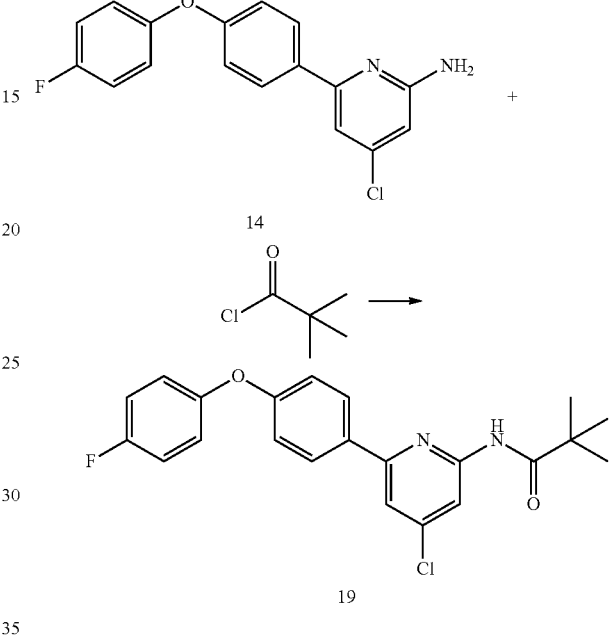

Compound 19: To a solution of compound 14 (10.02 mmol) in DCM was added iPr₂NEt (2.60 mL, 14.93 mmol) and pivaloyl chloride (1.35 mL, 10.96 mmol, Aldrich). The reaction was stirred overnight then washed successively with 50 mL saturated NaHCO₃ and 50 mL brine. The organic layer was dried over MgSO₄, filtered and evaporated in vacuo. The residue was chromatographed over silica gel eluting with 0-20% EtOAc in hexanes. The product fractions were isolated and evaporated in vacuo to give N-(4-chloro-6-(4-(4-fluorophenoxy)phenyl)pyridin-2-yl)pivalamide as a thick near-colorless oil (2.89 g, 7.25 mmol, 72% yield, LC/MS: m/z=399.0 [M+H]⁺).

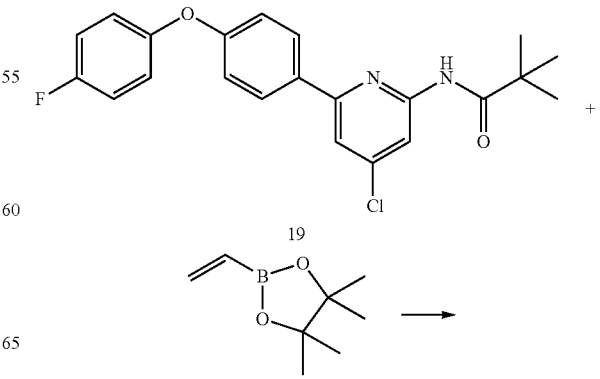

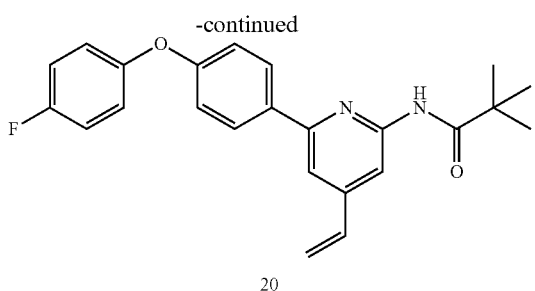

20

Compound 20: To compound 19 (2.89 g, 7.25 mmol) in a screw-cap pressure vessel was added a 1M TBAF solution (22 mL, 22 mmol, Aldrich), 4,4,5,5-tetramethyl-2-vinyl-1,3,2-dioxaborolane (1.85 mL, 10.91 mmol, Aldrich) and PdCl$_2$(dppf) (0.475 g, 0.58 mmol). The vessel was flushed with argon, capped and heated at 80° C. for 3 days. After cooling, the reaction was partitioned between 200 mL EtOAc and 100 mL water. The organic layer was washed once with 50 mL brine, dried over MgSO$_4$, filtered and evaporated in vacuo. The residue was chromatographed over silica gel eluting with 0-20% EtOAc in hexanes. The product fractions were isolated and evaporated in vacuo to give N-(6-(4-(4-fluorophenoxy)phenyl)-4-vinylpyridin-2-yl) pivalamide as a thick yellow oil (1.541 g, 3.95 mmol, 54% yield, LC/MS: m/z=391.2 [M+H]$^+$).

Scheme 12

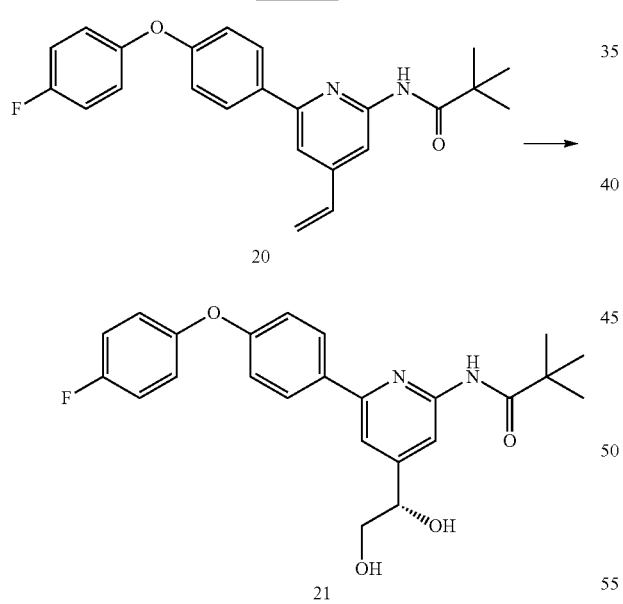

Compound 21: To a solution of compound 20 (1.451 g, 3.95 mmol) in iPrOH (15 mL) was added water (15 mL) and AD-Mix α (5.372 g). The reaction was stirred overnight then partitioned between 100 mL EtOAc and 50 mL water and the mixture filtered over a pad of celite. The organic layer was isolated and washed once more with 50 mL brine, dried over Na$_2$SO$_4$, filtered and evaporated in vacuo. The residue was chromatographed over silica gel eluting with 0-100% Acetone in hexanes. The product fractions were isolated and evaporated in vacuo to give (S)—N-(4-(1,2-dihydroxyethyl)-6-(4-(4-fluorophenoxy)phenyl)pyridin-2-yl)pivalamide as a cream-colored solid (1.184 g, 2.79 mmol, 71% yield, LC/MS: m/z=425.2 [M+H]$^+$).

Scheme 13

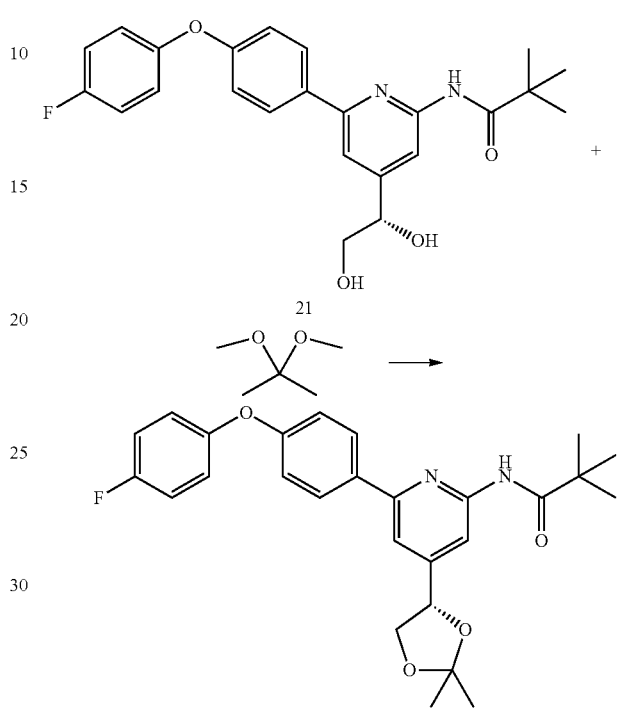

Compound 22: To compound 21 (1.179 g, 2.78 mmol) was added 2,2-dimethoxypropane (10 mL, 81.33 mmol, Aldrich) and TsOH.H$_2$O (0.055 g, 0.29 mmol, Aldrich). The reaction was stirred at ambient temperature for 4 days then 60° C. for 1 day. The reaction was evaporated in vacuo and the residue was chromatographed over silica gel eluting with 5-30% EtOAc in hexanes. The product fractions were isolated and evaporated in vacuo to give (S)—N-(4-(2,2-dimethyl-1,3-dioxolan-4-yl)-6-(4-(4-fluorophenoxy)phenyl)pyridin-2-yl)pivalamide as a thick colorless oil (0.959 g, 2.06 mmol, 74% yield, LC/MS: m/z=465.2 [M+H]$^+$).

Scheme 14

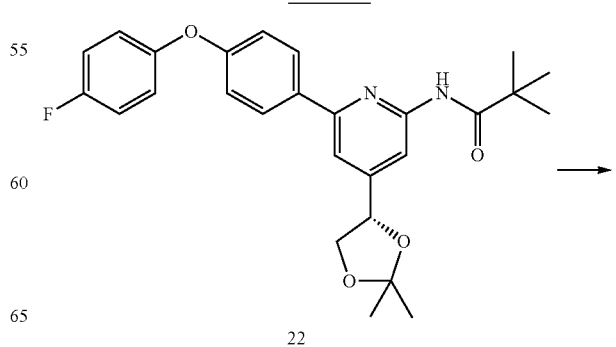

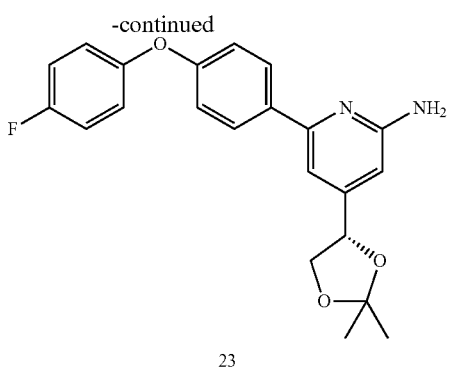

23

Compound 23: To compound 22 (0.959 g, 2.06 mmol) was added MeOH (12.5 mL), water (12.5 mL), and 85% KOH pellets (0.148 g, 2.24 mmol). The reaction was heated at 60° C. overnight, diluted with additional MeOH (50 mL) and the heating was increased to a reflux. After 3 days additional 85% KOH pellets (0.084 g, 1.27 mmol) were added and the refluxing continued for 3 more days. The reaction was then cooled and evaporated in vacuo until it appeared that most of the MeOH had been removed. The reaction mixture was partitioned between 50 mL EtOAc and 25 mL brine. The organic layer was washed again with 25 mL brine, dried with MgSO$_4$, filtered and evaporated in vacuo. The residue was chromatographed over silica gel eluting with 10-70% EtOAc in hexanes. The product fractions were isolated and evaporated in vacuo to give (S)-4-(2,2-dimethyl-1,3-dioxolan-4-yl)-6-(4-(4-fluorophenoxy)phenyl)pyridin-2-amine as a thick near-colorless oil (0.695 g, 1.83 mmol, 89% yield, LC/MS: m/z=381.2 [M+H]$^+$).

Scheme 15

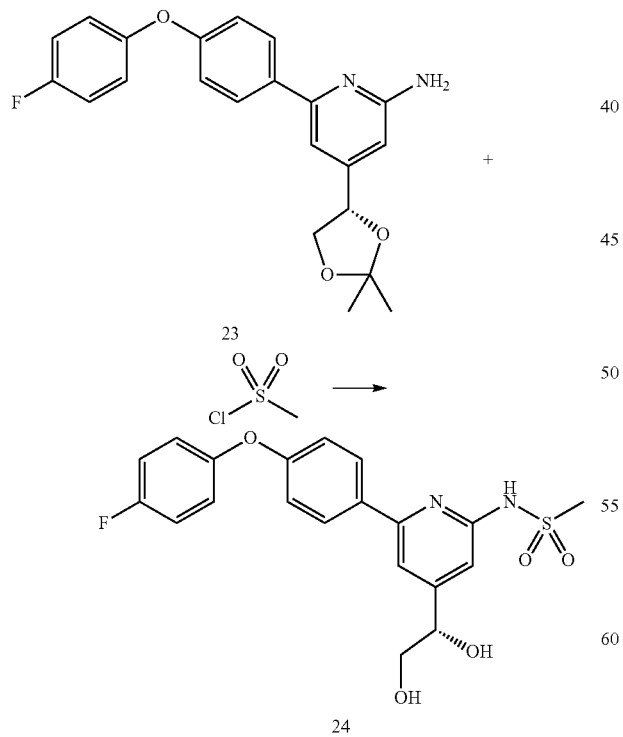

Compound 24: To a solution of compound 23 (0.097 g, 0.25 mmol) in 1:1 DCM/pyridine (2.5 mL) was added methanesulfonyl chloride (0.049 mL, 0.63 mmol). After 4 days the reaction was partitioned between 10 mL EtOAc and 10 mL saturated NaHCO$_3$. The organic layer was washed once with 10 mL brine. The organic layer was evaporated in vacuo and MeOH (5 mL) and 4N HCl in dioxane (2.0 mL) were added. After 1 hour the reaction was evaporated in vacuo. The residue was chromatographed using reverse-phase HPLC eluting with 20-90% acetonitrile in water, each containing 0.1% TFA. The product fractions were pooled and treated with Amberlite IRA-400(OH) resin to remove the TFA. The solution was frozen and lyophilized to give (S)—N-(4-(1,2-dihydroxyethyl)-6-(4-(4-fluorophenoxy)phenyl)pyridin-2-yl)methanesulfonamide (0.037 g, 0.088 mmol, 35% yield, LC/MS: m/z=419.2 [M+H]$^+$, $^1$H NMR (400 MHz, DMSO-d$_6$): 10.53 (s, 1H), 7.97 (d, J=8.8 Hz, 2H), 7.43 (s, 1H), 7.23-7.16 (m, 2H), 7.11-7.05 (m, 2H), 7.02 (d, J=8.8 Hz, 2H), 6.80 (s, 1H), 4.50 (t, J=5.6 Hz, 1H), 3.42 (d, J=6.0, 2H), 3.34 (s, 3H). Using the chemistry described above, the following compounds were prepared:

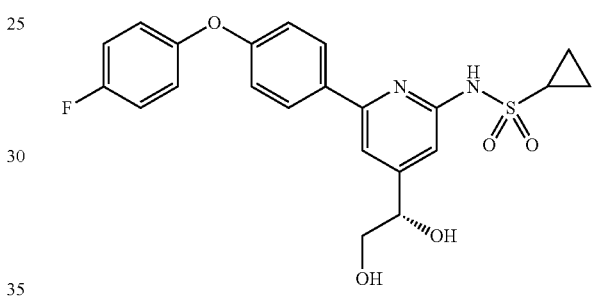

Compound 25: (S)—N-(4-(1,2-dihydroxyethyl)-6-(4-(4-fluorophenoxy)phenyl)pyridin-2-yl)cyclopropanesulfonamide: LC/MS: m/z=445.2 [M+H]$^+$, $^1$H NMR (400 MHz, DMSO-d$_6$): 10.48 (s, 1H), 7.99 (d, J=8.8 Hz, 2H), 7.43 (s, 1H), 7.24-7.16 (m, 2H), 7.11-7.05 (m, 2H), 7.01 (d, J=8.8 Hz, 2H), 6.84 (s, 1H), 4.50 (t, J=5.6 Hz, 1H), 3.43 (d, J=6.0 Hz, 2H), 3.16-3.08 (m, 1H), 1.05-0.99 (m, 2H), 0.99-0.93 (m, 2H).

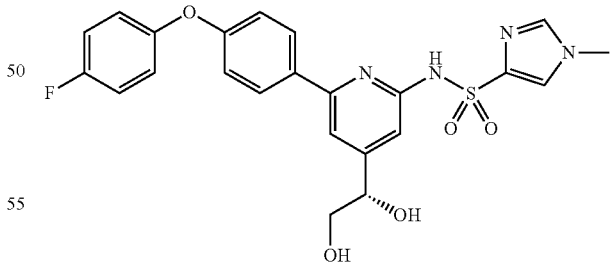

Compound 26: (S)—N-(4-(1,2-dihydroxyethyl)-6-(4-(4-fluorophenoxy)phenyl)pyridin-2-yl)-1-methyl-1H-imidazole-4-sulfonamide: LC/MS: m/z=485.2 [M+H]$^+$; $^1$H NMR (400 MHz, DMSO-d$_6$): 10.82 (s, 1H), 7.92 (s, 1H), 7.87 (d, J=8.8 Hz, 2H), 7.63 (d, J=1.2 Hz, 1H), 7.35 (s, 1H), 7.24-7.16 (m, 2H), 7.10-7.04 (m, 2H), 7.00 (d, J=8.4 Hz, 2H), 6.89 (s, 1H), 4.45 (t, J=6.0 Hz, 1H), 3.57 (s, 3H), 3.38 (d, J=6.0 Hz, 2H).

Example 8

Synthesis of N-(6-(4-(4-fluorophenoxy)phenyl)pyridin-2-yl)methanesulfonamide

Scheme 16

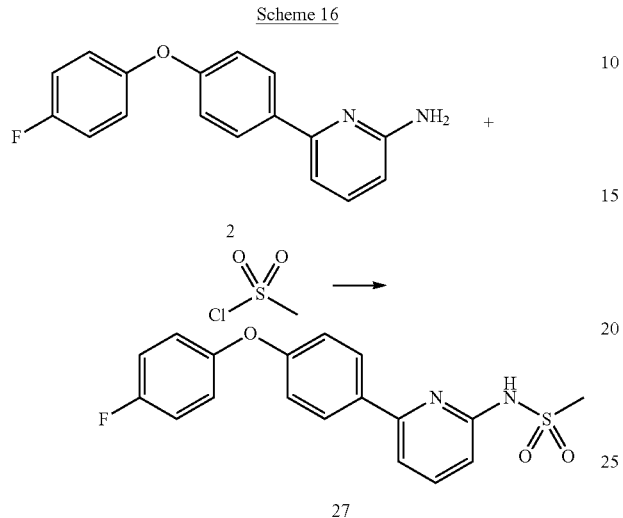

Compound 27: To a solution of compound 2 (0.071 g, 0.25 mmol) in 1:1 DCM/pyridine (2.5 mL) was added methanesulfonyl chloride (0.049 mL, 0.63 mmol). After 4 days the reaction was partitioned between 10 mL EtOAc and 10 mL saturated NaHCO$_3$. The organic layer was washed once with 10 mL brine, evaporated in vacuo, and MeOH (5 mL) and 4N HCl in dioxane (2.0 mL) were added. After 1 h the reaction mixture was evaporated in vacuo. The residue was chromatographed using reverse-phase HPLC eluting with 20-90% acetonitrile in water, each containing 0.1% TFA. The product fractions were pooled and treated with Amberlite IRA-400(OH) resin to remove the TFA. The solution was frozen and lyophilized to yield the product N-(6-(4-(4-fluorophenoxy)phenyl)pyridin-2-yl)methanesulfonamide (0.039 g, 0.109 mmol, 43% yield, LC/MS: m/z=359.2 [M+H]$^+$, $^1$H NMR (400 MHz, DMSO-d$_6$): 10.71 (s, 1H), 8.13 (d, J=8.8 Hz, 2H), 7.86 (t, J=8.0 Hz, 1H), 7.64 (d, J=7.6 Hz, 1H), 7.37-7.29 (m, 2H), 7.25-7.19 (m, 2H), 7.15 (d, J=8.8 Hz, 2H), 6.91 (d, J=8.4 Hz, 1H), 3.48 (s, 3H). Using the chemistry described above, the following compounds were prepared:

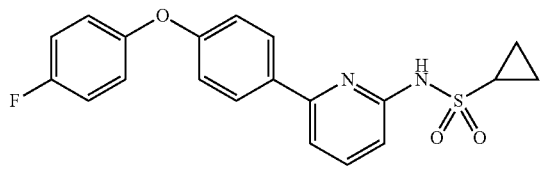 [SMILES: O=S(=O)(Nc1cccc(-c2ccc(Oc3ccc(F)cc3)cc2)n1)C1CC1]

Compound 28: N-(6-(4-(4-fluorophenoxy)phenyl)pyridin-2-yl)cyclopropane sulfonamide: LC/MS: m/z=385.2 [M+H]$^+$, $^1$H NMR (400 MHz, DMSO-d$_6$): 10.60 (s, 1H), 8.08 (d, J=8.8 Hz, 2H), 7.79 (t, J=7.6 Hz, 1H), 7.57 (d, J=7.6 Hz, 1H), 7.31-7.24 (m, 2H), 7.18-7.12 (m, 2H), 7.08 (d, J=8.8 Hz, 2H), 6.89 (d, J=8.0 Hz, 1H), 3.22-3.14 (m, 1H), 1.13-1.07 (m, 2H), 1.07-1.00 (m, 2H).

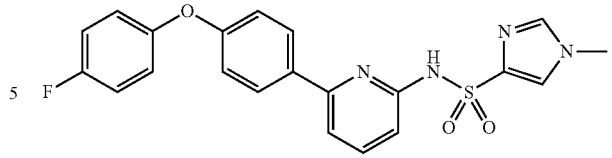

Compound 29: N-(6-(4-(4-fluorophenoxy)phenyl)pyridin-2-yl)-1-methyl-1H-imidazole-4-sulfonamide: LC/MS: m/z=425.2 [M+H]$^+$, $^1$H NMR (400 MHz, DMSO-d$_6$): 11.01 (s, 1H), 8.12-8.01 (m, 3H), 7.83-7.75 (m, 2H), 7.56 (d, J=7.2 Hz, 1H), 7.38-7.29 (m, 2H), 7.24-7.18 (m, 2H), 7.13 (d, J=8.8 Hz, 2H), 7.03 (d, J=8.0 Hz, 1H), 3.71 (s, 3H).

Example 9

Synthesis of (S)-2-acetamido-N-(6-(4-(4-fluorophenoxy)phenyl)pyridin-2-yl)-3-(1H-imidazol-4-yl)propanamide Scheme 17

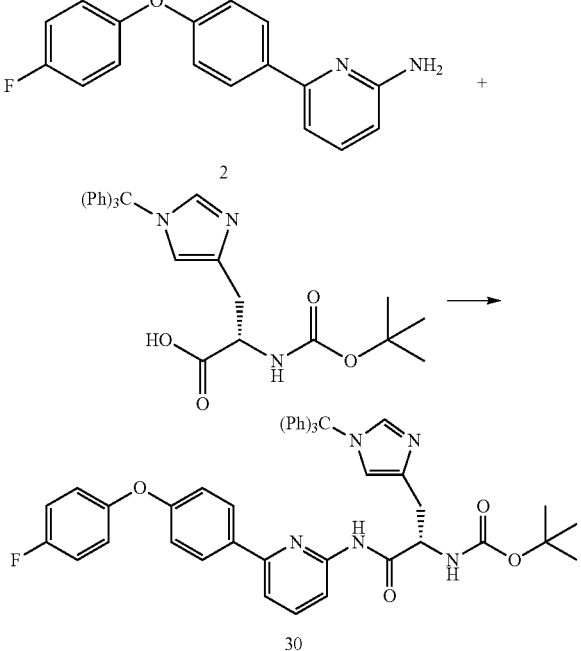

Compound 30: To a solution of (S)-2-((tert-butoxycarbonyl)amino)-3-(1-trityl-1H-imidazol-4-yl)propanoic acid (1.990 g, 4.00 mmol, Aldrich) in DCM (20 mL) was added HOBT (0.680 g, 5.03 mmol, Aldrich), EDC.HCl (0.961 g, 5.01 mmol, Aldrich) and iPr$_2$NEt (0.87 mL, 4.99 mmol). After 5 minutes a solution of compound 2 (1.118 g, 3.99 mmol) in DCM (25 mL) was added. After 4 days more iPr$_2$NEt (1.05 mL, 6.03 mmol) and HATU (1.667 g, 4.38 mmol, GenScript Corporation) were added. After 3 days the reaction mixture was washed successively with 25 mL water and 25 mL brine. The organic layer was dried over MgSO$_4$, filtered and evaporated in vacuo. The residue was chromatographed over silica gel eluting with 10-90% EtOAc in hexanes. The product fractions were isolated and evaporated in vacuo to give (S)-tert-butyl (1-((6-(4-(4-fluorophenoxy)

phenyl)pyridin-2-yl)amino)-1-oxo-3-(1-trityl-1H-imidazol-4-yl)propan-2-yl)carbamate as a cream-colored foam (1.809 g, 2.38 mmol, 60% yield, LC/MS: m/z=760.2 [M+H]⁺).

Scheme 18

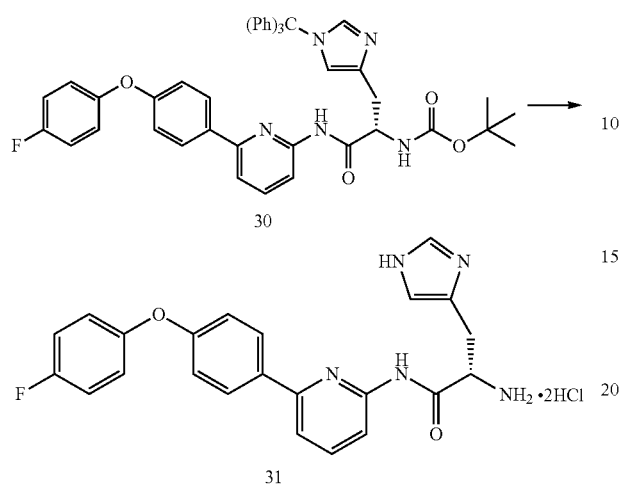

Compound 31: To compound 30 (1.809 g, 2.38 mmol) in dioxane (10 mL) was added 4M HCl in dioxane (2.5 mL, 10.0 mmol). After stirring overnight additional 4M HCl in dioxane (2.5 mL, 10.0 mmol) was added and the reaction was transferred to a sealed tube and heated at 60° C. for 3 days. After cooling, the reaction was diluted with 100 mL Et₂O and the solids filtered off and rinsed several times with Et₂O. The material was dried under a stream of nitrogen then under vacuum at 50° C. to give (S)-2-amino-N-(6-(4-(4-fluorophenoxy)phenyl)pyridin-2-yl)-3-(1H-imidazol-4-yl) propanamide as the bis-hydrochloride salt as a cream-colored powder (1.145 g, 2.34 mmol, 98% yield, LC/MS: m/z=418.2 [M+H]⁺, ¹H NMR (400 MHz, DMSO-d₆): 14.62 (br s, 1H), 14.42 (br s, 1H), 11.13 (s, 1H), 9.09 (s, 1H), 8.72 (br s, 3H), 8.09 (d, J=8.8 Hz, 2H), 7.98-7.90 (m, 2H), 7.73 (d, J=7.2 Hz, 1H), 7.54 (s, 1H), 7.31-7.26 (m, 2H), 7.18-7.14 (m, 2H), 7.10 (d, J=8.8 Hz, 2H), 4.59-4.50 (m, 1H), 3.47-3.40 (m, 1H), 3.36-3.28 (m, 1H).

Scheme 19

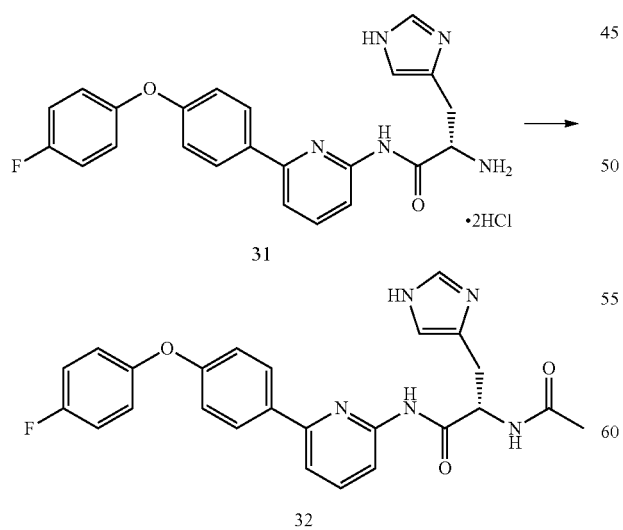

Compound 32: To a suspension of compound 31 (0.10 mmol) in DCM (1 mL) and acetonitrile (1 mL) with iPr₂NEt (0.058 mL, 0.33 mmol) was added acetyl chloride (0.009 mL, 0.13 mmol, Aldrich). After 2 hours more acetyl chloride (0.007 mL, 0.10 mmol) was added. After stirring overnight the reaction was quenched with MeOH and evaporated in vacuo. The residue was chromatographed using reverse-phase HPLC eluting with 20-90% acetonitrile in water, each containing 0.1% TFA. The product fractions were pooled and treated with Amberlite IRA-400(OH) resin to remove the TFA. The solution was frozen and lyophilized to give (S)-2-acetamido-N-(6-(4-(4-fluorophenoxy)phenyl)pyridin-2-yl)-3-(1H-imidazol-4-yl)propanamide (0.028 g, 0.061 mmol, 61% yield, LC/MS: m/z=460.2 [M+11]⁺, ¹H NMR (400 MHz, DMSO-d₆): 13.77 (br s, 1H), 10.44 (s, 1H), 8.60 (s, 1H), 8.29 (d, J=7.6 Hz, 1H), 8.02 (d, J=8.8 Hz, 2H), 7.90 (d, J=8.4 Hz, 1H), 7.80 (t, J=7.6 Hz, 1H), 7.59 (d, J=7.6 Hz, 1H), 7.25-7.16 (m, 3H), 7.12-7.06 (m, 2H), 7.02 (d, J=8.8 Hz, 2H), 4.84-4.76 (m, 1H), 3.11-3.04 (m, 1H), 2.98-2.88 (m, 1H), 1.81 (s, 3H).

Using the chemistry described above, the following compounds were prepared:

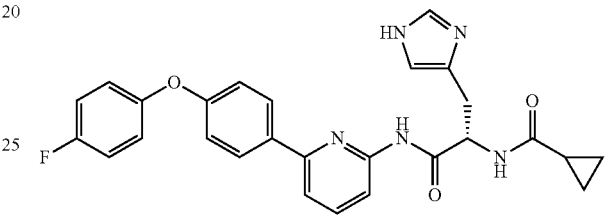

Compound 33: (S)—N-(1-((6-(4-(4-fluorophenoxy)phenyl)pyridin-2-yl)amino)-3-(1H-imidazol-4-yl)-1-oxopropan-2-yl)cyclopropanecarboxamide: LC/MS: m/z=486.2 [M+H]⁺, ¹H NMR (400 MHz, DMSO-d₆): 14.04 (br s, 1H), 10.46 (s, 1H), 8.91 (s, 1H), 8.56 (d, J=8.0 Hz, 1H), 8.01 (d, J=8.8 Hz, 2H), 7.91 (d, J=8.4 Hz, 1H), 7.81 (t, J=7.6 Hz, 1H), 7.60 (d, J=7.6 Hz, 1H), 7.33 (s, 1H), 7.25-7.17 (m, 2H), 7.12-7.06 (m, 2H), 7.02 (d, J=8.8 Hz, 2H), 4.91-4.82 (m, 1H), 3.16-3.09 (m, 1H), 3.01-2.93 (m, 1H), 1.66-1.58 (m, 1H), 0.67-0.55 (m, 4H).

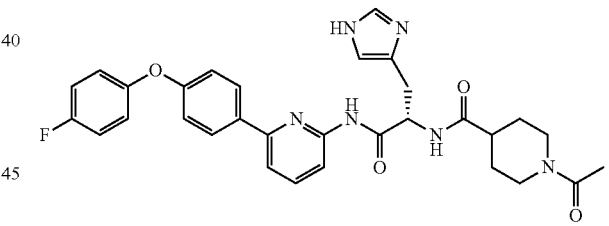

Compound 34: (S)-1-acetyl-N-(1-((6-(4-(4-fluorophenoxy)phenyl)pyridin-2-yl)amino)-3-(1H-imidazol-4-yl)-1-oxopropan-2-yl)piperidine-4-carboxamide: LC/MS: m/z=571.2 [M+H]⁺, ¹H NMR (400 MHz, DMSO-d₆): 14.02 (br s, 1H), 10.43 (d, J=4.4 Hz, 1H), 8.91 (s, 1H), 8.30-8.24 (m, 1H), 8.01 (d, J=8.4 Hz, 2H), 7.90 (d, J=8.0 Hz, 1H), 7.86-7.77 (m, 1H), 7.60 (d, J=7.6 Hz, 1H), 7.32 (s, 1H), 7.25-7.17 (m, 2H), 7.12-7.06 (m, 2H), 7.02 (d, J=8.8 Hz, 2H), 4.87-4.78 (m, 1H), 4.28-4.18 (m, 1H), 3.76-3.66 (m, 1H), 3.18-3.10 (m, 1H), 3.00-2.90 (m, 2H), 2.54-2.35 (m, 2H), 1.91 (s, 3H), 1.67-1.51 (m, 2H), 1.46-1.12 (m, 2H).

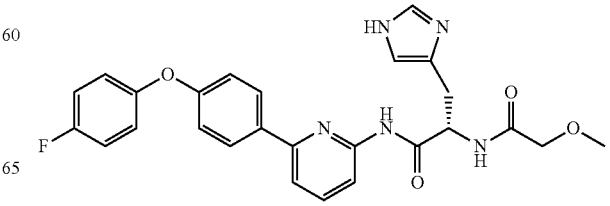

Compound 35: (S)—N-(6-(4-(4-fluorophenoxy)phenyl)pyridin-2-yl)-3-(1H-imidazol-4-yl)-2-(2-methoxyacetamido): LC/MS: m/z=490.2 [M+H]+, 1H NMR (400 MHz, DMSO-d6): 14.15 (br s, 1H), 10.51 (s, 1H), 8.92 (s, 1H), 8.12 (d, J=8.4 Hz, 1H), 8.02 (d, J=8.8 Hz, 2H), 7.90 (d, J=8.0 Hz, 1H), 7.84-7.78 (m, 1H), 7.61 (d, J=8.0 Hz, 1H), 7.33 (s, 1H), 7.26-7.17 (m, 2H), 7.13-7.05 (m, 2H), 7.02 (d, J=8.8 Hz, 2H), 4.92-4.83 (m, 1H), 3.80 (s, 2H), 3.23 (s, 3H), 3.22-3.15 (m, 1H), 3.13-3.05 (m, 1H).

Example 10

Synthesis of (S)—N-(6-(4-(4-fluorophenoxy)phenyl)pyridin-2-yl)-2-(2-hydroxy acetamido)-3-(1H-imidazol-4-yl)propanamide Scheme 20

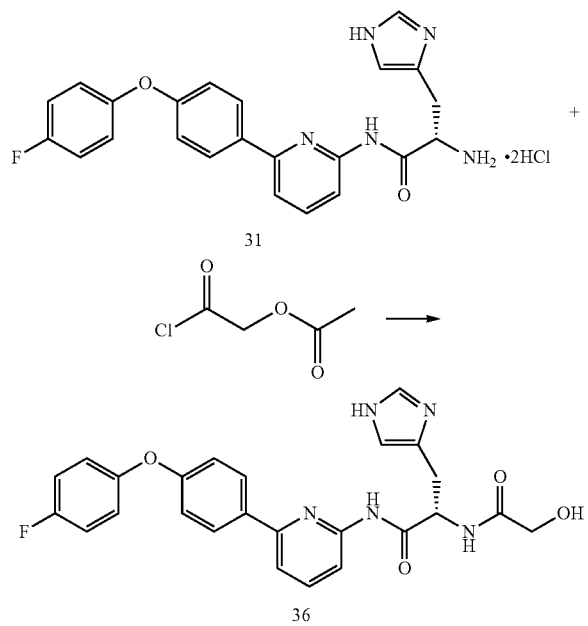

Compound 36: To a suspension of compound 31 (0.10 mmol) in DCM (1 mL) and acetonitrile (1 mL) with iPr2NEt (0.058 mL, 0.33 mmol) was added 2-chloro-2-oxoethyl acetate (0.011 mL, 0.12 mmol, Aldrich). After stirring overnight the reaction was quenched with MeOH and evaporated in vacuo. The residue was dissolved in 5:1 THF/water (2 mL) and LiOH.H2O (0.008 g, 0.19 mmol, Aldrich) was added. After 2 hours 1N NaOH (1.0 mL, 1.0 mmol) was added. After 1 hour the reaction was partitioned between DCM and water. The organic layer was separated and evaporated in vacuo. The residue was chromatographed using reverse-phase HPLC eluting with 20-90% acetonitrile in water, each containing 0.1% TFA. The product fractions were pooled and treated with Amberlite IRA-400(OH) resin to remove the TFA. The solution was frozen and lyophilized to give (S)—N-(6-(4-(4-fluorophenoxy)phenyl)pyridin-2-yl)-2-(2-hydroxyacetamido)-3-(1H-imidazol-4-yl)propanamide (0.007 g, 0.015 mmol, 15% yield, LC/MS: m/z=476.2 [M+H]+, 1H NMR (400 MHz, DMSO-d6): 14.10 (br s, 1H), 10.52 (s, 1H), 8.92 (d, J=1.2 Hz, 1H), 8.07 (d, J=8.4 Hz, 1H), 8.02 (d, J=8.8 Hz, 2H), 7.90 (d, J=8.0 Hz, 1H), 7.81 (t, J=8.0 Hz, 1H), 7.61 (d, J=7.6 Hz, 1H), 7.33 (s, 1H), 7.25-7.18 (m, 2H), 7.12-7.06 (m, 2H), 7.02 (d, J=8.8 Hz, 2H), 5.57 (br s, 1H), 4.91-4.83 (m, 1H), 3.80 (s, 2H), 3.24-3.15 (m, 1H), 3.14-3.06 (m, 1H). Using the chemistry described above the following compound was prepared substituting 1-chloro-2-methyl-1-oxopropan-2-yl acetate as the acid chloride component:

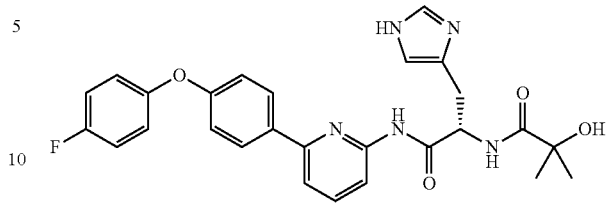

Compound 37: (S)—N-(6-(4-(4-fluorophenoxy)phenyl)pyridin-2-yl)-2-(2-hydroxy-2-methylpropanamido)-3-(1H-imidazol-4-yl)propanamide: LC/MS: m/z=504.2 [M+H]+, 1H NMR (400 MHz, DMSO-d6): 14.16 (br s, 1H), 10.46 (s, 1H), 8.92 (s, 1H), 8.05-7.99 (m, 3H), 7.91 (d, J=8.0 Hz, 1H), 7.82 (t, J=8.0 Hz, 1H), 7.61 (d, J=7.6 Hz, 1H), 7.31 (s, 1H), 7.25-7.18 (m, 2H), 7.12-7.06 (m, 2H), 7.03 (d, J=8.8 Hz, 2H), 5.53 (br s, 1H), 4.84-4.76 (m, 1H), 3.24-3.16 (m, 1H), 3.14-3.05 (m, 1H), 1.17 (s, 3H), 1.11 (s, 3H).

Example 11

Synthesis of (S)—N-(6-(4-(4-fluorophenoxy)phenyl)pyridin-2-yl)-3-(1H-imidazol-4-yl)-2-(methylsulfonamido)propanamide Scheme 21

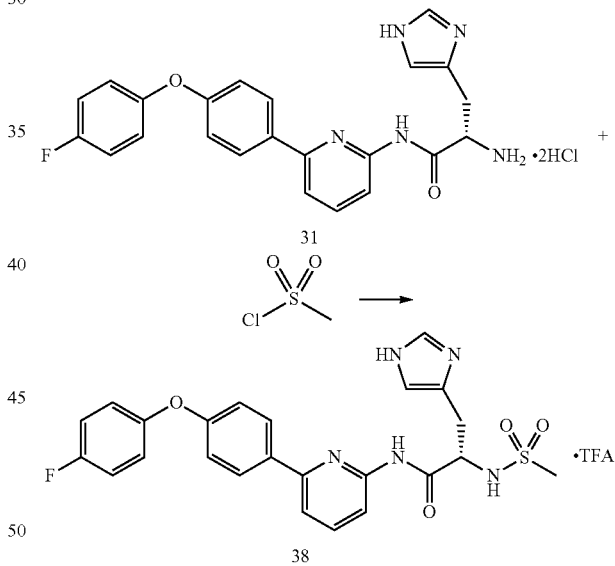

Compound 38: To a solution of compound 31 (0.098 g, 0.20 mmol) in 1:1 DCM/pyridine (2.5 mL) was added the methanesulfonyl chloride (0.016 mL, 0.21 mmol). After 2 hours additional methanesulfonyl chloride (0.007 mL, 0.09 mmol) was added. After 20 minutes the reaction was quenched with MeOH and evaporated in vacuo. The residue was chromatographed using reverse-phase HPLC eluting with 20-90% acetonitrile in water, each containing 0.1% TFA. The product fractions were pooled, frozen and lyophilized to give (S)—N-(6-(4-(4-fluorophenoxy)phenyl)pyridin-2-yl)-3-(1H-imidazol-4-yl)-2-(methylsulfonamido)propanamide as the trifluoroacetate salt as a light tan solid (0.011 g, 0.018 mmol, 9% yield, LC/MS: m/z=496.2 [M+H]+, 1H NMR (400 MHz, DMSO-d6): 14.08 (br s, 2H), 10.52 (s, 1H), 8.93 (d, J=1.2 Hz, 1H), 8.01 (d, J=8.8 Hz, 2H), 7.94 (d, J=8.0 Hz, 1H), 7.86-7.79 (m, 2H), 7.62 (d, J=7.6 Hz, 1H), 7.38 (s, 1H), 7.25-7.18 (m, 2H), 7.12-7.06 (m, 2H), 7.02 (d, J=8.8 Hz, 2H), 4.50-4.41 (m, 1H), 3.18-3.10 (m, 1H), 3.02-2.93 (m, 1H), 2.82 (s, 3H).

Example 12

Synthesis of give (S)-tert-butyl(1-amino-4-((6-(4-(4-fluorophenoxy)phenyl)pyridin-2-yl)amino)-1,4-dioxobutan-2-yl)carbamate and (S)-tert-butyl(4-amino-1-((6-(4-(4-fluorophenoxy)phenyl)pyridin-2-yl)amino)-1,4-dioxobutan-2-yl)carbamate Scheme 22

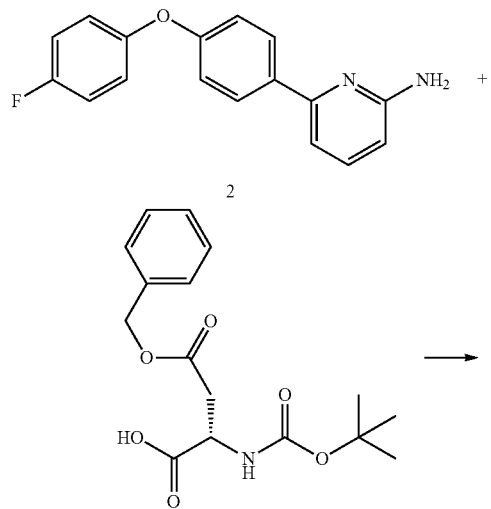

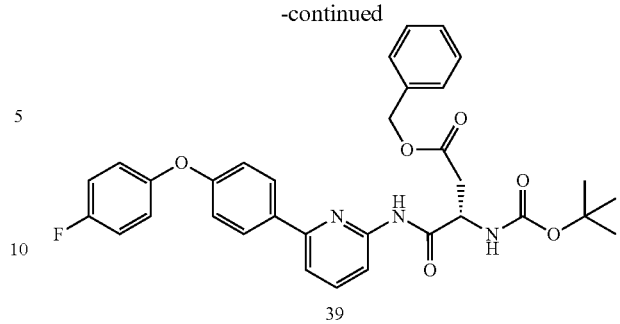

Compound 39: To a solution of (S)-4-(benzyloxy)-2-((tert-butoxycarbonyl)amino)-4-oxobutanoic acid (1.424 g, 4.40 mmol, Advanced ChemTech) in DMF (30 mL) was added iPr$_2$NEt (0.75 mL, 4.31 mmol) and HATU (1.680 g, 4.42 mmol). The reaction was stirred for 2 minutes then a solution of compound 2 (1.124 g, 4.01 mmol) in DMF (10 mL) with iPr$_2$NEt (0.75 mL, 4.31 mmol) was added. After stirring overnight the reaction was diluted with 400 mL water. The reaction mixture was extracted three times with 100 mL Et$_2$O. The combined organic layers were washed once with 50 mL brine, dried over MgSO$_4$, filtered and concentrated in vacuo. The residue was chromatographed over silica gel eluting with 0-40% EtOAc in hexanes. The product fractions were isolated and evaporated in vacuo to give (S)-benzyl 3-((tert-butoxycarbonyl)amino)-4-((6-(4-(4-fluorophenoxy)phenyl)pyridin-2-yl)amino)-4-oxobutanoate (1.413 g, 2.41 mmol, 60% yield, LC/MS: m/z=586.2 [M+H]$^+$).

Scheme 23

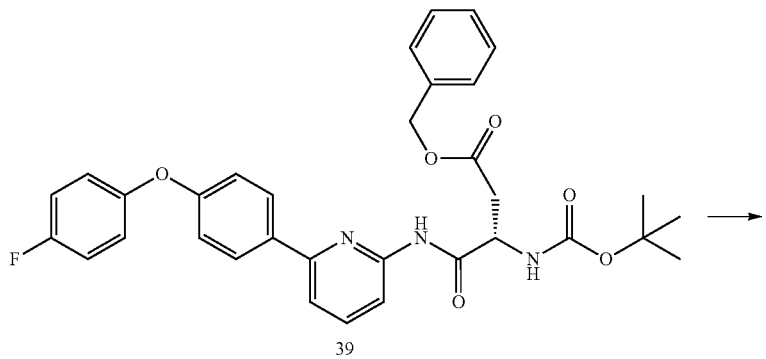

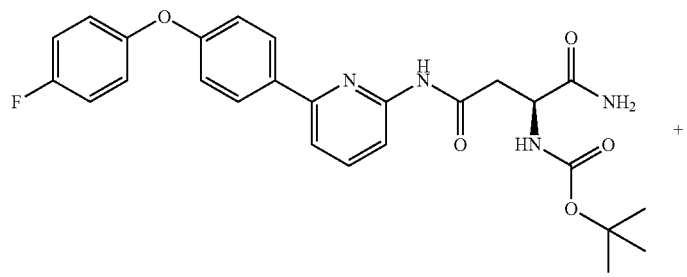

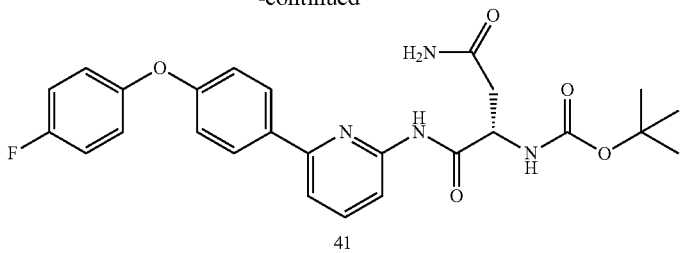

41

Compounds 40 and 41: To compound 39 (1.408 g, 2.40 mmol) was added 7M NH₃ in MeOH (25 mL, Aldrich). After 2 days the reaction mixture was diluted with 100 mL hexanes and 100 mL 1.74 M aqueous HCl was added. The solid that formed was collected and rinsed with water. The solid was repeatedly chromatographed over silica gel eluting with 50-100% EtOAc in hexanes to separate the two close running products. The product fractions were separately collected and concentrated in vacuo. The residues were each triturated with 2 mL EtOAc then dried under vacuum at 50° C. to give (S)-tert-butyl (1-amino-4-((6-(4-(4-fluorophenoxy)phenyl)pyridin-2-yl)amino)-1,4-dioxobutan-2-yl)carbamate as a white powder (0.077 g, 0.16 mmol, 6% yield, LC/MS: m/z=495.2 [M+H]⁺, ¹H NMR (400 MHz, DMSO-d₆): 10.40 (s, 1H), 8.09 (s, J=8.8 Hz, 2H), 8.00 (br d, J=7.6 Hz, 1H), 7.84 (t, J=8.0 Hz, 1H), 7.62 (d, J=8.0 Hz, 1H), 7.32-7.24 (m, 3H), 7.19-7.13 (m, 2H), 7.08 (d, J=8.8 Hz, 2H), 7.05 (br s, 1H), 6.93 (d, J=8.4 Hz, 1H), 4.37-4.29 (m, 1H), 2.84-2.63 (m, 2H), 1.35 (s, 9H); and (S)-tert-butyl (4-amino-1-((6-(4-(4-fluorophenoxy)phenyl)pyridin-2-yl)amino)-1,4-dioxobutan-2-yl)carbamate as a white powder (0.119 g, 0.24 mmol, 10% yield, LC/MS: m/z=495.2 [M+H]⁺, ¹H NMR (400 MHz, DMSO-d₆): 10.26 (s, 1H), 8.09 (d, J=8.8 Hz, 2H), 7.97 (d, J=8.0 Hz, 1H), 7.86 (d, J=8.0 Hz, 1H), 7.65 (d, J=7.6 Hz, 1H), 7.38 (s, 1H), 7.31-7.24 (m, 2H), 7.21-7.13 (m, 3H), 7.08 (d, J=8.8 Hz, 2H), 6.98 (s, 1H), 4.56-4.48 (m, 1H), 2.62-2.54 (m, 1H), 2.49-2.43 (m, 1H), 1.40 (s, 9H).

Example 13

Synthesis of N—((S)-1-((4-((S)-1,2-dihydroxyethyl)-6-(4-(4-fluorophenoxy)phenyl)pyridin-2-yl)amino)-4-methyl-1-oxopentan-2-yl)cyclopropanecarboxamide Scheme 24

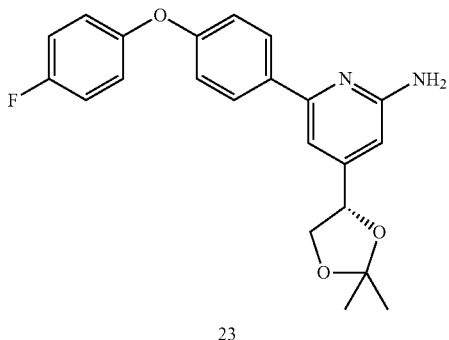

23

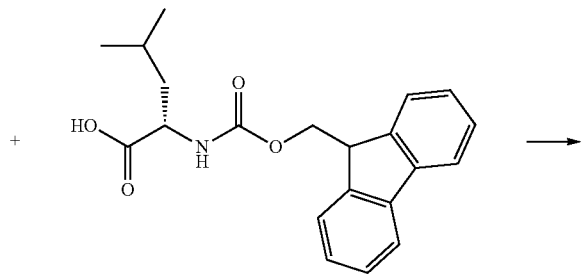

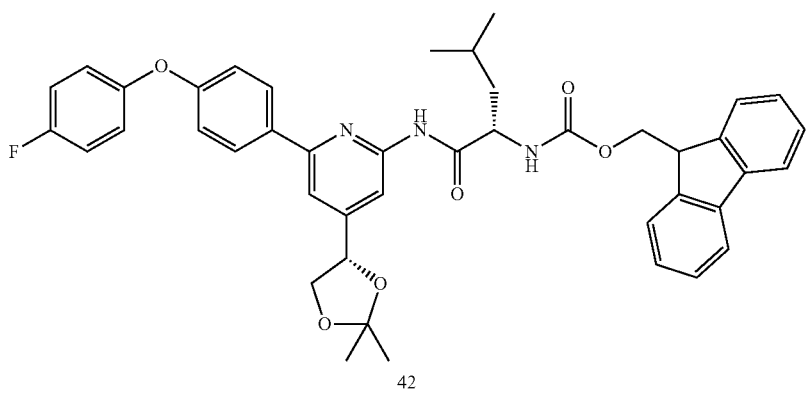

42

-continued

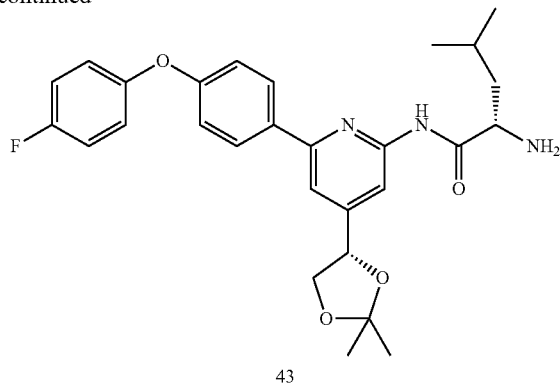

43

Compound 43: To a solution of (S)-2-((((9H-fluoren-9-yl)methoxy)carbonyl)amino)-4-methylpentanoic acid (0.407 g, 1.15 mmol, Advanced ChemTech) in DMF (10 mL) was added iPr₂NEt (0.20 mL, 1.15 mmol) and HATU (0.433 g, 1.14 mmol). After stirring for 2 minutes a solution of compound 23 (0.390 g, 1.03 mmol) in DMF (10 mL) with iPr₂NEt (0.20 mL, 1.15 mmol) was added. After stirring for 2 days, a solution of (S)-2-((((9H-fluoren-9-yl)methoxy) carbonyl)amino)-4-methylpentanoic acid (0.401 g, 1.13 mmol) in DMF (5 mL) with iPr₂NEt (0.20 mL, 1.15 mmol) and HATU (0.433 g, 1.14 mmol) was prepared and added to the main reaction. After 4 days the reaction was diluted with 250 mL water and solid precipitate (compound 42) was collected.

Compound 42 was dissolved in DCM (50 mL) and tris-aminoethyl amine (1.54 mL, 10.28 mmol, Aldrich) and DMF (10 mL) were added. After stirring overnight more DMF (10 mL) was added. After stirring overnight the reaction was diluted with 50 mL DCM, washed successively with 50 mL water/brine, 50 mL pH 5.5 phosphate buffer/brine, and 50 mL brine. The organic layer was dried over MgSO₄, filtered and concentrated in vacuo. The residue was chromatographed over silica gel eluting with 20-80% EtOAc in hexanes. The product fractions were isolated and evaporated in vacuo to give (S)-2-amino-N-(4-((S)-2,2-dimethyl-1,3-dioxolan-4-yl)-6-(4-(4-fluorophenoxy)phenyl)pyridin-2-yl)-4-methylpentanamide as a thick yellow oil (0.209 g, 0.42 mmol, 41% yield, LC/MS: m/z=494.2 [M+H]⁺).

Scheme 25

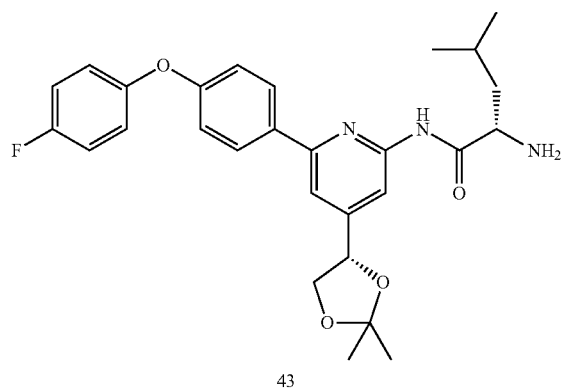

43

+

-continued

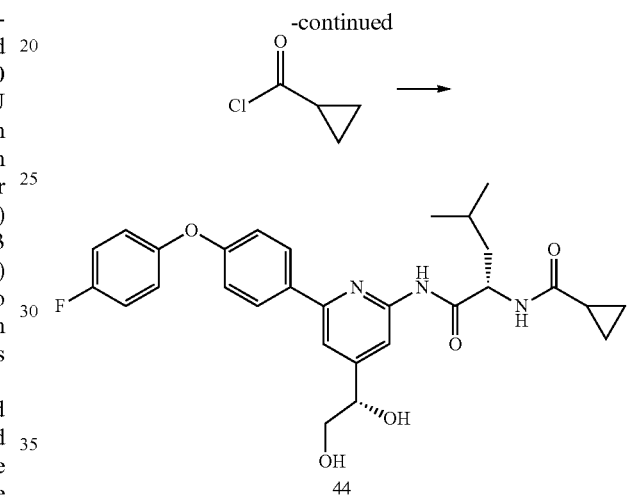

44

Compound 44: To a solution of compound 43 (0.104 g, 0.21 mmol) in DCM (5 mL) was added iPr₂NEt (0.044 mL, 0.25 mmol) and cyclopropanecarbonyl chloride (0.021 mL, 0.23 mmol). After stirring overnight the reaction was concentrated in vacuo then dissolved in MeOH (5 mL) and 4N HCl in dioxane (0.5 mL, 2.0 mmol) was added. After stirring overnight the reaction was concentrated in vacuo. The residue was chromatographed using reverse-phase HPLC eluting with 20-90% acetonitrile in water, each containing 0.1% TFA. The product fractions were pooled and treated with Amberlite IRA-400(OH) resin to remove the TFA. The solution was frozen and lyophilized to give N—((S)-1-((4-((S)-1,2-dihydroxyethyl)-6-(4-(4-fluorophenoxy)phenyl) pyridin-2-yl)amino)-4-methyl-1-oxopentan-2-yl)cyclopropane carboxamide (0.033 g, 0.063 mmol, 30% yield, LC/MS: m/z=522.2 [M+H]⁺, ¹H NMR (400 MHz, DMSO-d₆): 10.43 (s, 1H), 8.28 (d, J=8.0 Hz, 1H), 8.00 (d, J=8.8 Hz, 2H), 7.97 (s, 1H), 7.50 (s, 1H), 7.24-7.17 (m, 2H), 7.11-7.05 (m, 2H), 7.01 (d, J=8.8 Hz, 2H), 4.58-4.50 (m, 2H), 3.44 (d, J=6.0 Hz, 2H), 1.69-1.57 (m, 2H), 1.57-1.40 (m, 2H), 0.86 (d, J=6.8 Hz, 3H), 0.82 (d, J=6.4 Hz, 3H), 0.64-0.54 (m, 4H).

Using the chemistry described above the following compound was prepared:

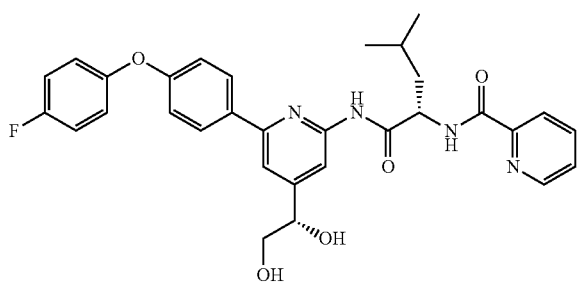 [SMILES: CC(C)C[C@H](NC(=O)c1ccccn1)C(=O)Nc1cc([C@H](O)CO)cc(-c2ccc(Oc3ccc(F)cc3)cc2)n1]

Compound 45: N—((S)-1-((4-((S)-1,2-dihydroxyethyl)-6-(4-(4-fluorophenoxy)phenyl)pyridin-2-yl)amino)-4-methyl-1-oxopentan-2-yl)picolinamide: LC/MS: m/z=559.2 [M+H]+, ¹H NMR (400 MHz, DMSO-d₆): 10.64 (s, 1H), 8.78 (d, J=8.8 Hz, 1H), 8.64 (dt, J=4.8, 1.2 Hz, 1H), 8.04-7.92 (m, 5H), 7.60-7.56 (m, 1H), 7.51 (s, 1H), 7.25-7.16 (m, 2H), 7.12-7.05 (m, 2H), 7.02 (d, J=8.8 Hz, 2H), 4.87-4.79 (m, 1H), 4.52 (t, J=5.6 Hz, 1H), 3.44 (d, J=6.0 Hz, 2H), 1.82-1.71 (m, 1H), 1.67-1.55 (m, 2H), 0.90-0.85 (m, 6H).

Example 14

Synthesis of 2-(4-((6-(4-(4-fluorophenoxy)phenyl)pyridin-2-yl)amino)piperidin-1-yl)acetic acid Scheme 26

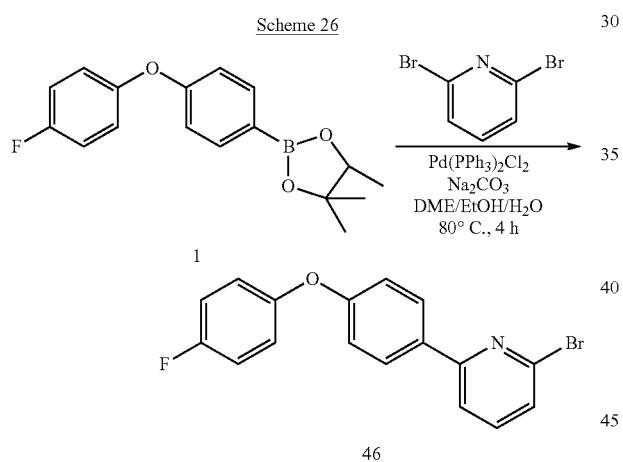

Compound 46: A 50 mL round bottom flask was charged with compound 1 (1.88 g, 6.0 mmol), 2,6-Dibromopyridine (1.42 g, 6.0 mmol), Pd(PPh₃)₂Cl₂ (210 mg, 0.3 mmol), Na₂CO₃ (0.95 g, 9.0 mmol) and DME/EtOH/H₂O (4 mL/2 mL/4 mL). The reaction mixture was purged with argon and then stirred at 80° C. under argon for 4 h. The reaction mixture was cooled to room temperature and extracted with EtOAc. The EtOAc was separated, dried over MgSO₄, filtered, and concentrated. The residue was subjected to flash column chromatography on silica gel using hexanes/EtOAc as the eluent to give compound 46 as white solid (1.55 g, yield 75%) (m/z+H) 345.

Scheme 27

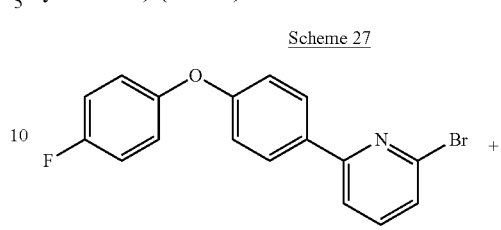

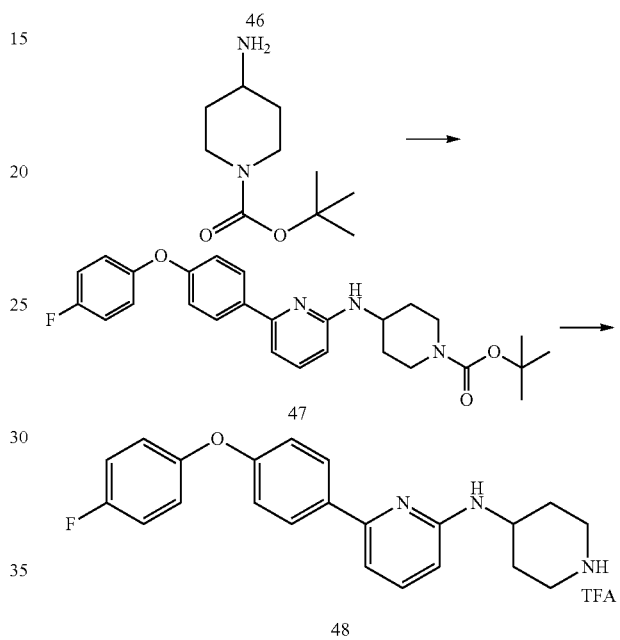

Compound 48: A 10 mL reaction flask was charged with compound 2 (100 mg, 0.3 mmol), 4-amino-1-Boc-piperidine (Aldrich, 200 mg, 0.6 mmol), Pd₂(dba)₃ (21 mg, 0.036 mmol), NaOBu-t (87 mg, 0.88 mmol), BINAP (29 mg, 0.14 mmol) and dioxane (3 mL). The reaction mixture was purged with argon and stirred at 100° C. for 2 h. The reaction mixture was cooled to room temperature and diluted with EtOAc. The EtOAc was separated, dried over MgSO₄, filtered, and concentrated. The residue was subjected to flash column chromatography on silica gel using hexanes/EtOAc as the eluent to give compound 47 as white solid (92 mg, yield 75%) (m/z+H) 407.

Compound 47 was dissolved in a mixture of DCM/TFA (2 mL/2 mL) and stirred at room temperature for 1 h. The solvent was removed and the residue was re-dissolved in DCM and concentrated to compound 48 as a TFA salt which was used for next step without further purification.

Scheme 28

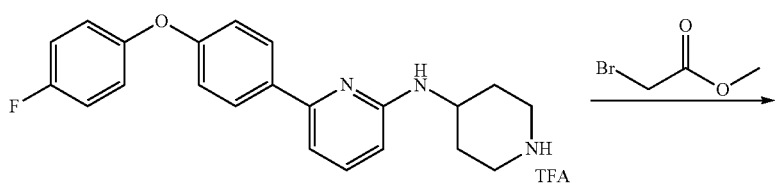

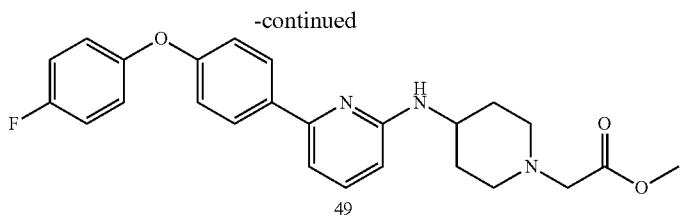

49

Compound 49: A 50 mL round bottom flask was charged with compound 48 (238 mg, 0.50 mmol), methyl bromoacetate (153 mg g, 1.0 mmol), K$_2$CO$_3$ (138 mg, 1 mmol) and DMF (2 mL). The mixture was stirred at 70° C. for 2 h. The reaction mixture was cooled to room temperature and extracted with EtOAc. The organic layer was separated, dried over MgSO$_4$, filtered, and concentrated. The residue was subjected to flash column chromatography on silica gel using hexanes/EtOAc as the eluent to give compound 49 as white solid (206 mg, yield 95%) (m/z+H) 436.

Scheme 29

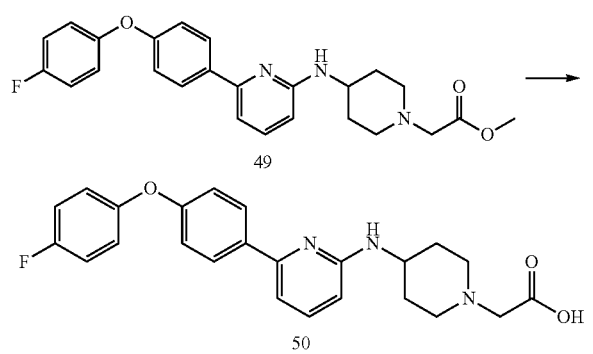

Compound 50: A 25 mL round bottom flask was charged with compound 49 (100 mg, 0.23 mmol), MeOH (2 mL) and NaOH (6N, 0.038 mL). The reaction mixture was stirred at 50° C. for 1 hr and then cooled to 0° C. using an ice bath. The pH of the mixture was adjusted to pH 1 using 6M HCl. The precipitate was collected and dried to give 2-(4-((6-(4-(4-fluorophenoxy)phenyl)pyridin-2-yl)amino)piperidin-1-yl)acetic acid as a white solid (80 mg, yield 95%). LC/MS: m/z=422 [M+H]$^+$; $^1$H NMR (400 MHz, CD$_3$OD): 7.9 (d, 2H), 7.4 (m, 1H), 6.8-7.1 (m, 7H), 6.4 (d, 1H), 4.2 (br, 1H), 2.8-3.6 (m, 6H), 1.4-2.3 (m, 4H).

Example 15

Synthesis of 1-(4-chloro-6-(4-(4-fluorophenoxy)phenyl)pyridin-2-yl)piperidine-4-carboxylic acid Scheme 30

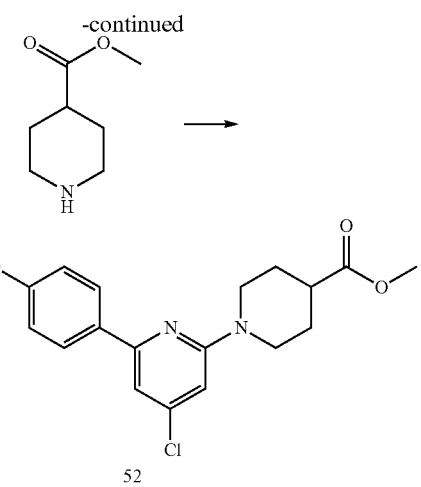

Compound 52: A 5 mL microwavable vial was charged with compound 51 (100 mg, 0.3 mmol), methyl piperidine-4-carboxylate (Aldrich, 43 mg, 0.3 mmol), DIEA (0.1 mL) and DMSO (1.0 mL). The reaction mixture was purged with argon and then stirred at 160° C. in the microwave for 20 minutes. The reaction mixture was cooled to room temperature and diluted with EtOAc. The EtOAc was separated, dried over MgSO$_4$, filtered, and concentrated. The residue was subjected to flash column chromatography on silica gel using hexanes/EtOAc as the eluent to give compound 52 as white solid (80 mg, yield 61%) (m/z+H) 441.

Scheme 31

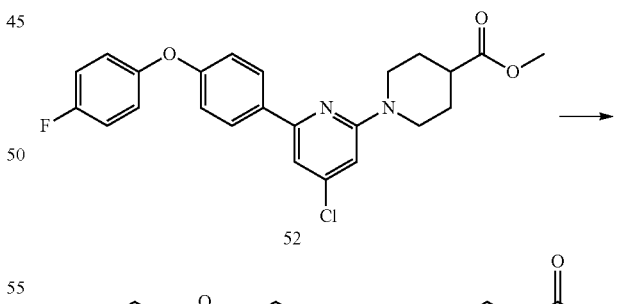

Compound 53: A 25 mL round bottom flask was charged with compound 52 (80 mg, 0.18 mmol), MeOH (2 mL) and NaOH (6N, 0.050 mL). The reaction mixture was stirred at 50° C. for 1 h and then cooled to 0° C. using an ice bath. The pH of the mixture was adjusted to pH 1 using 6M HCl. The precipitate was collected and dried to give 1-(4-chloro-6-(4-(4-fluorophenoxy)phenyl)pyridin-2-yl)piperidine-4-carboxylic acid as a white solid (75 mg, yield 98%). LC/MS: m/z=427 [M+H]$^+$; $^1$H NMR (400 MHz, CD$_3$OD): 7.9 (d, 2H), 6.8-7.1 (m, 7H), 6.7 (m, 1H), 3.8 (m, 2H); 3.1 (m, 2H); 2.5 (m, 1H); 1.6-2.1 (m, 4H).

Example 16

Synthesis of (S)—N-{6-[4-(4-fluoro-phenoxy)-phenyl]-pyridin-2-yl}-3-hydroxy-2-ureido-propionamide give ((S)-1-{6-[4-(4-fluoro-phenoxy)-phenyl]-pyridin-2-yl-carbamoyl}-2-hydroxy-ethyl)-carbamic acid tert-butyl ester as a white solid (3.3 g, 73% yield). LC/MS: m/z=468 [M+H]$^+$; $^1$H NMR (400 MHz, CD$_3$OD): 8.10-8.03 (m, 3H), 7.82 (t, J=8.1 Hz, 1H), 7.59 (d, J=7.89 Hz, 1H), 7.04-7.17 (m, 6H), 7.58-7.64 (m, 1H), 7.37-7.44 (s, 1H), 7.03-7.21 (m, 6H), 4.37 (br, s, 1H). 3.83-3.93 (m, 2H), 2.94-3.03 (dd, J=9.87, 14.03 Hz, 1H), 1.49 (s, 9H).

Compound 70: To compound 59 (2.5 g, 5.3 mmol) in dry dioxane (5 mL) was added 4.0N HCl in dioxane (14 mL, 53 mmol) at 0° C. The reaction mixture was stirred for 2 h at room temperature. After the reaction was complete, the solvent was evaporated. The crude residue was suspended in diethyl ether and filtered (this process repeated for 3 times) to give (S)-2-amino-N-{6-[4-(4-fluoro-phenoxy)-phenyl]-pridin-2-yl}-3-hydroxy-propionamide as the HCl salt (1.9 g,

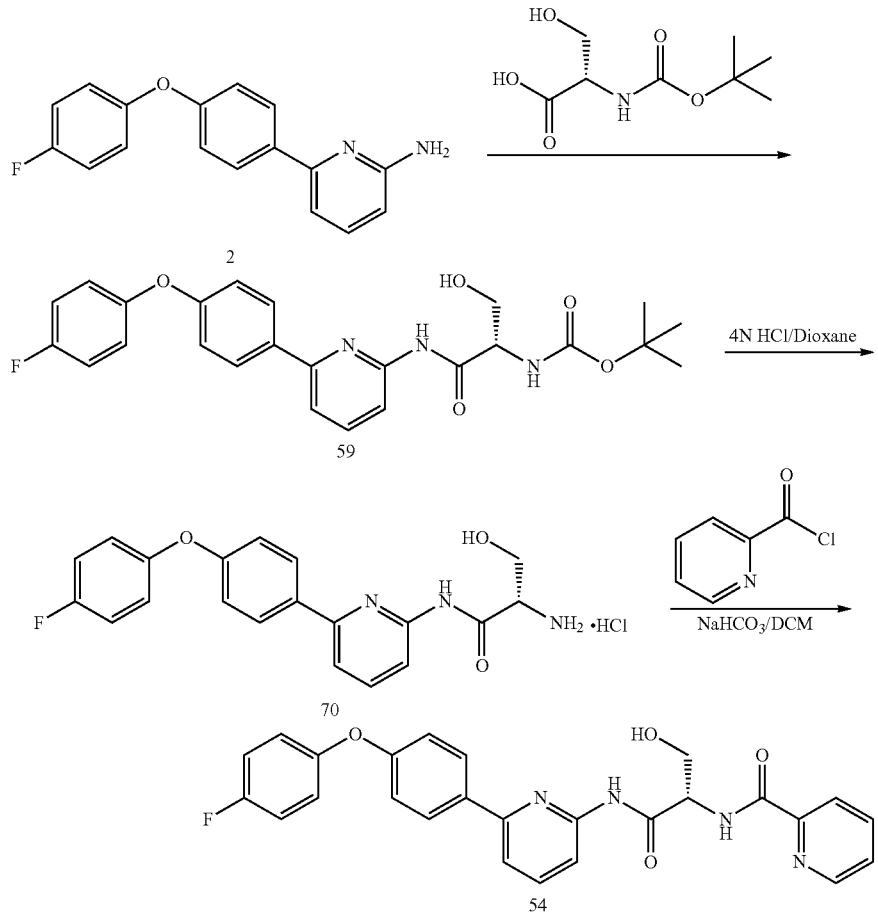

Scheme 32

Compound 59: A mixture of Boc-Ser-OH (purchased from Sigma-Aldrich, 2.7 g, 9.6 mmol) and HATU (purchased from GenScript Corporation, 5.6 g, 14.9 mmol) in a mixture of THF/DCM (160 mL) was stirred for 1 h and compound 2 (2.7 g, 9.6 mmol) was added thereto. The reaction mixture was stirred overnight at room temperature and the solvent was evaporated. The residue was dissolved in CH$_2$Cl$_2$ and washed with water. The organic phase was dried over anhydrous Na$_2$SO$_4$ and concentrated to give a semi-solid residue. The crude product was purified by column chromatography (silica gel, 30% EtOAc in hexane) to 88% yield). LC/MS: m/z=368 [M+H]$^+$; $^1$H NMR (400 MHz, CD$_3$OD): 8.17 (d, J=8.11 Hz, 1H), 8.05 (t, J=8.77 Hz, 1H), 7.83 (t, J=7.89 Hz, 1H), 7.59 (d, J=8.33 Hz, 1H), 7.04-7.18 (m, 6H), 3.84 (m, 2H), 3.65 (t, J=5.04 Hz, 1H).

Compound 54: To a suspension of compound 70 (as the HCl salt) (1.0 eq.) in 1:1 mixture of saturated NaHCO$_3$ and dichloromethane was added 2-pyridinecarboxylicacid chloride (93.0 mg, 0.52 mmol) at 0° C. The suspension was stirred at room temperature overnight. After the reaction was complete, the organic layer was separated and aqueous layer was extracted with EtOAc. The combined organic layers were dried over anhydrous Na₂SO₄ and the solvent was evaporated to give oily residue which was purified by preparative TLC to give pyridine-2-carboxylic acid ((S)-1-{6-[4-(4-fluoro-phenoxy)-phenyl]-pyridin-2-ylcarbamoyl}-2-hydroxy-ethyl)-amide. (119 mg, 53% yield). LC/MS: m/z=473 [M+H]⁺; ¹H NMR (400 MHz, DMSO-d₆): 10.71 (s, 1H), 8.88 (d, J=7.67 Hz, 1H), 8.72 (d, J=4.82 Hz, 1H), 8.01-8.17 (m, 6H), 7.87 (t, J=8.10 Hz, 1H), 7.63-7.68 (m, 2H), 7.04-7.34 (m, 6H), 5.29 (t, J=5.7 Hz, 1H), 4.86 (br, s, 1H), 3.93-3.99 (m, 1H), 3.80-3.87 (m, 1H).

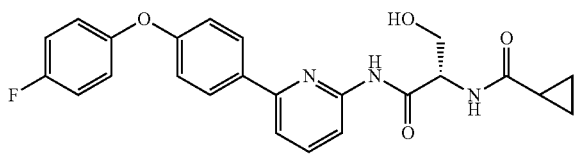 [SMILES: O=C(N[C@@H](CO)C(=O)Nc1cccc(-c2ccc(Oc3ccc(F)cc3)cc2)n1)C1CC1]

Compound 55: In similar fashion, compound 70 (as the HCl salt) (32 mg, 0.08 mmol) was treated with cyclopropylcarboxylicacid chloride (93.0 mg, 0.09 mmol) to give cyclopropanecarboxylic acid ((S)-1-{6-[4-(4-fluoro-phenoxy)-phenyl]-pyridin-2-ylcarbamoyl}-2-hydroxy-ethyl)-amide (21 mg, 61% yield). LC/MS: m/z=436 [M+H]⁺; ¹H NMR (400 MHz, CD₃OD): 8.04-8.10 (m, 3H), 7.82 (t, J=8.11 Hz, 1H), 7.59 (d, J=7.0 Hz, 1H), 7.0-7.19 (m, 6H), 4.68 (br, s, 1H), 3.86-3.98 (m, 2H), 1.73-1.82 (m, 1H), 0.89-0.94 (m, 2H), 0.80-0.87 (m, 2H).

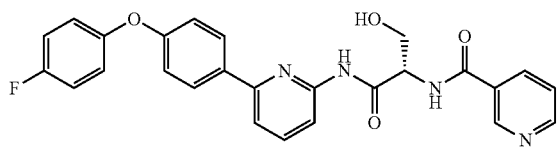 [SMILES: O=C(N[C@@H](CO)C(=O)Nc1cccc(-c2ccc(Oc3ccc(F)cc3)cc2)n1)c1cccnc1]

Compound 56: In similar fashion, compound 70 (as the HCl salt) (73 mg, 0.18 mmol) was treated with 3-pyridinecarboxylicacid chloride (52.0 mg, 0.29 mmol) to give N—((S)-1-{6-[4-(4-fluoro-phenoxy)-phenyl]-pyridin-2-yl-carbamoyl}-2-hydroxy-ethyl)-nicotinamide (53.4 mg, 62% yield). LC/MS: m/z=473 [M+H]⁺; ¹H NMR (400 MHz, DMSO-d₆): 10.59 (s, 1H), 9.09 (s, 1H), 8.72-8.82 (m, 2H), 8.27 (d, J=7.45 Hz, 1H), 8.11 (d, J=8.55 Hz, 2H), 8.02 (d, J=7.89 Hz, 1H), 7.86 (t, J=7.89 Hz, 1H), 7.65 (d, J=6.80 Hz, 1H), 7.00-7.30 (m, 6H), 5.19 (br, s, 1H), 4.84 (br, s, 1H), 3.87 (s, 2H).

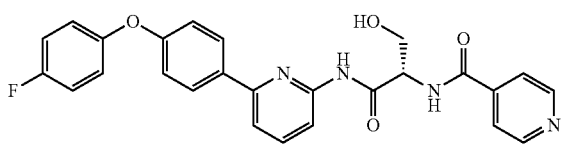 [SMILES: O=C(N[C@@H](CO)C(=O)Nc1cccc(-c2ccc(Oc3ccc(F)cc3)cc2)n1)c1ccncc1]

Compound 57: In similar fashion, compound 70 (as the HCl salt) (30 mg, 0.07 mmol) was treated with 4-pyridinecarboxylicacid chloride (14.5 mg, 0.08 mmol) to give N—((S)-1-{6-[4-(4-fluoro-phenoxy)-phenyl]-pyridin-2-yl-carbamoyl}-2-hydroxy-ethyl)-isonicotinamide (28 mg, 80% yield). LC/MS: m/z=473 [M+H]⁺; ¹H NMR (400 MHz, DMSO-d₆): 10.62 (s, 1H), 8.82 (d, J=6.58 Hz, 1H), 8.76 (d, J=6.14 Hz, 2H), 8.11 (d, J=8.99 Hz, 2H), 8.01 (d, J=7.89 Hz, 1H), 7.81-7.89 (m, 3H), 7.65 (d, J=7.24 Hz, 1H), 7.28 (t, J=8.55 Hz, 2H), 7.13-7.18 (m, 2H), 7.09 (d, J=8.99 Hz, 2H), 5.17 (br, s, 1H), 4.83 (br, s, 1H), 3.86 (s, 2H).

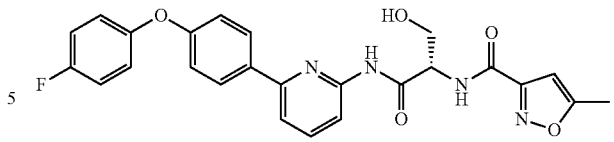

Compound 58: In similar fashion, compound 70 (as the HCl salt) (90 mg, 0.22 mmol) was treated with 5-methyl-isoxazole-3-carboxylic acid (35.7 mg, 0.25 mmol) to give 5-methyl-isoxazole-3-carboxylic acid ((S)-1-{6-[4-(4-fluoro-phenoxy)-phenyl]-pyridin-2-ylcarbamoyl}-2-hydroxy-ethyl)-amide (68 mg, 64% yield). LC/MS: m/z=477 [M+H]⁺; ¹H NMR (400 MHz, CDCl₃): 9.27 (s, 1H), 8.09 (d, J=7.23 Hz, 1H), 7.98 (d, J=7.23 Hz, 1H), 7.91 (d, J=8.99 Hz, 2H), 7.77 (t, J=8.11 Hz, 1H), 7.45 (d, J=7.67 Hz, 1H), 7.01-7.11 (m, 6H), 6.50 (s, 1H), 4.83-4.89 (s, 1H), 4.32 (d, J=9.41 Hz, 1H), 3.89 (br, s, 1H), 3.28 (br, s, 1H), 2.49 (s, 3H).

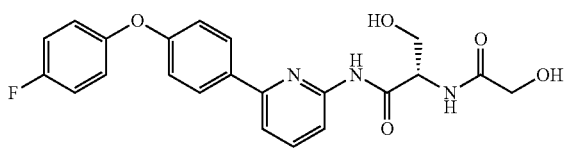 [SMILES: O=C(CO)N[C@@H](CO)C(=O)Nc1cccc(-c2ccc(Oc3ccc(F)cc3)cc2)n1]

Compound 60: To a suspension of compound 70 (as the HCl salt) (400 mg, 1.0 mmol) in dry dichloromethane (20 mL) was added HOBt (162 mg, 1.2 mmol) and EDC (229 mg, 1.2 mmol). The reaction mixture was stirred for 30 min at room temperature. Hydroxyacetic acid (76.05 mg, 1.0 mmol) and diisopropylethyl amine (0.2 mL) were added thereto. The reaction mixture was stirred overnight and washed with water. The solvent was evaporated and the residue was purified by preparative TLC (10% MeOH in DCM) to give (S)—N-{6-[4-(4-fluoro-phenoxy)-phenyl]-pyridin-2-yl}-3-hydroxy-2-(2-hydroxy-acetylamino)-propionamide (290 mg, 69% yield). LC/MS: m/z=426 [M+H]⁺; ¹H NMR (400 MHz, DMSO-d₆): 10.55 (s, 1H), 8.10 (d, J=8.99 Hz, 2H), 8.01 (d, J=8.33 Hz, 1H), 7.86 (dd, J=7.89, 16.04 Hz, 2H), 7.65 (d, J=7.89 Hz, 1H), 7.20-7.31 (m, 2H), 7.13-7.19 (m, 2H), 7.05-7.11 (m, 2H), 5.73 (t, J=5.38 Hz, 1H), 5.18 (t, J=5.7 Hz, 1H), 4.62-4.69 (br, s, 1H), 3.89 (d, J=5.7 Hz, 2H), 3.80-3.86 (m, 1H), 3.67-3.73 (m, 1H).

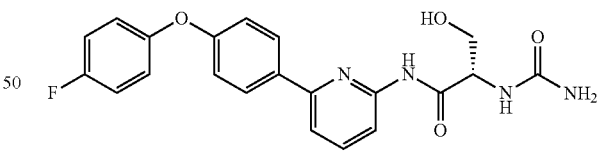

Compound 61: To a suspension of compound 70 (as the HCl salt) (150 mg, 0.37 mmol) in water (3.7 mL) was added potassium cyanate (90 mg, 1.11 mmol) at 0° C. The reaction mixture was stirred for 3 h at room temperature. Ethyl acetate (10 mL) was added thereto and organic layer was separated. The organic phase was dried over anhydrous Na₂SO₄ and the solvent was evaporated. The residue was purified by column chromatography (silica gel, 7% MeOH in DCM) to give (S)—N-{6-[4-(4-fluoro-phenoxy)-phenyl]-pyridin-2-yl}-3-hydroxy-2-ureido-propionamide (120 mg, 79% yield). LC/MS: m/z=411 [M+H]⁺; ¹H NMR (400 MHz, DMSO-d₆): 10.24 (s, 1H), 8.10 (d, J=8.77 Hz, 2H), 8.03 (d, J=8.11 Hz, 1H), 7.86 (t, J=7.89 Hz, 1H), 7.64 (d, J=7.67 Hz, 1H), 7.28 (t, J=8.55 Hz, 2H), 7.13-7.19 (t, J=8.55 Hz, 2H), 7.09 (d, J=8.77 Hz, 2H), 6.37 (d, J=8.11, 1H), 5.80 (s, 2H), 5.07 (t, J=5.26 Hz, 1H), 4.37-4.44 (br, s, 1H), 3.74-3.80 (m, 1H), 3.57-3.63 (m, 1H).

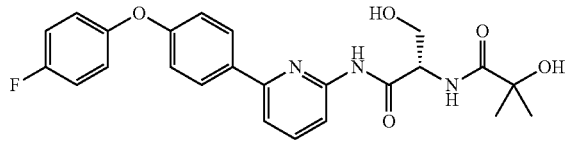 [SMILES: CC(C)(O)C(=O)N[C@@H](CO)C(=O)Nc1cccc(-c2ccc(Oc3ccc(F)cc3)cc2)n1]

Compound 92: In a similar fashion, compound 70 (as the HCl salt) (200 mg, 0.50 mmol) was treated with alpha-hydroxyisobutyric acid (52 mg, 0.5 mmol) in the presence of EDC (114 mg, 0.6 mmol), HOBt (81 mg, 0.6 mmol), and DIEA (0.1 mL, 0.5 mmol) in dry DCM. The reaction mixture was stirred for overnight at room temperature. After the work-up, the oily residue was purified by preparative TLC to give (S)—N-(6-(4-(4-fluorophenoxy)phenyl)pyridin-2-yl)-3-hydroxy-2-(2-hydroxy-2-methylpropanamido)propanamide (125 mg, 56%). $^1$H NMR (400 MHz, CD$_3$OD): 8.05 (3H, d, J=8.99 Hz), 8.02-8.07 (2H, m), 7.80 (1H, t, J=8.10 Hz), 7.57 (6H, d, J=7.9 Hz), 6.99-7.16 (6H, m), 4.58-4.62 (1H, br), 4.00 (1H, dd, J=4.6, 11.2 Hz), 3.87 (1H, dd, J=5.0, 11.2 Hz), 1.41 (6H, d, J=5.3 Hz). LC/MS: m/z=454.0 [M+H]$^+$.

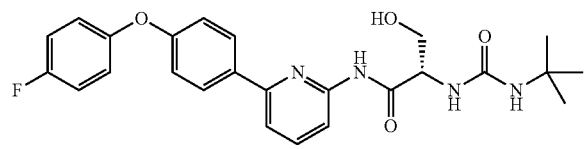 [SMILES: CC(C)(C)NC(=O)N[C@@H](CO)C(=O)Nc1cccc(-c2ccc(Oc3ccc(F)cc3)cc2)n1]

Compound 89: In a similar fashion, compound 70 (as the HCl salt) (25 mg, 0.50 mmol) in a mixture of DCM/sat.NaHCO$_3$ (1:1, 3 mL) was treated with t-butyl isocyanate (0.04 mL, 0.19 mmol) and stirred for 2 h at 0° C. After the reaction was complete, the mixture was diluted with DCM and extracted with ethyl acetate. The organic phase was dried with anhydrous Na$_2$CO$_3$ and concentrated. The residue was purified by preparative TLC (DCM:MeOH=1:10) to give (S)-2-(3-(tert-butyl)ureido)-N-(6-(4-(4-fluorophenoxy)phenyl)pyridin-2-yl)-3-hydroxypropanamide (15 mg, 54%). $^1$H-NMR (400 MHz, CD$_3$OD): 7.86 (1H, d, J=8.30 Hz), 7.82 (2H, d, J=8.70 Hz), 7.60 (1H, t, J=8.10 Hz), 7.36 (1H, d, J=7.6 Hz), 6.79-6.97 (6H, m), 6.07 (1H, br), 4.21 (1H, t, d=4.6 Hz), 3.73 (1H, dd, J=4.6, 11.0 Hz), 3.57 (1H, dd, J=5.0, 11.1 Hz), 1.41 (9H, s). LC/MS: m/z=467.1 [M+H]$^+$.

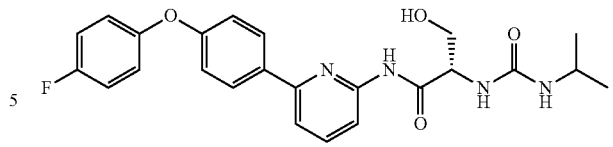

Compound 91: In a similar fashion, compound 70 (as the HCl salt) (200 mg, 0.5 mmol) in a mixture of DCM/sat. NaHCO$_3$ (1:1, 10 mL) was treated with isopropyl isocyanate (127.5 mg, 1.5 mmol) and stirred for overnight at room temperature. After the work up, the crude residue was purified by preparative TLC (DCM: MeOH=1:10) to give (S)—N-(6-(4-(4-fluorophenoxy)phenyl)pyridin-2-yl)-3-hydroxy-2-(3-isopropylureido)propanamide (153 mg, 68%). $^1$H-NMR (400 MHz, CD$_3$OD): 8.09 (1H, d, J=8.30 Hz), 8.05 (2H, d, J=9.05 Hz), 7.82 (1H, t, J=7.7 Hz), 7.36 (1H, d, J=7.6 Hz), 7.58 (1H, d, J=7.67 Hz), 7.02-7.19 (6H, m), 4.49 (1H, t, J=4.6 Hz), 4.0 (1H, dd, J=4.6, 11.0 Hz), 3.57-3.88 (2H, m), 3.33 (6H, m). LC/MS: m/z=453.1 [M+H]$^+$.

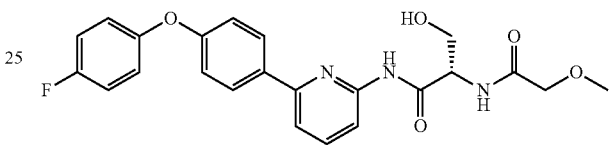

Compound 93: In a similar fashion, compound 70 (as the HCl salt) (100 mg, 0.25 mmol) was treated with methoxyacetic acid (0.02 mL, 0.25 mmol) in the presence of HATU (94 mg, 0.25 mmol) and DIEA (0.1 mL, 0.5 mmol) in a mixture of DCM/THF (5 mL). The reaction mixture was stirred overnight at room temperature. After the work-up, the oily residue was purified by preparative TLC to give (S)—N-(6-(4-(4-fluorophenoxy)phenyl)pyridin-2-yl)-3-hydroxy-2-(2-methoxy-acetamido)propanamide (109 mg, 56%). $^1$H NMR (400 MHz, CD$_3$OD): 8.06 (3H, d, J=9.00 Hz), 7.83 (1H, t, J=7.60 Hz), 7.60 (1H, d, J=7.67 Hz), 7.03-7.19 (6H, m), 4.74 (1H, br), 4.01 (2H, s), 3.98 (1H, d, J=4.60 Hz), 3.91 (1H, dd, J=5.0, 11.0 Hz), 3.50 (3H, s). LC/MS: m/z=440.1 [M+H]$^+$.

Example 17

Synthesis of (S)-2-acetylamino-N-{6-[4-(4-fluorophenoxy)-phenyl]-pyridin-2-yl}-3-pyridin-3-yl-propionamide Scheme 33

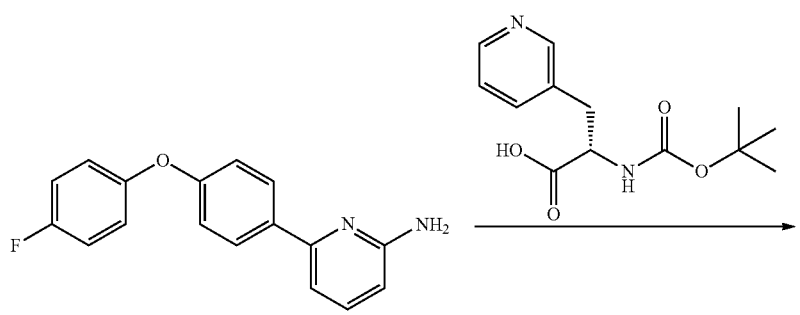

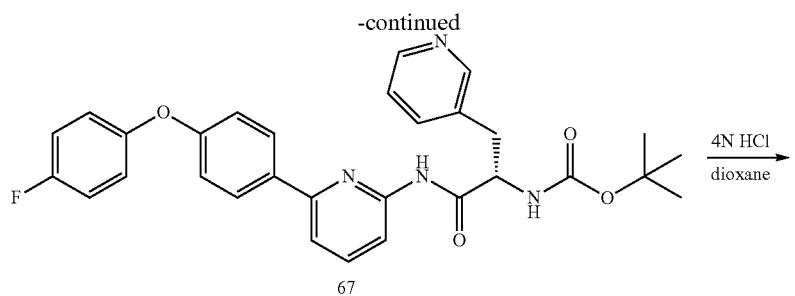

67

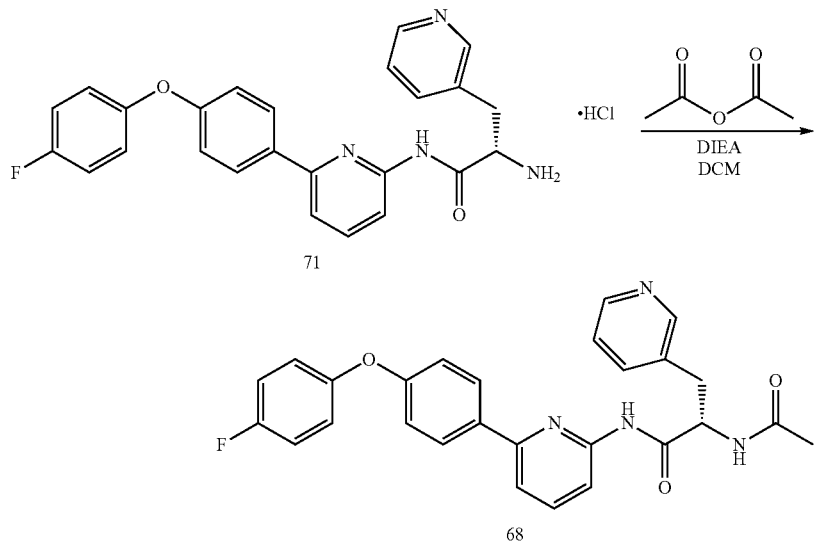

71

68

Compound 67: A mixture of Boc-3-(3-pyridyl)-Ala-OH (purchased from Sigma-Aldrich, 1.0 g, 3.76 mmol) and EDC (860 mg, 4.5 mmol), HOBt (607.5 mg, 4.5 mmol) in DCM (100 mL) was stirred for 30 min and compound 2 (1.05 g, 3.75 mmol) was added thereto. After the reaction was complete, water was added. The organic phase was separated, dried over anhydrous $Na_2SO_4$, filtered, and concentrated to give pale yellow residue. The crude residue was purified by column chromatography (silica gel, 5% MeOH in DCM) to give ((S)-1-{6-[4-(4-fluoro-phenoxy)-phenyl]-pyridin-2-ylcarbamoyl}-2-pyridin-3-yl-ethyl)-carbamic acid tert-butyl ester (1.0 g, 51% yield). LC/MS: m/z=529 [M+H]$^+$; $^1$H NMR (400 MHz, $CD_3OD$): 8.51 (s, 1H), 8.42 (s, 1H), 8.06 (d, J=8.99 Hz, 3H), 7.80-7.90 (m, 2H), 7.58-7.64 (m, 1H), 7.37-7.44 (s, 1H), 7.03-7.21 (m, 6H), 4.56-4.65 (br, s, 1H). 3.24-3.30 (m, 1H), 2.94-3.03 (dd, J=9.87, 14.03 Hz, 1H), 1.39 (s, 9H).

Compound 71: To compound 67 (250 mg, 0.47 mmol) in dioxane was added 4.0N HCl in dioxane (3 mL). The reaction mixture was stirred at room temperature for 3 h. The solvent was evaporated and the residue was washed with diethyl ether several times to give (S)-2-amino-N-{6-[4-(4-fluoro-phenoxy)-phenyl]-pyridin-2-yl}-3-pyridin-3-yl-propionamide as the HCl salt (140 mg, 69% yield) which was used for the next step without further purification. LC/MS: m/z=429 [M+H]$^+$.

Compound 68: A suspension of compound 71 (as the HCl salt) (200 mg, 0.43 mmol) in dry DCM (8.6 mL) was cooled to 0° C. under a $N_2$ atmosphere and DIEA (0.17 mL, 0.95 mmol) and acetic anhydride (0.09 mL, 0.86 mmol) were added. The reaction mixture was allowed to stir overnight at the room temperature and the solvent was evaporated. The crude product was purified by preparative TLC (10% MeOH in DCM) and then recrystallized (30% EtOAc in hexane) to give (S)-2-acetylamino-N-{6-[4-(4-fluoro-phenoxy)-phenyl]-pyridin-2-yl}-3-pyridin-3-yl-propionamide as a white solid (120 mg, 59% yield). LC/MS: m/z=471 [M+H]$^+$; $^1$H NMR (400 MHz, $CD_3OD$): 8.50 (s, 1H), 8.40 (d, J=4.8 Hz, 1H), 8.05 (m, 3H), 7.70-7.86 (m, 2H), 7.58 (d, J=7.67 Hz, 1H), 7.36-7.41 (m, 1H), 7.01-7.41 (m, 6H), 3.25-3.31 (m, 1H), 3.01-3.08 (m, 1H), 1.96 (s, 3H).

Example 18

Synthesis of (S)-2-acetylamino-N-{6-[4-(4-fluoro-phenoxy)-phenyl]-pyridin-2-yl}-3-hydroxy-butyramide Scheme 34

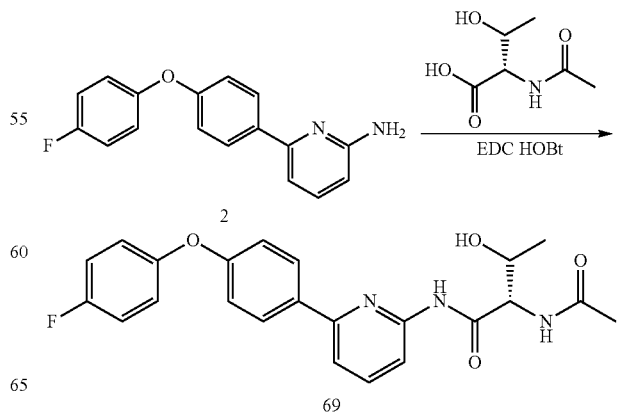

69

Compound 69: A mixture of AcThr-OH (purchased from Sigma-Aldrich, 250 mg, 1.6 mmol) and HATU (purchased from GenScript Corporation, 303 mg, 0.8 mmol) in a mixture of THF/DCM (60 mL) was stirred for 30 min and compound 2 (448 mg, 1.6 mmol) was added thereto. The mixture was stirred overnight at room temperature and then the solvent was evaporated. The resulting residue was dissolved in $CH_2Cl_2$ and washed with water. The organic phase was dried over anhydrous $Na_2SO_4$ and concentrated to give oily residue. The crude residue was purified by preparative TLC (10% MeOH in DCM) to give (S)-2-acetylamino-N-{6-[4-(4-fluoro-phenoxy)-phenyl]-pyridin-2-yl}-3-hydroxy-butyramide as a white solid (120 mg, 32% yield). LC/MS: m/z=424 [M+H]$^+$; $^1$H NMR (400 MHz, $CD_3OD$): 7.99-8.07 (m, 3H), 7.80 (t, J=8.07 Hz, 1H), 7.56 (d, J=7.34 Hz, 1H), 7.01-7.16 (m, 6H), 4.57 (s, 1H), 4.25-4.29 (m, 1H), 2.09 (s, 3H), 1.24 (d, J=6.60 Hz, 3H).

Example 19

Synthesis of 2,3-dihydroxy-N-(6-(4-(4-(trifluoromethyl)phenoxy)phenyl)pyridin-2-yl)propanamide

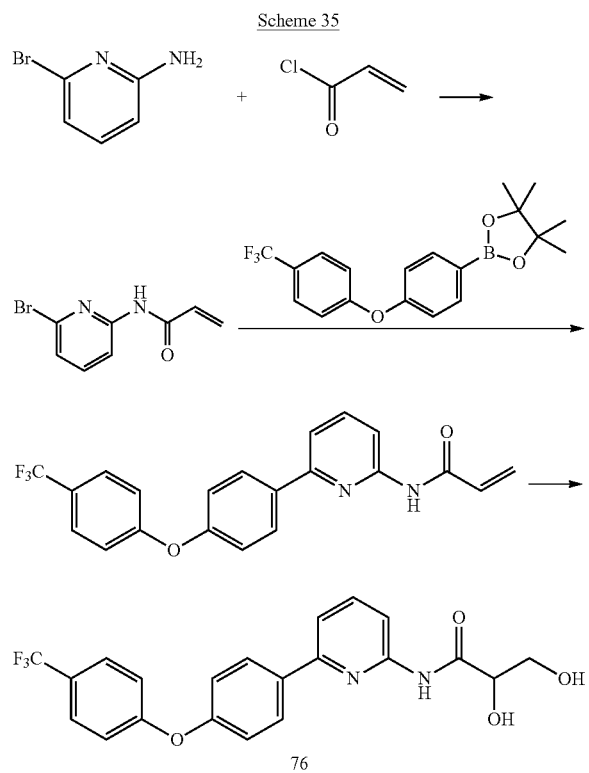

2-Amino-6-bromopyridine (5 g, 0.028 mol) was added to 70 mL of dichloromethane in a 100 mL 3-neck round-bottom flask. Triethylamine (4.0 mL, 0.028 mole) was added and the mixture cooled to 0-5° C. with an ice/water bath. At this temperature acryloyl chloride (2.6 g, 0.028 mole) was added drop wise. After complete addition the reaction mixture was allowed to reach room temperature and stirred overnight at room temperature under nitrogen atmosphere. TLC after 16 h indicated that 10% starting material remained unreacted. Water was added (25 mL) and the layers were separated. The organic layer was washed with brine, dried over sodium sulfate, filtered, and concentrated under reduced pressure to obtain the crude product, which was purified by 60-120 mesh silica gel column chromatography using 0-10% ethyl acetate heptane as eluent to give 5.1 g (78%) N-(6-bromopyridin-2-yl)acrylamide.

4,4,5,5-tetramethyl-2-(4-(4-(trifluoromethyl)phenoxy)phenyl)-1,3,2-dioxaborolane (1.76 g, 4.8 mmol) and N-(6-bromopyridin-2-yl)acrylamide (1.0 g, 4.4 mmol) were added to 15 mL of THF in a 50 mL 3-neck round bottom flask under nitrogen atmosphere. Pd(dppf)Cl$_2$ (105 mg, 0.14 mmol) and TBAF (9.0 mL, 1M in THF, 9 mmol) were added and the reaction mixture was stirred at 60° C. for 16 h. TLC indicated that 5-10% starting material remained unreacted. The solvent was removed under reduced pressure and the residue was partitioned between ethyl acetate and water. The organic layer was washed with brine, dried over sodium sulfate, filtered, and concentrated under reduced pressure to obtain the crude product, which was purified by 230-400 mesh silica gel column chromatography using 0-15% ethyl acetate as eluent to give N-(6-(4-(4-(trifluoromethyl)phenoxy)phenyl)pyridin-2-yl)acrylamide as a gummy solid). Trituration with hexane gave a free flowing solid 0.7 g (41%).

N-(6-(4-(4-(trifluoromethyl)phenoxy)phenyl)pyridin-2-yl)acrylamide (0.39 g, 1 mmol) was suspended in a mixture of 8 mL of acetone and 2 mL of water in a 50 mL 3-neck round bottom flask. The reaction mixture was cooled to 0-10° C. with an ice/water bath. At this temperature, NMO (145 mg, 1.24 mmol) and OsO$_4$ (14 mg, 0.059 mmol) were added and the reaction mixture was stirred at the same temperature for 6 h. TLC indicated that the reaction was complete. The reaction mixture was diluted with ethyl acetate and the resulting solution washed with aqueous sodium bisulfite and brine and dried over sodium sulfate. Evaporation under reduced pressure yielded the crude product, which was purified 60-120 mesh silica gel chromatography using 0-20% ethyl acetate: heptane to yield the desired compound as a thick oily solid which was triturated with hexane to give 180 mg (43%) 2,3-dihydroxy-N-(6-(4-(4-(trifluoromethyl)phenoxy)phenyl)pyridin-2-yl)propanamide (Compound 76) as a free flowing solid. LC/MS: m/z=419.3 [M+H]$^+$, $^1$H NMR (400 MHz, DMSO-d$_6$): 9.62 (1H, s), 8.25-8.00 (3H, m), 7.95 (1H, m), 7.80-7.70 (3H, m), 7.30-7.25 (4H, m), 6.06 (1H, s), 4.92 (1H, m), 4.17-4.12 (1H, m), 3.69-3.64 (2H, m).

Using the synthetic methodology described above, the following compounds were prepared:

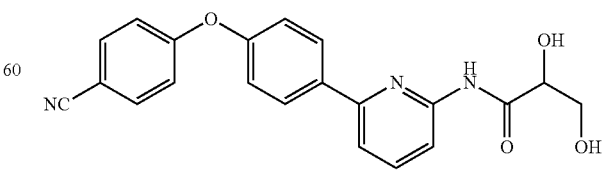

N-(6-(4-(4-cyanophenoxy)phenyl)pyridin-2-yl)-2,3-dihydroxypropanamide (Compound 73): LC/MS: m/z=376.2

[M+H]⁺, ¹H NMR (400 MHz, DMSO-d₆): 9.60 (1H, s), 8.22-8.12 (2H, m), 8.12-8.05 (1H, m), 7.95-7.82 (3H, m), 7.75-7.70 (1H, m), 7.30-7.17 (4H, m), 6.07-6.02 (1H, m), 4.92-4.87 (1H, m), 4.17-4.12 (1H, m), 3.67-3.62 (2H, m).

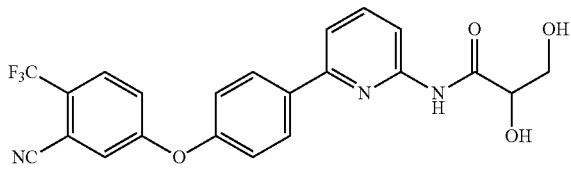 [SMILES: N#Cc1cc(Oc2ccc(-c3cccc(NC(=O)C(O)CO)n3)cc2)ccc1C(F)(F)F]

N-(6-(4-(3-cyano-4-(trifluoromethyl)phenoxy)phenyl) pyridin-2-yl)-2,3-dihydroxypropanamide (Compound 74): LC/MS: m/z=4444.3 [M+H]⁺, ¹H NMR (400 MHz, DMSO-d₆): 9.62 (1H, s), 8.25-8.15 (2H, m), 8.15-8.05 (1H, m), 8.05-7.85 (3H, m), 7.80-7.70 (1H, m), 7.38-7.22 (2H, m), 6.07-6.02 (1H, m), 4.90-4.85 (1H, m), 4.17-4.12 (1H, m), 3.67-3.62 (2H, m).

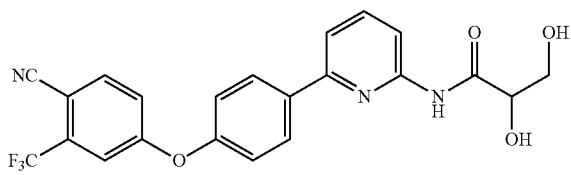 [SMILES: N#Cc1ccc(Oc2ccc(-c3cccc(NC(=O)C(O)CO)n3)cc2)cc1C(F)(F)F]

N-(6-(4-(4-cyano-3-(trifluoromethyl)phenoxy)phenyl) pyridin-2-yl)-2,3-dihydroxypropanamide (Compound 75): LC/MS: m/z=4444.3 [M+H]⁺, ¹H NMR (400 MHz, DMSO-d₆): 9.62 (1H, s), 8.27-8.13 (3H, m), 8.13-8.08 (1H, m), 7.98-7.90 (1H, m), 7.76-7.72 (1H, m), 7.65-7.60 (1H, m), 7.45-7.38 (1H, m), 7.38-7.30 (1H, m), 6.10-6.03 (1H, m), 4.90-4.85 (1H, m), 4.17-4.12 (1H, m), 3.67-3.62 (2H, m).

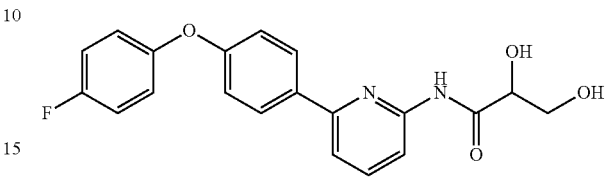

N-(6-(4-(4-fluorophenoxy)phenyl)pyridin-2-yl)-2,3-dihydroxypropanamide (Compound 72): LC/MS: m/z=369.1 [M+H]⁺, ¹H NMR (400 MHz, DMSO-d₆): 9.57 (1H, s), 8.09 (2H, d, J=9.0 Hz), 8.05 (1H, d, J=8.1 Hz), 7.89 (1H, t, J=7.9 Hz), 7.68 (1H, d, J=7.9 Hz), 7.31-7.24 (2H, m), 7.19-7.12 (2H, m), 7.07 (2H, d, J=9.0 Hz), 6.06 (1H, d, J=5.7 Hz), 4.92 (1H, t, J=5.5 Hz), 4.17-4.12 (1H, m), 3.69-3.64 (2H, m).

Example 20

Synthesis of (S)-2-((4-chloro-6-(4-(4-fluorophenoxy)phenyl)pyridin-2-yl)amino) propanamide Scheme 36

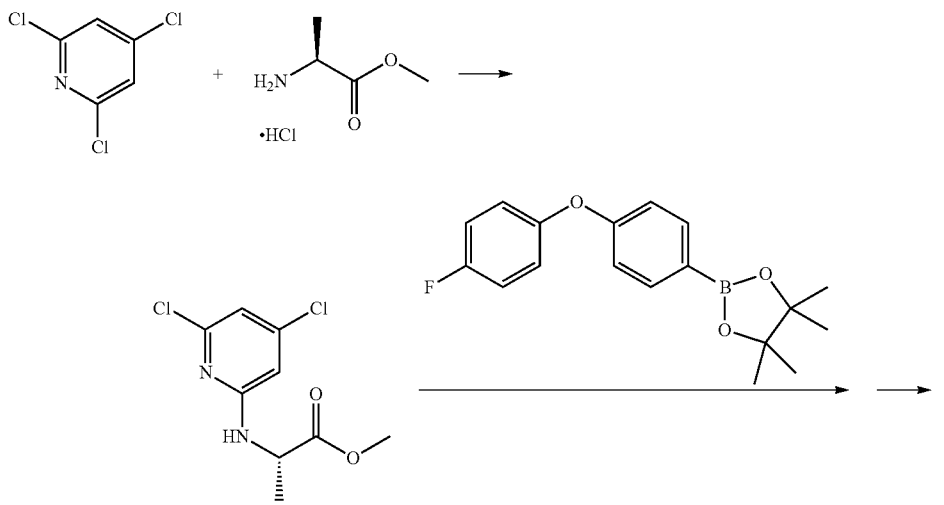

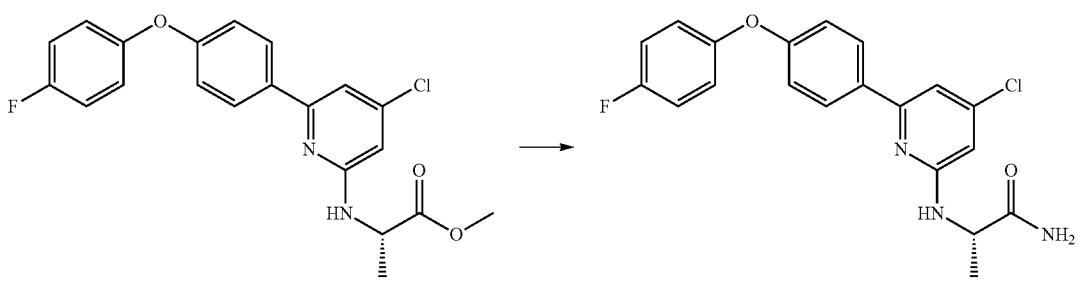

To a solution of the 2,4,6-trichloropyridine (10.694 g, 58.62 mmol) in acetonitrile (100 mL) was added (S)-methyl 2-aminopropanoate hydrochloride (8.198 g, 58.73 mmol) and iPr₂NEt (22.5 mL, 129 mmol). The mixture was heated at reflux for 4 days then additional (S)-methyl 2-aminopropanoate hydrochloride (8.184 g, 58.63 mmol) and iPr₂NEt (10.2 mL, 58.6 mmol) were added. Heating was continued for 5 more days then additional (S)-methyl 2-aminopropanoate hydrochloride (8.191 g, 58.68 mmol) and iPr₂NEt (20 mL, 115 mmol) was added. Heating was continued for 5 more days then the reaction was cooled. The reaction was concentrated in vacuo and the residue partitioned between 250 mL EtOAc and 100 mL water to give a gelatinous precipitate. The precipitate was filtered and rinsed with additional EtOAc. The organic filtrate was isolated and washed once with 100 mL brine. The filter cake containing the gelatinous precipitate was washed with MeOH and these washings were combined with the other portion of organic filtrate and evaporated in vacuo. This residue was dissolved in DCM, dried with MgSO₄, filtered and evaporated in vacuo. The residue was chromatographed over silica gel with 0-50% EtOAc in hexanes. The isomer fractions were isolated and evaporated in vacuo to give (S)-methyl 2-((4,6-dichloropyridin-2-yl)amino)propanoate as a pale tan solid (3.582 g, 14.38 mmol, 25% yield). LC/MS: m/z=249.2 [M+H]⁺.

To a mixture of (S)-methyl 2-((4,6-dichloropyridin-2-yl)amino)propanoate (1.245 g, 5.00 mmol) in dioxane (25 mL) was added 2-(4-(4-fluorophenoxy)phenyl)-4,4,5,5-tetramethyl-1,3,2-dioxaborolane (1.571 g, 5.00 mmol), 2M aqueous Na₂CO₃ (5.0 mL, 10 mmol), and PdCl₂(dppf) (0.218 g, 0.267 mmol). The reaction vessel was flushed with argon, sealed, and heated at 80° C. overnight. After cooling, the reaction mixture was evaporated in vacuo and the residue chromatographed over silica gel with 0-30% EtOAc in hexanes. The product fractions were evaporated in vacuo to give semi-pure (S)-methyl 2-((4-chloro-6-(4-(4-fluorophenoxy)phenyl)pyridin-2-yl)amino)propanoate which was carried on as-is.

To the semi-pure (S)-methyl 2-((4-chloro-6-(4-(4-fluorophenoxy)phenyl)pyridin-2-yl)amino)propanoate (approximately 5.0 mmol) was added 7M NH₃ in MeOH (25 mL, 175 mmol) in a pressure reaction vessel. The vessel was sealed and heated at 50° C. for 3 days then at 80° C. for 2 additional days. After cooling, the reaction mixture was evaporated in vacuo and the residue chromatographed over silica gel with 25-50% acetone in hexanes. The product fractions were evaporated in vacuo to give nearly pure (S)-2-((4-chloro-6-(4-(4-fluorophenoxy)phenyl)pyridin-2-yl)amino)propanamide as an oil. 1.126 g of this material was reserved for additional reactions and 0.109 g was further purified via reverse-phase chromatography with a 40-100% acetonitrile in water (+0.1% TFA) gradient. The product fractions were pooled and lyophilized to give pure (S)-2-((4-chloro-6-(4-(4-fluorophenoxy)phenyl)pyridin-2-yl)amino)propanamide (Compound 79) as the trifluoroacetate salt (0.073 g). LC/MS: m/z=386.1 [M+H]⁺, ¹H NMR (400 MHz, DMSO-d₆): 8.08 (2H, d, J=8.8 Hz), 7.43 (1H, s), 7.31-7.23 (2H, m), 7.17-7.11 (3H, m), ~7.0 (1H, v. broad s), 6.99 (2H, d, J=8.6 Hz), 6.94 (1H, s), 6.58 (1H, d, J=1.3 Hz), 4.43-4.35 (1H, m), 1.33 (3H, d, J=7.0 Hz).

Example 21

Synthesis of (S)-2-((1-amino-1-oxopropan-2-yl)amino)-6-(4-(4-fluorophenoxy)phenyl)isonicotinamide Scheme 37

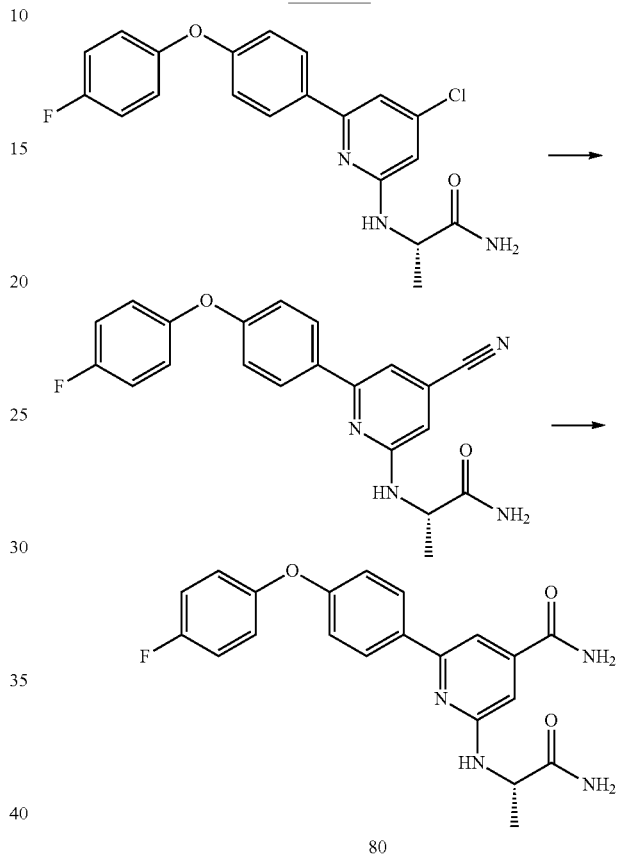

80

To a solution of (S)-2-((4-chloro-6-(4-(4-fluorophenoxy)phenyl)pyridin-2-yl)amino)propanamide (0.624 g, 1.62 mmol) in DMF (10 mL) was added Zn(CN)₂ (0.115 g, 0.98 mmol), Zn powder (0.027 g, 0.41 mmol, <150 μm), and PdCl₂(dppf) (0.068 g, 0.083 mmol). The reaction vessel was flushed with argon, sealed, and heated at 120° C. overnight. After cooling, the reaction mixture was evaporated in vacuo and the residue chromatographed over silica gel with 25-75% acetone in hexanes. The product fractions were evaporated in vacuo to give (S)-2-((4-cyano-6-(4-(4-fluorophenoxy)phenyl)pyridin-2-yl)amino)propanamide as a tan-orange solid (0.541 g, 1.44 mmol, 89% yield). LC/MS: m/z=377.2 [M+H]⁺.

To a suspension of (S)-2-((4-cyano-6-(4-(4-fluorophenoxy)phenyl)pyridin-2-yl)amino)propanamide (0.541 g, 1.44 mmol) in EtOH (5 mL) and water (5 mL) was added PtH(PMe₂O)₂H(PMe₂OH) (spatula tip amount). The reaction vessel was flushed with argon, sealed, and heated at 100° C. overnight. After cooling, the reaction mixture was evaporated in vacuo. The residue was dissolved in MeOH and filtered over a nylon disk and again evaporated in vacuo. The residue was chromatographed over silica gel with 75-100% acetone in hexanes. The product fractions were isolated and evaporated in vacuo. The resulting oil was triturated with 5 mL 10% EtOAc/hexanes, filtered and dried under vacuum at 40° C. to give (S)-2-((1-amino-1-oxopropan-2-yl)amino)-6-(4-(4-fluorophenoxy)phenyl)isonicotinamide (Compound 80) as a light yellow powder (0.361 g, 0.915 mmol, 64% yield). LC/MS: m/z=395.1 [M+H]$^+$, $^1$H NMR (400 MHz, DMSO-d$_6$): 8.11 (2H, d, J=8.6 Hz), 8.08 (1H, s), 7.54 (1H, s), 7.45 (1H, s), 7.36 (1H, s), 7.30-7.23 (2H, m), 7.17-7.10 (2H, m), 7.03 (2H, d, J=8.8 Hz), 6.95 (1H, br d, J=6.8 Hz), 6.92-6.88 (2H, m), 4.43-4.34 (1H, m), 1.34 (3H, d, J=7.0 Hz).

Example 22

Synthesis of (E)-N-(6-(4-(4-fluorophenoxy)phenyl)pyridin-2-yl)-2-phenylethenesulfonamide In a 50-mL vial with a screw-top septum, 6-(4-(4-fluorophenoxy)phenyl)pyridin-2-amine (1.5 g, 5.36 mmol) was dissolved in pyridine (4 mL) and cooled in an ice bath. To the solution was added 2-phenylethenesulfonyl chloride (Aldrich, 1.6 g, 8 mmol) dissolved in pyridine (3 mL). The reaction mixture was stirred at room temperature for 18 h, the precipitate was collected by vacuum filtration, and the filter cake was washed with 20 mL cold methanol to give (E)-N-(6-(4-(4-fluorophenoxy)phenyl)pyridin-2-yl)-2-phenylethenesulfonamide (Compound 97) (907 mg, white solid). $^1$H NMR (400 MHz, (CD$_3$)$_2$SO): 10.94-10.88 (1H, m), 8.05-7.97 (2H, m), 7.79-7.66 (4H, m), 7.56-7.45 (2H, m), 7.43-7.33 (3H, m), 7.32-7.24 (2H, s), 7.16-7.08 (2H, m), 6.99-6.92 (2H, m), 6.91-6.84 (1H, m). LCMS: m/z=447 [M+H$^+$]$^+$.

Example 23

Synthesis of 2S,3S)—N-(6-(4-(4-fluorophenoxy)phenyl)pyridin-2-yl)-3-hydroxy-2-(2-hydroxyacetamido)butanamide

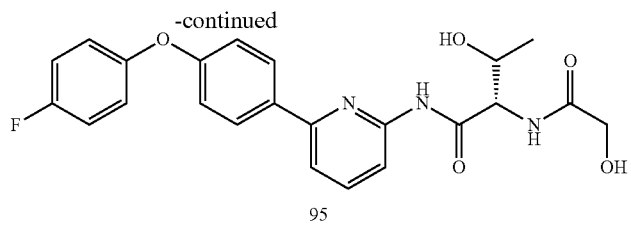

95

In similar fashion shown in Scheme 32 of EXAMPLE 16, a mixture of Boc-Thr-OH (purchased from Sigma-Aldrich, 219 mg, 1.0 mmol) and HATU (purchased from GenScript Corporation, 606 mg, 1.60 mmol) in a mixture of THF/DCM (10 mL) was stirred for 1 h and compound 2 (280 mg, 1.0 mmol) was added thereto. The reaction mixture was stirred overnight at room temperature. After the work-up, the residue was purified by column chromatography (silica gel, 30% EtOAc in hexane) to give ((S)-1-{6-[4-(4-fluoro-phenoxy)-phenyl]-pyridin-2-ylcarbamoyl}-2-hydroxy-propyl)-carbamic acid tert-butyl ester (Compound 109) (392 mg, 81.5% yield). Rf=0.6, LC/MS: m/z=482.1 [M+H]$^+$.

To compound 109 (392 mg, 0.81 mmol) in dry dioxane (3 mL) was added 4.0N HCl in dioxane (2 mL, 8.1 mmol) at 0° C. The reaction mixture was stirred for 2 h at room temperature to give (S)-2-amino-N-{6-[4-(4-fluoro-phenoxy)-phenyl]-pridin-2-yl}-3-hydroxy-propionamide (Compound 110) as the HCl salt (312 mg, 92% yield) which was used for the next step without further purification.

(2S,3S)—N-(6-(4-(4-fluorophenoxy)phenyl)pyridin-2-yl)-3-hydroxy-2-amino-butanamide (as the HCl salt) (194 mg, 0.47 mmol) was treated with glycolic acid (35.7 mg, 0.47 mmol) in the presence of HATU (90.7 mg, 0.47 mmol), DIEA (0.17 mL, 0.93 mmol) in a mixture of DCM/THF (5 mL). The mixture was stirred overnight at room temperature. After the work-up, the oily residue was purified by preparative TLC to give (2S,3S)—N-(6-(4-(4-fluorophenoxy)phenyl)pyridin-2-yl)-3-hydroxy-2-(2-hydroxyacetamido)butanamide (Compound 95) (98 mg, 48%). $^1$H NMR (400 MHz, CD$_3$OD): 8.07 (3H, d, J=9.00 Hz), 7.85 (1H, t, J=7.99 Hz), 7.60 (1H, d, J=7.90 Hz), 7.01-7.19 (6H, m), 4.63 (1H, br), 4.32-4.40 (1H, m), 4.11 (2H, s), 1.27 (3H, d, J=6.39 Hz). LC/MS: m/z=440.1 [M+H]$^+$.

Example 24

Synthesis of (S)-2-acetamido-N-(4-(4-(4-fluorophenoxy)phenyl)pyridine-2-yl)-3-(1-methyl-1H-imidazol-4-yl)propanamide Scheme 40

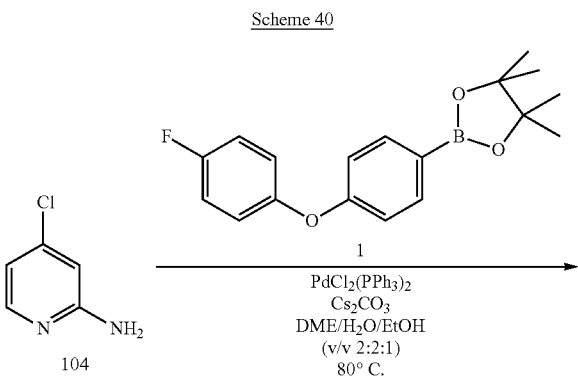

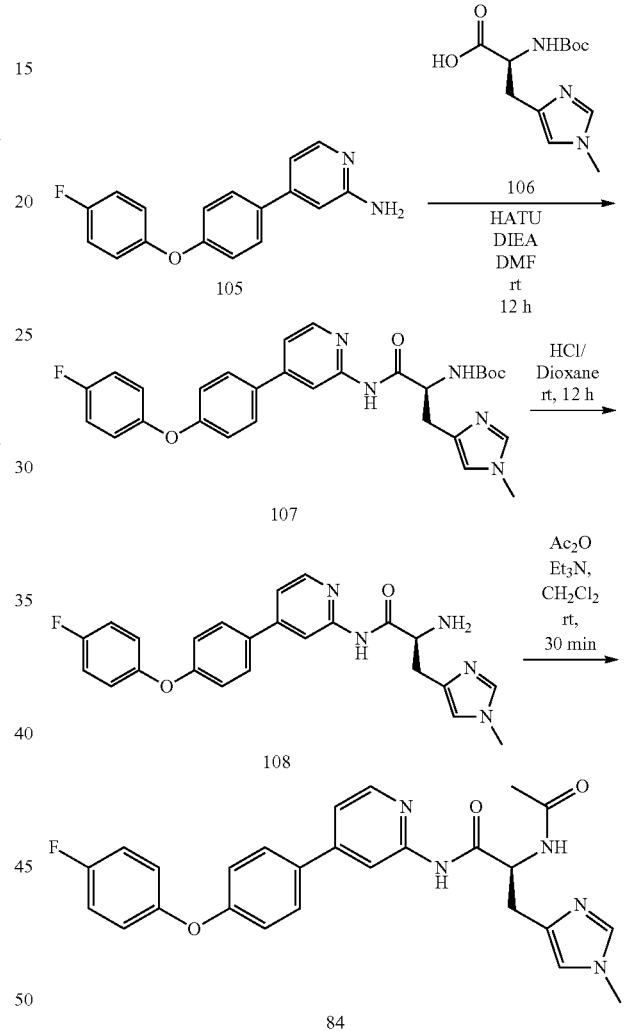

A sealed reaction vessel containing compound 104 (488 g, 3.8 mmol), compound 1 (1 g, 3.18 mmol), PdCl$_2$(PPh$_3$)$_2$ (179 mg, 0.25 mmol), Cs$_2$CO$_3$ (2 g, 6.4 mmol) in a mixed solvent of DME (6 mL), ethanol (3 mL) and water (6 mL) was heated at 80° C. for 2 hours. After cooling to room temperature, the mixture was diluted with EtOAc (20 mL) and brine (20 mL). After separation of the organic layer, the aqueous layer was further extracted with EtOAc (20 mL). The combined organic layers were dried with Na$_2$SO$_4$, filtered, and concentrated. The resulting residue was purified on Combiflash (40 g silica gel, 0-100% EtOAc/Hexane) to give compound 105 as a brown solid (338 mg, 38%). A mixture of compound 105 (338 mg, 1.2 mmol), compound 106 (260 mg, 1.2 mmol), HATU (454 mg, 1.2 mmol), and DIEA (0.663 mL, 3.6 mmol) in DMF (5 mL) was stirred at room temperature for 12 h. The mixture was loaded on silica gel and purified with Combiflash (5-10% MeOH/CH$_2$Cl$_2$) to give compound 107 in low yield. A solution of compound 107 in EtOAc was treated with 4 N HCl/dioxane at room temperature for 12 h and compound 108 was obtained by pipetting off the clear solution. Compound 108 was suspended in CH$_2$Cl$_2$ (1 mL), and to the suspension was added Ac$_2$O (0.05 mL) and Et$_3$N (0.5 mL). The mixture was stirred for 30 min, and then concentrated to dryness. The residue was purified with reverse phase (C-18) column on Combiflash to give (S)-2-acetamido-N-(4-(4-(4-fluorophenoxy)phenyl)pyridine-2-yl)-3-(1-methyl-1H-imidazol-4-yl)propanamide (Compound 84) as the TFA salt (10 mg). $^1$H NMR (400 MHz, CD$_3$OD): 8.82 (1H, s), 8.36 (1H, dd, J=2.4, 5.6 Hz), 8.30 (1H, s), 7.78 (2H, m), 7.54 (1H, m), 7.42 (1H, s), 7.21-7.10 (6H, m), 4.93 (1H, m), 3.91 (3H, s), 3.38 (1H, m), 3.15 (1H, m), 2.06 (3H, s). LC/MS: m/z=474 [M+H]$^+$.

Example 25

Synthesis of (R)-2-(3-(6-(4-(4-fluorophenoxy)phenyl)pyridin-2-yl)ureido)succinamide was added to the reaction mixture dropwise and then stirred at room temperature for 14 h. The reaction mixture was diluted with DCM and 1N HCl and the organic layer was collected, washed with brine, dried over Na$_2$SO$_4$ and concentrated under rotary evaporation. The crude product was subjected to flash column chromatography on silica gel (DCM/MeOH) to give compound 112 as white solid (100 mg, yield 62%).

Compound 112 (100 mg, 0.22 mmol) was dissolved in 1 mL of DCM and 5 mL of 7N NH$_3$ in MeOH was added. The resulting mixture was stirred at room temperature for 14 h. The solvent was removed under rotary evaporation and the residue was subjected to flash column chromatography on silica gel (DCM/MeOH) to give (R)-2-(3-(6-(4-(4-fluorophenoxy)phenyl)pyridin-2-yl)ureido)succinamide (Compound 102) as white solid (70 mg, yield 73%). $^1$H NMR (400 MHz, DMSO-d$_6$): 9.30 (1H, s), 8.55 (1H, br), 8.10 (2H, m), 7.70 (1H, m), 7.10-7.50 (11H, m), 6.85 (1H, s), 4.55 (1H, m), 2.55 (2H, m). LC/MS: m/z=438 [M+H]$^+$.

Example 26

The following Compounds of the Invention were prepared using the methodology described in the EXAMPLES above:

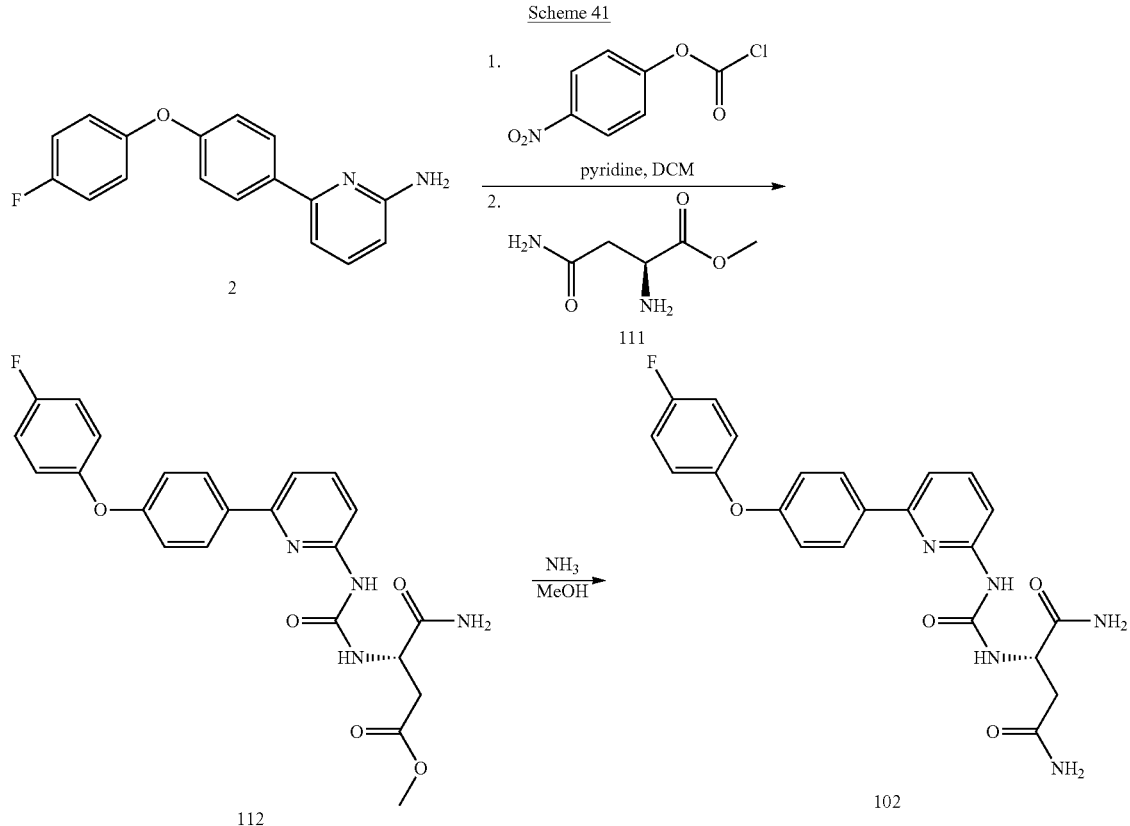

A solution of compound 2 (100 mg, 0.36 mmol) in DCM (5 mL) was slowly added to a DCM (5 mL) solution containing 4-nitro phenoxy chloroformate (72 mg, 0.36 mmol) and pyridine (57 mg, 0.72 mmol) cooled in an ice bath. After the addition, the ice bath was removed and the reaction mixture was stirred at room temperature for 2 h. A DCM solution (5 mL) containing the amine ester compound III (53 mg, 0.36 mmol) and pyridine (29 mg, 0.36 mmol)

(S)-2-acetamido-N-(6-(4-(4-fluorophenoxy)phenyl)pyridin-2-yl)-3-(1H-imidazol-4-yl)propanamide (Compound 32): $^1$H NMR (400 MHz, DMSO-d$_6$): 11.60 (1H, br), 10.35 (1H, br), 8.20 (1H, br), 8.10 (2H, d, J=8.2 Hz), 7.90 (1H, d, J=8.2 Hz), 7.77 (1H, t, J=8.2 Hz), 7.57 (1H, d, J=8.2 Hz), 7.47 (1H, s), 7.20 (2H, t, J=8.2 Hz), 7.09 (2H, m), 7.01 (2H, d, J=8.2 Hz), 6.78 (1H, br), 4.68 (1H, s), 2.70-3.01 (2H, m), 1.82 (3H, s). LC/MS: m/z=460 [M+H]$^+$.

(S)-2-acetamido-N-(6-(4-(4-fluorophenoxy)phenyl)pyridin-2-yl)-3-(1-methyl-1H-imidazol-4-yl)propanamide (Compound 77): $^1$H NMR (400 MHz, CD$_3$OD): 7.87-7.99 (3H, m), 7.65 (1H, m), 7.40 (1H, m), 6.85-7.05 (6H, m), 6.80 (1H, s), 4.70 (1H, s), 3.51 (3H, s), 2.80-3.10 (2H, m), 1.82 (3H, s). LC/MS: m/z=474 [M+H]$^+$.

(R)—N-(6-(4-(4-fluorophenoxy)phenyl)pyridin-2-yl)-2-(2-hydroxy-2-methylpropanamido)-3-(1-methyl-1H-imidazol-4-yl)propanamide (Compound 78): $^1$H NMR (400 MHz, CD$_3$OD): δ 8.70 (1H, s), 7.90 (3H, m), 7.71 (1H, m), 7.50 (1H, m), 7.25 (1H, s), 6.90-7.10 (6H, m), 3.80 (3H, s), 2.90-3.20 (3H, m), 1.21 (6H, s). LC/MS: m/z=518 [M+H]$^+$ (S)—N-(6-(4-(4-fluorophenoxy)phenyl)pyridin-2-yl)-3-(1-methyl-1H-imidazol-4-yl)-2-propionamidopropanamide (Compound 81): $^1$H NMR (400 MHz, CD$_3$OD): 7.90 (3H, m), 7.71 (1H, m), 7.50 (1H, m), 7.30-7.55 (2H, m), 6.80-7.10 (6H, m), 6.75 (1H, s), 4.70 (1H, s), 3.55 (3H, s), 2.90-3.20 (2H, m), 1.05 (3H, t, J=8.2 Hz). LC/MS: m/z=488 [M+H]$^+$.

(S)—N-(6-(4-(4-fluorophenoxy)phenyl)pyridin-2-yl)-2-isobutyramido-3-(1-methyl-1H-imidazol-4-yl)propanamide (Compound 82): $^1$H NMR (400 MHz, CD$_3$OD): δ 7.80-8.05 (3H, m), 7.71 (1H, m), 7.50 (1H, m), 7.40 (2H, m), 6.80-7.10 (6H, m), 6.75 (1H, s), 4.70 (1H, s), 3.50 (3H, s), 2.75-3.00 (2H, m), 2.40 (1H, m), 1.01 (6H, m). LC/MS: m/z=502 [M+H]$^+$.

(S)—N-(6-(4-(4-fluorophenoxy)phenyl)pyridin-2-yl)-3-(1-methyl-1H-imidazol-4-yl)-2-pivalamidopropanamide (Compound 83): $^1$H NMR (400 MHz, CD$_3$OD): 7.80-8.05 (3H, m), 7.65 (1H, m), 7.40 (2H, m), 6.80-7.10 (6H, m), 6.75 (1H, s), 4.70 (1H, s), 3.55 (3H, s), 2.75-3.05 (2H, m), 1.11 (9H, s). LC/MS: m/z=516 [M+H]$^+$.

(S)—N-(1-((6-(4-(4-fluorophenoxy)phenyl)pyridin-2-yl)amino)-3-(1-methyl-1H-imidazol-4-yl)-1-oxopropan-2-yl)cyclopropanecarboxamide (Compound 85): $^1$H NMR (400 MHz, CD$_3$OD): 7.80-8.05 (3H, m), 7.70 (1H, m), 7.40 (2H, m), 6.80-7.10 (6H, m), 6.75 (1H, s), 4.70 (1H, s), 3.50 (3H, s), 2.75-3.00 (2H, m), 1.55 (1H, m), 0.55-0.85 (4H, m). LC/MS: m/z=500 [M+H]$^+$.

(S)-3,3,3-trifluoro-N-(1-((6-(4-(4-fluorophenoxy)phenyl)pyridin-2-yl)amino)-3-(1-methyl-1H-imidazol-4-yl)-1-oxopropan-2-yl)propanamide (Compound 86): $^1$H NMR (400 MHz, CD$_3$OD): 7.80-8.05 (3H, m), 7.70 (1H, m), 7.40 (2H, m), 6.80-7.10 (6H, m), 6.75 (1H, s), 4.70 (1H, s), 3.50 (3H, s), 2.75-3.25 (4H, m). LC/MS: m/z=542 [M+H]$^+$.

(S)-2-acetamido-N-(6-(4-(4-fluorophenoxy)phenyl)pyridin-2-yl)-3-(1-methyl-1H-imidazol-5-yl)propanamide (Compound 87): $^1$H NMR (400 MHz, CD$_3$OD): 8.90 (1H, s), 8.10 (3H, m), 7.80 (1H, m), 7.50 (1H, m), 7.20 (1H, s), 6.95-7.23 (6H, m), 5.05 (1H, m), 4.00 (3H, s), 3.10-3.40 (2H, m), 2.05 (3H, s). LC/MS: m/z=474 [M+H]$^+$ (R)—N-(1-((6-(4-(4-fluorophenoxy)phenyl)pyridin-2-yl)amino)-3-(1-methyl-1H-imidazol-4-yl)-1-oxopropan-2-yl)-4-(trifluoromethyl)benzamide (Compound 88): $^1$H NMR (400 MHz, CD$_3$OD): 8.65 (1H, s), 7.85-8.05 (5H, m), 7.70 (3H, m), 7.50 (1H, m), 7.30 (1H, s), 6.80-7.10 (6H, m), 5.05 (1H, m), 3.80 (3H, s), 3.20-3.45 (2H, m). LC/MS: m/z=604 [M+H]$^+$.

(R)-2-acetamido-3-(1-methyl-1H-imidazol-4-yl)-N-(6-(4-((5-(trifluoromethyl)pyridin-2-yl)oxy)phenyl)pyridin-2-yl)propanamide (Compound 94): $^1$H NMR (400 MHz, CD$_3$OD): 8.80 (1H, s), 8.40 (1H, s), 7.95-8.15 (4H, m), 7.80 (1H, m) 7.60 (1H, m), 7.35 (1H, s), 7.10-7.30 (3H, m), 4.95 (1H, m), 3.90 (3H, s), 3.05-3.30 (2H, m), 2.10 (3H, s). LC/MS: m/z=525 [M+H]$^+$.

N-(6-(4-(4-fluorophenoxy)phenyl)pyridin-2-yl)-1-methyl-1H-benzo[d]imidazole-6-carboxamide (Compound 98): $^1$H NMR (400 MHz, DMSO-d$_6$): 10.6 (1H, s), 8.41 (1H, m), 8.28 (1H, m), 8.12 (2H, m), 8.05 (1H, d, J=8.4 Hz), 7.95 (1H, dd, J=2, 8.8 Hz), 7.84 (1H, t, J=8 Hz), 7.64 (2H, m), 7.21 (2H, m), 7.10 (2H, m), 7.02 (2H, m), 3.84 (3H, s). LC/MS: m/z=439[M+H]$^+$.

(S)-2-(3-(6-(4-(4-fluorophenoxy)phenyl)pyridin-2-yl)ureido)-3-(1-methyl-1H-imidazol-4-yl)propanamide (Compound 99): $^1$H NMR (400 MHz, CD$_3$OD): 7.80 (2H, m), 7.55 (1H, m), 7.22 (2H, m), 6.80-7.05 (6H, m), 6.70 (1H, m), 6.52 (1H, s), 4.62 (1H, m), 3.32 (3H, s), 3.15 (3H, s), 2.90 (2H, m). LC/MS: m/z=475 [M+H]$^+$.

(S)-methyl 2-(3-(6-(4-(4-fluorophenoxy)phenyl)pyridin-2-yl)ureido)-3-(1-methyl-1H-imidazol-4-yl)propanoate (Compound 100): $^1$H NMR (400 MHz, CD$_3$OD): δ 7.80 (2H, m), 7.60 (1H, m), 7.25 (1H, m), 6.80-7.10 (6H, m), 6.75 (1H, m), 6.52 (1H, s), 4.62 (1H, m), 3.32 (3H, s), 3.15 (3H, s), 2.90 (2H, m). LC/MS: m/z=490 [M+H]$^+$.

(R)-2-(3-(6-(4-(4-fluorophenoxy)phenyl)pyridin-2-yl)ureido)-3-(1H-indol-2-yl)propanamide (Compound 101): $^1$H NMR (400 MHz, DMSO-d$_6$): 10.65 (1H, s), 9.20 (1H, s), 8.70 (1H, br), 7.80 (2H, m), 7.40-7.70 (3H, m), 7.35 (1H, m), 7.15-7.25 (3H, m), 7.00-7.15 (4H, m), 6.95 (2H, m), 6.70 (3H, m), 4.50 (1H, m), 2.70-2.90 (2H, m). LC/MS: m/z=510 [M+H]$^+$.

(R)-2-(3-(6-(4-(4-fluorophenoxy)phenyl)pyridin-2-yl)ureido)-3-(1H-imidazol-5-yl)propanamide (Compound 103): $^1$H NMR (400 MHz, DMSO-d$_6$): 11.62 (1H, s), 9.40 (1H, s), 8.70 (1H, br), 8.01 (2H, s), 7.70 (1H, m), 7.50 (3H, m), 6.95-7.25 (8H, m), 6.70 (1H, m), 4.50 (1H, m), 2.60-3.00 (2H, m). LC/MS: m/z=461 [M+H]$^+$.

Example 27

Representative Compounds of the Invention have been tested in the FLIPR® or FLIPR$^{TETRA}$® sodium dye assay with KCl assay and/or electrophysiology (EP) assay for sodium channel blocking activity, which is described in detail above. Representative values are presented in TABLE 4.

TABLE 4

| Evaluation of compounds as sodium channel (Na$_v$) blockers | | | |
|---|---|---|---|
| Compound | Na$_v$1.7 Activity (µM) | | |
| Example No. | FLIPR assay IC$_{50}$ (µM) ± SEM | EP assay K$_i$ | EP assay K$_r$ |
| 3 | 0.042 ± 0.02 | 0.194 ± 0.070 | |
| 4 | 0.064 ± 0.02 | 0.130 ± 0.030 | |
| 7 | 0.067 ± 0.007 | 0.059 ± 0.010 | 18.000 ± 1.000 |
| 8 | 0.036 ± 0.004 | | |
| 9 | 0.091 ± 0.02 | | |
| 10 | 0.091 ± 0.03 | | |
| 11 | 0.086 ± 0.02 | | |
| 12 | 0.096 ± 0.004 | 0.257 ± 0.060 | 5.063 |
| 13 | 0.075 ± 0.017 | 0.075 ± 0.020 | 10.2000 ± 0.200 |
| 15 | 0.26 ± 0.07 | | |
| 17 | 0.094 ± 0.03 | | |
| 18 | 1.5 ± 0.3 | | |
| 24 | 2.9 ± 0.8 | | |
| 26 | >20 | | |
| 27 | 0.34 ± 0.05 | | |
| 28 | 0.22 ± 0.07 | | |
| 29 | 0.32 ± 0.05 | | |
| 31 | 0.18 ± 0.02 | | |
| 32 | 0.086 ± 0.02 | 0.025 ± 0.000 | 0.580 ± 0.100 |
| 33 | 0.11 ± 0.02 | 0.206 ± 0.040 | 5.309 ± 0.560 |

TABLE 4-continued

Evaluation of compounds as sodium channel (Na$_v$) blockers

| Compound | Na$_v$1.7 Activity (μM) | | |
|---|---|---|---|
| Example No. | FLIPR assay IC$_{50}$ (μM) ± SEM | EP assay K$_i$ | EP assay K$_r$ |
| 34 | 0.58 ± 0.05 | | |
| 35 | 0.13 ± 0.02 | | |
| 36 | 0.14 ± 0.01 | | |
| 37 | 0.12 ± 0.03 | | |
| 38 | 0.14 ± 0.03 | 0.019 ± 0.010 | 1.196 ± 0.310 |
| 40 | 0.13 ± 0.03 | | |
| 41 | 0.066 ± 0.008 | | |
| 44 | 0.059 ± 0.12 | | |
| 45 | 0.30 ± 0.07 | | |
| 50 | 2.24 ± 0.15 | | |
| 53 | 7.34 ± 0.68 | | |
| 54 | 0.07 ± 0.02 | | |
| 55 | 0.06 ± 0.006 | | |
| 56 | 0.14 ± 0.05 | 0.195 ± 0.070 | 32.235 ± 8.380 |
| 57 | 0.16 ± 0.03 | | |
| 58 | 0.11 ± 0.04 | | |
| 59 | 0.31 ± 0.07 | | |
| 60 | 0.46 ± 0.08 | 0.113 ± 0.050 | 4.944 ± 0.810 |
| 61 | 0.12 ± 0.05 | | |
| 62 | 1.34 ± 0.21 | | |
| 63 | 1.15 ± 0.07 | | |
| 64 | 0.12 ± 0.01 | | |
| 65 | >20 | | |
| 66 | 5.0 ± 0.88 | 1.374 ± 0.170 | |
| 70 | 0.27 ± 0.032 | 0.046 ± 0.000 | 0.803 ± 0.200 |
| 72 | 0.074 0.003 | 0.143 ± 0.030 | 8.914 ± 1.210 |
| 73 | 0.358 ± 0.020 | | |
| 74 | 0.678 ± 0.043 | | |
| 75 | 0.609 ± 0.027 | | |
| 76 | >20 | | |
| 77 | 0.111 ± 0.007 | | |
| 78 | 0.608 ± 0.075 | | |
| 79 | 0.276 ± 0.079 | | |
| 80 | 1.341 ± 0.277 | | |
| 81 | 0.064 ± 0.010 | | |
| 82 | 0.046 ± 0.005 | | |
| 83 | 0.020 ± 0.002 | | |
| 84 | 0.290 ± 0.025 | | |
| 85 | 0.111 ± 0.011 | | |
| 86 | 0.084 ± 0.007 | | |
| 87 | 0.140 ± 0.002 | | |
| 88 | 0.159 ± 0.024 | | |
| 89 | 0.134 ± 0.018 | | |
| 90 | 0.070 ± 0.012 | | |
| 91 | 0.275 ± 0.030 | | |
| 92 | 0.198 ± 0.053 | | |
| 93 | 0.113 ± 0.027 | | |
| 94 | 0.335 ± 0.068 | | |
| 95 | 0.172 ± 0.016 | | |
| 96 | >20 | | |
| 97 | 1.440 ± 0.194 | | |
| 98 | >20 | | |
| 99 | 0.667 ± 0.162 | | |
| 100 | 0.226 ± 0.020 | | |
| 101 | 4.021 ± 0.366 | | |
| 102 | 0.613 ± 0.029 | | |
| 103 | 1.619 ± 0.226 | | |

Having now fully described this invention, it will be understood by those of ordinary skill in the art that the same can be performed within a wide and equivalent range of conditions, formulations and other parameters without affecting the scope of the invention or any embodiment thereof.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

All patents and publications cited herein are fully incorporated by reference herein in their entirety.

What is claimed is:

1. A compound of Formula III:

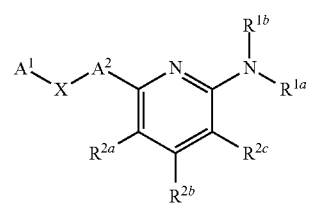

or a pharmaceutically acceptable salt or solvate thereof, wherein:

$A^1$-X-$A^2$- is:

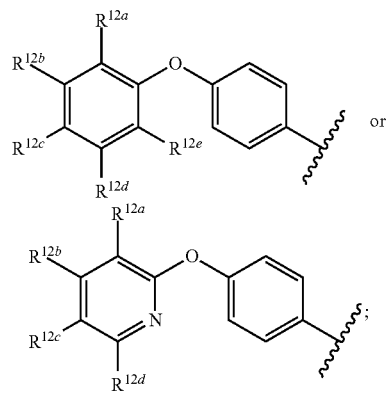

Wherein
$R^{12a}$ and $R^{12e}$ are hydrogen;
$R^{12b}$, $R^{12c}$, and $R^{12d}$, which can be identical or different, are selected from the group consisting of:
  a) hydrogen;
  b) halo;
  c) cyano; and
  d) haloalkyl;
$R^{1a}$ is selected from the group consisting of:
  a) (heterocyclo)alkyl;
  b) heterocyclo optionally substituted by carboxyalkyl;
  c) —SO$_2$R$^6$; and
  d) —COR$^7$;
$R^6$ is selected from the group consisting of:
  a) alkyl;
  b) cycloalkyl;
  c) heteroaryl optionally substituted by alkyl;
  d) amino; and
  e) alkenyl optionally substituted by aryl;
$R^7$ is selected from the group consisting of:
  a) heteroaryl optionally substituted by one or two substituents independently selected from the group of hydroxy, alkyl, amino, alkylamino, and dialkylamino;

b)

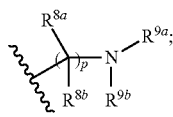

and
c) hydroxyalkyl;
wherein:
p is 0, 1, or 2;
each $R^{8a}$ and $R^{8b}$, which can be identical or different, are selected from the group consisting of:
a) hydrogen;
b) alkyl;
c) aralkyl;
d) (heteroaryl)alkyl;
e) (carboxamido)alkyl;
f) hydroxyalkyl;
g) aryl optionally substituted by alkyl;
h) heteroaryl optionally substituted by alkyl; and
i) carboxamido;
$R^{9a}$ is selected from the group consisting of:
a) hydrogen;
b) alkyl optionally substituted by one or two substituents independently selected from the group consisting of (alkoxy)carbonyl, carboxamido, and heteroaryl, wherein said heteroaryl is further optionally substituted by alkyl;
c) —$COR^{10}$;
d) —$SO_2R^{11}$; and
e) —$R^{25}$;
wherein:
$R^{19}$ is selected from the group consisting of:
a) alkyl;
b) alkoxyalkyl;
c) hydroxyalkyl;
d) heteroalkyl;
e) cycloalkyl;
f) aryl optionally substituted by alkyl or haloalkyl;
g) heterocyclo optionally substituted by carbonylalkyl;
h) heteroaryl optionally substituted by alkyl;
i) amino;
j) alkylamino;
k) dialkylamino;
l) alkoxy; and
m) haloalkyl
$R^{11}$ is alkyl;
$R^{9b}$ is selected from the group consisting of hydrogen and alkyl; or
$R^{1b}$ is selected from the group consisting of:
a) hydrogen; and
b) hydroxyalkyl; or
$R^{1a}$ and $R^{1b}$ taken together with the nitrogen atom to which they are attached form a 3- to 8-membered heterocyclo optionally substituted by one or two substituents independently selected from the group of hydroxy, carboxy, and carboxyalkyl;
$R^{2a}$, $R^{2b}$, and $R^{2c}$, which can be identical or different, are selected from the group consisting of:
a) hydrogen;
b) halo;
c) haloalkyl;
d) hydroxyalkyl; and
e) carboxamido;

$R^{25}$ is:

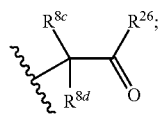

$R^{8c}$ and $R^{8d}$, which can be identical or different, are selected from the group consisting of:
a) hydrogen;
b) alkyl;
c) aralkyl;
d) (heterocyclo)alkyl;
e) (heteroaryl)alkyl; and
i) (carboxamido)alkyl;
$R^{26}$ is selected from the group consisting of:
a) hydroxy;
b) alkoxy;
c) amino;
d) alkylamino; and
e) dialkylamino.

2. The compound of claim 1, wherein $R^{1a}$ is —$SO_2R^6$, or a pharmaceutically acceptable salt or solvate thereof.

3. The compound of claim 1, wherein $R^{1a}$ is —$COR^7$ and $R^7$ is:

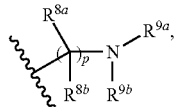

and wherein p is 1 or 2, or a pharmaceutically acceptable salt or solvate thereof.

4. The compound of claim 1 having Formula V:

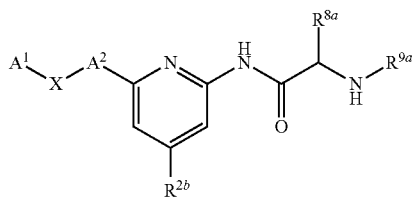

or a pharmaceutically acceptable salt or solvate thereof.

5. The compound of claim 4, wherein $R^{9a}$ is —$COR^{10}$, or a pharmaceutically acceptable salt or solvate thereof.

6. The compound of claim 1 having Formula IX:

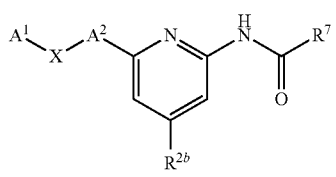

wherein $R^7$ is hydroxyalkyl, or a pharmaceutically acceptable salt or solvate thereof.

7. The compound of claim 1 having Formula X:

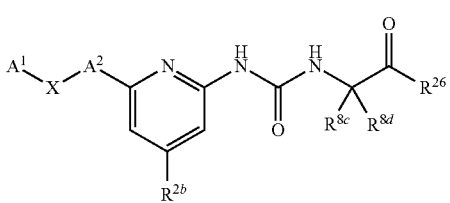

or a pharmaceutically acceptable salt or solvate thereof.

8. The compound of claim 1 wherein $A^1$-X-$A^2$- is:

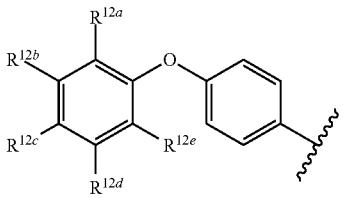

wherein:
$R^{12a}$, and $R^{12e}$ are hydrogen;
$R^{12b}$, $R^{12c}$, and $R^{12d}$, which can be identical or different, are selected from the group consisting of:
  a) hydrogen;
  b) halo;
  c) cyano; and
  d) haloalkyl;
or a pharmaceutically acceptable salt or solvate thereof.

9. A compound selected from the group consisting of:
(S)-2-acetamido-N-(6-(4-(4-fluorophenoxy)phenyl)pyridin-2-yl)-4-methylpentanamide;
(S)-2-acetamido-N-(6-(4-(4-fluorophenoxy)phenyl)pyridin-2-yl)-3-phenylpropanamide;
(S)—N-(1-((6-(4-(4-fluorophenoxy)phenyl)pyridin-2-yl)amino)-4-methyl-1-oxopentan-2-yl)picolinamide;
(S)—N-(1-((6-(4-(4-fluorophenoxy)phenyl)pyridin-2-yl)amino)-4-methyl-1-oxopentan-2-yl)cyclopropanecarboxamide;
(S)—N-(6-(4-(4-fluorophenoxy)phenyl)pyridin-2-yl)-2-(2-(2-methoxyethoxy)acetamido)-4-methylpentanamide;
(S)—N-(1-((6-(4-(4-fluorophenoxy)phenyl)pyridin-2-yl)amino)-4-methyl-1-oxopentan-2-yl)nicotinamide;
(S)—N-(6-(4-(4-fluorophenoxy)phenyl)pyridin-2-yl)-2-(3-isopropylureido)-4-methylpentanamide;
(S)—N-(6-(4-(4-fluorophenoxy)phenyl)pyridin-2-yl)-4-methyl-2-ureidopentanamide;
N-(4-chloro-6-(4-(4-fluorophenoxy)phenyl)pyridin-2-yl)methanesulfonamide;
(S)—N-(4-chloro-6-(4-(4-fluorophenoxy)phenyl)pyridin-2-yl)-N-(2,3-dihydroxypropyl) methanesulfonamide;
N-(4-chloro-6-(4-(4-fluorophenoxy)phenyl)pyridin-2-yl)sulfamide;
(S)—N-(4-(1,2-dihydroxyethyl)-6-(4-(4-fluorophenoxy)phenyl)pyridin-2-yl)methanesulfonamide;
(S)—N-(4-(1,2-dihydroxyethyl)-6-(4-(4-fluorophenoxy)phenyl)pyridin-2-yl)-1-methyl-1H-imidazole-4-sulfonamide;
N-(6-(4-(4-fluorophenoxy)phenyl)pyridin-2-yl)methanesulfonamide;
N-(6-(4-(4-fluorophenoxy)phenyl)pyridin-2-yl)cyclopropanesulfonamide;
N-(6-(4-(4-fluorophenoxy)phenyl)pyridin-2-yl)-1-methyl-1H-imidazole-4-sulfonamide;
(S)-2-amino-N-(6-(4-(4-fluorophenoxy)phenyl)pyridin-2-yl)-3-(1H-imidazol-4-yl) propanamide;
(S)-2-acetamido-N-(6-(4-(4-fluorophenoxy)phenyl)pyridin-2-yl)-3-(1H-imidazol-4-yl)propanamide;
(S)—N-(1-((6-(4-(4-fluorophenoxy)phenyl)pyridin-2-yl)amino)-3-(1H-imidazol-4-yl)-1-oxopropan-2-yl)cyclopropanecarboxamide;
(S)-1-acetyl-N-(1-((6-(4-(4-fluorophenoxy)phenyl)pyridin-2-yl)amino)-3-(1H-imidazol-4-yl)-1-oxopropan-2-yl)piperidine-4-carboxamide;
(S)—N-(6-(4-(4-fluorophenoxy)phenyl)pyridin-2-yl)-3-(1H-imidazol-4-yl)-2-(2-methoxyacetamido)propanamide;
(S)—N-(6-(4-(4-fluorophenoxy)phenyl)pyridin-2-yl)-2-(2-hydroxyacetamido)-3-(1H-imidazol-4-yl)propanamide;
(S)—N-(6-(4-(4-fluorophenoxy)phenyl)pyridin-2-yl)-2-(2-hydroxy-2-methylpropanamido)-3-(1H-imidazol-4-yl)propanamide;
(S)—N-(6-(4-(4-fluorophenoxy)phenyl)pyridin-2-yl)-3-(1H-imidazol-4-yl)-2-(methylsulfonamido)propanamide;
(S)-tert-butyl(1-amino-4-((6-(4-(4-fluorophenoxy)phenyl)pyridin-2-yl)amino)-1,4-dioxobutan-2-yl)carbamate;
(S)-tert-butyl(4-amino-1-((6-(4-(4-fluorophenoxy)phenyl)pyridin-2-yl)amino)-1,4-dioxobutan-2-yl)carbamate;
N—((S)-1-((4-((S)-1,2-dihydroxyethyl)-6-(4-(4-fluorophenoxy)phenyl)pyridin-2-yl)amino)-4-methyl-1-oxopentan-2-yl)cyclopropanecarboxamide;
N—((S)-1-((4-((S)-1,2-dihydroxyethyl)-6-(4-(4-fluorophenoxy)phenyl)pyridin-2-yl)amino)-4-methyl-1-oxopentan-2-yl)picolinamide;
2-(4-((6-(4-(4-fluorophenoxy)phenyl)pyridin-2-yl)amino)piperidin-1-yl)acetic acid;
1-(4-chloro-6-(4-(4-fluorophenoxy)phenyl)pyridin-2-yl)piperidine-4-carboxylic acid;
(2S,4R)-1-(3-chloro-5-(4-(4-fluorophenoxy)phenyl)pyridin-2-yl)-4-hydroxypyrrolidine-2-carboxylic acid;
(2S,4R)-1-(4-chloro-6-(4-(4-fluorophenoxy)phenyl)pyridin-2-yl)-4-hydroxypyrrolidine-2-carboxylic acid;
1-(2-((4-chloro-6-(4-(4-fluorophenoxy)phenyl)pyridin-2-yl)amino)ethyl)imidazolidin-2-one;
2-amino-N-(6-(4-(4-fluorophenoxy)phenyl)pyridin-2-yl)-6-hydroxypyrimidine-4-carboxamide;
(S)-1-(2-((4-(1,2-dihydroxyethyl)-6-(4-(4-fluorophenoxy)phenyl)pyridin-2-yl)amino)ethyl)imidazolidin-2-one,
pyridine-2-carboxylic acid ((S)-1-{6-[4-(4-fluoro-phenoxy)-phenyl]-pyridin-2-ylcarbamoyl}-2-hydroxy-ethyl)-amide,
cyclopropanecarboxylic acid ((S)-1-{6-[4-(4-fluoro-phenoxy)-phenyl]-pyridin-2-ylcarbamoyl}-2-hydroxy-ethyl)-amide,
N—((S)-1-{6-[4-(4-fluoro-phenoxy)-phenyl]-pyridin-2-ylcarbamoyl}-2-hydroxy-ethyl)-nicotinamide,
N—((S)-1-{6-[4-(4-fluoro-phenoxy)-phenyl]-pyridin-2-ylcarbamoyl}-2-hydroxy-ethyl)-isonicotinamide, 5-methyl-isoxazole-3-carboxylic acid ((S)-1-{6-[4-(4-fluoro-phenoxy)-phenyl]-pyridin-2-ylcarbamoyl}-2-hydroxy-ethyl)-amide,
((S)-1-{6-[4-(4-fluoro-phenoxy)-phenyl]-pyridin-2-ylcarbamoyl}-2-hydroxy-ethyl)-carbamic acid tert-butyl ester,
(S)—N-{6-[4-(4-fluoro-phenoxy)-phenyl]-pyridin-2-yl}-3-hydroxy-2-(2-hydroxy-acetylamino)-propionamide,
(S)—N-{6-[4-(4-fluoro-phenoxy)-phenyl]-pyridin-2-yl}-3-hydroxy-2-ureido-propionamide,
((S)-1-{6-[4-(4-fluoro-phenoxy)-phenyl]-pyridin-2-ylcarbamoyl}-2-pyridin-3-yl-ethyl)-carbamic acid tert-butyl ester,
(S)-2-acetylamino-N-{6-[4-(4-fluoro-phenoxy)-phenyl]-pyridin-2-yl}-3-pyridin-3-yl-propionamide,
(S)-2-acetylamino-N-{6-[4-(4-fluoro-phenoxy)-phenyl]-pyridin-2-yl}-3-hydroxy-butyramide,
(S)-2-amino-N-{6-[4-(4-fluoro-phenoxy)-phenyl]-pridin-2-yl}-3-hydroxy-propionamide, and
(S)-2-amino-N-{6-[4-(4-fluoro-phenoxy)-phenyl]-pyridin-2-yl}-3-pyridin-3-yl-propionamide,
or a pharmaceutically acceptable salt or solvate thereof.

10. A compound selected from the group consisting of:
N-(6-(4-(4-fluorophenoxy)phenyl)pyridin-2-yl)-2,3-dihydroxypropanamide,
N-(6-(4-(4-cyanophenoxy)phenyl)pyridin-2-yl)-2,3-di hydroxypropanamide,
N-(6-(4-(3-cyano-4-(trifluoromethyl)phenoxy)phenyl)pyridin-2-yl)-2,3-dihydroxypropanamide,
N-(6-(4-(4-cyano-3-(trifluoromethyl)phenoxy)phenyl)pyridin-2-yl)-2,3-dihydroxypropanamide,
2,3-dihydroxy-N-(6-(4-(4-(trifluoromethyl)phenoxy)phenyl)pyridin-2-yl) propanamide,
(S)-2-acetamido-N-(6-(4-(4-fluorophenoxy)phenyl)pyridin-2-yl)-3-(1-methyl-1H-imidazol-4-yl)propanamide,
(R)—N-(6-(4-(4-fluorophenoxy)phenyl)pyridin-2-yl)-2-(2-hydroxy-2-methylpropanamido)-3-(1-methyl-1H-imidazol-4-yl)propanamide,
(S)-2-((4-chloro-6-(4-(4-fluorophenoxy)phenyl)pyridin-2-yl)amino) propanamide,
(S)-2-((1-amino-1-oxopropan-2-yl)amino)-6-(4-(4-fluorophenoxy)phenyl) isonicotinamide,
(S)—N-(6-(4-(4-fluorophenoxy)phenyl)pyridin-2-yl)-3-(1-methyl-1H-imidazol-4-yl)-2-propionamidopropanamide,
(S)—N-(6-(4-(4-fluorophenoxy)phenyl)pyridin-2-yl)-2-isobutyramido-3-(1-methyl-1H-imidazol-4-yl)propanamide,
(S)—N-(6-(4-(4-fluorophenoxy)phenyl)pyridin-2-yl)-3-(1-methyl-1H-imidazol-4-yl)-2-pivalamidopropanamide,
(S)-2-acetamido-N-(4-(4-(4-fluorophenoxy)phenyl)pyridin-2-yl)-3-(1-methyl-1H-imidazol-4-yl)propanamide,
(S)—N-(1-((6-(4-(4-fluorophenoxy)phenyl)pyridin-2-yl)amino)-3-(1-methyl-1H-imidazol-4-yl)-1-oxopropan-2-yl)cyclopropanecarboxamide,
(S)-3,3,3-trifluoro-N-(1-((6-(4-(4-fluorophenoxy)phenyl)pyridin-2-yl)amino)-3-(1-methyl-1H-imidazol-4-yl)-1-oxopropan-2-yl)propanamide,
(S)-2-acetamido-N-(6-(4-(4-fluorophenoxy)phenyl)pyridin-2-yl)-3-(1-methyl-1H-imidazol-5-yl)propanamide,
(R)—N-(1-((6-(4-(4-fluorophenoxy)phenyl)pyridin-2-yl)amino)-3-(1-methyl-1H-imidazol-4-yl)-1-oxopropan-2-yl)-4-(trifluoromethyl)benzamide,
(S)-2-(3-(tert-butyl)ureido)-N-(6-(4-(4-fluorophenoxy)phenyl)pyridin-2-yl)-3-hydroxypropanamide,
(S)—N-(6-(4-(4-fluorophenoxy)phenyl)pyridin-2-yl)-2-(2-hydroxyacetamido)-4-methylpentanamide,
(S)—N-(6-(4-(4-fluorophenoxy)phenyl)pyridin-2-yl)-3-hydroxy-2-(3-isopropylureido)propanamide,
(S)—N-(6-(4-(4-fluorophenoxy)phenyl)pyridin-2-yl)-3-hydroxy-2-(2-hydroxy-2-methylpropanamido)propanamide,
(S)—N-(6-(4-(4-fluorophenoxy)phenyl)pyridin-2-yl)-3-hydroxy-2-(2-methoxyacetamido)propanamide,
(R)-2-acetamido-3-(1-methyl-1H-imidazol-4-yl)-N-(6-(4-((5-(trifluoromethyl) pyridin-2-yl)oxy)phenyl)pyridin-2-yl)propanamide,
(2S,3S)—N-(6-(4-(4-fluorophenoxy)phenyl)pyridin-2-yl)-3-hydroxy-2-(2-hydroxyacetamido)butanamide,
2,3-dihydroxy-N-(6-(4-((5-(trifluoromethyl)pyridin-2-yl)oxy)phenyl)pyridin-2-yl)propanamide,
(E)-N-(6-(4-(4-fluorophenoxy)phenyl)pyridin-2-yl)-2-phenylethene sulfonamide,
N-(6-(4-(4-fluorophenoxy)phenyl)pyridin-2-yl)-1-methyl-1H-benzo[d]imidazole-6-carboxamide,
(S)-2-(3-(6-(4-(4-fluorophenoxy)phenyl)pyridin-2-yl) ureido)-3-(1-methyl-1H-imidazol-4-yl)propanamide,
(S)-methyl 2-(3-(6-(4-(4-fluorophenoxy)phenyl)pyridin-2-yl)ureido)-3-(1-methyl-1H-imidazol-4-yl)propanoate,
(R)-2-(3-(6-(4-(4-fluorophenoxy)phenyl)pyridin-2-yl) ureido)-3-(1H-indol-2-yl) propanamide,
(R)-2-(3-(6-(4-(4-fluorophenoxy)phenyl)pyridin-2-yl) ureido)succinamide, and
(R)-2-(3-(6-(4-(4-fluorophenoxy)phenyl)pyridin-2-yl) ureido)-3-(1H-imidazol-5-yl) propanamide,
or a pharmaceutically acceptable salt or solvate thereof.

11. A pharmaceutical composition comprising the compound of claim 1 and a pharmaceutically acceptable carrier.

12. A method for treating pain in a mammal, comprising administering an effective amount of a compound as claimed in claim 1 to a mammal in need of such treatment.

13. A method of modulating $Na_v0.7$ sodium channels in a mammal, comprising administering to the mammal at least one compound as claimed in claim 1.

14. The compound as claimed in claim 1, wherein the compound is $^3H$, $^{11}C$, or $^{14}C$ radiolabeled, or a pharmaceutically acceptable salt or solvate thereof.

15. A method of screening a candidate compound for the ability to bind to a binding site on a protein using a radiolabeled compound of claim 14, comprising a) introducing a fixed concentration of the radiolabeled compound to a soluble or membrane-associated protein or fragment thereof to form a mixture; b) titrating the mixture with a candidate compound; and c) determining the binding of the candidate compound to said binding site.

16. The compound of claim 1, wherein $R^{1b}$ is hydrogen and $R^{1a}$ is an optionally substituted heterocyclo.

17. The compound of claim 1, wherein $R^{1a}$ and $R^{1b}$ are taken together with the nitrogen atom to which they are attached form an optionally substituted heterocyclo.

18. The compound of claim 1, wherein $A^1$-X-$A^2$- is:

19. The compound of claim 18, wherein $R^{12c}$ is halo or haloalkyl.

20. The compound of claim 4, wherein $R^{8a}$ is selected from the group consisting of hydrogen, $C_{1-6}$ alkyl, hydroxyalkyl, (carboxamide)alkyl, aralkyl, and (heteroaryl)alkyl, or a pharmaceutically acceptable salt or solvate thereof.

21. The compound of claim 20, wherein $R^{8a}$ is (carboxamide)alkyl selected from the group consisting of —$CH_2CONH_2$, —$C(H)CH_3CONH_2$, and —$CH_2CON(H)CH_3$.

22. The compound of claim 20, wherein $R^{8a}$ is (heteroaryl)alkyl or monohydroxyalkyl.

23. The compound of claim 4, wherein R2b is selected from the group consisting of hydrogen, halo, and hydroxyalkyl, or a pharmaceutically acceptable salt or solvate thereof.

24. The compound of claim 1, wherein $R^{12c}$ is halo or haloalkyl, and all of $R^{12a}$, $R^{12b}$, $R^{12d}$, and $R^{12e}$ are hydrogen.

\* \* \* \* \*